US012473567B2

(12) United States Patent
Bartlett et al.

(10) Patent No.: US 12,473,567 B2
(45) **Date of Patent: *Nov. 18, 2025**

(54) NON-IMMUNOGENIC CIRCULAR, NON-VIRAL DNA VECTORS

(71) Applicant: Rampart Bioscience, Inc., Monrovia, CA (US)

(72) Inventors: Jeffrey S. Bartlett, Colombus, OH (US); Ming Yan, Encino, CA (US)

(73) Assignee: Rampart Bioscience, Inc., Monrovia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/060,511

(22) Filed: Feb. 21, 2025

(65) Prior Publication Data

US 2025/0179517 A1 Jun. 5, 2025

Related U.S. Application Data

(63) Continuation of application No. 19/015,381, filed on Jan. 9, 2025, which is a continuation of application No. PCT/US2023/070238, filed on Jul. 14, 2023.

(60) Provisional application No. 63/390,515, filed on Jul. 19, 2022.

(51) Int. Cl.

| | |
|---|---|
| ***C12N 15/85*** | (2006.01) |
| ***A61K 9/51*** | (2006.01) |
| ***A61K 48/00*** | (2006.01) |

(52) U.S. Cl.

CPC ............ *C12N 15/85* (2013.01); *A61K 9/5123* (2013.01); *A61K 48/0066* (2013.01); *C12N 2750/14143* (2013.01); *C12N 2800/107* (2013.01); *C12N 2820/55* (2013.01)

(58) Field of Classification Search

CPC .......... C12N 15/85; C12N 2750/14143; C12N 2800/107; C12N 2820/55; A61K 9/5123; A61K 48/0066; A61K 48/0016; A61K 48/005

See application file for complete search history.

(56) References Cited

U.S. PATENT DOCUMENTS

| | | | | |
|---|---|---|---|---|
| 5,478,745 | A | 12/1995 | Samulski et al. | |
| 5,869,305 | A | 2/1999 | Samulski et al. | |
| 6,977,174 | B2 * | 12/2005 | Crouzet | C07K 14/501 435/325 |
| 7,763,712 | B2 | 7/2010 | Crine et al. | |
| 7,803,622 | B2 | 9/2010 | Engelhardt et al. | |
| 7,960,529 | B2 | 6/2011 | Crine et al. | |
| 8,691,208 | B2 | 4/2014 | Tomatsu et al. | |
| 9,598,703 | B2 | 3/2017 | Garcia et al. | |
| 9,988,620 | B2 | 6/2018 | Crine et al. | |
| 10,000,532 | B2 | 6/2018 | Crine et al. | |
| 10,047,365 | B2 | 8/2018 | Williams | |
| 10,167,478 | B2 | 1/2019 | Williams | |
| 10,590,434 | B2 | 3/2020 | Martin Molina et al. | |
| 10,822,596 | B2 | 11/2020 | Hatch | |
| 10,844,388 | B2 | 11/2020 | Williams | |
| 11,015,210 | B2 | 5/2021 | Faust et al. | |
| 11,098,313 | B2 | 8/2021 | Williams | |
| 11,149,302 | B2 | 10/2021 | Rothwell et al. | |
| 11,324,839 | B2 | 5/2022 | Schnepp et al. | |
| 11,602,569 | B2 | 3/2023 | Schnepp et al. | |
| 11,634,742 | B2 | 4/2023 | de Beer et al. | |
| 11,766,490 | B2 | 9/2023 | Schnepp et al. | |
| 11,851,665 | B2 | 12/2023 | Williams | |
| 2003/0032092 | A1 | 2/2003 | Blanche et al. | |
| 2008/0305073 | A1 | 12/2008 | Barone et al. | |
| 2010/0233814 | A1 | 9/2010 | Williams | |
| 2011/0250694 | A1 | 10/2011 | Williams | |
| 2020/0069817 | A1 | 3/2020 | Liu et al. | |
| 2021/0002667 | A1 | 1/2021 | Schnepp et al. | |
| 2021/0010021 | A1 * | 1/2021 | Williams | C12N 15/86 |
| 2021/0169994 | A1 | 6/2021 | Voegtli et al. | |

(Continued)

FOREIGN PATENT DOCUMENTS

| | | | |
|---|---|---|---|
| EP | 0828519 | B1 | 10/2008 |
| EP | 3768846 | B1 | 6/2023 |

(Continued)

OTHER PUBLICATIONS

Lusby (34(2) Journal of Virology 402-409 (1980) (Year: 1980).*
U.S. Appl. No. 19/015,381, Bartlett, et al., filed Jan. 9, 2025.
U.S. Appl. No. 19/016,927, Bartlett, et al., filed Jan. 10, 2025.
Nafissi et al., "Construction and Characterization of an in-vivo Linear Covalently Closed DNA Vector Production System" Microbial Cell Factories, 11:154, 2012.

(Continued)

*Primary Examiner* — Neil P Hammell
*Assistant Examiner* — Kyle T Rega
(74) *Attorney, Agent, or Firm* — Knowles Intellectual Property Strategies, LLC

(57) ABSTRACT

The present disclosure relates to circular, non-viral DNA vectors, compositions including one or more of the disclosed vectors, and methods for delivering and/or expressing one or more therapeutic genes (e.g., proteins) in mammals, e.g., human patients. In some embodiments, the present disclosure is directed to circular, non-viral DNA vectors, such as circular non-viral DNA vectors including at least two inverted repeat sequences, where the at least two inverted repeat sequences are separated by a non-repeated nucleotide sequence which is not part of the at least two inverted repeat sequences. In some embodiments, the disclosed circular, non-viral DNA vectors do not include a "DD element." In some embodiments, the disclosed circular, non-viral DNA vectors do not include a "DD element," but include at least a portion of a bacterial origin of replication.

27 Claims, 34 Drawing Sheets

Specification includes a Sequence Listing.

(56) References Cited

U.S. PATENT DOCUMENTS

| | | | |
|---|---|---|---|
| 2021/0269828 | A1 | 9/2021 | Samulski |
| 2021/0330817 | A1 | 10/2021 | Schnepp et al. |
| 2022/0090129 | A1 | 3/2022 | Miller et al. |
| 2022/0098633 | A1 | 3/2022 | de Beer et al. |
| 2022/0243201 | A1 | 8/2022 | Maghodia et al. |
| 2022/0356490 | A1 | 11/2022 | Liu et al. |
| 2024/0092905 | A1 | 3/2024 | Sevy et al. |

FOREIGN PATENT DOCUMENTS

| | | | | |
|---|---|---|---|---|
| WO | WO 99/28340 | A2 | 6/1999 | |
| WO | WO 99/60146 | A1 | 11/1999 | |
| WO | WO 2005/084180 | A2 | 9/2005 | |
| WO | WO-2009/025866 | A1 | 2/2009 | |
| WO | WO 2014/035457 | A1 | 3/2014 | |
| WO | WO 2014/077863 | A1 | 5/2014 | |
| WO | WO 2014/077866 | A1 | 5/2014 | |
| WO | WO-2014/100798 | A1 | 6/2014 | |
| WO | WO 2016/025884 | A1 | 2/2016 | |
| WO | WO 2018/127462 | A1 | 7/2018 | |
| WO | WO 2018/213828 | A1 | 11/2018 | |
| WO | WO-2019057774 | A1 * | 3/2019 | ............. C12N 15/85 |
| WO | WO 2019/143885 | A1 | 7/2019 | |
| WO | WO 2019/183248 | A1 | 9/2019 | |
| WO | WO 2020/033863 | A1 | 2/2020 | |
| WO | WO 2020/217057 | A1 | 10/2020 | |
| WO | WO 2021/022327 | A1 | 2/2021 | |
| WO | WO 2021/058984 | A1 | 4/2021 | |
| WO | WO 2021/119218 | A1 | 6/2021 | |
| WO | WO 2022/023284 | A1 | 2/2022 | |
| WO | WO 2022/051555 | A2 | 3/2022 | |
| WO | WO 2022/058755 | A1 | 3/2022 | |
| WO | WO 2022/087494 | A1 | 4/2022 | |
| WO | WO 2022/103852 | A1 | 5/2022 | |
| WO | WO 2022/147573 | A1 | 7/2022 | |
| WO | WO 2022/223556 | A1 | 10/2022 | |
| WO | WO 2022/271965 | A2 | 12/2022 | |
| WO | WO 2023/028441 | A1 | 3/2023 | |
| WO | WO 2023/028455 | A1 | 3/2023 | |
| WO | WO 2020/132396 | A1 | 4/2023 | |
| WO | WO 2023/056070 | A2 | 4/2023 | |
| WO | WO 2023/060088 | A1 | 4/2023 | |
| WO | WO 2023/122303 | A2 | 6/2023 | |
| WO | WO 2023/135273 | A2 | 7/2023 | |
| WO | WO 2023/178294 | A2 | 9/2023 | |
| WO | WO 2024/020320 | A2 | 1/2024 | |
| WO | WO-2025/090786 | A1 | 5/2025 | |

OTHER PUBLICATIONS

Bansal et al., "Non-canonical DNA structures: Diversity and disease association." Frontiers in Genetics 13: 959258, Sep. 6, 2022.
Bochman et al., "DNA secondary structures: stability and function of G-quadruplex structures." Nature Reviews/Genetics, p. 1-11, Oct. 3, 2012.
Bowater et al., "Interaction of Proteins with Inverted Repeats and Cruciform Structures in Nucleic Acids." Int. J. Mol. Sci., 23, 6171, 2022.
Brazda et al., "Cruciform structures are common DNA feature important for regulating biological processes." BMC Mol. Biol., 12:33, 2011.
Buck et al., "Recombinant Adeno-Associated viral Vectors (rAAV)-Vector Elements in Ocular Gene Therapy Clinical Trials and Transgene Expression and Bioactivity Assays." Intl. J. of Mol. Sciences, 21, 4197, 2020.
Choi et al., "Effects of Adeno-Associated Virus DNA Hairpin Structure on Recombination." J. of Virol., p. 6801-6807; vol. 79, No. 11, Jun. 2005.
Duan et al., "Circular Intermediates of Recombinant Adeno-Associated Virus Have Defined Structural Characteristics Responsible for Long-Term Episomal Persistence in Muscle Tissue." J. of Virol., p. 8568-8577, Nov. 1998.
Durymanov et al., "Non-viral Delivery of Nucleic Acids: Insight Into Mechanisms of Overcoming Intracellular Barriers." Front. Pharmacol. 9:971, Aug. 2021.
Earley et al., "Adeno-Associated Virus Serotype-Specific Inverted Terminal Repeat Sequence Role in Vector Transgene Expression." Hum Gene Ther., 31(3-4): 151-162, Feb. 2020.
Faust et al., CpG-depleted adeno-associated virus vectors evade immune detection. J Clin Invest, 123:2994-3001, 2013.
Finer et al., "A brief account of viral vectors and their promise for gene therapy." Gene Ther., 24(1):1-2), 2017.
Goncalves et al., "DNA Minicircles Connected via G-Quadruplex Interaction Modules." Small, 6, No. 12, 1347-1352, 2010.
Hardee et al., "Advances in Non-15 Viral DNA Vectors for Gene Therapy." Genes 8(2), 65, 2017.
Hodgson et al., "Recent advances in non-viral vectors for gene therapy & vaccination." Cell Gene Therapy Insights, 3(2), 95-101, 2017.
Inagaki et al., "Chromosomal instability mediated by non-B DNA: Cruciform confirmation and not DNA sequence is responsible for recurrent translocation in humans." Genome Research 19:191-198; 2009.
Islas et al., "Design of microaerobically inducible miniR 1 plasmids." mLife, vol. 2, Issue 1; 101-104, Mar. 2023.
Kay et al., "A robust system for production of minicircle DNA vectors." Nat. Biotechnol., 28, 1287-1289, 2010.
Kurahashi et al., "Cruciform DNA Structure Underlies the Etiology for Palindrome-mediated Human Chromosomal translocations." J Biol Chem., 279(34):35377-35383, Aug. 20, 2004.
Li et al., "Production and characterization of novel recombinant adeno-associated virus replicative-form genomes: A eukaryotic source of DNA for gene transfer." PLoS One 8, e69879, 2013.
Li et al., "Interaction In Vitro of Type III Intermediate Filament Proteins with Supercoiled Plasmid DNA and Modulation of Eukaryotic DNA Topoisomerase I and II Activities." DNA and Cell Biology vol. 21, No. 10, p. 743-769, 2002.
Lim et al., High spontaneous integration rates of end-modified linear DNAs upon 5 mammalian cell transfection. Sci Rep 13, 6835, 2023.
Loot et al., "Cellular pathways controlling integron cassette site folding." EMBO, 29, 2623-2634, 2010.
Lu et al., "The extragenic spacer length between the 5' and 3' ends of the transgene expression cassette affects transgene silencing from plasmid-based vectors." Mol. Ther. J. Am. Soc. Gene Ther., 20, 2111-2119, 2012.
Maniar et al., "Minicircle DNA Vectors Achieve Sustained Expression Reflected by Active Chromatin and Transcriptional Level." Mol. Ther., 21, 131-138, 2013.
Mayer et al., "Construction of DNA Architecture with RNA Hairpins." Angw. Chem. Int. Ed., 47, 971-973, 2008.
Mclean et al., "The Role of DNA Sequence in the Formation of Z-DNA Versus Cruciforms in Plasmids." J. Biol. Chem. vol. 263, No. 15, pp. 7370-7377, May 25, 1988.
Nielsen et al., "A reproducible method for identification of human genomic DNA autonomously replicating sequences." Mol. Gen. Genet., 242:280-288, 1994.
Ou-Yang et al., "Cruciform DNA Structures Act as Legible Templates for Accelerating Homologous Recombination in Transgenic Animals." Int. J. Mol. Sci., 23, 3973, 2022.
Pan et al., "Rational engineering of a functional CpG-free ITR for AAV gene therapy." Gene Ther., 29(6): 333-345, Jun. 2022.
Pandya et al., "Regulatory role of Non-canonical DNA Polymorphisms in human genome and their relevance in Cancer." BBA-Reviews on Cancer 1876, 188594, 2021.
Pierce et al., "High throughput Single-Cell Chromatin Accessibility CRISPR Screens Enable Unbiased Identification of Regulatory Networks in Cancer." Nature Communications, 12:2969, May 2021.
Puras et al., "Protamine/DNA/Niosome Ternary Nonviral Vectors for Gene Delivery to the Retina: The Role of Protamine." Mol. Pharm., 12, 3658-3671, 2015.
Rasched et al., "DNA Minicircles with Gaps for Versatile Functionalization." Angw. Chem. Int. Ed., 47, 967-970, 2008.
Samulski et al., "AAV-mediated gene therapy for research and therapeutic purposes." Annu. Rev. 5 Virol. 1, 427-451, 2014.

(56) References Cited

OTHER PUBLICATIONS

Samulski et al., Cloning of adeno-associated virus into pBR322: Rescue of intact virus from the recombinant plasmid in human cells.: PNAS USA vol. 79, pp. 2077-2081, Mar. 1982.
Sarkar et al., "A novel approach to design of cis-acting DNA structural elements for regulation of gene expression in vivo." Current Science, Vil. 60, Nos. 9 & 10, 25, p. 586-591, May 1991.
Schnepp et al., "Infectious Molecular Clones of Adeno-Associated Virus Isolated Directly from Human Tissues." J. of Virol., p. 1456-1464, vol. 83, No. 3, Feb. 2009.
Thibault et al., "Production of DNA minicircles less than 250 base pairs through a novel concentrated DNA circularization assay enabling minicircle design with NF-kB inhibition activity." Nucleic Acid Research, vol. 45, No. 5, e26, 2017.
Tolmachov, O.E. "Self-entanglement of long linear DNA vectors using transient non-B-DNA attachment points: A new concept for improvement of non-viral therapeutic gene delivery." Medical Hypotheses 78, 632-635, 2012.
Van Gaal et al., "Plasmid Engineering for Controlled and Sustained Gene Expression for Nonviral Gene Therapy." Pharm. Res., 23, 1053-1074, 2006.
Williams, J.A., "Vector Design for Improved DNA Efficacy, Safety and Production." Vaccines, 1, 224-249, 2013.
Williams et al., "Improving cell and gene therapy safety and performance using next-generation Nanoplasmid vectors." Molecular Therapy: Nucleic Acids vol. 32, p. 494-503, Jun. 2023.
Xiao et al., "A Novel 165-Base Pair Terminal Repeat Sequence is the Sole CIS Requirement for the Adeno-Associated Virus Life Cycle." J. of Virol., vol. 71, No. 2, p. 941-948, Feb. 1997.
Zhang et al., "Letter to the Editor: "D" matters in recombinant AAV packaging." Mol. Ther. vol. 29, No. 6, p. 1937-1939, Jun. 2021.
Zhao et al., "Viral vector-based gene therapies in the clinic." Bioeng Transl Med., 7(1): 30 e10258, Jan. 2022.
International Search Report and Written Opinion of PCT/US23/70238, dated Feb. 13, 2024.
US-2025/0146015-A1, May 8, 2025, Bartlett et al., U.S. Appl. No. 19/015,381.
US-2025/0146016-A1, May 8, 2025, Barlett et al., U.S. Appl. No. 19/016,927.
US-2025/0188487-A1, Jun. 12, 2025, Bartlett et al., U.S. Appl. No. 19/064,383.
Athman et al., "A Computational Analysis of Alternative Splicing Across Mammalian Tissues Reveals Circadian and Ultradian Rhythms in Splicing Events" pp. 1-25, International Journal of Molecular Sciences, Aug. 15, 2019.

* cited by examiner

| Length | 607 | 709 | 652 |
|---|---|---|---|
| Predicted Gibbs free energy (KJ/mol) | -289 | -451.3 | -417.8 |
| Normalized predicted Gibbs free energy (KJ/mol/bp) | -0.47611 | -0.63653 | -0.6408 |
| Predicted Tm (400nM DNA 50mM salt Mg 2.5mM) | 91.58°C 45.8 % GC | 93.37°C 49.51 % GC | 94.1°C 51.23 % GC |

FIG. 2E

SEQUENCE LISTING

```
Sequence total quantity: 95
SEQ ID NO: 1           moltype = DNA  length = 130
FEATURE                Location/Qualifiers
misc_feature           1..130
                       note = Synthetic: 5' Inverted Repeat Sequence derived from
                        AAV2 ITR
source                 1..130
                       mol_type = other DNA
                       organism = synthetic construct
SEQUENCE: 1
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag                                                         130

SEQ ID NO: 2           moltype = DNA  length = 130
FEATURE                Location/Qualifiers
misc_feature           1..130
                       note = Synthetic: 3' Inverted Repeat Sequence derived from
                        AAV2 ITR
source                 1..130
                       mol_type = other DNA
                       organism = synthetic construct
SEQUENCE: 2
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct                                                         130

SEQ ID NO: 3           moltype = DNA  length = 128
FEATURE                Location/Qualifiers
misc_feature           1..128
                       note = Synthetic: 5' Inverted Repeat Sequence derived from
                        AAV1 ITR
```

```
source                  1..128
                        mol_type = other DNA
                        organism = synthetic construct
SEQUENCE: 3
ttaccccctag tgatggagtt gcccactccc tctctgcgcg ctcgctcgct cggtggggcc  60
tgcggaccaa aggtccgcag acggcagagc tctgctctgc cggccccacc gagcgagcga  120
gcgcgcag                                                            128

SEQ ID NO: 4            moltype = DNA  length = 128
FEATURE                 Location/Qualifiers
misc_feature            1..128
                        note = Synthetic: 3' Inverted Repeat Sequence derived from
                         AAV1 ITR
source                  1..128
                        mol_type = other DNA
                        organism = synthetic construct
SEQUENCE: 4
ctgcgcgctc gctcgctcgg tggggccggc agagcagagc tctgccgtct gcggaccttt  60
ggtccgcagg ccccaccgag cgagcgagcg cgcagagagg gagtgggcaa ctccatcact  120
aggggtaa                                                            128

SEQ ID NO: 5            moltype = DNA  length = 133
FEATURE                 Location/Qualifiers
misc_feature            1..133
                        note = Synthetic: 5' Inverted Repeat Sequence derived from
                         AAV3 ITR
source                  1..133
                        mol_type = other DNA
                        organism = synthetic construct
SEQUENCE: 5
gccatacctc tagtgatgga gttgcccact ccctctatgc gcactcgctc gctcggtggg  60
gcctggcgac caaaggtcgc cagacggacg tgctttgcac gtccggcccc accgagcgag  120
cgagtgcgca tag                                                      133

SEQ ID NO: 6            moltype = DNA  length = 133
FEATURE                 Location/Qualifiers
misc_feature            1..133
                        note = Synthetic: 3' Inverted Repeat Sequence derived from
                         AAV3 ITR
source                  1..133
                        mol_type = other DNA
                        organism = synthetic construct
SEQUENCE: 6
ctatgcgcac tcgctcgctc ggtggggccg gacgtgcaaa gcacgtccgt ctggcgacct  60
ttggtcgcca ggccccaccg agcgagcgag tgcgcataga gggagtgggc aactccatca  120
ctagaggtat ggc                                                      133

SEQ ID NO: 7            moltype = DNA  length = 133
FEATURE                 Location/Qualifiers
misc_feature            1..133
                        note = Synthetic: 5' Inverted Repeat Sequence derived from
                         AAV4 ITR
source                  1..133
                        mol_type = other DNA
                        organism = synthetic construct
SEQUENCE: 7
gggcaaacct agatgatgga gttggccact ccctctatgc gcgctcgctc actcactcgg  60
ccctggagac caaaggtctc cagactgccg gcctctggcc ggcagggccg agtgagtgag  120
cgagcgcgca tag                                                      133

SEQ ID NO: 8            moltype = DNA  length = 133
FEATURE                 Location/Qualifiers
misc_feature            1..133
                        note = Synthetic: 3' Inverted Repeat Sequence derived from
                         AAV4 ITR
source                  1..133
                        mol_type = other DNA
                        organism = synthetic construct
SEQUENCE: 8
ctatgcgcgc tcgctcactc actcggccct gccggccaga ggccggcagt ctggagacct  60
ttggtctcca gggccgagtg agtgagcgag cgcgcataga gggagtggcc aactccatca  120
tctaggtttg ccc                                                      133

SEQ ID NO: 9            moltype = DNA  length = 129
FEATURE                 Location/Qualifiers
misc_feature            1..129
                        note = Synthetic: 5' Inverted Repeat Sequence derived from
                         AAV6 ITR
source                  1..129
```

```
                        mol_type = other DNA
                        organism = synthetic construct
SEQUENCE: 9
ataccoctag tgatggagtt gcccactccc tctatgcgcg ctcgctcgct cgtggggcct  60
gcggaccaaa ggtccgcaga cggcagagct ctgctctgcc ggccccaccg agcgagcgag  120
cgcgcatag                                                           129

SEQ ID NO: 10           moltype = DNA  length = 129
FEATURE                 Location/Qualifiers
misc_feature            1..129
                        note = Synthetic: 3' Inverted Repeat Sequence derived from
                         AAV6 ITR
source                  1..129
                        mol_type = other DNA
                        organism = synthetic construct
SEQUENCE: 10
ctatgcgcgc tcgctcgctc ggtggggccg gcagagcaga gctctgccgt ctgcggacct  60
ttggtccgca ggccccacga gcgagcgagc gcgcatagag ggagtgggca actccatcac  120
taggggtat                                                           129

SEQ ID NO: 11           moltype = DNA  length = 132
FEATURE                 Location/Qualifiers
misc_feature            1..132
                        note = Synthetic: 5' Inverted Repeat Sequence derived from
                         AAV7 ITR
source                  1..132
                        mol_type = other DNA
                        organism = synthetic construct
SEQUENCE: 11
cggtacccct agtgagggag ttggccactc cctctatgcg cgctcgctcg ctcggtgggg  60
cctgcggacc aaaggtccgc agacggcaga gctctgctct gccggcccca ccgagcgagc  120
gagcgcgcat ag                                                       132

SEQ ID NO: 12           moltype = DNA  length = 132
FEATURE                 Location/Qualifiers
misc_feature            1..132
                        note = Synthetic: 3' Inverted Repeat Sequence derived from
                         AAV7 ITR
source                  1..132
                        mol_type = other DNA
                        organism = synthetic construct
SEQUENCE: 12
ctatgcgcgc tcgctcgctc ggtggggccg gcagagcaga gctctgccgt ctgcggacct  60
ttggtccgca ggccccaccg agcgagcgag cgcgcataga gggagtggcc aactccctca  120
ctaggggtac cg                                                       132

SEQ ID NO: 13           moltype = DNA  length = 129
FEATURE                 Location/Qualifiers
misc_feature            1..129
                        note = Synthetic: Zero-CpG 5' Inverted Repeat Sequence
                         Variant 1 derived from AAV2 ITR
source                  1..129
                        mol_type = other DNA
                        organism = synthetic construct
SEQUENCE: 13
ttaattaagg ctaggaaccc ctagtgatgg agttggccac tccctctctg ccctctccct  60
ctctcactga ggcctgggga ccaaaggtcc ccagactgca gagctttgct ctgcaggcct  120
cagtgagag                                                           129

SEQ ID NO: 14           moltype = DNA  length = 129
FEATURE                 Location/Qualifiers
misc_feature            1..129
                        note = Synthetic: Zero-CpG 3' Inverted Repeat Sequence
                         Variant 1 derived from AAV2 ITR
source                  1..129
                        mol_type = other DNA
                        organism = synthetic construct
SEQUENCE: 14
ctctcactga ggcctgcaga gcaaagctct gcagtctggg gacctttggt ccccaggcct  60
cagtgagaga gggagagggc agagagggag tggccaactc catcactagg ggttcctagc  120
cttaattaa                                                           129

SEQ ID NO: 15           moltype = DNA  length = 132
FEATURE                 Location/Qualifiers
misc_feature            1..132
                        note = Synthetic: Zero-CpG 5' Inverted Repeat Sequence
                         Variant 2 derived from AAV2 ITR
source                  1..132
                        mol_type = other DNA
```

```
                         organism = synthetic construct
SEQUENCE: 15
aggaacccct agtgatggag ttggccactc cctctctgca ctctctctct ctcactgagg  60
cctggggacc aaaggtcccc agactgcaga gctttgctct gcaggcctca gtgagagaga  120
gagagtgcag ag                                                      132

SEQ ID NO: 16            moltype = DNA  length = 129
FEATURE                  Location/Qualifiers
misc_feature             1..129
                         note = Synthetic: Zero-CpG 3' Inverted Repeat Sequence
                          Variant 2 derived from AAV2 ITR
source                   1..129
                         mol_type = other DNA
                         organism = synthetic construct
SEQUENCE: 16
ctctcactga ggcctgcaga gcaaagctct gcagtctggg gacctttggt ccccaggcct  60
cagtgagaga gggagagggc agagagggag tggccaactc catcactagg ggttcctagc  120
cttaattaa                                                          129

SEQ ID NO: 17            moltype = DNA  length = 129
FEATURE                  Location/Qualifiers
misc_feature             1..129
                         note = Synthetic: Zero-CpG 5' Inverted Repeat Sequence
                          Variant 3 derived from AAV2 ITR
source                   1..129
                         mol_type = other DNA
                         organism = synthetic construct
SEQUENCE: 17
ttaattaagg ctaggaaccc ctagtgatgg agttggccac tccctctctg ccctctccct  60
ctctcactga ggcctgggga ccaaaggtcc ccagactgca gagctttgct ctgcaggcct  120
cagtgagag                                                          129

SEQ ID NO: 18            moltype = DNA  length = 129
FEATURE                  Location/Qualifiers
misc_feature             1..129
                         note = Synthetic: Zero-CpG 3' Inverted Repeat Sequence
                          Variant 3 derived from AAV2 ITR
source                   1..129
                         mol_type = other DNA
                         organism = synthetic construct
SEQUENCE: 18
ctctcactga ggcctgcaga gcaaagctct gcagtctggg gacctttggt ccccaggcct  60
cagtgagaga gggagagggc agagagggag tggccaactc catcactagg ggttcctagc  120
cttaattaa                                                          129

SEQ ID NO: 19            moltype = AA  length = 502
FEATURE                  Location/Qualifiers
REGION                   1..502
                         note = Synthetic: sTNALP
source                   1..502
                         mol_type = protein
                         organism = synthetic construct
SEQUENCE: 19
MISPFLVLAI GTCLTNSLVP EKEKDPKYWR DQAQETLKYA LELQKLNTNV AKNVIMFLGD  60
GMGVSTVTAA RILKGQLHHN PGEETRLEMD KFPFVALSKT YNTNAQVPDS AGTATAYLCG  120
VKANEGTVGV SAATERSRCN TTQGNEVTSI LRWAKDAGKS VGIVTTTRVN HATPSAAYAH  180
SADRDWYSDN EMPPEALSQG CKDIAYQLMH NIRDIDVIMG GGRKYMYPKN KTDVEYESDE  240
KARGTRLDGL DLVDTWKSFK PRYKHSHFIW NRTELLTLDP HNVDYLLGLF EPGDMQYELN  300
RNNVTDPSLS EMVVVAIQIL RKNPKGFFLL VEGGRIDHGH HEGKAKQALH EAVEMDRAIG  360
QAGSLTSSED TLTVVTADHS HVFTFGGYTP RGNSIFGLAP MLSDTDKKPF TAILYGNGPG  420
YKVVGGEREN VSMVDYAHNN YQAQSAVPLR HETHGGEDVA VFSKGPMAHL LHGVHEQNYV  480
PHVMAYAACI GANLGHCAPA SS                                           502

SEQ ID NO: 20            moltype = AA  length = 512
FEATURE                  Location/Qualifiers
REGION                   1..512
                         note = Synthetic: TNALP-D10
source                   1..512
                         mol_type = protein
                         organism = synthetic construct
SEQUENCE: 20
MISPFLVLAI GTCLTNSLVP EKEKDPKYWR DQAQETLKYA LELQKLNTNV AKNVIMFLGD  60
GMGVSTVTAA RILKGQLHHN PGEETRLEMD KFPFVALSKT YNTNAQVPDS AGTATAYLCG  120
VKANEGTVGV SAATERSRCN TTQGNEVTSI LRWAKDAGKS VGIVTTTRVN HATPSAAYAH  180
SADRDWYSDN EMPPEALSQG CKDIAYQLMH NIRDIDVIMG GGRKYMYPKN KTDVEYESDE  240
KARGTRLDGL DLVDTWKSFK PRYKHSHFIW NRTELLTLDP HNVDYLLGLF EPGDMQYELN  300
RNNVTDPSLS EMVVVAIQIL RKNPKGFFLL VEGGRIDHGH HEGKAKQALH EAVEMDRAIG  360
QAGSLTSSED TLTVVTADHS HVFTFGGYTP RGNSIFGLAP MLSDTDKKPF TAILYGNGPG  420
YKVVGGEREN VSMVDYAHNN YQAQSAVPLR HETHGGEDVA VFSKGPMAHL LHGVHEQNYV  480
```

```
PHVMAYAACI GANLGHCAPA SSDDDDDDDD DD                               512

SEQ ID NO: 21          moltype = AA  length = 520
FEATURE                Location/Qualifiers
REGION                 1..520
                       note = Synthetic: sTNALP-(DSS)6
source                 1..520
                       mol_type = protein
                       organism = synthetic construct
SEQUENCE: 21
MISPFLVLAI GTCLTNSLVP EKEKDPKYWR DQAQETLKYA LELQKLNTNV AKNVIMFLGD  60
GMGVSTVTAA RILKGQLHHN PGEETRLEMD KFPFVALSKT YNTNAQVPDS AGTATAYLCG  120
VKANEGTVGV SAATERSRCN TTQGNEVTSI LRWAKDAGKS VGIVTTTRVN HATPSAAYAH  180
SADRDWYSDN EMPPEALSQG CKDIAYQLMH NIRDIDVIMG GGRKYMYPKN KTDVEYESDE  240
KARGTRLDGL DLVDTWKSFK PRYKHSHFIW NRTELLTLDP HNVDYLLGLF EPGDMQYELN  300
RNNVTDPSLS EMVVVAIQIL RKNPKGFFLL VEGGRIDHGH HEGKAKQALH EAVEMDRAIG  360
QAGSLTSSED TLTVVTADHS HVFTFGGYTP RGNSIFGLAP MLSDTDKKPF TAILYGNGPG  420
YKVVGGEREN VSMVDYAHNN YQAQSAVPLR HETHGGEDVA VFSKGPMAHL LHGVHEQNYV  480
PHVMAYAACI GANLGHCAPA SSDSSDSSDS SDSSDSSDSS                       520

SEQ ID NO: 22          moltype = AA  length = 231
FEATURE                Location/Qualifiers
REGION                 1..231
                       note = Synthetic: Fc Domain
source                 1..231
                       mol_type = protein
                       organism = synthetic construct
SEQUENCE: 22
LKDKTHTCPP CPAPELLGGP SVFLFPPKPK DTLMISRTPE VTCVVVDVSH EDPEVKFNWY  60
VDGVEVHNAK TKPREEQYNS TYRVVSVLTV LHQDWLNGKE YKCKVSNKAL PAPIEKTISK  120
AKGQPREPQV YTLPPSREEM TKNQVSLTCL VKGFYPSDIA VEWESNGQPE NNYKTTPPVL  180
DSDGSFFLYS KLTVDKSRWQ QGNVFSCSVM HEALHNHYTQ KSLSLSPGKD I           231

SEQ ID NO: 23          moltype = AA  length = 524
FEATURE                Location/Qualifiers
REGION                 1..524
                       note = misc_feature - HUMAN Alkaline phosphatase,
                        tissue-nonspecific isozyme
source                 1..524
                       mol_type = protein
                       organism = Homo sapiens
SEQUENCE: 23
MISPFLVLAI GTCLTNSLVP EKEKDPKYWR DQAQETLKYA LELQKLNTNV AKNVIMFLGD  60
GMGVSTVTAA RILKGQLHHN PGEETRLEMD KFPFVALSKT YNTNAQVPDS AGTATAYLCG  120
VKANEGTVGV SAATERSRCN TTQGNEVTSI LRWAKDAGKS VGIVTTTRVN HATPSAAYAH  180
SADRDWYSDN EMPPEALSQG CKDIAYQLMH NIRDIDVIMG GGRKYMYPKN KTDVEYESDE  240
KARGTRLDGL DLVDTWKSFK PRYKHSHFIW NRTELLTLDP HNVDYLLGLF EPGDMQYELN  300
RNNVTDPSLS EMVVVAIQIL RKNPKGFFLL VEGGRIDHGH HEGKAKQALH EAVEMDRAIG  360
QAGSLTSSED TLTVVTADHS HVFTFGGYTP RGNSIFGLAP MLSDTDKKPF TAILYGNGPG  420
YKVVGGEREN VSMVDYAHNN YQAQSAVPLR HETHGGEDVA VFSKGPMAHL LHGVHEQNYV  480
PHVMAYAACI GANLGHCAPA SSAGSLAAGP LLLALALYPL SVLF                   524

SEQ ID NO: 24          moltype = AA  length = 484
FEATURE                Location/Qualifiers
REGION                 1..484
                       note = Synthetic: secretive TNALP without GPI
source                 1..484
                       mol_type = protein
                       organism = synthetic construct
SEQUENCE: 24
VPEKEKDPKY WRDQAQETLK YALELQKLNT NVAKNVIMFL GDGMGVSTVT AARILKGQLH  60
HNPGEETRLE MDKFPFVALS KTYNTNAQVP DSAGTATAYL CGVKANEGTV GVSAATERSR  120
CNTTQGNEVT SILRWAKDAG KSVGIVTTTR VNHATPSAAY AHSADRDWYS DNEMPPEALS  180
QGCKDIAYQL MHNIRDIDVI MGGGRKYMYP KNKTDVEYES DEKARGTRLD GLDLVDTWKS  240
FKPRYKHSHF IWNRTELLTL DPHNVDYLLG LFEPGDMQYE LNRNNVTDPS LSEMVVVAIQ  300
ILRKNPKGFF LLVEGGRIDH GHHEGKAKQA LHEAVEMDRA IGQAGSLTSS EDTLTVVTAD  360
HSHVFTFGGY TPRGNSIFGL APMLSDTDKK PFTAILYGNG PGYKVVGGER ENVSMVDYAH  420
NNYQAQSAVP LRHETHGGED VAVFSKGPMA HLLHGVHEQN YVPHVMAYAA CIGANLGHCA  480
PASS                                                              484

SEQ ID NO: 25          moltype = AA  length = 18
FEATURE                Location/Qualifiers
REGION                 1..18
                       note = Synthetic: signal peptide
source                 1..18
                       mol_type = protein
                       organism = synthetic construct
SEQUENCE: 25
MISPFLVLAI GTCLTNSL                                               18
```

```
SEQ ID NO: 26          moltype = AA  length = 22
FEATURE                Location/Qualifiers
REGION                 1..22
                       note = Synthetic: GPI anchor
source                 1..22
                       mol_type = protein
                       organism = synthetic construct
SEQUENCE: 26
AGSLAAGPLL LALALYPLSV LF                                           22

SEQ ID NO: 27          moltype = AA  length = 22
FEATURE                Location/Qualifiers
REGION                 1..22
                       note = Synthetic: mutated GPI anchor
source                 1..22
                       mol_type = protein
                       organism = synthetic construct
SEQUENCE: 27
AGSLAADPAA TAAALYPLSV LF                                           22

SEQ ID NO: 28          moltype = DNA  length = 5118
FEATURE                Location/Qualifiers
misc_feature           1..5118
                       note = Synthetic: (M012) Halo sTNALP vector comprising a
                        cruciform structure IR-R6K Ori-IR and EF1A-driven
                        sTNALP-Fc-(DSS)6 transgene
source                 1..5118
                       mol_type = other DNA
                       organism = synthetic construct
SEQUENCE: 28
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctagc ggctccggtg cccgtcagtg ggcagagcgc  240
acatcgccca cagtccccga gaagttgggg ggaggggtcg gcaattgaac cggtgcctag  300
agaaggtggc gcggggtaaa ctgggaaagt gatgtcgtgt actggctccg cctttttccc  360
gagggtgggg gagaaccgta tataagtgca gtagtcgccg tgaacgttct ttttcgcaac  420
gggtttgccg ccagaacaca ggtaagtgcc gtgtgtggtt cccgcgggcc tggcctcttt  480
acgggttatg gcccttgcgt gccttgaatt acttccactg gctgcagtac gtgattcttg  540
atcccgagct tcgggttgga agtgggtggg agagttcgag gccttgcgct taaggagccc  600
cttcgcctcg tgcttgagtt gaggcctggc ctgggcgctg gggccgccgc gtgcgaatct  660
ggtggcacct tcgcgcctgt ctcgctgctt tcgataagtc tctagccatt taaaattttt  720
gatgacctgc tgcgacgctt tttttctggc aagatagtct tgtaaatgcg ggccaagatc  780
tgcacactgg tatttcggtt tttggggccg cgggcggcga cggggcccgt gcgtcccagc  840
gcacatgttc ggcgaggcgg ggcctgcgag cgcggccacc gagaatcgga cgggggtagt  900
ctcaagctgg ccggcctgct ctggtgcctg gcctcgcgcc gccgtgtatc gccccgccct  960
gggcggcaag gctggcccgg tcggcaccag ttgcgtgagc ggaaagatgg ccgcttcccg  1020
gccctgctgc agggagctca aaatggagga cgcggcgctc gggagagcgg gcgggtgagt  1080
cacccacaca aaggaaaagg gcctttccgt cctcagccgt cgcttcatgt gactccacgg  1140
agtaccgggc gccgtccagg cacctcgatt agttctcgag cttttggagt acgtcgtctt  1200
taggttgggg ggaggggttt tatgcgatgg agtttcccca cactgagtgg gtggagactg  1260
aagttaggcc agcttggcac ttgatgtaat tctccttgga atttgccctt tttgagtttg  1320
gatcttggtt cattctcaag cctcagacag tggttcaaag tttttttctt ccatttcagg  1380
tgtcgtgagc tagcgccacc atggatatgc gcgtacccgc tcaacttctg ggtttgttgc  1440
tgctttggct caggggagcc cgctgtgccg cgcttgtccc tgaaaaggag aaggacccca  1500
aatattggag agaccaggct caggaaaccc tcaagtacgc tcttgaactg caaaagctta  1560
atactaacgt ggctaaaaac gtgataatgt tcttgggggga cggaatgggg gtttcaaccg  1620
ttaccgcggc cagaatcttg aaagggcagc tgcaccataa cccaggcgaa gaaacgaggc  1680
tggagatgga caaatttcca ttcgtggcgc tttctaagac ctacaacact aacgcccagg  1740
tccctgactc agctggtacg gccactgcct acctttgtgg agtgaaggca aatgagggga  1800
ctgttggtgt ttccgcagct actgagagat ctcggtgtaa tacgactcaa ggtaatgaag  1860
ttacatccat actccgatgg gcaaaagacg cgggcaaatc tgttgggatt gttacaacta  1920
ctagggtgaa ccatgcgaca ccctctgcag cttatgcgca cagtgccgac cgagactggt  1980
attcagataa tgagatgcca cccgaggccc ttagccaggg ctgcaaggac atagcctatc  2040
aattgatgca caatatcaga gacatagacg ttataatggg tggtggtcgc aagtacatgt  2100
accccaaaaa caaaaccgac gtagagtatg aatccgatga aaaagctagg ggcaccagac  2160
tcgacggact tgatctggtt gatacatgga agagcttcaa gcccagatac aagcattcac  2220
atttcatctg gaacaggacc gaacttctca cattggaccc ccacaatgtt gactatctcc  2280
tcggtttgtt tgaaccaggg gatatgcagt atgagctcaa tcggaacaac gtcactgacc  2340
ccagtttgag tgaaatggtc gttgttgcaa tacaaatttt gaggaaaaat ccaaaggggt  2400
ttttcttgtt ggtagagggc ggacggatag atcacgggca ccacgaaggc aaagcaaaac  2460
aggccctgca cgaagccgtt gaaatggatc gcgctatcgg tcaagccggc tccctgacga  2520
gtagtgaaga taccttgacc gtcgtcactg cggatcatag ccacgttttt acctttgggg  2580
gatacacccc caggggcaac tcaatttttg gacttgcacc gatgctcagc gacacagata  2640
aaaagccttt tactgcgatt ctgtatggca acggccctgg atacaaagta gtagggggtg  2700
aaagggaaaa cgtcagcatg gtggactatg cacacaataa ttatcaggcg cagtccgctg  2760
ttccgctgcg gcatgagact cacgggggag aggacgttgc tgtcttttcc aagggaccaa  2820
tggctcatct tctccatgga gtccatgagc aaaattatgt ccctcatgtc atggcatacg  2880
```

```
ctgcatgtat aggagcaaat ctcgggcact gtgcaccggc gtcctccctc aaagacaaaa  2940
cacacacttg tccaccttgc ccggcacctg aacttctggg cggcccgagc gttttttttgt  3000
tccctcctaa acctaaggac acgctcatga tcagccgcac gccagaggtt acctgtgtag  3060
tggtggatgt cagccacgag gatccggaag taaaattcaa ctggtatgta gatggggtgg  3120
aggttcacaa tgccaaaacc aagccacgag aggaacagta caatagtact taccgggtcg  3180
tgtctgtatt gaccgtcctg catcaggatt ggttgaacgg gaaagaatat aagtgcaagg  3240
tgagcaacaa agcacttccg gccccaatag agaaaacaat tagtaaagca aaaggacaac  3300
cacgggaacc gcaagtttat acactgccgc cctctcgaga cgagctgacc aaaaatcagg  3360
ttagccttac atgtttggtc aaggggttct acccgagtga tattgcagtg gaatgggaat  3420
ccaacggtca accagaaaat aactacaaaa ctactccgcc ggtgttggat tcagacggct  3480
ctttctttct gtatagcaaa ctcactgttg acaagtcaag atggcagcag ggcaatgtat  3540
ttagctgtag tgttatgcac gaagctcttc ataaccacta cacacaaaag tcactttctc  3600
tttccccagg aaaagacatc gattccagcg acagttcaga cagctctgac agctccgatt  3660
cctccgactc aagttgaaag cttggatcca atcaacctct ggattacaaa atttgtgaaa  3720
gattgactgg tattcttaac tatgttgctc cttttacgct atgtggatac gctgctttaa  3780
tgcctttgta tcatgctatt gcttcccgta tggctttcat tttctcctcc ttgtataaat  3840
cctggttgct gtctctttat gaggagttgt ggcccgttgt caggcaacgt ggcgtggtgt  3900
gcactgtgtt tgctgacgca acccccactg gttggggcat tgccaccacc tgtcagctcc  3960
tttccgggac tttcgctttc cccctcccta ttgccacggc ggaactcatc gccgcctgcc  4020
ttgcccgctg ctggacaggg gctcggctgt tgggcactga caattccgtg gtgttgtcgg  4080
ggaaatcatc gtcctttcct tggctgctcg cctgtgttgc cacctggatt ctgcgcggga  4140
cgtccttctg ctacgtccct tcggccctca atccagcgga ccttccttcc cgcggcctgc  4200
tgccggctct gcggcctctt ccgcgtcttc gagatctgcc tcgactgtgc cttctagttg  4260
ccagccatct gttgtttgcc cctcccccgt gccttccttg accctggaag gtgccactcc  4320
cactgtcctt tcctaataaa atgaggaaat tgcatcgcat tgtctgagta ggtgtcattc  4380
tattctgggg ggtggggtgg ggcaggacag caagggggag gattgggaag acaatagcag  4440
gcatgctggg gactcgagtt aagggcgaat tcccgataag gatcttccta gagcatggct  4500
acgtagataa gtagcatggc gggttaatca ttaactacaa ggaaccccta gtgatggagt  4560
tggccactcc ctctctgcgc gctcgctcgc tcactgaggc cgggcgacca aaggtcgccc  4620
gacgcccggg ctttgcccgg gcggcctcag tgagcgagcg agcgcgcagc cttaattaat  4680
accgttcgta taatgtatgc tatacgaacg gtactgcagt gtcagccgtt aagtgttcct  4740
gtgtcactca aaattgcttt gagaggctct aagggcttct cagtgcgtta catccctggc  4800
ttgttgtcca caaccgttaa accttaaaag ctttaaaagc cttatatatt cttttttttc  4860
ttataaaact taaaacctta gaggctattt aagttgctga tttatattaa ttttattgtt  4920
caaacatgag agcttagtac gtgaaacatg agagcttagt acgttagcca tgagagctta  4980
gtacgttagc catgagggtt tagttcgtta aacatgagag cttagtacgt taaacatgag  5040
agcttagtac gtgaaacatg agagcttagt acgtactatc aacaggttga actgctgatc  5100
ttcagatctt aattaagg                                                5118
```

```
SEQ ID NO: 29           moltype = DNA  length = 4857
FEATURE                 Location/Qualifiers
misc_feature            1..4857
                        note = Synthetic: (M013) Halo sTNALP vector comprising A
                         CRUCIFORM structure and EF1A-driven sTNALP-Fc-(DSS)6
                         transgene
source                  1..4857
                        mol_type = other DNA
                        organism = synthetic construct
SEQUENCE: 29
ctaggaaccc ctagtgatgg agttggccac tccctctctg cgcgctcgct cgctcactga  60
ggccgggcga ccaaaggtcg cccgacgccc gggctttgcc cgggcggcct cagtgagcga  120
gcgagcgcgc agagagggag tggccaactc catcactagg ggtttccttt aattaaggct  180
ccggtgcccg tcagtgggca gagcgcacat cgcccacagt ccccgagaag ttggggggag  240
gggtcggcaa ttgaaccggt gcctagagaa ggtggcgcgg ggtaaactgg gaaagtgatg  300
tcgtgtactg gctccgcctt tttcccgagg gtgggggaga accgtatata agtgcagtag  360
tcgccgtgaa cgttcttttt cgcaacgggt ttgccgccag aacacaggta agtgccgtgt  420
gtggttcccg cgggcctggc ctctttacgg gttatggccc ttgcgtgcct tgaattactt  480
ccactggctg cagtacgtga ttcttgatcc cgagcttcgg gttggaagtg ggtgggagag  540
ttcgaggcct tgcgcttaag gagccccttc gcctcgtgct tgagttgagg cctggcctgg  600
gcgctggggc cgccgcgtgc gaatctggtg gcaccttcgc gcctgtctcg ctgctttcga  660
taagtctcta gccatttaaa atttttgatg acctgctgcg acgctttttt tctggcaaga  720
tagtcttgta aatgcgggcc aagatctgca cactggtatt tcggtttttg gggccgcggg  780
cggcgacggg gcccgtgcgt cccagcgcac atgttcggcg aggcggggcc tgcgagcgcg  840
gccaccgaga atcggacggg ggtagtctca agctggccgg cctgctctgg tgcctggcct  900
cgcgccgccg tgtatcgccc cgccctgggc ggcaaggctg gcccggtcgg caccagttgc  960
gtgagcggaa agatggccgc ttcccggccc tgctgcaggg agctcaaaat ggaggacgcg  1020
gcgctcggga gagcgggcgg gtgagtcacc cacacaaagg aaaagggcct ttccgtcctc  1080
agccgtcgct tcatgtgact ccacggagta ccgggcgccg tccaggcacc tcgattagtt  1140
ctcgagcttt tggagtacgt cgtctttagg ttggggggag gggttttatg cgatggagtt  1200
tccccacact gagtgggtgg agactgaagt taggccagct tggcacttga tgtaattctc  1260
cttggaattt gccctttttg agtttggatc ttggttcatt ctcaagcctc agacagtggt  1320
tcaaagtttt tttcttccat ttcaggtgtc gtgagctagc gccaccatgg atatgcgcgt  1380
acccgctcaa cttctgggtt tgttgctgct ttggctcagg ggagcccgct gtgccgcgct  1440
tgtccctgaa aaggagaagg accccaaata ttggagagac caggctcagg aaaccctcaa  1500
gtacgctctt gaactgcaaa agcttaatac taacgtggct aaaaacgtga taatgttctt  1560
gggggacgga atgggggttt caaccgttac cgcggccaga atcttgaaag ggcagctgca  1620
ccataaccca ggcgaagaaa cgaggctgga gatggacaaa tttccattcg tggcgctttc  1680
taagacctac aacactaacg cccaggtccc tgactcagct ggtacggcca ctgcctacct  1740
ttgtggagtg aaggcaaatg aggggactgt tggtgtttcc gcagctactg agagatctcg  1800
```

```
gtgtaatacg actcaaggta atgaagttac atccatactc cgatgggcaa aagacgcggg  1860
caaatctgtt gggattgtta caactactag ggtgaaccat gcgacaccct ctgcagctta  1920
tgcgcacagt gccgaccgag actggtattc agataatgag atgccacccg aggcccttag  1980
ccagggctgc aaggacatag cctatcaatt gatgcacaat atcagagaca tagacgttat  2040
aatgggtggt ggtcgcaagt acatgtaccc caaaaacaaa accgacgtag agtatgaatc  2100
cgatgaaaaa gctaggggca ccagactcga cggacttgat ctggttgata catggaagag  2160
cttcaagccc agatacaagc attcacattt catctggaac aggaccgaac ttctcacatt  2220
ggacccccac aatgttgact atctcctcgg tttgtttgaa ccaggggata tgcagtatga  2280
gctcaatcgg aacaacgtca ctgaccccag tttgagtgaa atggtcgttg ttgcaataca  2340
aattttgagg aaaaatccaa aggggttttt cttgttggta gagggcggac ggatagatca  2400
cgggcaccac gaaggcaaag caaaacaggc cctgcacgaa gccgttgaaa tggatcgcgc  2460
tatcggtcaa gccggctccc tgacgagtag tgaagatacc ttgaccgtcg tcactgcgga  2520
tcatagccac gtttttacct ttgggggata cacccccagg ggcaactcaa tttttggact  2580
tgcaccgatg ctcagcgaca cagataaaaa gccttttact gcgattctgt atggcaacgg  2640
ccctggatac aaagtagtag ggggtgaaag ggaaaacgtc agcatggtgg actatgcaca  2700
caataattat caggcgcagt ccgctgttcc gctgcggcat gagactcacg ggggagagga  2760
cgttgctgtc ttttccaagg gaccaatggc tcatcttctc catggagtcc atgagcaaaa  2820
ttatgtccct catgtcatgg catacgctgc atgtatagga gcaaatctcg ggcactgtgc  2880
accggcgtcc tccctcaaag acaaaacaca cacttgtcca ccttgcccgg cacctgaact  2940
tctgggcggc ccgagcgttt ttttgttccc tcctaaacct aaggacacgc tcatgatcag  3000
ccgcacgcca gaggttacct gtgtagtggt ggatgtcagc cacgaggatc cggaagtaaa  3060
attcaactgg tatgtagatg gggtggaggt tcacaatgcc aaaaccaagc cacgagagga  3120
acagtacaat agtacttacc gggtcgtgtc tgtattgacc gtcctgcatc aggattggtt  3180
gaacgggaaa gaatataagt gcaaggtgag caacaaagca cttccggccc caatagagaa  3240
aacaattagt aaagcaaaag gacaaccacg ggaaccgcaa gtttatacac tgccgccctc  3300
tcgagacgag ctgaccaaaa atcaggttag ccttacatgt ttggtcaagg ggttctaccc  3360
gagtgatatt gcagtggaat gggaatccaa cggtcaacca gaaaataact acaaaactac  3420
tccgccggtg ttggattcag acggctcttt ctttctgtat agcaaactca ctgttgacaa  3480
gtcaagatgg cagcagggca atgtatttag ctgtagtgtt atgcacgaag ctcttcataa  3540
ccactacaca caaaagtcac tttctctttc cccaggaaaa gacatcgatt ccagcgacag  3600
ttcagacagc tctgacagct ccgattcctc cgactcaagt tgaaagcttg gatccaatca  3660
acctctggat tacaaaattt gtgaaagatt gactggtatt cttaactatg ttgctccttt  3720
tacgctatgt ggatacgctg ctttaatgcc tttgtatcat gctattgctt cccgtatggc  3780
tttcattttc tcctccttgt ataaatcctg gttgctgtct ctttatgagg agttgtggcc  3840
cgttgtcagg caacgtggcg tggtgtgcac tgtgtttgct gacgcaaccc ccactggttg  3900
gggcattgcc accacctgtc agctcctttc cgggactttc gctttccccc tccctattgc  3960
cacggcggaa ctcatcgccg cctgccttgc ccgctgctgg acaggggctc ggctgttggg  4020
cactgacaat tccgtggtgt tgtcggggaa atcatcgtcc tttccttggc tgctcgcctg  4080
tgttgccacc tggattctgc gcgggacgtc cttctgctac gtcccttcgg ccctcaatcc  4140
agcggacctt ccttcccgcg gcctgctgcc ggctctgcgg cctcttccgc gtcttcgaga  4200
tctgcctcga ctgtgccttc tagttgccag ccatctgttg tttgcccctc ccccgtgcct  4260
tccttgaccc tggaaggtgc cactcccact gtcctttcct aataaaatga ggaaattgca  4320
tcgcattgtc tgagtaggtg tcattctatt ctggggggtg gggtggggca ggacagcaag  4380
ggggaggatt gggaagacaa tagcaggcat gctggggata ccgttcgtat aatgtatgct  4440
atacgaacgg tactgcagtg tcagccgtta agtgttcctg tgtcactcaa aattgctttg  4500
agaggctcta agggcttctc agtgcgttac atccctggct tgttgtccac aaccgttaaa  4560
ccttaaaagc tttaaaagcc ttatatattc ttttttttct tataaaactt aaaaccttag  4620
aggctattta agttgctgat ttatattaat tttattgttc aaacatgaga gcttagtacg  4680
tgaaacatga gagcttagta cgttagccat gagagcttag tacgttagcc atgagggttt  4740
agttcgttaa acatgagagc ttagtacgtt aaacatgaga gcttagtacg tgaaacatga  4800
gagcttagta cgtactatca acaggttgaa ctgctgatct tcagatctta attaagg     4857
```

```
SEQ ID NO: 30          moltype = DNA  length = 4233
FEATURE                Location/Qualifiers
misc_feature           1..4233
                       note = Synthetic: (M014) Halo firefly luciferase vector
                        comprising a cruciform structure and EF1A-driven firefly
                        luciferase reporter transgene
source                 1..4233
                       mol_type = other DNA
                       organism = synthetic construct
SEQUENCE: 30
ctaggaaccc ctagtgatgg agttggccac tccctctctg cgcgctcgct cgctcactga  60
ggccgggcga ccaaaggtcg cccgacgccc gggctttgcc cgggcggcct cagtgagcga  120
gcgagcgcgc agagagggag tggccaactc catcactagg ggttcctttt aattaaggct  180
ccggtgcccg tcagtgggca gagcgcacat cgcccacagt ccccgagaag ttggggggag  240
gggtcggcaa ttgaaccggt gcctagagaa ggtggcgcgg ggtaaactgg gaaagtgatg  300
tcgtgtactg gctccgcctt tttcccgagg gtgggggaga accgtatata agtgcagtag  360
tcgccgtgaa cgttcttttt cgcaacgggt ttgccgccag aacacaggta agtgccgtgt  420
gtggttcccg cgggcctggc ctctttacgg gttatggccc ttgcgtgcct tgaattactt  480
ccactggctg cagtacgtga ttcttgatcc cgagcttcgg gttggaagtg ggtgggagag  540
ttcgaggcct tgcgcttaag gagccccttc gcctcgtgct tgagttgagg cctggcctgg  600
gcgctggggc cgccgcgtgc gaatctggtg gcaccttcgc gcctgtctcg ctgctttcga  660
taagtctcta gccatttaaa atttttgatg acctgctgcg acgctttttt tctggcaaga  720
tagtcttgta aatgcgggcc aagatctgca cactggtatt tcggtttttg ggccgcgggg  780
cggcgacggg gcccgtgcgt cccagcgcac atgttcggcg aggcggggcc tgcgagcgcg  840
gccaccgaga atcggacggg ggtagtctca agctggccgg cctgctctgg tgcctggcct  900
cgcgccgccg tgtatcgccc cgccctgggc ggcaaggctg gcccggtcgg caccagttgc  960
gtgagcggaa agatggccgc ttcccggccc tgctgcaggg agctcaaaat ggaggacgcg  1020
```

```
gcgctcggga gagcgggcgg gtgagtcacc cacacaaagg aaaagggcct ttccgtcctc  1080
agccgtcgct tcatgtgact ccacggagta ccgggcgccg tccaggcacc tcgattagtt  1140
ctcgagcttt tggagtacgt cgtctttagg ttggggggag gggttttatg cgatggagtt  1200
tccccacact gagtgggtgg agactgaagt taggccagct tggcacttga tgtaattctc  1260
cttggaattt gccctttttg agtttggatc ttggttcatt ctcaagcctc agacagtggt  1320
tcaaagtttt tttcttccat ttcaggtgtc gtgagctagc gccaccatgg aagacgccaa  1380
aaacataaag aaaggcccgg cgccattcta tccgctggaa gatggaaccg ctggagagca  1440
actgcataag gctatgaaga gatacgccct ggttcctgga acaattgctt ttacagatgc  1500
acatatcgag gtggacatca cttacgctga gtacttcgaa atgtccgttc ggttggcaga  1560
agctatgaaa cgatatgggc tgaatacaaa tcacagaatc gtcgtatgca gtgaaaactc  1620
tcttcaattc tttatgccgg tgttgggcgc gttatttatc ggagttgcag ttgcgcccgc  1680
gaacgacatt tataatgaac gtgaattgct caacagtatg ggcatttcgc agcctaccgt  1740
ggtgttcgtt tccaaaaagg ggttgcaaaa aattttgaac gtgcaaaaaa agctcccaat  1800
catccaaaaa attattatca tggattctaa aacggattac cagggatttc agtcgatgta  1860
cacgttcgtc acatctcatc tacctcccgg ttttaatgaa tacgattttg tgccagagtc  1920
cttcgatagg gacaagacaa ttgcactgat catgaactcc tctggatcta ctggtctgcc  1980
taaaggtgtc gctctgcctc atagaactgc ctgcgtgaga ttctcgcatg ccagagatcc  2040
tatttttggc aatcaaatca ttccggatac tgcgatttta agtgttgttc cattccatca  2100
cggttttgga atgtttacta cactcggata tttgatatgt ggatttcgag tcgtcttaat  2160
gtatagattt gaagaagagc tgtttctgag gagccttcag gattacaaga ttcaaagtgc  2220
gctgctggtg ccaaccctat tctccttctt cgccaaaagc actctgattg acaaatacga  2280
tttatctaat ttacacgaaa ttgcttctgg tggcgctccc ctctctaagg aagtcgggga  2340
agcggttgcc aagaggttcc atctgccagg tatcaggcaa ggatatgggc tcactgagac  2400
tacatcagct attctgatta cacccgaggg ggatgataaa ccgggcgcgg tcggtaaagt  2460
tgttccattt tttgaagcga aggttgtgga tctggatacc gggaaaacgc tgggcgttaa  2520
tcaaagaggc gaactgtgtg tgagaggtcc tatgattatg tccggttatg taaacaatcc  2580
ggaagcgacc aacgccttga ttgacaagga tggatggcta cattctggag acatagctta  2640
ctgggacgaa gacgaacact tcttcatcgt tgaccgcctg aagtctctga ttaagtacaa  2700
aggctatcag gtggctcccg ctgaattgga atccatcttg ctccaacacc ccaacatctt  2760
cgacgcaggt gtcgcaggtc ttcccgacga tgacgccggt gaacttcccg ccgccgttgt  2820
tgttttggag cacggaaaga cgatgacgga aaaagagatc gtggattacg tcgccagtca  2880
agtaacaacc gcgaaaaagt tgcgcggagg agttgtgttt gtggacgaag taccgaaagg  2940
tcttaccgga aaactcgacg caagaaaaat cagagagatc ctcataaagg ccaagaaggg  3000
cggaaagatc gccgtgtgaa agcttggatc caatcaacct ctggattaca aaatttgtga  3060
aagattgact ggtattctta actatgttgc tccttttacg ctatgtggat acgctgcttt  3120
aatgcctttg tatcatgcta ttgcttcccg tatggctttc attttctcct ccttgtataa  3180
atcctggttg ctgtctcttt atgaggagtt gtggcccgtt gtcaggcaac gtggcgtggt  3240
gtgcactgtg tttgctgacg caacccccac tggttggggc attgccacca cctgtcagct  3300
cctttccggg actttcgctt tccccctccc tattgccacg gcggaactca tcgccgcctg  3360
ccttgcccgc tgctggacag gggctcggct gttgggcact gacaattccg tggtgttgtc  3420
ggggaaatca tcgtcctttc cttggctgct cgcctgtgtt gccacctgga ttctgcgcgg  3480
gacgtccttc tgctacgtcc cttcggccct caatccagcg gaccttcctt cccgcggcct  3540
gctgccggct ctgcggcctc ttccgcgtct tcgagatctg cctcgactgt gccttctagt  3600
tgccagccat ctgttgtttg cccctccccc gtgccttcct tgaccctgga aggtgccact  3660
cccactgtcc tttcctaata aaatgaggaa attgcatcgc attgtctgag taggtgtcat  3720
tctattctgg ggggtggggt ggggcaggac agcaaggggg aggattggga agacaatagc  3780
aggcatgctg gggataccgt tcgtataatg tatgctatac gaacggtact gcagtgtcag  3840
ccgttaagtg ttcctgtgtc actcaaaatt gctttgagag gctctaaggg cttctcagtg  3900
cgttacatcc ctggcttgtt gtccacaacc gttaaacctt aaaagcttta aaagccttat  3960
atattctttt ttttcttata aaacttaaaa ccttagaggc tatttaagtt gctgatttat  4020
attaatttta ttgttcaaac atgagagctt agtacgtgaa acatgagagc ttagtacgtt  4080
agccatgaga gcttagtacg ttagccatga gggtttagtt cgttaaacat gagagcttag  4140
tacgttaaac atgagagctt agtacgtgaa acatgagagc ttagtacgta ctatcaacag  4200
gttgaactgc tgatcttcag atcttaatta agg                               4233

SEQ ID NO: 31           moltype = DNA  length = 5708
FEATURE                 Location/Qualifiers
misc_feature            1..5708
                        note = Synthetic: P021 EF1a-driven firefly luciferase
                         reporter control vector
source                  1..5708
                        mol_type = other DNA
                        organism = synthetic construct
SEQUENCE: 31
taactataac ggtcctaagg tagcgaaccc ccaactgaga gaactcaaag gttaccccag  60
ttggggttaa ttaaggctcc ggtgcccgtc agtgggcaga gcgcacatcg cccacagtcc  120
ccgagaagtt ggggggaggg gtcggcaatt gaaccggtgc ctagagaagg tggcgcgggg  180
taaactggga aagtgatgtc gtgtactggc tccgcctttt tcccgagggt gggggagaac  240
cgtatataag tgcagtagtc gccgtgaacg ttcttttttcg caacgggttt gccgccagaa  300
cacaggtaag tgccgtgtgt ggttcccgcg ggcctggcct ctttacgggt tatggccctt  360
gcgtgccttg aattacttcc actggctgca gtacgtgatt cttgatcccg agcttcgggt  420
tggaagtggg tgggagagtt cgaggccttg cgcttaagga gccccttcgc ctcgtgcttg  480
agttgaggcc tggcctgggc gctggggccg ccgcgtgcga atctggtggc accttcgcgc  540
ctgtctcgct gctttcgata agtctctagc catttaaaat ttttgatgac ctgctgcgac  600
gcttttttttc tggcaagata gtcttgtaaa tgcgggccaa gatctgcaca ctggtatttc  660
ggtttttggg gccgcgggcg gcgacggggc ccgtgcgtcc cagcgcacat gttcggcgag  720
gcggggcctg cgagcgcggc caccgagaat cggacggggg tagtctcaag ctggccggcc  780
tgctctggtg cctggcctcg cgccgccgtg tatcgccccg ccctgggcgg caaggctggc  840
ccggtcggca ccagttgcgt gagcggaaag atggccgctt cccggccctg ctgcagggag  900
```

-continued

```
ctcaaaatgg aggacgcggc gctcgggaga gcgggcgggt gagtcaccca cacaaaggaa  960
aagggccttt ccgtcctcag ccgtcgcttc atgtgactcc acggagtacc gggcgccgtc  1020
caggcacctc gattagttct cgagcttttg gagtacgtcg tctttaggtt ggggggaggg  1080
gttttatgcg atggagtttc cccacactga gtgggtggag actgaagtta ggccagcttg  1140
gcacttgatg taattctcct tggaatttgc cctttttgag tttggatctt ggttcattct  1200
caagcctcag acagtggttc aaagtttttt tcttccattt caggtgtcgt gagctagcgc  1260
caccatggaa gacgccaaaa acataaagaa aggcccggcg ccattctatc cgctggaaga  1320
tggaaccgct ggagagcaac tgcataaggc tatgaagaga tacgccctgg ttcctggaac  1380
aattgctttt acagatgcac atatcgaggt ggacatcact tacgctgagt acttcgaaat  1440
gtccgttcgg ttggcagaag ctatgaaacg atatgggctg aatacaaatc acagaatcgt  1500
cgtatgcagt gaaaactctc ttcaattctt tatgccggtg ttgggcgcgt tatttatcgg  1560
agttgcagtt gcgcccgcga acgacattta taatgaacgt gaattgctca acagtatggg  1620
catttcgcag cctaccgtgg tgttcgtttc caaaaagggg ttgcaaaaaa ttttgaacgt  1680
gcaaaaaaag ctcccaatca tccaaaaaat tattatcatg gattctaaaa cggattacca  1740
gggatttcag tcgatgtaca cgttcgtcac atctcatcta cctcccggtt ttaatgaata  1800
cgattttgtg ccagagtcct tcgataggga caagacaatt gcactgatca tgaactcctc  1860
tggatctact ggtctgccta aaggtgtcgc tctgcctcat agaactgcct gcgtgagatt  1920
ctcgcatgcc agagatccta tttttggcaa tcaaatcatt ccggatactg cgattttaag  1980
tgttgttcca ttccatcacg gttttggaat gtttactaca ctcggatatt tgatatgtgg  2040
atttcgagtc gtcttaatgt atagatttga agaagagctg tttctgagga gccttcagga  2100
ttacaagatt caaagtgcgc tgctggtgcc aaccctattc tccttcttcg ccaaaagcac  2160
tctgattgac aaatacgatt tatctaattt acacgaaatt gcttctggtg gcgctcccct  2220
ctctaaggaa gtcggggaag cggttgccaa gaggttccat ctgccaggta tcaggcaagg  2280
atatgggctc actgagacta catcagctat tctgattaca cccgaggggg atgataaacc  2340
gggcgcggtc ggtaaagttg ttccattttt tgaagcgaag gttgtggatc tggataccgg  2400
gaaaacgctg ggcgttaatc aaagaggcga actgtgtgtg agaggtccta tgattatgtc  2460
cggttatgta aacaatccgg aagcgaccaa cgccttgatt gacaaggatg gatggctaca  2520
ttctggagac atagcttact gggacgaaga cgaacacttc ttcatcgttg accgcctgaa  2580
gtctctgatt aagtacaaag gctatcaggt ggctcccgct gaattggaat ccatcttgct  2640
ccaacacccc aacatcttcg acgcaggtgt cgcaggtctt cccgacgatg acgccggtga  2700
acttcccgcc gccgttgttg ttttggagca cggaaagacg atgacggaaa aagagatcgt  2760
ggattacgtc gccagtcaag taacaaccgc gaaaaagttg cgcggaggag ttgtgtttgt  2820
ggacgaagta ccgaaaggtc ttaccggaaa actcgacgca agaaaaatca gagagatcct  2880
cataaaggcc aagaagggcg gaaagatcgc cgtgtgatga gaattcgttt aaacccgctg  2940
atcagcctcg actgtgcctt ctagttgcca gccatctgtt gtttgcccct cccccgtgcc  3000
ttccttgacc ctggaaggtg ccactcccac tgtcctttcc taataaaatg aggaaattgc  3060
atcgcattgt ctgagtaggt gtcattctat tctggggggt ggggtggggc aggacagcaa  3120
gggggaggat tgggaagaca atagcaggca tgctggggat gcggtgggct ctatggcttc  3180
tgaggcggaa agaaccagct ggggctccgc gcccggggag cccaagggca cgccctggca  3240
cctagggggt atccccgtat accgtcgacc tctagctaga gcttggcgta atcatggtca  3300
tagctgtttc ctgtgtgaaa ttgttatccg ctcacaattc cacacaacat acgagccgga  3360
agcataaagt gtaaagcctg gggtgcctaa tgagtgagct aactcacatt aattgcgttg  3420
cgctcactgc ccgctttcca gtcgggaaac ctgtcgtgcc agctgcatta atgaatcggc  3480
caacgcgcgg ggagaggcgg tttgcgtatt gggcgctctt ccgcttcctc gctcactgac  3540
tcgctgcgct cggtcgttcg gctgcggcga gcggtatcag ctcactcaaa ggcggtaata  3600
cggttatcca cagaatcagg ggataacgca ggaaagaaca tgtgagcaaa aggccagcaa  3660
aaggccagga accgtaaaaa ggccgcgttg ctggcgtttt tccataggct ccgcccccct  3720
gacgagcatc acaaaaatcg acgctcaagt cagaggtggc gaaacccgac aggactataa  3780
agataccagg cgtttccccc tggaagctcc ctcgtgcgct ctcctgttcc gaccctgccg  3840
cttaccggat acctgtccgc ctttctccct tcgggaagcg tggcgctttc tcatagctca  3900
cgctgtaggt atctcagttc ggtgtaggtc gttcgctcca agctgggctg tgtgcacgaa  3960
ccccccgttc agcccgaccg ctgcgcctta tccggtaact atcgtcttga gtccaacccg  4020
gtaagacacg acttatcgcc actggcagca gccactggta acaggattag cagagcgagg  4080
tatgtaggcg gtgctacaga gttcttgaag tggtggccta actacggcta cactagaaga  4140
acagtatttg gtatctgcgc tctgctgaag ccagttacct tcggaaaaag agttggtagc  4200
tcttgatccg gcaaacaaac caccgctggt agcggtggtt tttttgtttg caagcagcag  4260
attacgcgca gaaaaaaagg atctcaagaa gatcctttga tcttttctac ggggtctgac  4320
gctcagtgga acgaaaactc acgttaaggg attttggtca tgagattatc aaaaaggatc  4380
ttcacctaga tccttttaaa ttaaaaatga agttttaaat caatctaaag tatatatgag  4440
taaacttggt ctgacagtta ccaatgctta atcagtgagg cacctatctc agcgatctgt  4500
ctatttcgtt catccatagt tgcctgactc cccgtcgtgt agataactac gatacgggag  4560
ggcttaccat ctggccccag tgctgcaatg ataccgcgag acccacgctc accggctcca  4620
gatttatcag caataaacca gccagccgga agggccgagc gcagaagtgg tcctgcaact  4680
ttatccgcct ccatccagtc tattaattgt tgccgggaag ctagagtaag tagttcgcca  4740
gttaatagtt tgcgcaacgt tgttgccatt gctacaggca tcgtggtgtc acgctcgtcg  4800
tttggtatgg cttcattcag ctccggttcc caacgatcaa ggcgagttac atgatccccc  4860
atgttgtgca aaaaagcggt tagctccttc ggtcctccga tcgttgtcag aagtaagttg  4920
gccgcagtgt tatcactcat ggttatggca gcactgcata attctcttac tgtcatgcca  4980
tccgtaagat gcttttctgt gactggtgag tactcaacca agtcattctg agaatagtgt  5040
atgcggcgac cgagttgctc ttgcccggcg tcaatacggg ataataccgc gccacatagc  5100
agaactttaa aagtgctcat cattggaaaa cgttcttcgg ggcgaaaact ctcaaggatc  5160
ttaccgctgt tgagatccag ttcgatgtaa cccactcgtg cacccaactg atcttcagca  5220
tcttttactt tcaccagcgt ttctgggtga gcaaaaacag gaaggcaaaa tgccgcaaaa  5280
aagggaataa gggcgacacg gaaatgttga atactcatac tcttcctttt tcaatattat  5340
tgaagcattt atcagggtta ttgtctcatg agcggataca tatttgaatg tatttagaaa  5400
aataaacaaa taggggttcc gcgcacattt ccccgaaaag tgccacctga cgtcgacgga  5460
tcgggagatc tcccgatccc ctatggtgca ctctcagtac aatctgctct gatgccgcat  5520
agttaagcca gtatctgctc cctgcttgtg tgttggaggt cgctgagtag tgcgcgagca  5580
aaatttaagc tacaacaagg caaggcttga ccgacaattg catgaagaat ctgcttaggg  5640
```

-continued

```
ttaggcgttt tgcgctgctt cgcgatgtac gggccagata tacgcgttga cattgattat  5700
tgactagt                                                           5708

SEQ ID NO: 32          moltype = DNA  length = 7413
FEATURE                Location/Qualifiers
misc_feature           1..7413
                       note = Synthetic: P006 GFP-dsREDE2 reporter construct
                        comprising a cruciform structure
source                 1..7413
                       mol_type = other DNA
                       organism = synthetic construct
SEQUENCE: 32
acgcgttgac attgattatt gactagttaa ctataacggt cctaaggtag cgaacccccca  60
actgagagaa ctcaaaggtt accccagttg ggtaaaata cagcatagca aaactttaac  120
ctccaaatca agcctctact tgaatccttt tctgagggat gaataaggca taggcatcag  180
gggctgttgc caatgtgcat tagctgtttg cagcctcacc ttctttcatg gagtttaaga  240
tatagtgtat tttcccaagg tttgaactag ctcttcattt ctttatgttt taaatgcact  300
gacctcccac attccctttt tagtaaaata ttcagaaata atttaaatac atcattgcaa  360
tgaaaataaa tgttttttat taggcagaat ccagatgctc aaggcccttc ataatatccc  420
ccagtttagt agttggactt agggaacaaa ggaacccttta atagaaattg gacagcaaga  480
aagcgagctt agtgatactt gtgggccagg gcattagcca caccagccac cactttctga  540
taggcagcct gcactggtgg ggtgaattcg aagcttgagc tcgagatcct actagtagga  600
tctgagtccg gattacttgt acagctcgtc catgccgtga gtgatcccgg cggcggtcac  660
gaactccagc aggaccatgt gatcgcgctt ctcgttgggg tctttgctca gggcggactg  720
ggtgctcagg tagtggttgt cgggcagcag cacggggccg tcgccgatgg gggtgttctg  780
ctggtagtgg tcggcgagct gcacgctgcc gtcctcgatg ttgtggcgga tcttgaagtt  840
caccttgatg ccgttcttct gcttgtcggc catgatatag acgttgtggc tgttgtagtt  900
gtactccagc ttgtgcccca ggatgttgcc gtcctccttg aagtcgatgc ccttcagctc  960
gatgcggttc accagggtgt cgccctgcag gaggaggaac ccctagtgat ggagttggcc  1020
actccctctc tgcgcgctcg ctcgctcact gaggccgggc gaccaaaggt cgcccgacgc  1080
ccgggctttg cccgggcggc ctcagtgagc gagcgagcgc gcagagaggg agtggccaac  1140
tccatcacta ggggtttcct ttcttacctc gaacttcacc tcggcgcggg tcttgtagtt  1200
gccgtcgtcc ttgaagaaga tggtgcgctc ctggacgtag ccttcgggca tggcggactt  1260
gaagaagtcg tgctgcttca tgtggtcggg gtagcggctg aagcactgca cgccgtaggt  1320
gaaggtggtc acgagggtgg gccagggcac gggcagcttg ccggtggtgc agatgaactt  1380
cagggtcagc ttgccgtagg tggcatcgcc ctcgccctcg ccggacacgc tgaacttgtg  1440
gccgtttacg tcgccgtcca gctcgaccag gatgggcacc accccggtga acagctcctc  1500
gcccttgctc accatggtgg cgaccggtag cgtgctttgc caaagtgatg ggccagcaca  1560
cagaccagca cgttgcccag gagctgtggg aggaagataa gaggtatgaa catgattagc  1620
aaaagggcct agcttggact cagaataatc cagccttatc ccaaccataa aataaaagca  1680
gaatggtagc tggattgtag ctgctattag caatatgaaa cctcttacat cagttacaat  1740
ttatatgcag aaatatttat atgcagaaat attgctattg ccttaaccca gaaattatca  1800
ctgttattct ttagaatggt gcaaagaggc atgatacatt gtatcattat tgccctgaaa  1860
gaaagagatt agggaaagta ttagaaataa gataaacaaa aaagtatatt aaaagaagaa  1920
agcatttttt aaaattacaa atgcaaaatt accctgattt ggtcaatatg tgtaccctgt  1980
tacttctccc cttcctatga catgaactta accatagaaa agaaggggaa agaaaacatc  2040
aagggtccca tagactcacc ctgaagttct caggatccga gctcggtacc acatgtaagc  2100
ttcgagggga ggctggatcg gtcccggtgt cttctatgga ggtcaaaaca gcgtggatgg  2160
cgtctccagg cgatctgacg gttcactaaa cgagctctgc ttatatagac ctcccaccgt  2220
acacgcctac cgcccatttg cgtcaatggg gcggagttgt tacgacattt tggaaagtcc  2280
cgttgatttt ggtgccaaaa caaactccca ttgacgtcaa tggggtggag acttggaaat  2340
ccccgtgagt caaaccgcta tccacgccca ttgatgtact gccaaaaccg catcaccatg  2400
gtaatagcga tgactaatac gtagatgtac tgccaagtag gaaagtccca taaggtcatg  2460
tactgggcat aatgccaggc gggccattta ccgtcattga cgtcaatagg gggcgtactt  2520
ggcatatgat acacttgatg tactgccaag tgggcagttt accgtaaata gtccacccat  2580
tgacgtcaat ggaaagtccc tattggcgtt actatgggaa catacgtcat tattgacgtc  2640
aatgggcggg ggtcgttggg cggtcagcca ggcgggccat ttaccgtaag ttatgtaacg  2700
cggaactcca tatatgggct atgaactaat gaccccgtaa ttgattacta ttaataacta  2760
gtcaataatc aatgtcttaa ttaaggctcc ggtgcccgtc agtgggcaga gcgcacatcg  2820
cccacagtcc ccgagaagtt ggggggaggg gtcggcaatt gaaccggtgc ctagagaagg  2880
tggcgcgggg taaactggga aagtgatgtc gtgtactggc tccgcctttt tcccgagggt  2940
gggggagaac cgtatataag tgcagtagtc gccgtgaacg ttcttttttcg caacgggttt  3000
gccgccagaa cacaggtaag tgccgtgtgt ggttcccgcg ggcctggcct ctttacgggt  3060
tatggccctt gcgtgccttg aattacttcc actggctgca gtacgtgatt cttgatcccg  3120
agcttcgggt tggaagtggg tgggagagtt cgaggccttg cgcttaagga gccccttcgc  3180
ctcgtgcttg agttgaggcc tggcctgggc gctggggccg ccgcgtgcga atctggtggc  3240
accttcgcgc ctgtctcgct gctttcgata agtctctagc catttaaaat ttttgatgac  3300
ctgctgcgac gcttttttttc tggcaagata gtcttgtaaa tgcgggccaa gatctgcaca  3360
ctggtatttc ggtttttggg gccgcgggcg gcgacggggc ccgtgcgtcc cagcgcacat  3420
gttcggcgag gcggggcctg cgagcgcggc caccgagaat cggacggggg tagtctcaag  3480
ctggccggcc tgctctggtg cctggcctcg cgccgccgtg tatcgccccg ccctgggcgg  3540
caaggctggc ccggtcggca ccagttgcgt gagcggaaag atggccgctt cccggccctg  3600
ctgcagggag ctcaaaatgg aggacgcggc gctcgggaga gcgggcgggt gagtcaccca  3660
cacaaaggaa aagggccttt ccgtcctcag ccgtcgcttc atgtgactcc acggagtacc  3720
gggcgccgtc caggcacctc gattagttct cgagcttttg gagtacgtcg tctttaggtt  3780
ggggggaggg gttttatgcg atggagtttc cccacactga gtgggtggag actgaagtta  3840
ggccagcttg gcacttgatg taattctcct tggaatttgc cctttttgag tttggatctt  3900
ggttcattct caagcctcag acagtggttc aaagtttttt tcttccattt caggtgtcgt  3960
gagctagcgc caccatggat agcactgaga acgtcatcaa gcccttcatg cgcttcaagg  4020
```

```
tgcacatgga gggctccgtg aacggccacg agttcgagat cgagggcgag ggcgagggca  4080
agccctacga gggcacccag accgccaagc tgcaggtgac caagggcggc cccctgccct  4140
tcgcctggga catcctgtcc ccccagttcc agtacggctc caaggtgtac gtgaagcacc  4200
ccgccgacat ccccgactac aagaagctgt ccttccccga gggcttcaag tgggagcgcg  4260
tgatgaactt cgaggacggc ggcgtggtga ccgtgaccca ggactcctcc ctgcaggacg  4320
gcaccttcat ctaccacgtg aagttcatcg gcgtgaactt cccctccgac ggccccgtaa  4380
tgcagaagaa gactctgggc tgggagccct ccaccgagcg cctgtacccc cgcgacggcg  4440
tgctgaaggg cgagatccac aaggcgctga agctgaaggg cggcggccac tacctggtgg  4500
agttcaagtc aatctacatg gccaagaagc ccgtgaagct gcccggctac tactacgtgg  4560
actccaagct ggacatcacc tcccacaacg aggactacac cgtggtggag cagtacgagc  4620
gcgccgaggc ccgccaccac ctgttccagt gagaattcgt ttaaacccgc tgatcagcct  4680
cgactgtgcc ttctagttgc cagccatctg ttgtttgccc ctcccccgtg ccttccttga  4740
ccctggaagg tgccactccc actgtccttt cctaataaaa tgaggaaatt gcatcgcatt  4800
gtctgagtag gtgtcattct attctggggg gtggggtggg gcaggacagc aagggggagg  4860
attgggaaga caatagcagg catgctgggg atgcggtggg ctctatggct tctgaggcgg  4920
aaagaaccag ctggggctcc gcgcccgggg agcccaaggg cacgccctgg cacctagggg  4980
gtatccccgt ataccgtcga cctctagcta gagcttggcg taatcatggt catagctgtt  5040
tcctgtgtga aattgttatc cgctcacaat tccacacaac atacgagccg gaagcataaa  5100
gtgtaaagcc tggggtgcct aatgagtgag ctaactcaca ttaattgcgt tgcgctcact  5160
gcccgctttc cagtcgggaa acctgtcgtg ccagctgcat taatgaatcg gccaacgcgc  5220
ggggagaggc ggtttgcgta ttgggcgctc ttccgcttcc tcgctcactg actcgctgcg  5280
ctcggtcgtt cggctgcggc gagcggtatc agctcactca aaggcggtaa tacggttatc  5340
cacagaatca ggggataacg caggaaagaa catgtgagca aaaggccagc aaaaggccag  5400
gaaccgtaaa aaggccgcgt tgctggcgtt tttccatagg ctccgccccc ctgacgagca  5460
tcacaaaaat cgacgctcaa gtcagaggtg gcgaaacccg acaggactat aaagatacca  5520
ggcgtttccc cctggaagct ccctcgtgcg ctctcctgtt ccgaccctgc cgcttaccgg  5580
atacctgtcc gcctttctcc cttcgggaag cgtggcgctt tctcatagct cacgctgtag  5640
gtatctcagt tcggtgtagg tcgttcgctc caagctgggc tgtgtgcacg aaccccccgt  5700
tcagcccgac cgctgcgcct tatccggtaa ctatcgtctt gagtccaacc cggtaagaca  5760
cgacttatcg ccactggcag cagccactgg taacaggatt agcagagcga ggtatgtagg  5820
cggtgctaca gagttcttga agtggtggcc taactacggc tacactagaa gaacagtatt  5880
tggtatctgc gctctgctga agccagttac cttcggaaaa agagttggta gctcttgatc  5940
cggcaaacaa accaccgctg gtagcggtgg tttttttgtt tgcaagcagc agattacgcg  6000
cagaaaaaaa ggatctcaag aagatccttt gatcttttct acggggtctg acgctcagtg  6060
gaacgaaaac tcacgttaag ggattttggt catgagatta tcaaaaagga tcttcaccta  6120
gatcctttta aattaaaaat gaagttttaa atcaatctaa agtatatatg agtaaacttg  6180
gtctgacagt taccaatgct taatcagtga ggcacctatc tcagcgatct gtctatttcg  6240
ttcatccata gttgcctgac tccccgtcgt gtagataact acgatacggg agggcttacc  6300
atctggcccc agtgctgcaa tgataccgcg agacccacgc tcaccggctc cagatttatc  6360
agcaataaac cagccagccg gaagggccga gcgcagaagt ggtcctgcaa ctttatccgc  6420
ctccatccag tctattaatt gttgccggga agctagagta agtagttcgc cagttaatag  6480
tttgcgcaac gttgttgcca ttgctacagg catcgtggtg tcacgctcgt cgtttggtat  6540
ggcttcattc agctccggtt cccaacgatc aaggcgagtt acatgatccc ccatgttgtg  6600
caaaaaagcg gttagctcct tcggtcctcc gatcgttgtc agaagtaagt tggccgcagt  6660
gttatcactc atggttatgg cagcactgca taattctctt actgtcatgc catccgtaag  6720
atgcttttct gtgactggtg agtactcaac caagtcattc tgagaatagt gtatgcggcg  6780
accgagttgc tcttgcccgg cgtcaatacg ggataatacc gcgccacata gcagaacttt  6840
aaaagtgctc atcattggaa aacgttcttc ggggcgaaaa ctctcaagga tcttaccgct  6900
gttgagatcc agttcgatgt aacccactcg tgcacccaac tgatcttcag catcttttac  6960
tttcaccagc gtttctgggt gagcaaaaac aggaaggcaa aatgccgcaa aaaagggaat  7020
aagggcgaca cggaaatgtt gaatactcat actcttcctt tttcaatatt attgaagcat  7080
ttatcagggt tattgtctca tgagcggata catatttgaa tgtatttaga aaaataaaca  7140
aataggggtt ccgcgcacat ttccccgaaa agtgccacct gacgtcgacg gatcgggaga  7200
tctcccgatc ccctatggtg cactctcagt acaatctgct ctgatgccgc atagttaagc  7260
cagtatctgc tccctgcttg tgtgttggag gtcgctgagt agtgcgcgag caaaatttaa  7320
gctacaacaa ggcaaggctt gaccgacaat tgcatgaaga atctgcttag ggttaggcgt  7380
tttgcgctgc ttcgcgatgt acgggccaga tat                               7413
```

```
SEQ ID NO: 33          moltype = DNA  length = 6332
FEATURE                Location/Qualifiers
misc_feature           1..6332
                       note = Synthetic: P020 sTNALP-Fc-(DSS)6 construct
source                 1..6332
                       mol_type = other DNA
                       organism = synthetic construct
SEQUENCE: 33
taactataac ggtcctaagg tagcgaaccc ccaactgaga gaactcaaag gttaccccag  60
ttggggttaa ttaaggctcc ggtgcccgtc agtgggcaga gcgcacatcg cccacagtcc  120
ccgagaagtt ggggggaggg gtcggcaatt gaaccggtgc ctagagaagg tggcgcgggg  180
taaactggga aagtgatgtc gtgtactggc tccgcctttt tcccgagggt gggggagaac  240
cgtatataag tgcagtagtc gccgtgaacg ttcttttttcg caacgggttt gccgccagaa  300
cacaggtaag tgccgtgtgt ggttcccgcg ggcctggcct ctttacgggt tatggccctt  360
gcgtgccttg aattacttcc actggctgca gtacgtgatt cttgatcccg agcttcgggt  420
tggaagtggg tgggagagtt cgaggccttg cgcttaagga gccccttcgc ctcgtgcttg  480
agttgaggcc tggcctgggc gctggggccg ccgcgtgcga atctggtggc accttcgcgc  540
ctgtctcgct gctttcgata agtctctagc catttaaaat tttgatgac ctgctgcgac  600
gctttttttc tggcaagata gtcttgtaaa tgcgggccaa gatctgcaca ctggtatttc  660
ggtttttggg gccgcgggcg gcgacggggc ccgtgcgtcc cagcgcacat gttcggcgag  720
gcggggcctg cgagcgcggc caccgagaat cggacggggg tagtctcaag ctggccggcc  780
```

-continued

```
tgctctggtg cctggcctcg cgccgccgtg tatcgccccg ccctgggcgg caaggctggc  840
ccggtcggca ccagttgcgt gagcggaaag atggccgctt cccggccctg ctgcagggag  900
ctcaaaatgg aggacgcggc gctcgggaga gcgggcgggt gagtcaccca cacaaaggaa  960
aagggccttt ccgtcctcag ccgtcgcttc atgtgactcc acggagtacc gggcgccgtc  1020
caggcacctc gattagttct cgagcttttg gagtacgtcg tctttaggtt ggggggaggg  1080
gttttatgcg atggagtttc cccacactga gtgggtggag actgaagtta ggccagcttg  1140
gcacttgatg taattctcct tggaatttgc ccttttttgag tttggatctt ggttcattct  1200
caagcctcag acagtggttc aaagtttttt tcttccattt caggtgtcgt gagctagcgc  1260
caccatggat atgcgcgtac ccgctcaact tctgggtttg ttgctgcttt ggctcagggg  1320
agcccgctgt gccgcgcttg tccctgaaaa ggagaaggac cccaaatatt ggagagacca  1380
ggctcaggaa accctcaagt acgctcttga actgcaaaag cttaatacta acgtggctaa  1440
aaacgtgata atgttcttgg gggacggaat gggggtttca accgttaccg cggccagaat  1500
cttgaaaggg cagctgcacc ataacccagg cgaagaaacg aggctggaga tggacaaatt  1560
tccattcgtg gcgctttcta agacctacaa cactaacgcc caggtccctg actcagctgg  1620
tacggccact gcctaccttt gtggagtgaa ggcaaatgag ggactgttg gtgtttccgc  1680
agctactgag agatctcggt gtaatacgac tcaaggtaat gaagttacat ccatactccg  1740
atgggcaaaa gacgcgggca aatctgttgg gattgttaca actactaggg tgaaccatgc  1800
gacaccctct gcagcttatg cgcacagtgc cgaccgagac tggtattcag ataatgagat  1860
gccacccgag gcccttagcc aggctgcaa ggacatagcc tatcaattga tgcacaatat  1920
cagagacata gacgttataa tgggtggtgg tcgcaagtac atgtacccca aaaacaaaac  1980
cgacgtagag tatgaatccg atgaaaaagc tagggggcacc agactcgacg gacttgatct  2040
ggttgataca tggaagagct tcaagcccag atacaagcat tcacatttca tctggaacag  2100
gaccgaactt ctcacattgg acccccacaa tgttgactat ctcctcggtt tgtttgaacc  2160
aggggatatg cagtatgagc tcaatcggaa caacgtcact gaccccagtt tgagtgaaat  2220
ggtcgttgtt gcaatacaaa ttttgaggaa aaatccaaag ggtttttct tgttggtaga  2280
gggcggacgg atagatcacg ggcaccacga aggcaaagca aaacaggccc tgcacgaagc  2340
cgttgaaatg gatcgcgcta tcggtcaagc cggctccctg acgagtagtg aagatacctt  2400
gaccgtcgtc actgcggatc atagccacgt ttttaccttt gggggataca cccccagggg  2460
caactcaatt tttggacttg caccgatgct cagcgacaca gataaaaagc cttttactgc  2520
gattctgtat ggcaacggcc ctggatacaa agtagtaggg ggtgaaaggg aaaacgtcag  2580
catggtggac tatgcacaca ataattatca ggcgcagtcc gctgttccgc tgcggcatga  2640
gactcacggg ggagaggacg ttgctgtctt ttccaaggga ccaatggctc atcttctcca  2700
tggagtccat gagcaaaatt atgtccctca tgtcatggca tacgctgcat gtataggagc  2760
aaatctcggg cactgtgcac cggcgtcctc cctcaaagac aaaacacaca cttgtccacc  2820
ttgcccggca cctgaacttc tgggcggccc gagcgttttt ttgttccctc ctaaacctaa  2880
ggacacgctc atgatcagcc gcacgccaga ggttacctgt gtagtggtgg atgtcagcca  2940
cgaggatccg gaagtaaaat tcaactggta tgtagatggg gtggaggttc acaatgccaa  3000
aaccaagcca cgagaggaac agtacaatag tacttaccgg gtcgtgtctg tattgaccgt  3060
cctgcatcag gattggttga acgggaaaga atataagtgc aaggtgagca acaaagcact  3120
tccggcccca atagagaaaa caattagtaa agcaaaagga caaccacggg aaccgcaagt  3180
ttatacactg ccgccctctc gagacgagct gaccaaaaat caggttagcc ttacatgttt  3240
ggtcaagggg ttctacccga gtgatattgc agtggaatgg gaatccaacg gtcaaccaga  3300
aaataactac aaaactactc cgccggtgtt ggattcagac ggctctttct ttctgtatag  3360
caaactcact gttgacaagt caagatggca gcagggcaat gtatttagct gtagtgttat  3420
gcacgaagct cttcataacc actacacaca aaagtcactt tctctttccc caggaaaaga  3480
catcgattcc agcgacagtt cagacagctc tgacagctcc gattcctccg actcaagttg  3540
atgagaattc gtttaaaccc gctgatcagc ctcgactgtg ccttctagtt gccagccatc  3600
tgttgtttgc ccctcccccg tgccttcctt gaccctggaa ggtgccactc ccactgtcct  3660
ttcctaataa aatgaggaaa ttgcatcgca ttgtctgagt aggtgtcatt ctattctggg  3720
gggtggggtg gggcaggaca gcaaggggga ggattgggaa gacaatagca ggcatgctgg  3780
ggatgcggtg ggctctatgg cttctgaggc ggaaagaacc agctggggct ccgcgcccgg  3840
ggagcccaag ggcacgccct ggcacctagg gggtatcccc gtataccgtc gacctctagc  3900
tagagcttgg cgtaatcatg gtcatagctg tttcctgtgt gaaattgtta tccgctcaca  3960
attccacaca acatacgagc cggaagcata aagtgtaaag cctggggtgc ctaatgagtg  4020
agctaactca cattaattgc gttgcgctca ctgcccgctt tccagtcggg aaacctgtcg  4080
tgccagctgc attaatgaat cggccaacgc gcggggagag gcggtttgcg tattgggcgc  4140
tcttccgctt cctcgctcac tgactcgctg cgctcggtcg ttcggctgcg gcgagcggta  4200
tcagctcact caaaggcggt aatacggtta tccacagaat caggggataa cgcaggaaag  4260
aacatgtgag caaaaggcca gcaaaaggcc aggaaccgta aaaaggccgc gttgctggcg  4320
tttttccata ggctccgccc ccctgacgag catcacaaaa atcgacgctc aagtcagagg  4380
tggcgaaacc cgacaggact ataaagatac caggcgtttc cccctggaag ctccctcgtg  4440
cgctctcctg ttccgaccct gccgcttacc ggatacctgt ccgcctttct cccttcggga  4500
agcgtggcgc tttctcatag ctcacgctgt aggtatctca gttcggtgta ggtcgttcgc  4560
tccaagctgg gctgtgtgca cgaacccccc gttcagcccg accgctgcgc cttatccggt  4620
aactatcgtc ttgagtccaa cccggtaaga cacgacttat cgccactggc agcagccact  4680
ggtaacagga ttagcagagc gaggtatgta ggcggtgcta cagagttctt gaagtggtgg  4740
cctaactacg gctacactag aagaacagta tttggtatct gcgctctgct gaagccagtt  4800
accttcggaa aaagagttgg tagctcttga tccggcaaac aaaccaccgc tggtagcggt  4860
ggtttttttg tttgcaagca gcagattacg cgcagaaaaa aaggatctca agaagatcct  4920
ttgatctttt ctacggggtc tgacgctcag tggaacgaaa actcacgtta agggattttg  4980
gtcatgagat tatcaaaaag gatcttcacc tagatccttt taaattaaaa atgaagtttt  5040
aaatcaatct aaagtatata tgagtaaact tggtctgaca gttaccaatg cttaatcagt  5100
gaggcaccta tctcagcgat ctgtctattt cgttcatcca tagttgcctg actccccgtc  5160
gtgtagataa ctacgatacg ggagggctta ccatctggcc ccagtgctgc aatgataccg  5220
cgagacccac gctcaccggc tccagattta tcagcaataa accagccagc cggaagggcc  5280
gagcgcagaa gtggtcctgc aactttatcc gcctccatcc agtctattaa ttgttgccgg  5340
gaagctagag taagtagttc gccagttaat agtttgcgca acgttgttgc cattgctaca  5400
ggcatcgtgg tgtcacgctc gtcgtttggt atggcttcat tcagctccgg ttcccaacga  5460
tcaaggcgag ttacatgatc ccccatgttg tgcaaaaaag cggttagctc cttcggtcct  5520
```

ccgatcgttg tcagaagtaa gttggccgca gtgttatcac tcatggttat ggcagcactg 5580
cataattctc ttactgtcat gccatccgta agatgctttt ctgtgactgg tgagtactca 5640
accaagtcat tctgagaata gtgtatgcgg cgaccgagtt gctcttgccc ggcgtcaata 5700
cgggataata ccgcgccaca tagcagaact ttaaaagtgc tcatcattgg aaaacgttct 5760
tcggggcgaa aactctcaag gatcttaccg ctgttgagat ccagttcgat gtaacccact 5820
cgtgcaccca actgatcttc agcatctttt actttcacca gcgtttctgg gtgagcaaaa 5880
acaggaaggc aaaatgccgc aaaaaaggga ataagggcga cacggaaatg ttgaatactc 5940
atactcttcc tttttcaata ttattgaagc atttatcagg gttattgtct catgagcgga 6000
tacatatttg aatgtattta gaaaaataaa caaatagggg ttccgcgcac atttccccga 6060
aaagtgccac ctgacgtcga cggatcggga gatctcccga tcccctatgg tgcactctca 6120
gtacaatctg ctctgatgcc gcatagttaa gccagtatct gctccctgct tgtgtgttgg 6180
aggtcgctga gtagtgcgcg agcaaaattt aagctacaac aaggcaaggc ttgaccgaca 6240
attgcatgaa gaatctgctt agggttaggc gttttgcgct gcttcgcgat gtacgggcca 6300
gatatacgcg ttgacattga ttattgacta gt 6332

SEQ ID NO: 34 moltype = DNA length = 11405
FEATURE Location/Qualifiers
misc_feature 1..11405
note = Synthetic: Fw12-EF1a-sTNALP-Fc-(DSS)6 lentiviral construct
source 1..11405
mol_type = other DNA
organism = synthetic construct
SEQUENCE: 34
gtactgggtc tctctggtta gaccagatct gagcctggga gctctctggc taactaggga 60
acccactgct taagcctcaa taaagcttgc cttgagtgct tcaagtagtg tgtgcccgtc 120
tgttgtgtga ctctggtaac tagagatccc tcagaccctt ttagtcagtg tggaaaatct 180
ctagcagtgg cgcccgaaca gggacttgaa agcgaaaggg aaaccagagg agctctctcg 240
acgcaggact cggcttgctg aagcgcgcac ggcaagaggc gaggggcggc gactggtgag 300
tacgccaaaa attttgacta gcggaggcta gaaggagaga gatgggtgcg agagcgtcag 360
tattaagcgg gggagaatta gatcgcgatg ggaaaaaatt cggttaaggc cagggggaaa 420
gaaaaaatat aaattaaaac atatagtatg ggcaagcagg gagctagaac gattcgcagt 480
taatcctggc ctgttagaaa catcagaagg ctgtagacaa atactgggac agctacaacc 540
atcccttcag acaggatcag aagaacttag atcattatat aatacagtag caaccctcta 600
ttgtgtgcat caaaggatag agataaaaga caccaaggaa gctttagaca agatagagga 660
agagcaaaac aaaagtaaga ccaccgcaca gcaagcggcc gctgatcttc agacctggag 720
gaggagatat gagggacaat tggagaagtg aattatataa atataaagta gtaaaaattg 780
aaccattagg agtagcaccc accaaggcaa agagaagagt ggtgcagaga gaaaaaagag 840
cagtgggaat aggagctttg ttccttgggt tcttgggagc agcaggaagc actatgggcg 900
cagcgtcaat gacgctgacg gtacaggcca gacaattatt gtctggtata gtgcagcagc 960
agaacaattt gctgagggct attgaggcgc aacagcatct gttgcaactc acagtctggg 1020
gcatcaagca gctccaggca agaatcctgg ctgtggaaag atacctaaag gatcaacagc 1080
tcctggggat ttggggttgc tctggaaaac tcatttgcac cactgctgtg ccttggaatg 1140
ctagttggag taataaatct ctggaacaga tttggaatca cacgacctgg atggagtggg 1200
acagagaaat taacaattac acaagcttaa tacactcctt aattgaagaa tcgcaaaacc 1260
agcaagaaaa gaatgaacaa gaattattgg aattagataa atgggcaagt ttgtggaatt 1320
ggtttaacat aacaaattgg ctgtggtata taaaattatt cataatgata gtaggaggct 1380
tggtaggttt aagaatagtt tttgctgtac tttctatagt gaatagagtt aggcagggat 1440
attcaccatt atcgtttcag acccacctcc caaccccgag gggacccgac aggcccgaag 1500
gaatagaaga agaaggtgga gagagagaca gagacagatc cattcgatta gtgaacggat 1560
cggcactgcg tgcgccaatt ctgcagacaa atggcagtat tcatccacaa ttttaaaaga 1620
aaaggggga ttggggggta cagtgcaggg gaaagaatag tagacataat agcaacagac 1680
atacaaacta aagaattaca aaaacaaatt acaaaaattc aaaattttcg ggtttattac 1740
agggacagca gagatccagt ttggttaatt aaggctccgg tgcccgtcag tgggcagagc 1800
gcacatcgcc cacagtcccc gagaagttgg ggggaggggt cggcaattga accggtgcct 1860
agagaaggtg gcgcggggta aactgggaaa gtgatgtcgt gtactggctc cgcctttttc 1920
ccgagggtgg gggagaaccg tatataagtg cagtagtcgc cgtgaacgtt ctttttcgca 1980
acgggtttgc cgccagaaca caggtaagtg ccgtgtgtgg ttcccgcggg cctggcctct 2040
ttacgggtta tggcccttgc gtgccttgaa ttacttccac tggctgcagt acgtgattct 2100
tgatcccgag cttcgggttg gaagtgggtg ggagagttcg aggccttgcg cttaaggagc 2160
cccttcgcct cgtgcttgag ttgaggcctg gcctgggcgc tggggccgcc gcgtgcgaat 2220
ctggtggcac cttcgcgcct gtctcgctgc tttcgataag tctctagcca tttaaaattt 2280
ttgatgacct gctgcgacgc tttttttctg gcaagatagt cttgtaaatg cgggccaaga 2340
tctgcacact ggtatttcgg tttttggggc cgcgggcggc gacggggccc gtgcgtccca 2400
gcgcacatgt tcggcgaggc ggggcctgcg agcgcggcca ccgagaatcg gacgggggta 2460
gtctcaagct ggccggcctg ctctggtgcc tggcctcgcg ccgccgtgta tcgccccgcc 2520
ctgggcggca aggctggccc ggtcggcacc agttgcgtga gcggaaagat ggccgcttcc 2580
cggccctgct gcagggagct caaaatggag gacgcggcgc tcgggagagc gggcgggtga 2640
gtcacccaca caaaggaaaa gggcctttcc gtcctcagcc gtcgcttcat gtgactccac 2700
ggagtaccgg gcgccgtcca ggcacctcga ttagttctcg agcttttgga gtacgtcgtc 2760
tttaggttgg ggggaggggt tttatgcgat ggagtttccc cacactgagt gggtggagac 2820
tgaagttagg ccagcttggc acttgatgta attctccttg gaatttgccc tttttgagtt 2880
tggatcttgg ttcattctca agcctcagac agtggttcaa agtttttttc ttccatttca 2940
ggtgtcgtga gctagcgcca ccatggatat gcgcgtaccc gctcaacttc tgggtttgtt 3000
gctgctttgg ctcaggggag cccgctgtgc cgcgcttgtc cctgaaaagg agaaggaccc 3060
caaatattgg agagaccagg ctcaggaaac cctcaagtac gctcttgaac tgcaaaagct 3120
taatactaac gtggctaaaa acgtgataat gttcttgggg gacggaatgg gggtttcaac 3180
cgttaccgcg gccagaatct tgaaagggca gctgcaccat aacccaggcg aagaaacgag 3240
gctggagatg gacaaatttc cattcgtggc gctttctaag acctacaaca ctaacgccca 3300

```
ggtccctgac tcagctggta cggccactgc ctacctttgt ggagtgaagg caaatgaggg  3360
gactgttggt gtttccgcag ctactgagag atctcggtgt aatacgactc aaggtaatga  3420
agttacatcc atactccgat gggcaaaaga cgcgggcaaa tctgttggga ttgttacaac  3480
tactagggtg aaccatgcga caccctctgc agcttatgcg cacagtgccg accgagactg  3540
gtattcagat aatgagatgc caccccgaggc ccttagccag ggctgcaagg acatagccta  3600
tcaattgatg cacaatatca gagacataga cgttataatg ggtggtggtc gcaagtacat  3660
gtaccccaaa aacaaaaccg acgtagagta tgaatccgat gaaaaagcta ggggcaccag  3720
actcgacgga cttgatctgg ttgatacatg gaagagcttc aagcccagat acaagcattc  3780
acatttcatc tggaacagga ccgaacttct cacattggac ccccacaatg ttgactatct  3840
cctcggtttg tttgaaccag ggatatgca gtatgagctc aatcggaaca acgtcactga  3900
ccccagtttg agtgaaatgg tcgttgttgc aatacaaatt ttgaggaaaa atccaaaggg  3960
gtttttcttg ttggtagagg gcggacggat agatcacggg caccacgaag gcaaagcaaa  4020
acaggccctg cacgaagccg ttgaaatgga tcgcgctatc ggtcaagccg gctccctgac  4080
gagtagtgaa gataccttga ccgtcgtcac tgcggatcat agccacgttt ttacctttgg  4140
gggatacacc cccaggggca actcaatttt tggacttgca ccgatgctca gcgacacaga  4200
taaaaagcct tttactgcga ttctgtatgg caacggccct ggatacaaag tagtaggggg  4260
tgaaagggaa aacgtcagca tggtggacta tgcacacaat aattatcagg cgcagtccgc  4320
tgttccgctg cggcatgaga ctcacggggg agaggacgtt gctgtctttt ccaagggacc  4380
aatggctcat cttctccatg gagtccatga gcaaaattat gtccctcatg tcatggcata  4440
cgctgcatgt ataggagcaa atctcgggca ctgtgcaccg gcgtcctccc tcaaagacaa  4500
aacacacact tgtccacctt gcccggcacc tgaacttctg ggcggcccga gcgttttttt  4560
gttccctcct aaacctaagg acacgctcat gatcagccgc acgccagagg ttacctgtgt  4620
agtggtggat gtcagccacg aggatccgga agtaaaattc aactggtatg tagatggggt  4680
ggaggttcac aatgccaaaa ccaagccacg agaggaacag tacaatagta cttaccgggt  4740
cgtgtctgta ttgaccgtcc tgcatcagga ttggttgaac gggaaagaat ataagtgcaa  4800
ggtgagcaac aaagcacttc cggccccaat agagaaaaca attagtaaag caaaaggaca  4860
accacgggaa ccgcaagttt atacactgcc gccctctcga gacgagctga ccaaaaatca  4920
ggttagcctt acatgtttgg tcaaggggtt ctacccgagt gatattgcag tggaatggga  4980
atccaacggt caaccagaaa ataactacaa aactactccg ccggtgttgg attcagacgg  5040
ctctttcttt ctgtatagca aactcactgt tgacaagtca agatggcagc agggcaatgt  5100
atttagctgt agtgttatgc acgaagctct tcataaccac tacacacaaa agtcactttc  5160
tctttcccca ggaaaagaca tcgattccag cgacagttca gacagctctg acagctccga  5220
ttcctccgac tcaagttgag aattcgatat caagcttatc gataatcaac ctctggatta  5280
caaaatttgt gaaagattga ctggtattct taactatgtt gctcctttta cgctatgtgg  5340
atacgctgct ttaatgcctt tgtatcatgc tattgcttcc cgtatggctt tcattttctc  5400
ctccttgtat aaatcctggt tgctgtctct ttatgaggag ttgtggcccg ttgtcaggca  5460
acgtggcgtg gtgtgcactg tgtttgctga cgcaaccccc actggttggg gcattgccac  5520
cacctgtcag ctcctttccg ggactttcgc tttccccctc cctattgcca cggcggaact  5580
catcgccgcc tgccttgccc gctgctggac aggggctcgg ctgttgggca ctgacaattc  5640
cgtggtgttg tcggggaaat catcgtcctt tccttggctg ctcgcctgtg ttgccacctg  5700
gattctgcgc gggacgtcct tctgctacgt cccttcggcc ctcaatccag cggaccttcc  5760
ttcccgcggc ctgctgccgg ctctgcggcc tcttccgcgt cttcgccttc gccctcagac  5820
gagtcggatc tccctttggg ccgcctcccc gcatcgatac cgtcgacctc gatcgagacc  5880
tagaaaaaca tggagcaatc acaagtagca atacagcagc taccaatgct gattgtgcct  5940
ggctagaagc acaagaggag gaggaggtgg gttttccagt cacacctcag gtacctttaa  6000
gaccaatgac ttacaaggca gctgtagatc ttagccactt tttaaaagaa aaggggggac  6060
tggaagggct aattcactcc caacgaagac aagatatcct tgatctgtgg atctaccaca  6120
cacaaggcta cttccctgat tggcagaact acacaccagg gccagggatc agatatccac  6180
tgacctttgg atggtgctac aagctagtac cagttgagca agagaaggta gaagaagcca  6240
atgaaggaga gaacacccgc ttgttacacc ctgtgagcct gcatgggatg gatgacccgg  6300
agagagaagt attagagtgg aggtttgaca gccgcctagc atttcatcac atggcccgag  6360
agctgcatcc ggactgtact gggtctctct ggttagacca gatctgagcc tgggagctct  6420
ctggctaact agggaaccca ctgcttaagc ctcaataaag cttgccttga gtgcttcaag  6480
tagtgtgtgc ccgtctgttg tgtgactctg gtaactagag atccctcaga cccttttagt  6540
cagtgtggaa aatctctagc agggcccgtt taaacccgct gatcagcctc gactgtgcct  6600
tctagttgcc agccatctgt tgtttgcccc tcccccgtgc cttccttgac cctggaaggt  6660
gccactccca ctgtcctttc ctaataaaat gaggaaattg catcgcattg tctgagtagg  6720
tgtcattcta ttctgggggg tggggtgggg caggacagca agggggagga ttgggaagac  6780
aatagcaggc atgctgggga tgcggtgggc tctatggctt ctgaggcgga aagaaccagc  6840
tggggctcta gggggtatcc ccacgcgccc tgtagcggcg cattaagcgc ggcgggtgtg  6900
gtggttacgc gcagcgtgac cgctacactt gccagcgccc tagcgcccgc tcctttcgct  6960
ttcttccctt cctttctcgc cacgttcgcc ggctttcccc gtcaagctct aaatcggggg  7020
ctccctttag ggttccgatt tagtgcttta cggcacctcg accccaaaaa acttgattag  7080
ggtgatggtt cacgtagtgg gccatcgccc tgatagacgg tttttcgccc tttgacgttg  7140
gagtccacgt tctttaatag tggactcttg ttccaaactg gaacaacact caaccctatc  7200
tcggtctatt cttttgattt ataagggatt ttgccgattt cggcctattg gttaaaaaat  7260
gagctgattt aacaaaaatt taacgcgaat taattctgtg gaatgtgtgt cagttagggt  7320
gtggaaagtc cccaggctcc ccagcaggca gaagtatgca aagcatgcat ctcaattagt  7380
cagcaaccag gtgtggaaag tccccaggct ccccagcagg cagaagtatg caaagcatgc  7440
atctcaatta gtcagcaacc atagtcccgc ccctaactcc gcccatcccg cccctaactc  7500
cgcccagttc cgcccattct ccgccccatg gctgactaat tttttttatt tatgcagagg  7560
ccgaggccgc ctctgcctct gagctattcc agaagtagtg aggaggcttt tttggaggcc  7620
taggcttttg caaaaagctc ccgggagctt gtatatccat tttcggatct gatcagcacg  7680
tgttgacaat taatcatcgg catagtatat cggcatagta taatacgaca aggtgaggaa  7740
ctaaaccatg gccaagttga ccagtgccgt tccggtgctc accgcgcgcg acgtcgccgg  7800
agcggtcgag ttctggaccg accggctcgg gttctcccgg gacttcgtgg aggacgactt  7860
cgccggtgtg gtccgggacg acgtgaccct gttcatcagc gcggtccagg accaggtggt  7920
gccggacaac accctggcct gggtgtgggt gcgcggcctg gacgagctgt acgccgagtg  7980
gtcggaggtc gtgtccacga acttccggga cgcctccggg ccggccatga ccgagatcgg  8040
```

```
cgagcagccg tgggggcggg agttcgccct gcgcgacccg gccggcaact gcgtgcactt  8100
cgtggccgag gagcaggact gacacgtgct acgagatttc gattccaccg ccgccttcta  8160
tgaaaggttg ggcttcggaa tcgttttccg ggacgccggc tggatgatcc tccagcgcgg  8220
ggatctcatg ctggagttct tcgcccaccc caacttgttt attgcagctt ataatggtta  8280
caaataaagc aatagcatca caaatttcac aaataaagca tttttttcac tgcattctag  8340
ttgtggtttg tccaaactca tcaatgtatc ttatcatgtc tgtataccgt cgacctctag  8400
ctagagcttg gcgtaatcat ggtcatagct gtttcctgtg tgaaattgtt atccgctcac  8460
aattccacac aacatacgag ccggaagcat aaagtgtaaa gcctggggtg cctaatgagt  8520
gagctaactc acattaattg cgttgcgctc actgcccgct ttccagtcgg gaaacctgtc  8580
gtgccagctg cattaatgaa tcggccaacg cgcggggaga ggcggtttgc gtattgggcg  8640
ctcttccgct tcctcgctca ctgactcgct gcgctcggtc gttcggctgc ggcgagcggt  8700
atcagctcac tcaaaggcgg taatacggtt atccacagaa tcaggggata acgcaggaaa  8760
gaacatgtga gcaaaaggcc agcaaaaggc caggaaccgt aaaaaggccg cgttgctggc  8820
gtttttccat aggctccgcc cccctgacga gcatcacaaa aatcgacgct caagtcagag  8880
gtggcgaaac ccgacaggac tataaagata ccaggcgttt ccccctggaa gctccctcgt  8940
gcgctctcct gttccgaccc tgccgcttac cggatacctg tccgcctttc tcccttcggg  9000
aagcgtggcg ctttctcata gctcacgctg taggtatctc agttcggtgt aggtcgttcg  9060
ctccaagctg ggctgtgtgc acgaaccccc cgttcagccc gaccgctgcg ccttatccgg  9120
taactatcgt cttgagtcca acccggtaag acacgactta tcgccactgg cagcagccac  9180
tggtaacagg attagcagag cgaggtatgt aggcggtgct acagagttct tgaagtggtg  9240
gcctaactac ggctacacta gaagaacagt atttggtatc tgcgctctgc tgaagccagt  9300
taccttcgga aaaagagttg gtagctcttg atccggcaaa caaaccaccg ctggtagcgg  9360
tggttttttt gtttgcaagc agcagattac gcgcagaaaa aaaggatctc aagaagatcc  9420
tttgatcttt tctacggggt ctgacgctca gtggaacgaa aactcacgtt aagggatttt  9480
ggtcatgaga ttatcaaaaa ggatcttcac ctagatcctt ttaaattaaa aatgaagttt  9540
taaatcaatc taaagtatat atgagtaaac ttggtctgac agttaccaat gcttaatcag  9600
tgaggcacct atctcagcga tctgtctatt tcgttcatcc atagttgcct gactccccgt  9660
cgtgtagata actacgatac gggagggctt accatctggc cccagtgctg caatgatacc  9720
gcgagaccca cgctcaccgg ctccagattt atcagcaata aaccagccag ccggaagggc  9780
cgagcgcaga agtggtcctg caactttatc cgcctccatc cagtctatta attgttgccg  9840
ggaagctaga gtaagtagtt cgccagttaa tagtttgcgc aacgttgttg ccattgctac  9900
aggcatcgtg gtgtcacgct cgtcgtttgg tatggcttca ttcagctccg gttcccaacg  9960
atcaaggcga gttacatgat cccccatgtt gtgcaaaaaa gcggttagct ccttcggtcc  10020
tccgatcgtt gtcagaagta agttggccgc agtgttatca ctcatggtta tggcagcact  10080
gcataattct cttactgtca tgccatccgt aagatgcttt tctgtgactg gtgagtactc  10140
aaccaagtca ttctgagaat agtgtatgcg gcgaccgagt tgctcttgcc cggcgtcaat  10200
acgggataat accgcgccac atagcagaac tttaaaagtg ctcatcattg gaaaacgttc  10260
ttcggggcga aaactctcaa ggatcttacc gctgttgaga tccagttcga tgtaacccac  10320
tcgtgcaccc aactgatctt cagcatcttt tactttcacc agcgtttctg ggtgagcaaa  10380
aacaggaagg caaaatgccg caaaaaaggg aataagggcg acacggaaat gttgaatact  10440
catactcttc ctttttcaat attattgaag catttatcag ggttattgtc tcatgagcgg  10500
atacatattt gaatgtattt agaaaaataa acaaataggg gttccgcgca catttccccg  10560
aaaagtgcca cctgacgtcg acggatcggg agatctcccg atcccctatg gtgcactctc  10620
agtacaatct gctctgatgc cgcatagtta agccagtatc tgctccctgc ttgtgtgttg  10680
gaggtcgctg agtagtgcgc gagcaaaatt taagctacaa caaggcaagg cttgaccgac  10740
aattgcatga agaatctgct tagggttagg cgttttgcgc tgcttcgcga tgtacgggcc  10800
agatatacgc gttgacattg attattgact agttattaat agtaatcaat tacggggtca  10860
ttagttcata gcccatatat ggagttccgc gttacataac ttacggtaaa tggcccgcct  10920
ggctgaccgc ccaacgaccc ccgcccattg acgtcaataa tgacgtatgt tcccatagta  10980
acgccaatag ggactttcca ttgacgtcaa tgggtggagt atttacggta aactgcccac  11040
ttggcagtac atcaagtgta tcatatgcca agtacgcccc ctattgacgt caatgacggt  11100
aaatggcccg cctggcatta tgcccagtac atgaccttat gggactttcc tacttggcag  11160
tacatctacg tattagtcat cgctattacc atggtgatgc ggttttggca gtacatcaat  11220
gggcgtggat agcggtttga ctcacgggga tttccaagtc tccaccccat tgacgtcaat  11280
gggagtttgt tttggcacca aaatcaacgg gactttccaa aatgtcgtaa caactccgcc  11340
ccattgacgc aaatgggcgg taggcgtgta cggtgggagg tctatataag cagcgcgttt  11400
tgcct                                                              11405
```

```
SEQ ID NO: 35          moltype = DNA  length = 709
FEATURE                Location/Qualifiers
misc_feature           1..709
                       note = Synthetic: Two inverted repeat sequences separated
                        by a minimal R6K gamma origin
source                 1..709
                       mol_type = other DNA
                       organism = synthetic construct
SEQUENCE: 35
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag ccttaattaa taccgttcgt ataatgtatg ctatacgaac ggtactgcag  180
tgtcagccgt taagtgttcc tgtgtcactc aaaattgctt tgagaggctc taagggcttc  240
tcagtgcgtt acatccctgg cttgttgtcc acaaccgtta aaccttaaaa gctttaaaag  300
ccttatatat tctttttttt cttataaaac ttaaaacctt agaggctatt taagttgctg  360
atttatatta attttattgt tcaaacatga gagcttagta cgtgaaacat gagagcttag  420
tacgttagcc atgagagctt agtacgttag ccatgagggt ttagttcgtt aaacatgaga  480
gcttagtacg ttaaacatga gagcttagta cgtgaaacat gagagcttag tacgtactat  540
caacaggttg aactgctgat cttcagatct taattaaggc tgcgcgctcg ctcgctcact  600
gaggccgccc gggcaaagcc cgggcgtcgg gcgacctttg gtcgcccggc ctcagtgagc  660
gagcgagcgc gcagagaggg agtggccaac tccatcacta ggggttcct             709
```

```
SEQ ID NO: 36          moltype = DNA  length = 128
FEATURE                Location/Qualifiers
misc_feature           1..128
                       note = Synthetic: AAV2 inverted
source                 1..128
                       mol_type = other DNA
                       organism = synthetic construct
SEQUENCE: 36
gcgcgctcgc tcgctcactg aggccgcccg ggcaaagccc gggcgtcggg cgacctttgg  60
tcgcccggcc tcagtgagcg agcgagcgcg cagagaggga gtggccaact ccatcactag  120
gggttcct                                                           128

SEQ ID NO: 37          moltype = DNA  length = 166
FEATURE                Location/Qualifiers
misc_feature           1..166
                       note = Synthetic: AAV2 A CRUCIFORM structure with a DD
                        element
source                 1..166
                       mol_type = other DNA
                       organism = synthetic construct
SEQUENCE: 37
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag agagggagtg gccaactcca tcactagggg tttcct                 166

SEQ ID NO: 38          moltype = DNA  length = 4681
FEATURE                Location/Qualifiers
misc_feature           1..4681
                       note = Synthetic: MF-EF1a-sTNALP control construct
source                 1..4681
                       mol_type = other DNA
                       organism = synthetic construct
SEQUENCE: 38
gcctagagaa ggtggcgcgg ggtaaactgg gaaagtgatg tcgtgtactg gctccgcctt  60
tttcccgagg gtgggggaga accgtatata agtgcagtag tcgccgtgaa cgttcttttt  120
cgcaacgggt ttgccgccag aacacaggta agtgccgtgt gtggttcccg cgggcctggc  180
ctctttacgg gttatggccc ttgcgtgcct tgaattactt ccactggctg cagtacgtga  240
ttcttgatcc cgagcttcgg gttggaagtg ggtgggagag ttcgaggcct tgcgcttaag  300
gagccccttc gcctcgtgct tgagttgagg cctggcctgg gcgctggggc cgccgcgtgc  360
gaatctggtg gcaccttcgc gcctgtctcg ctgctttcga taagtctcta gccatttaaa  420
atttttgatg acctgctgcg acgctttttt tctggcaaga tagtcttgta aatgcgggcc  480
aagatctgca cactggtatt tcggtttttg gggccgcggg cggcgacggg gcccgtgcgt  540
cccagcgcac atgttcggcg aggcggggcc tgcgagcgcg gccaccgaga atcggacggg  600
ggtagtctca agctggccgg cctgctctgg tgcctggcct cgcgccgccg tgtatcgccc  660
cgccctgggc ggcaaggctg gcccggtcgg caccagttgc gtgagcggaa agatggccgc  720
ttcccggccc tgctgcaggg agctcaaaat ggaggacgcg gcgctcggga gagcgggcgg  780
gtgagtcacc cacacaaagg aaaagggcct ttccgtcctc agccgtcgct tcatgtgact  840
ccacggagta ccgggcgccg tccaggcacc tcgattagtt ctcgagcttt tggagtacgt  900
cgtctttagg ttggggggag gggttttatg cgatggagtt tccccacact gagtgggtgg  960
agactgaagt taggccagct tggcacttga tgtaattctc cttggaattt gccctttttg  1020
agtttggatc ttggttcatt ctcaagcctc agacagtggt tcaaagtttt tttcttccat  1080
ttcaggtgtc gtgagctagc gccaccatgg atatgcgcgt acccgctcaa cttctgggtt  1140
tgttgctgct ttggctcagg ggagcccgct gtgccgcgct tgtccctgaa aaggagaagg  1200
accccaaata ttggagagac caggctcagg aaaccctcaa gtacgctctt gaactgcaaa  1260
agcttaatac taacgtggct aaaaacgtga taatgttctt gggggacgga atgggggttt  1320
caaccgttac cgcggccaga atcttgaaag ggcagctgca ccataaccca ggcgaagaaa  1380
cgaggctgga gatggacaaa tttccattcg tggcgctttc taagacctac aacactaacg  1440
cccaggtccc tgactcagct ggtacggcca ctgcctacct ttgtggagtg aaggcaaatg  1500
aggggactgt tggtgtttcc gcagctactg agagatctcg gtgtaatacg actcaaggta  1560
atgaagttac atccatactc cgatgggcaa aagacgcggg caaatctgtt gggattgtta  1620
caactactag ggtgaaccat gcgacaccct ctgcagctta tgcgcacagt gccgaccgag  1680
actggtattc agataatgag atgccacccg aggcccttag ccagggctgc aaggacatag  1740
cctatcaatt gatgcacaat atcagagaca tagacgttat aatgggtggt ggtcgcaagt  1800
acatgtaccc caaaaacaaa accgacgtag agtatgaatc cgatgaaaaa gctaggggca  1860
ccagactcga cggacttgat ctggttgata catggaagag cttcaagccc agatacaagc  1920
attcacattt catctggaac aggaccgaac ttctcacatt ggacccccac aatgttgact  1980
atctcctcgg tttgtttgaa ccaggggata tgcagtatga gctcaatcgg aacaacgtca  2040
ctgaccccag tttgagtgaa atggtcgttg ttgcaataca aattttgagg aaaaatccaa  2100
aggggttttt cttgttggta gagggcggac ggatagatca cgggcaccac gaaggcaaag  2160
caaaacaggc cctgcacgaa gccgttgaaa tggatcgcgc tatcggtcaa gccggctccc  2220
tgacgagtag tgaagatacc ttgaccgtcg tcactgcgga tcatagccac gtttttacct  2280
ttgggggata cacccccagg ggcaactcaa tttttggact tgcaccgatg ctcagcgaca  2340
cagataaaaa gccttttact gcgattctgt atggcaacgg ccctggatac aaagtagtag  2400
ggggtgaaag ggaaaacgtc agcatggtgg actatgcaca caataattat caggcgcagt  2460
ccgctgttcc gctgcggcat gagactcacg ggggagagga cgttgctgtc ttttccaagg  2520
gaccaatggc tcatcttctc catggagtcc atgagcaaaa ttatgtccct catgtcatgg  2580
catacgctgc atgtatagga gcaaatctcg ggcactgtgc accggcgtcc tccctcaaag  2640
acaaaacaca cacttgtcca ccttgcccgg cacctgaact tctgggcggc ccgagcgttt  2700
```

```
ttttgttccc tcctaaacct aaggacacgc tcatgatcag ccgcacgcca gaggttacct  2760
gtgtagtggt ggatgtcagc cacgaggatc cggaagtaaa attcaactgg tatgtagatg  2820
gggtggaggt tcacaatgcc aaaaccaagc cacgagagga acagtacaat agtacttacc  2880
gggtcgtgtc tgtattgacc gtcctgcatc aggattggtt gaacgggaaa gaatataagt  2940
gcaaggtgag caacaaagca cttccggccc caatagagaa aacaattagt aaagcaaaag  3000
gacaaccacg ggaaccgcaa gtttatacac tgccgccctc tcgagacgag ctgaccaaaa  3060
atcaggttag ccttacatgt ttggtcaagg ggttctaccc gagtgatatt gcagtggaat  3120
gggaatccaa cggtcaacca gaaaataact acaaaactac tccgccggtg ttggattcag  3180
acggctcttt ctttctgtat agcaaactca ctgttgacaa gtcaagatgg cagcagggca  3240
atgtatttag ctgtagtgtt atgcacgaag ctcttcataa ccactacaca caaaagtcac  3300
tttctctttc cccaggaaaa gacatcgatt ccagcgacag ttcagacagc tctgacagct  3360
ccgattcctc cgactcaagt tgaaagcttg gatccaatca acctctggat tacaaaattt  3420
gtgaaagatt gactggtatt cttaactatg ttgctccttt tacgctatgt ggatacgctg  3480
ctttaatgcc tttgtatcat gctattgctt cccgtatggc tttcattttc tcctccttgt  3540
ataaatcctg gttgctgtct ctttatgagg agttgtggcc cgttgtcagg caacgtggcg  3600
tggtgtgcac tgtgtttgct gacgcaaccc ccactggttg gggcattgcc accacctgtc  3660
agctcctttc cgggactttc gctttccccc tccctattgc cacggcggaa ctcatcgccg  3720
cctgccttgc ccgctgctgg acaggggctc ggctgttggg cactgacaat tccgtggtgt  3780
tgtcggggaa atcatcgtcc tttccttggc tgctcgcctg tgttgccacc tggattctgc  3840
gcgggacgtc cttctgctac gtcccttcgg ccctcaatcc agcggacctt ccttcccgcg  3900
gcctgctgcc ggctctgcgg cctcttccgc gtcttcgaga tctgcctcga ctgtgccttc  3960
tagttgccag ccatctgttg tttgcccctc ccccgtgcct tccttgaccc tggaaggtgc  4020
cactcccact gtcctttcct aataaaatga ggaaattgca tcgcattgtc tgagtaggtg  4080
tcattctatt ctggggggtg gggtggggca ggacagcaag ggggaggatt gggaagacaa  4140
tagcaggcat gctggggata ccgttcgtat aatgtatgct atacgaacgg tactgcagtg  4200
tcagccgtta agtgttcctg tgtcactcaa aattgctttg agaggctcta agggcttctc  4260
agtgcgttac atccctggct tgttgtccac aaccgttaaa ccttaaaagc tttaaaagcc  4320
ttatatattc ttttttttct tataaaactt aaaaccttag aggctattta agttgctgat  4380
ttatattaat tttattgttc aaacatgaga gcttagtacg tgaaacatga gagcttagta  4440
cgttagccat gagagcttag tacgttagcc atgagggttt agttcgttaa acatgagagc  4500
ttagtacgtt aaacatgaga gcttagtacg tgaaacatga gagcttagta cgtactatca  4560
acaggttgaa ctgctgatct tcagatctta attaaggggc tccggtgccc gtcagtgggc  4620
agagcgcaca tcgcccacag tccccgagaa gttgggggga ggggtcggca attgaaccgg  4680
t                                                                  4681
```

```
SEQ ID NO: 39          moltype = DNA  length = 30
FEATURE                Location/Qualifiers
misc_feature           1..30
                       note = Synthetic: QTS - TLR9 inhibitory sequence
source                 1..30
                       mol_type = other DNA
                       organism = synthetic construct
SEQUENCE: 39
ttagggttag ggttagggtt agggttaggg                                   30
```

```
SEQ ID NO: 40          moltype = DNA  length = 5148
FEATURE                Location/Qualifiers
misc_feature           1..5148
                       note = Synthetic: Halo construct comprising R6K Ori
                        sequence between two inverted repeated sequences, one TLR9
                        inhibitory sequence, EF1a-driven sTNALP-Fc-(DSS)6 transgene
source                 1..5148
                       mol_type = other DNA
                       organism = synthetic construct
SEQUENCE: 40
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcttag ggttagggtt agggttaggg ttagggcccc ttaagctagc  240
ggctccggtg cccgtcagtg ggcagagcgc acatcgccca cagtccccga gaagttgggg  300
ggaggggtcg gcaattgaac cggtgcctag agaaggtggc gcggggtaaa ctgggaaagt  360
gatgtcgtgt actggctccg cctttttccc gagggtgggg gagaaccgta tataagtgca  420
gtagtcgccg tgaacgttct ttttcgcaac gggtttgccg ccagaacaca ggtaagtgcc  480
gtgtgtggtt cccgcgggcc tggcctcttt acgggttatg gcccttgcgt gccttgaatt  540
acttccactg gctgcagtac gtgattcttg atcccgagct tcgggttgga agtgggtggg  600
agagttcgag gccttgcgct taaggagccc cttcgcctcg tgcttgagtt gaggcctggc  660
ctgggcgctg gggccgccgc gtgcgaatct ggtggcacct tcgcgcctgt ctcgctgctt  720
tcgataagtc tctagccatt taaaattttt gatgacctgc tgcgacgctt tttttctggc  780
aagatagtct tgtaaatgcg ggccaagatc tgcacactgg tatttcggtt tttggggccg  840
cgggcggcga cggggcccgt gcgtcccagc gcacatgttc ggcgaggcgg ggcctgcgag  900
cgcggccacc gagaatcgga cgggggtagt ctcaagctgg ccggcctgct ctggtgcctg  960
gcctcgcgcc gccgtgtatc gccccgccct gggcggcaag gctggcccgg tcggcaccag  1020
ttgcgtgagc ggaaagatgg ccgcttcccg gccctgctgc agggagctca aaatggagga  1080
cgcggcgctc gggagagcgg gcgggtgagt cacccacaca aaggaaaagg gcctttccgt  1140
cctcagccgt cgcttcatgt gactccacgg agtaccgggc gccgtccagg cacctcgatt  1200
agttctcgag cttttggagt acgtcgtctt taggttgggg ggaggggttt tatgcgatgg  1260
agtttcccca cactgagtgg gtggagactg aagttaggcc agcttggcac ttgatgtaat  1320
tctccttgga atttgccctt tttgagtttg gatcttggtt cattctcaag cctcagacag  1380
tggttcaaag ttttttcttt ccatttcagg tgtcgtgagc tagcgccacc atggatatgc  1440
```

gcgtacccgc tcaacttctg ggtttgttgc tgctttggct caggggagcc cgctgtgccg 1500
cgcttgtccc tgaaaaggag aaggacccca aatattggag agaccaggct caggaaaccc 1560
tcaagtacgc tcttgaactg caaaagctta atactaacgt ggctaaaaac gtgataatgt 1620
tcttggggga cggaatgggg gtttcaaccg ttaccgcggc cagaatcttg aaagggcagc 1680
tgcaccataa cccaggcgaa gaaacgaggc tggagatgga caaatttcca ttcgtggcgc 1740
tttctaagac ctacaacact aacgcccagg tccctgactc agctggtacg gccactgcct 1800
acctttgtgg agtgaaggca aatgagggga ctgttggtgt ttccgcagct actgagagat 1860
ctcggtgtaa tacgactcaa ggtaatgaag ttacatccat actccgatgg gcaaaagacg 1920
cgggcaaatc tgttgggatt gttacaacta ctagggtgaa ccatgcgaca ccctctgcag 1980
cttatgcgca cagtgccgac cgagactggt attcagataa tgagatgcca cccgaggccc 2040
ttagccaggg ctgcaaggac atagcctatc aattgatgca caatatcaga gacatagacg 2100
ttataatggg tggtggtcgc aagtacatgt accccaaaaa caaaaccgac gtagagtatg 2160
aatccgatga aaaagctagg ggcaccagac tcgacggact tgatctggtt gatacatgga 2220
agagcttcaa gcccagatac aagcattcac atttcatctg gaacaggacc gaacttctca 2280
cattggaccc ccacaatgtt gactatctcc tcggtttgtt tgaaccaggg gatatgcagt 2340
atgagctcaa tcggaacaac gtcactgacc ccagtttgag tgaaatggtc gttgttgcaa 2400
tacaaatttt gaggaaaaat ccaaaggggt ttttcttgtt ggtagagggc ggacggatag 2460
atcacgggca ccacgaaggc aaagcaaaac aggccctgca cgaagccgtt gaaatggatc 2520
gcgctatcgg tcaagccggc tccctgacga gtagtgaaga taccttgacc gtcgtcactg 2580
cggatcatag ccacgttttt acctttgggg gatacacccc caggggcaac tcaatttttg 2640
gacttgcacc gatgctcagc gacacagata aaaagccttt tactgcgatt ctgtatggca 2700
acggccctgg atacaaagta gtagggggtg aaagggaaaa cgtcagcatg gtggactatg 2760
cacacaataa ttatcaggcg cagtccgctg ttccgctgcg gcatgagact cacgggggag 2820
aggacgttgc tgtcttttcc aagggaccaa tggctcatct tctccatgga gtccatgagc 2880
aaaattatgt ccctcatgtc atggcatacg ctgcatgtat aggagcaaat ctcgggcact 2940
gtgcaccggc gtcctccctc aaagacaaaa cacacacttg tccaccttgc ccggcacctg 3000
aacttctggg cggcccgagc gtttttttgt tccctcctaa acctaaggac acgctcatga 3060
tcagccgcac gccagaggtt acctgtgtag tggtggatgt cagccacgag gatccggaag 3120
taaaattcaa ctggtatgta gatggggtgg aggttcacaa tgccaaaacc aagccacgag 3180
aggaacagta caatagtact taccgggtcg tgtctgtatt gaccgtcctg catcaggatt 3240
ggttgaacgg gaaagaatat aagtgcaagg tgagcaacaa agcacttccg gccccaatag 3300
agaaaacaat tagtaaagca aaaggacaac cacgggaacc gcaagtttat acactgccgc 3360
cctctcgaga cgagctgacc aaaaatcagg ttagccttac atgtttggtc aaggggttct 3420
acccgagtga tattgcagtg gaatgggaat ccaacggtca accagaaaat aactacaaaa 3480
ctactccgcc ggtgttggat tcagacggct ctttctttct gtatagcaaa ctcactgttg 3540
acaagtcaag atggcagcag ggcaatgtat ttagctgtag tgttatgcac gaagctcttc 3600
ataaccacta cacacaaaag tcactttctc tttccccagg aaaagacatc gattccagcg 3660
acagttcaga cagctctgac agctccgatt cctccgactc aagttgaaag cttggatcca 3720
atcaacctct ggattacaaa atttgtgaaa gattgactgg tattcttaac tatgttgctc 3780
cttttacgct atgtggatac gctgctttaa tgcctttgta tcatgctatt gcttcccgta 3840
tggctttcat tttctcctcc ttgtataaat cctggttgct gtctctttat gaggagttgt 3900
ggcccgttgt caggcaacgt ggcgtggtgt gcactgtgtt tgctgacgca acccccactg 3960
gttggggcat tgccaccacc tgtcagctcc tttccgggac tttcgctttc cccctcccta 4020
ttgccacggc ggaactcatc gccgcctgcc ttgcccgctg ctggacaggg gctcggctgt 4080
tgggcactga caattccgtg gtgttgtcgg ggaaatcatc gtcctttcct tggctgctcg 4140
cctgtgttgc cacctggatt ctgcgcggga cgtccttctg ctacgtccct tcggccctca 4200
atccagcgga ccttccttcc cgcggcctgc tgccggctct gcggcctctt ccgcgtcttc 4260
gagatctgcc tcgactgtgc cttctagttg ccagccatct gttgtttgcc cctcccccgt 4320
gccttccttg accctggaag gtgccactcc cactgtcctt tcctaataaa atgaggaaat 4380
tgcatcgcat tgtctgagta ggtgtcattc tattctgggg ggtggggtgg ggcaggacag 4440
caagggggag gattgggaag acaatagcag gcatgctggg gactcgagtt aagggcgaat 4500
tcccgataag gatcttccta gagcatggct acgtagataa gtagcatggc gggttaatca 4560
ttaactacaa ggaaccccta gtgatggagt tggccactcc ctctctgcgc gctcgctcgc 4620
tcactgaggc cgggcgacca aaggtcgccc gacgcccggg ctttgcccgg gcggcctcag 4680
tgagcgagcg agcgcgcagc cttaattaat accgttcgta taatgtatgc tatacgaacg 4740
gtactgcagt gtcagccgtt aagtgttcct gtgtcactca aaattgcttt gagaggctct 4800
aagggcttct cagtgcgtta catccctggc ttgttgtcca caaccgttaa accttaaaag 4860
ctttaaaagc cttatatatt cttttttttc ttataaaact taaaacctta gaggctattt 4920
aagttgctga tttatattaa ttttattgtt caaacatgag agcttagtac gtgaaacatg 4980
agagcttagt acgttagcca tgagagctta gtacgttagc catgagggtt tagttcgtta 5040
aacatgagag cttagtacgt taaacatgag agcttagtac gtgaaacatg agagcttagt 5100
acgtactatc aacaggttga actgctgatc ttcagatctt aattaagg 5148

SEQ ID NO: 41 moltype = DNA length = 5178
FEATURE Location/Qualifiers
misc_feature 1..5178
note = Synthetic: Halo construct comprising ITR-R6K Ori-ITR
sequence, two TLR9 inhibitory sequences, EF1a-driven
sTNALP-Fc-(DSS)6 transgene
source 1..5178
mol_type = other DNA
organism = synthetic construct
SEQUENCE: 41
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcttag ggttagggtt agggttaggg ttaggggccc ttaagctagc 240
ggctccggtg cccgtcagtg ggcagagcgc acatcgccca cagtccccga gaagttgggg 300
ggaggggtcg gcaattgaac cggtgcctag agaaggtggc gcggggtaaa ctgggaaagt 360

```
gatgtcgtgt actggctccg ccttttttccc gagggtgggg gagaaccgta tataagtgca  420
gtagtcgccg tgaacgttct ttttcgcaac gggtttgccg ccagaacaca ggtaagtgcc  480
gtgtgtggtt cccgcgggcc tggcctcttt acgggttatg gcccttgcgt gccttgaatt  540
acttccactg gctgcagtac gtgattcttg atcccgagct tcgggttgga agtgggtggg  600
agagttcgag gccttgcgct taaggagccc cttcgcctcg tgcttgagtt gaggcctggc  660
ctgggcgctg gggccgccgc gtgcgaatct ggtggcacct tcgcgcctgt ctcgctgctt  720
tcgataagtc tctagccatt taaaattttt gatgacctgc tgcgacgctt tttttctggc  780
aagatagtct tgtaaatgcg ggccaagatc tgcacactgg tatttcggtt tttggggccg  840
cgggcggcga cggggcccgt gcgtcccagc gcacatgttc ggcgaggcgg ggcctgcgag  900
cgcggccacc gagaatcgga cgggggtagt ctcaagctgg ccggcctgct ctggtgcctg  960
gcctcgcgcc gccgtgtatc gccccgccct gggcggcaag gctggcccgg tcggcaccag  1020
ttgcgtgagc ggaaagatgg ccgcttcccg gccctgctgc agggagctca aaatggagga  1080
cgcggcgctc gggagagcgg gcgggtgagt cacccacaca aaggaaaagg gcctttccgt  1140
cctcagccgt cgcttcatgt gactccacgg agtaccgggc gccgtccagg cacctcgatt  1200
agttctcgag cttttggagt acgtcgtctt taggttgggg ggaggggttt tatgcgatgg  1260
agtttcccca cactgagtgg gtggagactg aagttaggcc agcttggcac ttgatgtaat  1320
tctccttgga atttgccctt tttgagtttg gatcttggtt cattctcaag cctcagacag  1380
tggttcaaag tttttttctt ccatttcagg tgtcgtgagc tagcgccacc atggatatgc  1440
gcgtacccgc tcaacttctg ggtttgttgc tgctttggct caggggagcc cgctgtgccg  1500
cgcttgtccc tgaaaaggag aaggacccca aatattggag agaccaggct caggaaaccc  1560
tcaagtacgc tcttgaactg caaaagctta atactaacgt ggctaaaaac gtgataatgt  1620
tcttgggggga cggaatgggg gtttcaaccg ttaccgcggc cagaatcttg aaagggcagc  1680
tgcaccataa cccaggcgaa gaaacgaggc tggagatgga caaatttcca ttcgtggcgc  1740
tttctaagac ctacaacact aacgcccagg tccctgactc agctggtacg gccactgcct  1800
acctttgtgg agtgaaggca aatgagggga ctgttggtgt ttccgcagct actgagagat  1860
ctcggtgtaa tacgactcaa ggtaatgaag ttacatccat actccgatgg gcaaaagacg  1920
cgggcaaatc tgttgggatt gttacaacta ctagggtgaa ccatgcgaca ccctctgcag  1980
cttatgcgca cagtgccgac cgagactggt attcagataa tgagatgcca cccgaggccc  2040
ttagccaggg ctgcaaggac atagcctatc aattgatgca caatatcaga gacatagacg  2100
ttataatggg tggtggtcgc aagtacatgt accccaaaaa caaaaaccgac gtagagtatg  2160
aatccgatga aaaagctagg ggcaccagac tcgacggact tgatctggtt gatacatgga  2220
agagcttcaa gcccagatac aagcattcac atttcatctg gaacaggacc gaacttctca  2280
cattggaccc ccacaatgtt gactatctcc tcggtttgtt tgaaccaggg gatatgcagt  2340
atgagctcaa tcggaacaac gtcactgacc ccagtttgag tgaaatggtc gttgttgcaa  2400
tacaaatttt gaggaaaaat ccaaaggggt ttttcttgtt ggtagagggc ggacggatag  2460
atcacgggca ccacgaaggc aaagcaaaac aggccctgca cgaagccgtt gaaatggatc  2520
gcgctatcgg tcaagccggc tccctgacga gtagtgaaga taccttgacc gtcgtcactg  2580
cggatcatag ccacgttttt acctttgggg gatacacccc caggggcaac tcaatttttg  2640
gacttgcacc gatgctcagc gacacagata aaaagccttt tactgcgatt ctgtatggca  2700
acggccctgg atacaaagta gtagggggtg aaagggaaaa cgtcagcatg gtggactatg  2760
cacacaataa ttatcaggcg cagtccgctg ttccgctgcg gcatgagact cacgggggag  2820
aggacgttgc tgtcttttcc aagggaccaa tggctcatct tctccatgga gtccatgagc  2880
aaaattatgt ccctcatgtc atggcatacg ctgcatgtat aggagcaaat ctcgggcact  2940
gtgcaccggc gtcctccctc aaagacaaaa cacacacttg tccaccttgc ccggcacctg  3000
aacttctggg cggcccgagc gtttttttgt tccctcctaa acctaaggac acgctcatga  3060
tcagccgcac gccagaggtt acctgtgtag tggtggatgt cagccacgag gatccggaag  3120
taaaattcaa ctggtatgta gatggggtgg aggttcacaa tgccaaaacc aagccacgag  3180
aggaacagta caatagtact taccgggtcg tgtctgtatt gaccgtcctg catcaggatt  3240
ggttgaacgg gaaagaatat aagtgcaagg tgagcaacaa agcacttccg gccccaatag  3300
agaaaacaat tagtaaagca aaaggacaac cacgggaacc gcaagtttat acactgccgc  3360
cctctcgaga cgagctgacc aaaaatcagg ttagccttac atgtttggtc aaggggttct  3420
acccgagtga tattgcagtg gaatgggaat ccaacggtca accagaaaat aactacaaaa  3480
ctactccgcc ggtgttggat tcagacggct ctttctttct gtatagcaaa ctcactgttg  3540
acaagtcaag atggcagcag ggcaatgtat ttagctgtag tgttatgcac gaagctcttc  3600
ataaccacta cacacaaaag tcactttctc tttccccagg aaaagacatc gattccagcg  3660
acagttcaga cagctctgac agctccgatt cctccgactc aagttgaaag cttggatcca  3720
atcaacctct ggattacaaa atttgtgaaa gattgactgg tattcttaac tatgttgctc  3780
cttttacgct atgtggatac gctgctttaa tgcctttgta tcatgctatt gcttcccgta  3840
tggctttcat tttctcctcc ttgtataaat cctggttgct gtctctttat gaggagttgt  3900
ggcccgttgt caggcaacgt ggcgtggtgt gcactgtgtt tgctgacgca acccccactg  3960
gttggggcat tgccaccacc tgtcagctcc tttccgggac tttcgctttc cccctcccta  4020
ttgccacggc ggaactcatc gccgcctgcc ttgcccgctg ctggacaggg gctcggctgt  4080
tgggcactga caattccgtg gtgttgtcgg ggaaatcatc gtcctttcct tggctgctcg  4140
cctgtgttgc cacctggatt ctgcgcggga cgtccttctg ctacgtccct tcggccctca  4200
atccagcgga ccttccttcc cgcggcctgc tgccggctct gcggcctctt ccgcgtcttc  4260
gagatctgcc tcgactgtgc cttctagttg ccagccatct gttgtttgcc cctcccccgt  4320
gccttccttg accctggaag gtgccactcc cactgtcctt tcctaataaa atgaggaaat  4380
tgcatcgcat tgtctgagta ggtgtcattc tattctgggg ggtggggtgg ggcaggacag  4440
caagggggag gattgggaag acaatagcag gcatgctggg gactcgagtt tagggttagg  4500
gttagggtta gggttagggt aagggcgaat tcccgataag gatcttccta gagcatggct  4560
acgtagataa gtagcatggc gggttaatca ttaactacaa ggaaccccta gtgatggagt  4620
tggccactcc ctctctgcgc gctcgctcgc tcactgaggc cgggcgacca aaggtcgccc  4680
gacgcccggg ctttgcccgg gcggcctcag tgagcgagcg agcgcgcagc cttaattaat  4740
accgttcgta taatgtatgc tatacgaacg gtactgcagt gtcagccgtt aagtgttcct  4800
gtgtcactca aaattgcttt gagaggctct aagggcttct cagtgcgtta catccctggc  4860
ttgttgtcca caaccgttaa accttaaaag ctttaaaagc cttatatatt cttttttttc  4920
ttataaaact taaaacctta gaggctattt aagttgctga tttatattaa ttttattgtt  4980
caaacatgag agcttagtac gtgaaacatg agagcttagt acgttagcca tgagagctta  5040
gtacgttagc catgagggtt tagttcgtta aacatgagag cttagtacgt taaacatgag  5100
```

-continued

```
agcttagtac gtgaaacatg agagcttagt acgtactatc aacaggttga actgctgatc  5160
ttcagatctt aattaagg                                                5178

SEQ ID NO: 42          moltype = DNA  length = 4932
FEATURE                Location/Qualifiers
misc_feature           1..4932
                       note = Synthetic: Halo construct comprising ITR-R6K Ori-ITR
                        sequence, EF1a-driven Zero-CpG PCSK9 Q152H transgene
source                 1..4932
                       mol_type = other DNA
                       organism = synthetic construct
SEQUENCE: 42
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctagc ggctccggtg cccgtcagtg ggcagagcgc  240
acatcgccca cagtccccga gaagttgggg ggaggggtcg gcaattgaac cggtgcctag  300
agaaggtggc gcggggtaaa ctgggaaagt gatgtcgtgt actggctccg cctttttccc  360
gagggtgggg gagaaccgta tataagtgca gtagtcgccg tgaacgttct ttttcgcaac  420
gggtttgccg ccagaacaca ggtaagtgcc gtgtgtggtt cccgcgggcc tggcctcttt  480
acgggttatg gcccttgcgt gccttgaatt acttccactg gctgcagtac gtgattcttg  540
atcccgagct tcgggttgga agtgggtggg agagttcgag gccttgcgct taaggagccc  600
cttcgcctcg tgcttgagtt gaggcctggc ctgggcgctg gggccgccgc gtgcgaatct  660
ggtggcacct tcgcgcctgt ctcgctgctt tcgataagtc tctagccatt taaaattttt  720
gatgacctgc tgcgacgctt tttttctggc aagatagtct tgtaaatgcg ggccaagatc  780
tgcacactgg tatttcggtt tttggggccg cgggcggcga cggggcccgt gcgtcccagc  840
gcacatgttc ggcgaggcgg ggcctgcgag cgcggccacc gagaatcgga cgggggtagt  900
ctcaagctgg ccggcctgct ctggtgcctg gcctcgcgcc gccgtgtatc gccccgccct  960
gggcggcaag gctggcccgg tcggcaccag ttgcgtgagc ggaaagatgg ccgcttcccg  1020
gccctgctgc agggagctca aaatggagga cgcggcgctc gggagagcgg gcgggtgagt  1080
cacccacaca aaggaaaagg gcctttccgt cctcagccgt cgcttcatgt gactccacgg  1140
agtaccgggc gccgtccagg cacctcgatt agttctcgag cttttggagt acgtcgtctt  1200
taggttgggg ggaggggttt tatgcgatgg agtttcccca cactgagtgg gtggagactg  1260
aagttaggcc agcttggcac ttgatgtaat tctccttgga atttgccctt tttgagtttg  1320
gatcttggtt cattctcaag cctcagacag tggttcaaag tttttttctt ccatttcagg  1380
tgtcgtgagc tagcgccacc atgggcacag tgagctccag aagatcttgg tggcctctgc  1440
ctctgctgct gctcctgctg ctgctgctgg gacctgctgg agctagagcc caggaggatg  1500
aagatggaga ctatgaggag ctggtgctgg ctctgagatc tgaggaagat ggtctggctg  1560
aagcccctga gcatggcacc acagctacct ttcacagatg tgccaaggac ccctggagac  1620
tgcctggcac ctatgtggtg gttcttaaag aggagacaca tctgagccag tctgagagaa  1680
cagccagaag actgcaggcc caagctgcta gaagaggtta tctgaccaag atcctgcatg  1740
tgtttcatgg ccttcttcct ggcttcctgg tcaagatgtc tggagatctg cttgagctgg  1800
ccctgaagct gccccatgtg gattacattg aggaggatag ctctgtgttt gcccactcta  1860
ttccttggaa cctggaaaga atcacccctc caagatatag agctgatgaa taccagcctc  1920
ctgatggagg cagcctggtg gaggtgtacc tgctggacac cagcatccag tctgaccaca  1980
gggagattga gggcagagtt atggtgacag attttgagaa tgtgccagaa gaggatggca  2040
ccagattcca cagacaagcc agcaagtgtg acagccatgg cacccacctg gctggagtgg  2100
tgtctggcag agatgctgga gtggccaagg gagccagcat gagaagcctg agagtgctga  2160
attgccaggg caagggcaca gtgtctggca ccctaattgg actggagttc atcagaaaga  2220
gccagctggt gcagcctgtg ggacctctgg ttgttctgct gcctctagct ggaggataca  2280
gcagagtgct gaatgctgcc tgccagagac tggctagagc tggagtggtg ctggtgactg  2340
ctgctggaaa tttcagagat gatgcctgcc tgtacagccc tgcctctgcc cctgaagtga  2400
tcacagtggg agctacaaat gcccaggacc aaccagtgac cctgggcacc ctgggaacca  2460
actttggcag atgtgtggac ctgtttgccc ctggagagga catcattgga gccagctcag  2520
attgctctac atgctttgtg agccaatctg gcacctcaca ggctgctgct catgtggctg  2580
gcattgctgc catgatgctg tctgcagaac ctgagctgac actggctgag ctgagacaga  2640
gactgatcca cttctctgct aaagatgtga tcaatgaggc ctggttccct gaagaccaga  2700
gagtgctgac acctaatctg gtggctgctc tgcctcccag cacccatgga gctggatggc  2760
agctgttctg cagaacagtg tggtctgccc actctggccc caccagaatg gccacagctg  2820
tggccagatg tgcccctgat gaggaactgc tcagctgcag cagctttagc agatctggca  2880
aaagaagagg agaaagaatg gaagcccagg gaggcaagct ggtgtgcaga gcccacaatg  2940
cctttggagg agaaggagtg tatgccattg ccagatgttg cctgctgccc caggccaact  3000
gctctgtgca cacagcccct ccagctgagg cctctatggg caccagagtg cactgccacc  3060
agcagggcca tgtgctgaca ggctgttcta gccattggga ggtggaagac ctgggaaccc  3120
acaagcctcc tgtgctgaga cccagaggcc agcctaacca gtgtgtgggc cacagagaag  3180
ccagcatcca tgccagttgt tgtcatgccc ctggcctgga atgcaaggtg aaggaacatg  3240
gcatcccagc tccacaggag caggtgacag tggcctgtga ggaaggctgg accctgacag  3300
gctgctctgc cctgcctggc acaagccatg tgctgggagc atatgctgtg gacaacacct  3360
gtgtggtgag aagcagggat gtgagcacaa caggcagcac ctctgaggga gctgttacag  3420
ctgtggccat ctgctgtaga tctagacact tggcccaggc ctctcaggag ctgcagtgag  3480
aattcgatat caagcttatc gataatcaac ctctggatta caaaatttgt gaaagattga  3540
ctggtattct taactatgtt gctcctttta cgctatgtgg atacgctgct ttaatgcctt  3600
tgtatcatgc tattgcttcc cgtatggctt tcattttctc ctccttgtat aaatcctggt  3660
tgctgtctct ttatgaggag ttgtggcccg ttgtcaggca acgtggcgtg gtgtgcactg  3720
tgtttgctga cgcaaccccc actggttggg gcattgccac cacctgtcag ctcctttccg  3780
ggactttcgc tttccccctc cctattgcca cggcggaact catcgccgcc tgccttgccc  3840
gctgctggac aggggctcgg ctgttgggca ctgacaattc cgtggtgttg tcggggaaat  3900
catcgtcctt tccttggctg ctcgcctgtg ttgccacctg gattctgcgc gggacgtcct  3960
tctgctacgt cccttcggcc ctcaatccag cggaccttcc ttcccgcggc ctgctgccgg  4020
```

```
ctctgcggcc tcttccgcgt cttcgagatc tgcctcgact gtgccttcta gttgccagcc  4080
atctgttgtt tgcccctccc ccgtgccttc cttgaccctg gaaggtgcca ctcccactgt  4140
cctttcctaa taaaatgagg aaattgcatc gcattgtctg agtaggtgtc attctattct  4200
ggggggtggg gtggggcagg acagcaaggg ggaggattgg gaagacaata gcaggcatgc  4260
tggggactcg agttaagggc gaattcccga taaggatctt cctagagcat ggctacgtag  4320
ataagtagca tggcgggtta atcattaact acaaggaacc cctagtgatg gagttggcca  4380
ctccctctct gcgcgctcgc tcgctcactg aggccgggcg accaaaggtc gcccgacgcc  4440
cgggctttgc ccgggcggcc tcagtgagcg agcgagcgcg cagccttaat taataccgtt  4500
cgtataatgt atgctatacg aacggtactg cagtgtcagc cgttaagtgt tcctgtgtca  4560
ctcaaaattg ctttgagagg ctctaagggc ttctcagtgc gttacatccc tggcttgttg  4620
tccacaaccg ttaaacctta aaagctttaa aagccttata tattcttttt tttcttataa  4680
aacttaaaac cttagaggct atttaagttg ctgatttata ttaattttat tgttcaaaca  4740
tgagagctta gtacgtgaaa catgagagct tagtacgtta gccatgagag cttagtacgt  4800
tagccatgag ggtttagttc gttaaacatg agagcttagt acgttaaaca tgagagctta  4860
gtacgtgaaa catgagagct tagtacgtac tatcaacagg ttgaactgct gatcttcaga  4920
tcttaattaa gg                                                      4932
```

```
SEQ ID NO: 43           moltype = DNA  length = 4371
FEATURE                 Location/Qualifiers
misc_feature            1..4371
                        note = Synthetic: Halo construct comprising IR-R6K Ori-IR
                         sequence, and EF1a-driven cynomolgus monkey sTNALP
                         transgene
source                  1..4371
                        mol_type = other DNA
                        organism = synthetic construct
SEQUENCE: 43
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagctagc ggctccggtg cccgtcagtg ggcagagcgc  240
acatcgccca cagtccccga gaagttgggg ggaggggtcg gcaattgaac cggtgcctag  300
agaaggtggc gcggggtaaa ctgggaaagt gatgtcgtgt actggctccg cctttttccc  360
gagggtgggg gagaaccgta tataagtgca gtagtcgccg tgaacgttct ttttcgcaac  420
gggtttgccg ccagaacaca ggtaagtgcc gtgtgtggtt cccgcgggcc tggcctcttt  480
acgggttatg gcccttgcgt gccttgaatt acttccactg gctgcagtac gtgattcttg  540
atcccgagct tcgggttgga agtgggtggg agagttcgag gccttgcgct taaggagccc  600
cttcgcctcg tgcttgagtt gaggcctggc ctgggcgctg gggccgccgc gtgcgaatct  660
ggtggcacct tcgcgcctgt ctcgctgctt tcgataagtc tctagccatt taaaattttt  720
gatgacctgc tgcgacgctt tttttctggc aagatagtct tgtaaatgcg ggccaagatc  780
tgcacactgg tatttcggtt tttggggccg cgggcggcga cggggcccgt gcgtcccagc  840
gcacatgttc ggcgaggcgg ggcctgcgag cgcggccacc gagaatcgga cgggggtagt  900
ctcaagctgg ccggcctgct ctggtgcctg gcctcgcgcc gccgtgtatc gccccgccct  960
gggcggcaag gctggcccgg tcggcaccag ttgcgtgagc ggaaagatgg ccgcttcccg  1020
gccctgctgc agggagctca aaatggagga cgcggcgctc gggagagcgg gcgggtgagt  1080
cacccacaca aaggaaaagg gcctttccgt cctcagccgt cgcttcatgt gactccacgg  1140
agtaccgggc gccgtccagg cacctcgatt agttctcgag cttttggagt acgtcgtctt  1200
taggttgggg ggaggggttt tatgcgatgg agtttcccca cactgagtgg gtggagactg  1260
aagttaggcc agcttggcac ttgatgtaat tctccttgga atttgccctt tttgagtttg  1320
gatcttggtt cattctcaag cctcagacag tggttcaaag tttttttctt ccatttcagg  1380
tgtcgtgagc tagcgccacc atggacatga gagtgcctgc ccagctgctg ggcctgctgc  1440
tgctgtggct gagaggagcc agatgtgctg ccctggtgcc tgagaaggag aaggacccca  1500
agtactggag agaccaggcc caggagaccc tgaagtatgc cctggagctg cagaagctga  1560
acaccaatgt ggccaagaat gtgatcatgt tcctgggaga tggcatggga gtgagcacag  1620
tgacagccac cagaatcctg aagggccagc tgcaccacaa ccctggagag gagaccagac  1680
tggagatgga caagttcccc tttgtggccc tgagcaagac ctacaacacc aatgcccagg  1740
tgcctgactc tgctggcaca gccacagcct acctgtgtgg agtgaaggcc aatgagggca  1800
cagtgggagt gtctgctgcc acagagagaa gcagatgcaa caccacccag ggcaatgagg  1860
tgaccagcat cctgagatgg gccaaggatg ctggcaagtc tgtgggcatt gtgaccacca  1920
ccagagtgaa ccatgccacc ccctctgctg cctatgccca ctctgctgac agagactggt  1980
actctgacaa tgagatgccc cctgaggccc tgagccaggg ctgcaaggac attgcctacc  2040
agctggtgca caacatcaga gacattgatg tgatcatggg aggaggcaga aagtacatgt  2100
accccaagaa caagacagat gtggagtatg agattgatga gaaggccaga ggcaccagac  2160
tggatggcct ggacctggtg aacatctgga agagcttcaa gcccagacac aagcacagcc  2220
acttcatctg gaacagaaca gagctgctga ccctggaccc ccacaatgtg gactacctgc  2280
tgggcctgtt tgagcctgga gacatggagt atgagctgaa cagaaacaat gtgacagacc  2340
ccagcctgtc tgagatggtg gtggtggcca tccagatcct gagaaagaac cccaagggct  2400
tcttcctgct ggtggaggga ggcagaattg accatggcca ccatgagggc aaggccaagc  2460
aggccctgca tgaggctgtg gagatggaca gagccattgg ccaggctggc agcatgacca  2520
gcctggagga caccctgaca gtggtgacag ctgaccacag ccatgtgttc acctttggag  2580
gctacacccc cagaggcaac agcatctttg gcctggcccc catgctgtct gacacagaca  2640
agaagccctt cacagccatc ctgtatggca atggccctgg ctacaaggtg gtgggaggag  2700
agagagagaa tgtgagcatg gtggactatg cccacaacaa ctaccaggcc cagtctgctg  2760
tgcccctgag acatgagacc catggaggag aggatgtggc tgtgttcagc aagggcccca  2820
tggcccacct gctgcatgga gtgcatgagc agaactacat cccccatgtg atggcctatg  2880
ctgcctgcat tggagccaac ctggaccact gtgcccctgc cagcagctga aagcttggat  2940
ccaatcaacc tctggattac aaaatttgtg aaagattgac tggtattctt aactatgttg  3000
ctccttttac gctatgtgga tacgctgctt taatgccttt gtatcatgct attgcttccc  3060
gtatggcttt cattttctcc tccttgtata aatcctggtt gctgtctctt tatgaggagt  3120
```

```
tgtggcccgt tgtcaggcaa cgtggcgtgg tgtgcactgt gtttgctgac gcaaccccca  3180
ctggttgggg cattgccacc acctgtcagc tcctttccgg gactttcgct ttccccctcc  3240
ctattgccac ggcggaactc atcgccgcct gccttgcccg ctgctggaca ggggctcggc  3300
tgttgggcac tgacaattcc gtggtgttgt cggggaaatc atcgtccttt ccttggctgc  3360
tcgcctgtgt tgccacctgg attctgcgcg ggacgtcctt ctgctacgtc ccttcggccc  3420
tcaatccagc ggaccttcct tcccgcggcc tgctgccggc tctgcggcct cttccgcgtc  3480
ttcgagatct gcctcgactg tgccttctag ttgccagcca tctgttgttt gcccctcccc  3540
cgtgccttcc ttgaccctgg aaggtgccac tcccactgtc ctttcctaat aaaatgagga  3600
aattgcatcg cattgtctga gtaggtgtca ttctattctg gggggtgggg tggggcagga  3660
cagcaagggg gaggattggg aagacaatag caggcatgct ggggactcga gttaagggcg  3720
aattcccgat aaggatcttc ctagagcatg gctacgtaga taagtagcat ggcgggttaa  3780
tcattaacta caaggaaccc ctagtgatgg agttggccac tccctctctg cgcgctcgct  3840
cgctcactga ggccgggcga ccaaaggtcg cccgacgccc gggctttgcc cgggcggcct  3900
cagtgagcga gcgagcgcgc agccttaatt aataccgttc gtataatgta tgctatacga  3960
acggtactgc agtgtcagcc gttaagtgtt cctgtgtcac tcaaaattgc tttgagaggc  4020
tctaagggct tctcagtgcg ttacatccct ggcttgttgt ccacaaccgt taaaccttaa  4080
aagctttaaa agccttatat attcttttttt ttcttataaa acttaaaacc ttagaggcta  4140
tttaagttgc tgatttatat taattttatt gttcaaacat gagagcttag tacgtgaaac  4200
atgagagctt agtacgttag ccatgagagc ttagtacgtt agccatgagg gtttagttcg  4260
ttaaacatga gagcttagta cgttaaacat gagagcttag tacgtgaaac atgagagctt  4320
agtacgtact atcaacaggt tgaactgctg atcttcagat cttaattaag g           4371
```

```
SEQ ID NO: 44          moltype = DNA  length = 4016
FEATURE                Location/Qualifiers
misc_feature           1..4016
                       note = Synthetic: Halo construct comprising A a cruiciform
                        structure with a DD elementCRUCIFORM, and human TBG
                        promoter-driven human sTNALP-Fc-(DSS)6 transgene
source                 1..4016
                       mol_type = other DNA
                       organism = synthetic construct
SEQUENCE: 44
ctaggaaccc ctagtgatgg agttggccac tccctctctg cgcgctcgct cgctcactga  60
ggccgggcga ccaaaggtcg cccgacgccc gggctttgcc cgggcggcct cagtgagcga  120
gcgagcgcgc agagagggag tggccaactc catcactagg ggtttccttt aattaactta  180
agtgcatgta taatttctac agaacctatt agaaaggatc acccagcctc tgcttttgta  240
caactttccc ttaaaaaact gccaattcca ctgctgtttg gcccaatagt gagaactttt  300
tcctgctgcc tcttggtgct tttgcctatg gcccctattc tgcctgctga agacactctt  360
gccagcatgg acttaaaccc ctccagctct gacaatcctc tttctctttt gttttacatg  420
aagggtctgg cagccaaagc aatcactcaa agttcaaacc ttatcatttt ttgctttgtt  480
cctcttggcc ttggttttgt acatcagctt tgaaaatacc atcccagggt taatgctggg  540
gttaatttat aactaagagt gctctagttt tgcaatacag gacatgctat aaatttaaat  600
aggtgagtct atgggaccct tgatgttttc tttccccttc ttttctatgg ttaagttcat  660
gtcataggaa ggggagaagt aacagggtac acatattgac caaatcaggg taattttgca  720
tttgtaattt taaaaaatgc tttcttcttt taatatactt ttttgttat cttatttcta  780
atactttccc taatctcttt ctttcagggc aataatgata caatgtatca tgcctctttg  840
caccattcta aagaataaca gtgataattt ctgggttaag gcaatagcaa tatttctgca  900
tataaatatt tctgcatata aattgtaact gatgtaagag gtttcatatt gctaatagca  960
gctacaatcc agctaccatt ctgcttttat tttatggttg ggataaggct ggattattct  1020
gagtccaagc taggcccttt tgctaatcat gttcatacct cttatcttcc tcccacaggt  1080
gctagcccac catggatatg agagtacctg ctcaacttct gggtttgttg ctgctttggc  1140
tcaggggagc cagatgtgct gccctggttc ctgagaagga aaaggacccc aagtactgga  1200
gagatcaggc acaggagaca ctgaagtatg ccctggagct gcagaagctg aataccaatg  1260
ttgccaaaaa tgtgatcatg ttcctgggag atgggatggg agtcagcaca gtgacagctg  1320
ctagaatcct gaagggacag ctgcatcata atcctggaga agagaccaga ctggaaatgg  1380
ataagttccc ctttgtggcc ctgagcaaga catataatac caatgcccaa gtgcctgatt  1440
ctgctggaac agctacagct tacctgtgtg gagtgaaggc caatgaggga acagtgggag  1500
tgtctgctgc cacagaaaga agcagatgca acaccaccca aggcaatgag gtgacaagca  1560
tcctgagatg ggccaaggat gctggcaaat ctgtgggcat tgtgacaaca accagagtga  1620
accatgccac cccatctgct gcttatgccc attctgctga cagagactgg tactctgaca  1680
atgagatgcc tccagaggct ctgtcccagg gttgtaaaga tattgcctat cagctgatgc  1740
acaacatcag agacattgat gtgatcatgg gaggaggcag gaagtacatg taccccaaga  1800
acaagacaga tgtggagtat gagtctgatg agaaggccag aggcacaaga ctggatggcc  1860
tggacctggt ggacacctgg aagtctttta agcccagata caagcacagc cacttcatct  1920
ggaacagaac agaactgctg accctggacc cccacaatgt ggactacctg ctgggcctgt  1980
ttgagcctgg agatatgcag tatgagctga atagaaacaa tgtgacagac ccctccctgt  2040
ctgaaatggt ggtggtggcc atccagatcc tgagaaagaa ccctaagggc tttttcctgc  2100
tggttgaggg aggaagaatt gaccatggcc atcatgaggg caaggctaag caggccctgc  2160
atgaggctgt ggagatggac agagccattg gccaagctgg ctctctgacc agctcagagg  2220
acaccctgac agtggtgaca gctgatcact ctcatgtgtt cacttttgga ggatataccc  2280
ctagaggcaa cagcatcttt ggcctggccc ctatgctgtc tgacacagac aaaaagccct  2340
tcacagccat cctgtatggc aatggcccag gatacaaggt ggtgggagga gagagagaga  2400
atgtgtctat ggtggactat gcacacaaca actaccaggc ccagtctgct gttcctctga  2460
gacatgaaac acatggaggg gaagatgtgg cagtgttttc taaaggccct atggctcacc  2520
tgctgcatgg agtccatgag cagaactatg tgccccatgt gatggcctat gctgcctgca  2580
ttggagcaaa cctgggccac tgtgcccctg ccagcagcct gaaagacaag acccacacat  2640
gtcctccctg ccctgcccct gagctgctgg gaggaccttc tgtgttcctg ttccctccaa  2700
agcctaaaga caccctgatg atcagcagaa cccctgaagt gacttgtgtg gtggtggatg  2760
tcagccatga agatccagaa gtgaaattca actggtatgt ggatggagtg gaggtgcaca  2820
```

```
atgccaaaac caagcctaga gaagaacagt acaacagcac ctacagagtg gtgtctgtgc  2880
tgacagtgct tcaccaggac tggctgaatg gcaaggaata caagtgcaag gtgagcaaca  2940
aggccctgcc tgctcctatt gagaagacca tcagcaaggc caagggacag cccagagaac  3000
ctcaggtcta caccctgcct cctagcagag atgagctgac aaagaaccag gtgagcctga  3060
catgcctggt gaagggcttc taccettctg atattgctgt ggaatgggag tctaatggcc  3120
aacctgaaaa caactacaag acaacacccc ctgtgctgga ctctgatggc agcttcttcc  3180
tgtactccaa actgacagtg gacaagtcca gatggcagca gggcaatgtg ttcagttgct  3240
ctgtcatgca tgaagccctg cacaaccact acacccagaa aagcctcagc ctgagccctg  3300
gaaaggatat tgactcctct gattcttctg acagctcaga ctcctctgat agctctgaca  3360
gctcttgaac tgtgccttct agttgccagc catctgttgt ttgcccctcc cccgtgcctt  3420
ccttgaccct ggaaggtgcc actcccactg tcctttccta ataaaatgag gaaattgcat  3480
cgcattgtct gagtaggtgt cattctattc tggggggtgg ggtggggcag gacagcaagg  3540
gggaggattg ggaagacaat agcaggcatg ctggggatac cgttcgtata atgtatgcta  3600
tacgaacggt actgcagtgt cagccgttaa gtgttcctgt gtcactcaaa attgctttga  3660
gaggctctaa gggcttctca gtgcgttaca tccctggctt gttgtccaca accgttaaac  3720
cttaaaagct ttaaaagcct tatatattct ttttttttct ataaaactta aaaccttaga  3780
ggctatttaa gttgctgatt tatattaatt ttattgttca aacatgagag cttagtacgt  3840
gaaacatgag agcttagtac gttagccatg agagcttagt acgttagcca tgagggttta  3900
gttcgttaaa catgagagct tagtacgtta aacatgagag cttagtacgt gaaacatgag  3960
agcttagtac gtactatcaa caggttgaac tgctgatctt cagatcttaa ttaagg      4016

SEQ ID NO: 45           moltype = DNA  length = 4266
FEATURE                 Location/Qualifiers
misc_feature            1..4266
                        note = Synthetic: Halo construct comprising IR-R6K Ori-IR
                         sequence, and human TBG liver-specific promoter-driven
                         Zero-CpG sTNALP-Fc-(DSS)6 transgene
source                  1..4266
                        mol_type = other DNA
                        organism = synthetic construct
SEQUENCE: 45
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagtgcat gtataatttc tacagaacct attagaaagg  240
atcacccagc ctctgctttt gtacaacttt cccttaaaaa actgccaatt ccactgctgt  300
ttggcccaat agtgagaact ttttcctgct gcctcttggt gcttttgcct atggccccta  360
ttctgcctgc tgaagacact cttgccagca tggacttaaa cccctccagc tctgacaatc  420
ctctttctct tttgttttac atgaagggtc tggcagccaa agcaatcact caaagttcaa  480
accttatcat tttttgcttt gttcctcttg gccttggttt tgtacatcag ctttgaaaat  540
accatcccag ggttaatgct ggggttaatt tataactaag agtgctctag ttttgcaata  600
caggacatgc tataaattta aataggtgag tctatgggac ccttgatgtt ttctttcccc  660
ttcttttcta tggttaagtt catgtcatag gaaggggaga agtaacaggg tacacatatt  720
gaccaaatca gggtaatttt gcatttgtaa ttttaaaaaa tgctttcttc ttttaatata  780
cttttttgtt tatcttattt ctaatacttt ccctaatctc tttctttcag ggcaataatg  840
atacaatgta tcatgcctct ttgcaccatt ctaaagaata acagtgataa tttctgggtt  900
aaggcaatag caatatttct gcatataaat atttctgcat ataaattgta actgatgtaa  960
gaggtttcat attgctaata gcagctacaa tccagctacc attctgcttt tattttatgg  1020
ttgggataag gctggattat tctgagtcca agctaggccc ttttgctaat catgttcata  1080
cctcttatct tcctcccaca ggtgctagcc caccatggat atgagagtac ctgctcaact  1140
tctgggtttg ttgctgcttt ggctcagggg agccagatgt gctgccctgg ttcctgagaa  1200
ggaaaaggac cccaagtact ggagagatca ggcacaggag acactgaagt atgccctgga  1260
gctgcagaag ctgaatacca atgttgccaa aaatgtgatc atgttcctgg gagatgggat  1320
gggagtcagc acagtgacag ctgctagaat cctgaaggga cagctgcatc ataatcctgg  1380
agaagagacc agactggaaa tggataagtt cccctttgtg gccctgagca agacatataa  1440
taccaatgcc caagtgcctg attctgctgg aacagctaca gcttacctgt gtggagtgaa  1500
ggccaatgag ggaacagtgg gagtgtctgc tgccacagaa agaagcagat gcaacaccac  1560
ccaaggcaat gaggtgacaa gcatcctgag atgggccaag gatgctggca aatctgtggg  1620
cattgtgaca acaaccagag tgaaccatgc cacccccatct gctgcttatg cccattctgc  1680
tgacagagac tggtactctg acaatgagat gcctccagag gctctgtccc agggttgtaa  1740
agatattgcc tatcagctga tgcacaacat cagagacatt gatgtgatca tgggaggagg  1800
caggaagtac atgtacccca agaacaagac agatgtggag tatgagtctg atgagaaggc  1860
cagaggcaca agactggatg gcctggacct ggtggacacc tggaagtctt ttaagcccag  1920
atacaagcac agccacttca tctggaacag aacagaactg ctgaccctgg acccccacaa  1980
tgtggactac ctgctgggcc tgtttgagcc tggagatatg cagtatgagc tgaatagaaa  2040
caatgtgaca gaccctcccc tgtctgaaat ggtggtggtg gccatccaga tcctgagaaa  2100
gaaccctaag ggcttttccc tgctggttga gggaggaaga attgaccatg gccatcatga  2160
gggcaaggct aagcaggccc tgcatgaggc tgtggagatg gacagagcca ttggccaagc  2220
tggctctctg accagctcag aggacaccct gacagtggtg acagctgatc actctcatgt  2280
gttcactttt ggaggatata cccctagagg caacagcatc tttggcctgg cccctatgct  2340
gtctgacaca gacaaaaagc ccttcacagc catcctgtat ggcaatggcc caggatacaa  2400
ggtggtggga ggagagagag agaatgtgtc tatggtggac tatgcacaca acaactacca  2460
ggcccagtct gctgttcctc tgagacatga aacacatgga ggggaagatg tggcagtgtt  2520
ttctaaaggc cctatggctc acctgctgca tggagtccat gagcagaact atgtgcccca  2580
tgtgatggcc tatgctgcct gcattggagc aaacctgggc cactgtgccc ctgccagcag  2640
cctgaaagac aagacccaca catgtcctcc ctgccctgcc cctgagctgc tgggaggacc  2700
ttctgtgttc ctgttccctc caaagcctaa agacaccctg atgatcagca gaacccctga  2760
agtgacttgt gtggtggtgg atgtcagcca tgaagatcca gaagtgaaat tcaactggta  2820
tgtggatgga gtggaggtgc acaatgccaa aaccaagcct agagaagaac agtacaacag  2880
```

```
cacctacaga gtggtgtctg tgctgacagt gcttcaccag gactggctga atggcaagga  2940
atacaagtgc aaggtgagca acaaggccct gcctgctcct attgagaaga ccatcagcaa  3000
ggccaaggga cagcccagag aacctcaggt ctacaccctg cctcctagca gagatgagct  3060
gacaaagaac caggtgagcc tgacatgcct ggtgaagggc ttctaccctt ctgatattgc  3120
tgtggaatgg gagtctaatg gccaacctga aaacaactac aagacaacac cccctgtgct  3180
ggactctgat ggcagcttct tcctgtactc caaactgaca gtggacaagt ccagatggca  3240
gcagggcaat gtgttcagtt gctctgtcat gcatgaagcc ctgcacaacc actacaccca  3300
gaaaagcctc agcctgagcc ctggaaagga tattgactcc tctgattctt ctgacagctc  3360
agactcctct gatagctctg acagctcttg aactgtgcct tctagttgcc agccatctgt  3420
tgtttgcccc tcccccgtgc cttccttgac cctggaaggt gccactccca ctgtcctttc  3480
ctaataaaat gaggaaattg catcgcattg tctgagtagg tgtcattcta ttctgggggg  3540
tggggtgggg caggacagca agggggagga ttgggaagac aatagcaggc atgctgggga  3600
ctcgagttaa gggcgaattc ccgataagga tcttcctaga gcatggctac gtagataagt  3660
agcatggcgg gttaatcatt aactacaagg aacccctagt gatggagttg gccactccct  3720
ctctgcgcgc tcgctcgctc actgaggccg ggcgaccaaa ggtcgcccga cgcccgggct  3780
ttgcccgggc ggcctcagtg agcgagcgag cgcgcagcct taattaatac cgttcgtata  3840
atgtatgcta tacgaacggt actgcagtgt cagccgttaa gtgttcctgt gtcactcaaa  3900
attgctttga gaggctctaa gggcttctca gtgcgttaca tccctggctt gttgtccaca  3960
accgttaaac cttaaaagct ttaaaagcct tatatattct ttttttttctt ataaaactta  4020
aaaccttaga ggctatttaa gttgctgatt tatattaatt ttattgttca aacatgagag  4080
cttagtacgt gaaacatgag agcttagtac gttagccatg agagcttagt acgttagcca  4140
tgagggttta gttcgttaaa catgagagct tagtacgtta aacatgagag cttagtacgt  4200
gaaacatgag agcttagtac gtactatcaa caggttgaac tgctgatctt cagatcttaa  4260
ttaagg                                                              4266

SEQ ID NO: 46           moltype = DNA  length = 4016
FEATURE                 Location/Qualifiers
misc_feature            1..4016
                        note = Synthetic: Halo construct comprising Zero-CpG A
                         CRUCIFORM variant 1, and human TBG liver-specific
                         promoter-driven Zero-CpG human sTNALP-Fc-(DSS)6 transgene
source                  1..4016
                        mol_type = other DNA
                        organism = synthetic construct
SEQUENCE: 46
ttaattaagg ctaggaaccc ctagtgatgg agttggccac tccctctctg ccctctccct  60
ctctcactga ggcctgggga ccaaaggtcc ccagactgca gagctttgct ctgcaggcct  120
cagtgagaga gggagagggc agagagggag tggccaactc catcactagg ggtttccttt  180
aattaactta agtgcatgta taatttctac agaacctatt agaaaggatc acccagcctc  240
tgcttttgta caactttccc ttaaaaaact gccaattcca ctgctgtttg gcccaatagt  300
gagaactttt tcctgctgcc tcttggtgct tttgcctatg gcccctattc tgcctgctga  360
agacactctt gccagcatgg acttaaaccc ctccagctct gacaatcctc tttctctttt  420
gttttacatg aagggtctgg cagccaaagc aatcactcaa agttcaaacc ttatcatttt  480
ttgctttgtt cctcttggcc ttggttttgt acatcagctt tgaaaatacc atcccagggt  540
taatgctggg gttaatttat aactaagagt gctctagttt tgcaatacag gacatgctat  600
aaatttaaat aggtgagtct atgggaccct tgatgtttc tttccccttc ttttctatgg  660
ttaagttcat gtcataggaa ggggagaagt aacagggtac acatattgac caaatcaggg  720
taattttgca tttgtaattt taaaaaatgc tttcttcttt taatatactt ttttgtttat  780
cttatttcta atactttccc taatctcttt ctttcagggc aataatgata caatgtatca  840
tgcctctttg caccattcta aagaataaca gtgataattt ctgggttaag gcaatagcaa  900
tatttctgca tataaatatt tctgcatata aattgtaact gatgtaagag gtttcatatt  960
gctaatagca gctacaatcc agctaccatt ctgcttttat tttatggttg ggataaggct  1020
ggattattct gagtccaagc taggcccttt tgctaatcat gttcatacct cttatcttcc  1080
tcccacaggt gctagcccac catggatatg agagtacctg ctcaacttct gggtttgttg  1140
ctgctttggc tcaggggagc cagatgtgct gccctggttc ctgagaagga aaaggacccc  1200
aagtactgga gagatcaggc acaggagaca ctgaagtatg ccctggagct gcagaagctg  1260
aataccaatg ttgccaaaaa tgtgatcatg ttcctgggag atgggatggg agtcagcaca  1320
gtgacagctg ctagaatcct gaagggacag ctgcatcata atcctggaga agagaccaga  1380
ctggaaatgg ataagttccc ctttgtggcc ctgagcaaga catataatac caatgcccaa  1440
gtgcctgatt ctgctggaac agctacagct tacctgtgtg gagtgaaggc caatgaggga  1500
acagtgggag tgtctgctgc cacagaaaga agcagatgca acaccaccca aggcaatgag  1560
gtgacaagca tcctgagatg ggccaaggat gctggcaaat ctgtgggcat tgtgacaaca  1620
accagagtga accatgccac cccatctgct gcttatgccc attctgctga cagagactgg  1680
tactctgaca atgagatgcc tccagaggct ctgtcccagg gttgtaaaga tattgcctat  1740
cagctgatgc acaacatcag agacattgat gtgatcatgg gaggaggcag gaagtacatg  1800
taccccaaga acaagacaga tgtggagtat gagtctgatg agaaggccag aggcacaaga  1860
ctggatggcc tggacctggt ggacacctgg aagtctttta agcccagata caagcacagc  1920
cacttcatct ggaacagaac agaactgctg accctggacc cccacaatgt ggactacctg  1980
ctgggcctgt ttgagcctgg agatatgcag tatgagctga atagaaacaa tgtgacagac  2040
ccctccctgt ctgaaatggt ggtggtggcc atccagatcc tgagaaagaa ccctaagggc  2100
tttttcctgc tggttgaggg aggaagaatt gaccatggcc atcatgaggg caaggctaag  2160
caggccctgc atgaggctgt ggagatggac agagccattg gccaagctgg ctctctgacc  2220
agctcagagg acaccctgac agtggtgaca gctgatcact ctcatgtgtt cacttttgga  2280
ggatataccc ctagaggcaa cagcatcttt ggcctggccc ctatgctgtc tgacacagac  2340
aaaaagccct tcacagccat cctgtatggc aatggcccag gatacaaggt ggtgggagga  2400
gagagagaga atgtgtctat ggtggactat gcacacaaca actaccaggc ccagtctgct  2460
gttcctctga gacatgaaac acatggaggg gaagatgtgg cagtgttttc taaaggccct  2520
atggctcacc tgctgcatgg agtccatgag cagaactatg tgccccatgt gatggcctat  2580
gctgcctgca ttggagcaaa cctgggccac tgtgcccctg ccagcagcct gaaagacaag  2640
```

```
acccacacat gtcctccctg ccctgcccct gagctgctgg gaggaccttc tgtgttcctg  2700
ttccctccaa agcctaaaga caccctgatg atcagcagaa cccctgaagt gacttgtgtg  2760
gtggtggatg tcagccatga agatccagaa gtgaaattca actggtatgt ggatggagtg  2820
gaggtgcaca atgccaaaac caagcctaga gaagaacagt acaacagcac ctacagagtg  2880
gtgtctgtgc tgacagtgct tcaccaggac tggctgaatg gcaaggaata caagtgcaag  2940
gtgagcaaca aggccctgcc tgctcctatt gagaagacca tcagcaaggc caagggacag  3000
cccagagaac ctcaggtcta caccctgcct cctagcagag atgagctgac aaagaaccag  3060
gtgagcctga catgcctggt gaagggcttc taccctctg atattgctgt ggaatgggag  3120
tctaatggcc aacctgaaaa caactacaag acaacacccc ctgtgctgga ctctgatggc  3180
agcttcttcc tgtactccaa actgacagtg gacaagtcca gatggcagca gggcaatgtg  3240
ttcagttgct ctgtcatgca tgaagccctg cacaaccact acacccagaa aagcctcagc  3300
ctgagccctg gaaaggatat tgactcctct gattcttctg acagctcaga ctcctctgat  3360
agctctgaca gctcttgaac tgtgccttct agttgccagc catctgttgt ttgcccctcc  3420
cccgtgcctt ccttgaccct ggaaggtgcc actcccactg tcctttccta ataaaatgag  3480
gaaattgcat cgcattgtct gagtaggtgt cattctattc tggggggtgg ggtggggcag  3540
gacagcaagg gggaggattg ggaagacaat agcaggcatg ctggggatac cgttcgtata  3600
atgtatgcta tacgaacggt actgcagtgt cagccgttaa gtgttcctgt gtcactcaaa  3660
attgctttga gaggctctaa gggcttctca gtgcgttaca tccctggctt gttgtccaca  3720
accgttaaac cttaaaagct ttaaaagcct tatatattct ttttttctt ataaaactta  3780
aaaccttaga ggctatttaa gttgctgatt tatattaatt ttattgttca aacatgagag  3840
cttagtacgt gaaacatgag agcttagtac gttagccatg agagcttagt acgttagcca  3900
tgagggttta gttcgttaaa catgagagct tagtacgtta aacatgagag cttagtacgt  3960
gaaacatgag agcttagtac gtactatcaa caggttgaac tgctgatctt cagatc      4016

SEQ ID NO: 47          moltype = DNA  length = 4016
FEATURE                Location/Qualifiers
misc_feature           1..4016
                       note = Synthetic: Halo construct comprising Zero-CpG A
                        CRUCIFORM structure variant 3, and human TBG
                        liver-specific promoter-driven Zero-CpG human
                        sTNALP-Fc-(DSS)6 transgene
source                 1..4016
                       mol_type = other DNA
                       organism = synthetic construct
SEQUENCE: 47
ttaattaagg ctaggaaccc ctagtgatgg agttggccac tccctctctg ctcactcact  60
cactcactga ggccagggca ccaaaggtgc cctgacagcc ctgctttgca gggctggcct  120
cagtgagtga gtgagtgagc agagagggag tggccaactc catcactagg ggtttccttt  180
aattaactta agtgcatgta taatttctac agaacctatt agaaaggatc acccagcctc  240
tgcttttgta caactttccc ttaaaaaact gccaattcca ctgctgtttg gcccaatagt  300
gagaactttt tcctgctgcc tcttggtgct tttgcctatg gcccctattc tgcctgctga  360
agacactctt gccagcatgg acttaaaccc ctccagctct gacaatcctc tttctctttt  420
gttttacatg aagggtctgg cagccaaagc aatcactcaa agttcaaacc ttatcatttt  480
ttgctttgtt cctcttggcc ttggttttgt acatcagctt tgaaaatacc atcccagggt  540
taatgctggg gttaatttat aactaagagt gctctagttt tgcaatacag gacatgctat  600
aaatttaaat aggtgagtct atgggaccct tgatgtttc tttccccttc ttttctatgg  660
ttaagttcat gtcataggaa ggggagaagt aacagggtac acatattgac caaatcaggg  720
taattttgca tttgtaattt taaaaaatgc tttcttcttt taatatactt ttttgtttat  780
cttatttcta atactttccc taatctcttt ctttcagggc aataatgata caatgtatca  840
tgcctctttg caccattcta aagaataaca gtgataattt ctgggttaag gcaatagcaa  900
tatttctgca tataaatatt tctgcatata aattgtaact gatgtaagag gtttcatatt  960
gctaatagca gctacaatcc agctaccatt ctgcttttat tttatggttg ggataaggct  1020
ggattattct gagtccaagc taggcccttt tgctaatcat gttcatacct cttatcttcc  1080
tcccacaggt gctagcccac catggatatg agagtacctg ctcaacttct gggtttgttg  1140
ctgctttggc tcaggggagc cagatgtgct gccctggttc ctgagaagga aaaggacccc  1200
aagtactgga gagatcaggc acaggagaca ctgaagtatg ccctggagct gcagaagctg  1260
aataccaatg ttgccaaaaa tgtgatcatg ttcctgggag atgggatggg agtcagcaca  1320
gtgacagctg ctagaatcct gaagggacag ctgcatcata atcctggaga agagaccaga  1380
ctggaaatgg ataagttccc ctttgtggcc ctgagcaaga catataatac caatgcccaa  1440
gtgcctgatt ctgctggaac agctacagct tacctgtgtg gagtgaaggc caatgaggga  1500
acagtgggag tgtctgctgc cacagaaaga agcagatgca acaccaccca aggcaatgag  1560
gtgacaagca tcctgagatg ggccaaggat gctggcaaat ctgtgggcat tgtgacaaca  1620
accagagtga accatgccac cccatctgct gcttatgccc attctgctga cagagactgg  1680
tactctgaca atgagatgcc tccagaggct ctgtcccagg gttgtaaaga tattgcctat  1740
cagctgatgc acaacatcag agacattgat gtgatcatgg gaggaggcag gaagtacatg  1800
taccccaaga acaagacaga tgtggagtat gagtctgatg agaaggccag aggcacaaga  1860
ctggatggcc tggacctggt ggacacctgg aagtctttta agcccagata caagcacagc  1920
cacttcatct ggaacagaac agaactgctg accctggacc cccacaatgt ggactacctg  1980
ctgggcctgt ttgagcctgg agatatgcag tatgagctga atagaaacaa tgtgacagac  2040
ccctccctgt ctgaaatggt ggtggtggcc atccagatcc tgagaaagaa ccctaagggc  2100
tttttcctgc tggttgaggg aggaagaatt gaccatggcc atcatgaggg caaggctaag  2160
caggccctgc atgaggctgt ggagatggac agagccattg gccaagctgg ctctctgacc  2220
agctcagagg acaccctgac agtggtgaca gctgatcact ctcatgtgtt cacttttgga  2280
ggatataccc ctagaggcaa cagcatcttt ggcctggccc ctatgctgtc tgacacagac  2340
aaaaagccct tcacagccat cctgtatggc aatggcccag gatacaaggt ggtgggagga  2400
gagagagaga atgtgtctat ggtggactat gcacacaaca actaccaggc ccagtctgct  2460
gttcctctga gacatgaaac acatggaggg gaagatgtgg cagtgttttc taaaggccct  2520
atggctcacc tgctgcatgg agtccatgag cagaactatg tgccccatgt gatggcctat  2580
gctgcctgca ttggagcaaa cctgggccac tgtgcccctg ccagcagcct gaaagacaag  2640
```

```
acccacacat gtcctccctg ccctgcccct gagctgctgg gaggaccttc tgtgttcctg  2700
ttccctccaa agcctaaaga caccctgatg atcagcagaa cccctgaagt gacttgtgtg  2760
gtggtggatg tcagccatga agatccagaa gtgaaattca actggtatgt ggatggagtg  2820
gaggtgcaca atgccaaaac caagcctaga gaagaacagt acaacagcac ctacagagtg  2880
gtgtctgtgc tgacagtgct tcaccaggac tggctgaatg gcaaggaata caagtgcaag  2940
gtgagcaaca aggccctgcc tgctcctatt gagaagacca tcagcaaggc caagggacag  3000
cccagagaac ctcaggtcta caccctgcct cctagcagag atgagctgac aaagaaccag  3060
gtgagcctga catgcctggt gaagggcttc tacccttctg atattgctgt ggaatgggag  3120
tctaatggcc aacctgaaaa caactacaag acaacacccc ctgtgctgga ctctgatggc  3180
agcttcttcc tgtactccaa actgacagtg gacaagtcca gatggcagca gggcaatgtg  3240
ttcagttgct ctgtcatgca tgaagccctg cacaaccact acacccagaa aagcctcagc  3300
ctgagccctg gaaaggatat tgactcctct gattcttctg acagctcaga ctcctctgat  3360
agctctgaca gctcttgaac tgtgccttct agttgccagc catctgttgt ttgcccctcc  3420
cccgtgcctt ccttgaccct ggaaggtgcc actcccactg tcctttccta ataaaatgag  3480
gaaattgcat cgcattgtct gagtaggtgt cattctattc tggggggtgg ggtggggcag  3540
gacagcaagg gggaggattg ggaagacaat agcaggcatg ctggggatac cgttcgtata  3600
atgtatgcta tacgaacggt actgcagtgt cagccgttaa gtgttcctgt gtcactcaaa  3660
attgctttga gaggctctaa gggcttctca gtgcgttaca tccctggctt gttgtccaca  3720
accgttaaac cttaaaagct ttaaaagcct tatatattct tttttttctt ataaaactta  3780
aaaccttaga ggctatttaa gttgctgatt tatattaatt ttattgttca aacatgagag  3840
cttagtacgt gaaacatgag agcttagtac gttagccatg agagcttagt acgttagcca  3900
tgagggttta gttcgttaaa catgagagct tagtacgtta aacatgagag cttagtacgt  3960
gaaacatgag agcttagtac gtactatcaa caggttgaac tgctgatctt cagatc      4016
```

```
SEQ ID NO: 48           moltype = DNA  length = 4244
FEATURE                 Location/Qualifiers
misc_feature            1..4244
                        note = Synthetic: Halo construct comprising Zero-CpG a
                         cruciformstructure variant 1, and human TBG liver-specific
                         promoter-driven Zero-CpG human sTNALP-Fc-(DSS)6 transgene
source                  1..4244
                        mol_type = other DNA
                        organism = synthetic construct
SEQUENCE: 48
ctaggaaccc ctagtgatgg agttggccac tccctctctg cgcgctcgct cgctcactga  60
ggccgggcga ccaaaggtcg cccgacgccc gggctttgcc cgggcggcct cagtgagcga  120
gcgagcgcgc agagagggag tggccaactc catcactagg ggttcctttt aattaagcct  180
gaaataacct ctgaaagagg aacttggtta ggtaccttct gaggctgaaa gaaccagctg  240
tggaatgtgt gtcagttagg gtgtggaaag tccccaggct ccccagcagg cagaagtatg  300
caaagcatgc atctcaatta gtcagcaacc aggtgtggaa agtccccagg ctccccagca  360
ggcagaagta tgcaaagcat gcatctcaat tagtcagcaa ccatagtccc tgcatgtata  420
atttctacag aacctattag aaaggatcac ccagcctctg cttttgtaca actttccctt  480
aaaaaactgc caattccact gctgtttggc ccaatagtga gaactttttc ctgctgcctc  540
ttggtgcttt tgcctatggc ccctattctg cctgctgaag acactcttgc cagcatggac  600
ttaaacccct ccagctctga caatcctctt tctcttttgt tttacatgaa gggtctggca  660
gccaaagcaa tcactcaaag ttcaaacctt atcatttttt gctttgttcc tcttggcctt  720
ggttttgtac atcagctttg aaaataccat cccagggtta atgctggggt taatttataa  780
ctaagagtgc tctagttttg caatacagga catgctataa atttaaatag gtgagtctat  840
gggacccttg atgttttctt tccccttctt ttctatggtt aagttcatgt cataggaagg  900
ggagaagtaa cagggtacac atattgacca aatcagggta attttgcatt tgtaatttta  960
aaaaatgctt tcttctttta atatactttt ttgtttatct tatttctaat actttcccta  1020
atctctttct ttcagggcaa taatgataca atgtatcatg cctctttgca ccattctaaa  1080
gaataacagt gataatttct gggttaaggc aatagcaata tttctgcata taaatatttc  1140
tgcatataaa ttgtaactga tgtaagaggt ttcatattgc taatagcagc tacaatccag  1200
ctaccattct gcttttattt tatggttggg ataaggctgg attattctga gtccaagcta  1260
ggcccttttg ctaatcatgt tcatacctct tatcttcctc ccacaggtgc tagcccacca  1320
tggatatgag agtacctgct caacttctgg gtttgttgct gctttggctc aggggagcca  1380
gatgtgctgc cctggttcct gagaaggaaa aggaccccaa gtactggaga gatcaggcac  1440
aggagacact gaagtatgcc ctggagctgc agaagctgaa taccaatgtt gccaaaaatg  1500
tgatcatgtt cctgggagat gggatgggag tcagcacagt gacagctgct agaatcctga  1560
agggacagct gcatcataat cctggagaag agaccagact ggaaatggat aagttcccct  1620
ttgtggccct gagcaagaca tataatacca atgcccaagt gcctgattct gctggaacag  1680
ctacagctta cctgtgtgga gtgaaggcca atgagggaac agtgggagtg tctgctgcca  1740
cagaaagaag cagatgcaac accacccaag gcaatgaggt gacaagcatc ctgagatggg  1800
ccaaggatgc tggcaaatct gtgggcattg tgacaacaac cagagtgaac catgccaccc  1860
catctgctgc ttatgcccat tctgctgaca gagactggta ctctgacaat gagatgcctc  1920
cagaggctct gtcccagggt tgtaaagata ttgcctatca gctgatgcac aacatcagag  1980
acattgatgt gatcatggga ggaggcagga agtacatgta ccccaagaac aagacagatg  2040
tggagtatga gtctgatgag aaggccagag gcacaagact ggatggcctg gacctggtgg  2100
acacctggaa gtcttttaag cccagataca agcacagcca cttcatctgg aacagaacag  2160
aactgctgac cctggacccc cacaatgtgg actacctgct gggcctgttt gagcctggag  2220
atatgcagta tgagctgaat agaaacaatg tgacagaccc ctccctgtct gaaatggtgg  2280
tggtggccat ccagatcctg agaaagaacc ctaagggctt tttcctgctg gttgagggag  2340
gaagaattga ccatggccat catgagggca aggctaagca ggccctgcat gaggctgtgg  2400
agatggacag agccattggc caagctggct ctctgaccag ctcagaggac accctgacag  2460
tggtgacagc tgatcactct catgtgttca cttttggagg atatacccct agaggcaaca  2520
gcatctttgg cctggcccct atgctgtctg acacagacaa aaagcccttc acagccatcc  2580
tgtatggcaa tggcccagga tacaaggtgg tgggaggaga gagagagaat gtgtctatgg  2640
tggactatgc acacaacaac taccaggccc agtctgctgt tcctctgaga catgaaacac  2700
```

```
atggagggga agatgtggca gtgttttcta aaggccctat ggctcacctg ctgcatggag  2760
tccatgagca gaactatgtg ccccatgtga tggcctatgc tgcctgcatt ggagcaaacc  2820
tgggccactg tgcccctgcc agcagcctga aagacaagac ccacacatgt cctccctgcc  2880
ctgcccctga gctgctggga ggaccttctg tgttcctgtt ccctccaaag cctaaagaca  2940
ccctgatgat cagcagaacc cctgaagtga cttgtgtggt ggtggatgtc agccatgaag  3000
atccagaagt gaaattcaac tggtatgtgg atggagtgga ggtgcacaat gccaaaacca  3060
agcctagaga agaacagtac aacagcacct acagagtggt gtctgtgctg acagtgcttc  3120
accaggactg gctgaatggc aaggaataca agtgcaaggt gagcaacaag gccctgcctg  3180
ctcctattga gaagaccatc agcaaggcca agggacagcc cagagaacct caggtctaca  3240
ccctgcctcc tagcagagat gagctgacaa agaaccaggt gagcctgaca tgcctggtga  3300
agggcttcta cccttctgat attgctgtgg aatgggagtc taatggccaa cctgaaaaca  3360
actacaagac aacacccccct gtgctggact ctgatggcag cttcttcctg tactccaaac  3420
tgacagtgga caagtccaga tggcagcagg gcaatgtgtt cagttgctct gtcatgcatg  3480
aagccctgca caaccactac acccagaaaa gcctcagcct gagccctgga aaggatattg  3540
actcctctga ttcttctgac agctcagact cctctgatag ctctgacagc tcttgaactg  3600
tgccttctag ttgccagcca tctgttgttt gcccctcccc cgtgccttcc ttgaccctgg  3660
aaggtgccac tcccactgtc ctttcctaat aaaatgagga aattgcatcg cattgtctga  3720
gtaggtgtca ttctattctg gggggtgggg tggggcagga cagcaagggg gaggattggg  3780
aagacaatag caggcatgct ggggataccg ttcgtataat gtatgctata cgaacggtac  3840
tgcagtgtca gccgttaagt gttcctgtgt cactcaaaat tgctttgaga ggctctaagg  3900
gcttctcagt gcgttacatc cctggcttgt tgtccacaac cgttaaacct taaaagcttt  3960
aaaagcctta tatattcttt tttttcttat aaaacttaaa accttagagg ctatttaagt  4020
tgctgattta tattaatttt attgttcaaa catgagagct tagtacgtga aacatgagag  4080
cttagtacgt tagccatgag agcttagtac gttagccatg agggtttagt tcgttaaaca  4140
tgagagctta gtacgttaaa catgagagct tagtacgtga aacatgagag cttagtacgt  4200
actatcaaca ggttgaactg ctgatcttca gatcttaatt aagg                  4244

SEQ ID NO: 49           moltype = DNA  length = 186
FEATURE                 Location/Qualifiers
misc_feature            1..186
                        note = Synthetic: Zero-CpG A cruciform structure 1
source                  1..186
                        mol_type = other DNA
                        organism = synthetic construct
SEQUENCE: 49
ttaattaagg ctaggaaccc ctagtgatgg agttggccac tccctctctg ccctctccct  60
ctctcactga ggcctgggga ccaaaggtcc ccagactgca gagctttgct ctgcaggcct  120
cagtgagaga gggagagggc agagagggag tggccaactc catcactagg ggtttccttt  180
aattaa                                                            186

SEQ ID NO: 50           moltype = DNA  length = 166
FEATURE                 Location/Qualifiers
misc_feature            1..166
                        note = Synthetic: Zero-CpG A cruciform structure 2
source                  1..166
                        mol_type = other DNA
                        organism = synthetic construct
SEQUENCE: 50
aggaacccct agtgatggag ttggccactc cctctctgca ctctctctct ctcactgagg  60
cctggggacc aaaggtcccc agactgcaga gctttgctct gcaggcctca gtgagagaga  120
gagagtgcag agagggagtg gccaactcca tcactagggg tttcct                166

SEQ ID NO: 51           moltype = DNA  length = 166
FEATURE                 Location/Qualifiers
misc_feature            1..166
                        note = Synthetic: Zero-CpG A cruciform structure 3
source                  1..166
                        mol_type = other DNA
                        organism = synthetic construct
SEQUENCE: 51
aggaacccct agtgatggag ttggccactc cctctctgct cactcactca ctcactgagg  60
ccagggcacc aaaggtgccc tgacagccct gctttgcagg gctggcctca gtgagtgagt  120
gagtgagcag agagggagtg gccaactcca tcactagggg tttcct                166

SEQ ID NO: 52           moltype = DNA  length = 2349
FEATURE                 Location/Qualifiers
misc_feature            1..2349
                        note = Synthetic: Zero-CpG human soluble TNALP-Fc-(DSS)6
source                  1..2349
                        mol_type = other DNA
                        organism = synthetic construct
SEQUENCE: 52
atggatatga gagtacctgc tcaacttctg ggtttgttgc tgctttggct caggggagcc  60
agatgtgctg ccctggttcc tgagaaggaa aaggacccca agtactggag agatcaggca  120
caggagacac tgaagtatgc cctggagctg cagaagctga ataccaatgt tgccaaaaat  180
gtgatcatgt tcctgggaga tgggatggga gtcagcacag tgacagctgc tagaatcctg  240
aagggacagc tgcatcataa tcctggagaa gagaccagac tggaaatgga taagttcccc  300
tttgtggccc tgagcaagac atataatacc aatgcccaag tgcctgattc tgctggaaca  360
gctacagctt acctgtgtgg agtgaaggcc aatgagggaa cagtgggagt gtctgctgcc  420
```

```
acagaaagaa gcagatgcaa caccacccaa ggcaatgagg tgacaagcat cctgagatgg  480
gccaaggatg ctggcaaatc tgtgggcatt gtgacaacaa ccagagtgaa ccatgccacc  540
ccatctgctg cttatgccca ttctgctgac agagactggt actctgacaa tgagatgcct  600
ccagaggctc tgtcccaggg ttgtaaagat attgcctatc agctgatgca caacatcaga  660
gacattgatg tgatcatggg aggaggcagg aagtacatgt accccaagaa caagacagat  720
gtggagtatg agtctgatga gaaggccaga ggcacaagac tggatggcct ggacctggtg  780
gacacctgga agtcttttaa gcccagatac aagcacagcc acttcatctg gaacagaaca  840
gaactgctga ccctggaccc ccacaatgtg gactacctgc tgggcctgtt tgagcctgga  900
gatatgcagt atgagctgaa tagaaacaat gtgacagacc cctccctgtc tgaaatggtg  960
gtggtggcca tccagatcct gagaaagaac cctaagggct tttcctgct ggttgaggga  1020
ggaagaattg accatggcca tcatgagggc aaggctaagc aggccctgca tgaggctgtg  1080
gagatggaca gagccattgg ccaagctggc tctctgacca gctcagagga caccctgaca  1140
gtggtgacag ctgatcactc tcatgtgttc acttttggag gatatacccc tagaggcaac  1200
agcatctttg gcctggcccc tatgctgtct gacacagaca aaaagccctt cacagccatc  1260
ctgtatggca atggcccagg atacaaggtg gtgggaggag agagagagaa tgtgtctatg  1320
gtggactatg cacacaacaa ctaccaggcc cagtctgctg ttcctctgag acatgaaaca  1380
catggagggg aagatgtggc agtgttttct aaaggcccta tggctcacct gctgcatgga  1440
gtccatgagc agaactatgt gccccatgtg atggcctatg ctgcctgcat tggagcaaac  1500
ctgggccact gtgcccctgc cagcagcctg aaagacaaga cccacacatg tcctccctgc  1560
cctgcccctg agctgctggg aggaccttct gtgttcctgt tccctccaaa gcctaaagac  1620
accctgatga tcagcagaac ccctgaagtg acttgtgtgg tggtggatgt cagccatgaa  1680
gatccagaag tgaaattcaa ctggtatgtg gatggagtgg aggtgcacaa tgccaaaacc  1740
aagcctagag aagaacagta caacagcacc tacagagtgg tgtctgtgct gacagtgctt  1800
caccaggact ggctgaatgg caaggaatac aagtgcaagg tgagcaacaa ggccctgcct  1860
gctcctattg agaagaccat cagcaaggcc aagggacagc ccagagaacc tcaggtctac  1920
accctgcctc ctagcagaga tgagctgaca aagaaccagg tgagcctgac atgcctggtg  1980
aagggcttct acccttctga tattgctgtg gaatgggagt ctaatggcca acctgaaaac  2040
aactacaaga caacaccccc tgtgctggac tctgatggca gcttcttcct gtactccaaa  2100
ctgacagtgg acaagtccag atggcagcag ggcaatgtgt tcagttgctc tgtcatgcat  2160
gaagccctgc acaaccacta cacccagaaa agcctcagcc tgagccctgg aaaggatatt  2220
gactcctctg attcttctga cagctcagac tcctctgata gctctgacag ctcttgaact  2280
gtgccttcta gttgccagcc atctgttgtt tgcccctccc ccgtgccttc cttgaccctg  2340
gaaggtgcc                                                          2349
```

```
SEQ ID NO: 53          moltype = DNA  length = 2079
FEATURE                Location/Qualifiers
misc_feature           1..2079
                       note = Synthetic: Zero-CpG human PCSK9 Q162H
source                 1..2079
                       mol_type = other DNA
                       organism = synthetic construct
SEQUENCE: 53
atgggcacag tgagctccag aagatcttgg tggcctctgc ctctgctgct gctcctgctg  60
ctgctgctgg gacctgctgg agctagagcc caggaggatg aagatggaga ctatgaggag  120
ctggtgctgg ctctgagatc tgaggaagat ggtctggctg aagcccctga gcatggcacc  180
acagctacct ttcacagatg tgccaaggac ccctggagac tgcctggcac ctatgtggtg  240
gttcttaaag aggagacaca tctgagccag tctgagagaa cagccagaag actgcaggcc  300
caagctgcta gaagaggtta tctgaccaag atcctgcatg tgtttcatgg ccttcttcct  360
ggcttcctgg tcaagatgtc tggagatctg cttgagctgg ccctgaagct gccccatgtg  420
gattacattg aggaggatag ctctgtgttt gcccactcta ttccttggaa cctggaaaga  480
atcacccctc caagatatag agctgatgaa taccagcctc ctgatggagg cagcctggtg  540
gaggtgtacc tgctggacac cagcatccag tctgaccaca gggagattga gggcagagtt  600
atggtgacag attttgagaa tgtgccagaa gaggatggca ccagattcca cagacaagcc  660
agcaagtgtg acagccatgg cacccacctg gctggagtgg tgtctggcag agatgctgga  720
gtggccaagg gagccagcat gagaagcctg agagtgctga attgccaggg caagggcaca  780
gtgtctggca ccctaattgg actggagttc atcagaaaga gccagctggt gcagcctgtg  840
ggacctctgg ttgttctgct gcctctagct ggaggataca gcagagtgct gaatgctgcc  900
tgccagagac tggctagagc tggagtggtg ctggtgactg ctgctggaaa tttcagagat  960
gatgcctgcc tgtacagccc tgcctctgcc cctgaagtga tcacagtggg agctacaaat  1020
gcccaggacc aaccagtgac cctgggcacc ctgggaacca actttggcag atgtgtggac  1080
ctgtttgccc ctggagagga catcattgga gccagctcag attgctctac atgctttgtg  1140
agccaatctg gcacctcaca ggctgctgct catgtggctg gcattgctgc catgatgctg  1200
tctgcagaac ctgagctgac actggctgag ctgagacaga gactgatcca cttctctgct  1260
aaagatgtga tcaatgaggc ctggttccct gaagaccaga gagtgctgac acctaatctg  1320
gtggctgctc tgcctcccag cacccatgga gctggatggc agctgttctg cagaacagtg  1380
tggtctgccc actctggccc caccagaatg gccacagctg tggccagatg tgcccctgat  1440
gaggaactgc tcagctgcag cagctttagc agatctggca aaagaagagg agaaagaatg  1500
gaagcccagg gaggcaagct ggtgtgcaga gcccacaatg cctttggagg agaaggagtg  1560
tatgccattg ccagatgttg cctgctgccc caggccaact gctctgtgca cacagcccct  1620
ccagctgagg cctctatggg caccagagtg cactgccacc agcagggcca tgtgctgaca  1680
ggctgttcta gccattggga ggtggaagac ctgggaaccc acaagcctcc tgtgctgaga  1740
cccagaggcc agcctaacca gtgtgtgggc cacagagaag ccagcatcca tgccagttgt  1800
tgtcatgccc ctggcctgga atgcaaggtg aaggaacatg gcatcccagc tccacaggag  1860
caggtgacag tggcctgtga ggaaggctgg accctgacag gctgctctgc cctgcctggc  1920
acaagccatg tgctgggagc atatgctgtg gacaacacct gtgtggtgag aagcagggat  1980
gtgagcacaa caggcagcac ctctgaggga gctgttacag ctgtggccat ctgctgtaga  2040
tctagacact tggcccaggc ctctcaggag ctgcagtga                         2079

SEQ ID NO: 54          moltype = DNA  length = 1524
```

```
FEATURE                Location/Qualifiers
misc_feature           1..1524
                       note = Synthetic: Zero-CpG cynomolgus monkey soluble TNALP
source                 1..1524
                       mol_type = other DNA
                       organism = synthetic construct
SEQUENCE: 54
atgagagtgc ctgcccagct gctgggcctg ctgctgctgt ggctgagagg agccagatgt  60
gctgccctgg tgcctgagaa ggagaaggac cccaagtact ggagagacca ggcccaggag  120
accctgaagt atgccctgga gctgcagaag ctgaacacca atgtggccaa gaatgtgatc  180
atgttcctgg gagatggcat gggagtgagc acagtgacag ccaccagaat cctgaagggc  240
cagctgcacc acaaccctgg agaggagacc agactggaga tggacaagtt cccctttgtg  300
gccctgagca agacctacaa caccaatgcc caggtgcctg actctgctgg cacagccaca  360
gcctacctgt gtggagtgaa ggccaatgag ggcacagtgg gagtgtctgc tgccacagag  420
agaagcagat gcaacaccac ccagggcaat gaggtgacca gcatcctgag atgggccaag  480
gatgctggca agtctgtggg cattgtgacc accaccagag tgaaccatgc cacccccctct  540
gctgcctatg cccactctgc tgacagagac tggtactctg acaatgagat gccccctgag  600
gccctgagcc agggctgcaa ggacattgcc taccagctgg tgcacaacat cagagacatt  660
gatgtgatca tgggaggagg cagaaagtac atgtacccca agaacaagac agatgtggag  720
tatgagattg atgagaaggc cagaggcacc agactggatg gcctggacct ggtgaacatc  780
tggaagagct tcaagcccag acacaagcac agccacttca tctggaacag aacagagctg  840
ctgaccctgg acccccacaa tgtggactac ctgctgggcc tgtttgagcc tggagacatg  900
gagtatgagc tgaacagaaa caatgtgaca gaccccagcc tgtctgagat ggtggtggtg  960
gccatccaga tcctgagaaa gaaccccaag ggcttcttcc tgctggtgga gggaggcaga  1020
attgaccatg gccaccatga gggcaaggcc aagcaggccc tgcatgaggc tgtggagatg  1080
gacagagcca ttggccaggc tggcagcatg accagcctgg aggacaccct gacagtggtg  1140
acagctgacc acagccatgt gttcaccttt ggaggctaca cccccagagg caacagcatc  1200
tttggcctgg cccccatgct gtctgacaca gacaagaagc ccttcacagc catcctgtat  1260
ggcaatggcc ctggctacaa ggtggtggga ggagagagag agaatgtgag catggtggac  1320
tatgcccaca acaactacca ggcccagtct gctgtgcccc tgagacatga gacccatgga  1380
ggagaggatg tggctgtgtt cagcaagggc cccatggccc acctgctgca tggagtgcat  1440
gagcagaact acatccccca tgtgatggcc tatgctgcct gcattggagc caacctggac  1500
cactgtgccc ctgccagcag ctga                                         1524

SEQ ID NO: 55          moltype = DNA  length = 7360
FEATURE                Location/Qualifiers
misc_feature           1..7360
                       note = Synthetic: P004 - a BC-deletion cruciform
                        structure-contained A dsGFP-dsRFP reporter construct
source                 1..7360
                       mol_type = other DNA
                       organism = synthetic construct
SEQUENCE: 55
acgcgttgac attgattatt gactagttaa ctataacggt cctaaggtag cgaacccccca  60
actgagagaa ctcaaaggtt accccagttg ggtaaaaata cagcatagca aactttaac  120
ctccaaatca agcctctact tgaatccttt tctgagggat gaataaggca taggcatcag  180
gggctgttgc caatgtgcat tagctgtttg cagcctcacc ttctttcatg gagtttaaga  240
tatagtgtat tttcccaagg tttgaactag ctcttcattt ctttatgttt taaatgcact  300
gacctcccac attccctttt tagtaaaata ttcagaaata atttaaatac atcattgcaa  360
tgaaaataaa tgttttttat taggcagaat ccagatgctc aaggcccttc ataatatccc  420
ccagtttagt agttggactt agggaacaaa ggaacctta atagaaattg gacagcaaga  480
aagcgagctt agtgatactt gtgggccagg gcattagcca caccagccac cactttctga  540
taggcagcct gcactggtgg ggtgaattcg aagcttgagc tcgagatcct actagtagga  600
tctgagtccg gattacttgt acagctcgtc catgccgtga gtgatcccgg cggcggtcac  660
gaactccagc aggaccatgt gatcgcgctt ctcgttgggg tctttgctca gggcggactg  720
ggtgctcagg tagtggttgt cgggcagcag cacggggccg tcgccgatgg gggtgttctg  780
ctggtagtgg tcggcgagct gcacgctgcc gtcctcgatg ttgtggcgga tcttgaagtt  840
caccttgatg ccgttcttct gcttgtcggc catgatatag acgttgtggc tgttgtagtt  900
gtactccagc ttgtgcccca ggatgttgcc gtcctccttg aagtcgatgc ccttcagctc  960
gatgcggttc accagggtgt cgccaggaac ccctagtgat ggagttggcc actccctctc  1020
tgcgcctcgc tcgctcactg aggccgcccc gggcctcagt gagcgagcga gcgcgcagag  1080
agggagtggc caactccatc actaggggtt tcctctcgaa cttcacctcg gcgcgggtct  1140
tgtagttgcc gtcgtccttg aagaagatgg tgcgctcctg gacgtagcct tcgggcatgg  1200
cggacttgaa gaagtcgtgc tgcttcatgt ggtcggggta gcggctgaag cactgcacgc  1260
cgtaggtgaa ggtggtcacg agggtgggcc agggcacggg cagcttgccg gtggtgcaga  1320
tgaacttcag ggtcagcttg ccgtaggtgg catcgccctc gccctcgccg gacacgctga  1380
acttgtggcc gtttacgtcg ccgtccagct cgaccaggat gggcaccacc ccggtgaaca  1440
gctcctcgcc cttgctcacc atggtggcga ccggtagcgt gctttgccaa agtgatgggc  1500
cagcacacag accagcacgt tgcccaggag ctgtgggagg aagataagag gtatgaacat  1560
gattagcaaa agggcctagc ttggactcag aataatccag ccttatccca accataaaat  1620
aaaagcagaa tggtagctgg attgtagctg ctattagcaa tatgaaacct cttacatcag  1680
ttacaattta tatgcagaaa tatttatatg cagaaatatt gctattgcct taacccagaa  1740
attatcactg ttattcttta gaatggtgca aagaggcatg atacattgta tcattattgc  1800
cctgaaagaa agagattagg gaaagtatta gaaataagat aaacaaaaaa gtatattaaa  1860
agaagaaagc attttttaaa attacaaatg caaaattacc ctgatttggt caatatgtgt  1920
accctgttac ttctcccctt cctatgacat gaacttaacc atagaaaaga aggggaaaga  1980
aaacatcaag ggtcccatag actcaccctg aagttctcag gatccgagct cggtaccaca  2040
tgtaagcttc gaggggaggc tggatcggtc ccggtgtctt ctatggaggt caaaacagcg  2100
tggatggcgt ctccaggcga tctgacggtt cactaaacga gctctgctta tatagacctc  2160
```

```
ccaccgtaca cgcctaccgc ccatttgcgt caatggggcg gagttgttac gacattttgg  2220
aaagtcccgt tgattttggt gccaaaacaa actcccattg acgtcaatgg ggtggagact  2280
tggaaatccc cgtgagtcaa accgctatcc acgcccattg atgtactgcc aaaaccgcat  2340
caccatggta atagcgatga ctaatacgta gatgtactgc caagtaggaa agtcccataa  2400
ggtcatgtac tgggcataat gccaggcggg ccatttaccg tcattgacgt caatagggggg  2460
cgtacttggc atatgataca cttgatgtac tgccaagtgg gcagtttacc gtaaatagtc  2520
cacccattga cgtcaatgga aagtccctat tggcgttact atgggaacat acgtcattat  2580
tgacgtcaat gggcgggggt cgttgggcgg tcagccaggc gggccattta ccgtaagtta  2640
tgtaacgcgg aactccatat atgggctatg aactaatgac cccgtaattg attactatta  2700
ataactagtc aataatcaat gtcttaatta aggctccggt gcccgtcagt gggcagagcg  2760
cacatcgccc acagtccccg agaagttggg gggagggggtc ggcaattgaa ccggtgccta  2820
gagaaggtgg cgcggggtaa actgggaaag tgatgtcgtg tactggctcc gccttttttcc  2880
cgagggtggg ggagaaccgt atataagtgc agtagtcgcc gtgaacgttc tttttcgcaa  2940
cgggtttgcc gccagaacac aggtaagtgc cgtgtgtggt tcccgcgggc ctggcctctt  3000
tacgggttat ggcccttgcg tgccttgaat tacttccact ggctgcagta cgtgattctt  3060
gatcccgagc ttcgggttgg aagtgggtgg gagagttcga ggccttgcgc ttaaggagcc  3120
ccttcgcctc gtgcttgagt tgaggcctgg cctgggcgct ggggccgccg cgtgcgaatc  3180
tggtggcacc ttcgcgcctg tctcgctgct ttcgataagt ctctagccat ttaaaatttt  3240
tgatgacctg ctgcgacgct ttttttctgg caagatagtc ttgtaaatgc gggccaagat  3300
ctgcacactg gtatttcggt ttttggggcc gcgggcggcg acggggcccg tgcgtcccag  3360
cgcacatgtt cggcgaggcg gggcctgcga gcgcggccac cgagaatcgg acgggggtag  3420
tctcaagctg gccggcctgc tctggtgcct ggcctcgcgc cgccgtgtat cgccccgccc  3480
tgggcggcaa ggctggcccg gtcggcacca gttgcgtgag cggaaagatg gccgcttccc  3540
ggccctgctg cagggagctc aaaatggagg acgcggcgct cgggagagcg ggcgggtgag  3600
tcacccacac aaaggaaaag ggcctttccg tcctcagccg tcgcttcatg tgactccacg  3660
gagtaccggg cgccgtccag gcacctcgat tagttctcga gcttttggag tacgtcgtct  3720
ttaggttggg gggagggggtt ttatgcgatg gagtttcccc acactgagtg ggtggagact  3780
gaagttaggc cagcttggca cttgatgtaa ttctccttgg aatttgccct ttttgagttt  3840
ggatcttggt tcattctcaa gcctcagaca gtggttcaaa gtttttttct tccatttcag  3900
gtgtcgtgag ctagcgccac catggatagc actgagaacg tcatcaagcc cttcatgcgc  3960
ttcaaggtgc acatggaggg ctccgtgaac ggccacgagt tcgagatcga gggcgagggc  4020
gagggcaagc cctacgaggg cacccagacc gccaagctgc aggtgaccaa gggcggcccc  4080
ctgcccttcg cctgggacat cctgtccccc cagttccagt acggctccaa ggtgtacgtg  4140
aagcaccccg ccgacatccc cgactacaag aagctgtcct tccccgaggg cttcaagtgg  4200
gagcgcgtga tgaacttcga ggacggcggc gtggtgaccg tgacccagga ctcctccctg  4260
caggacggca ccttcatcta ccacgtgaag ttcatcggcg tgaacttccc ctccgacggc  4320
cccgtaatgc agaagaagac tctgggctgg gagccctcca ccgagcgcct gtaccccccgc  4380
gacggcgtgc tgaagggcga gatccacaag gcgctgaagc tgaagggcgg cggccactac  4440
ctggtggagt tcaagtcaat ctacatggcc aagaagcccg tgaagctgcc cggctactac  4500
tacgtggact ccaagctgga catcacctcc cacaacgagg actacaccgt ggtggagcag  4560
tacgagcgcg ccgaggcccg ccaccacctg ttccagtgag aattcgttta aacccgctga  4620
tcagcctcga ctgtgccttc tagttgccag ccatctgttg tttgcccctc ccccgtgcct  4680
tccttgaccc tggaaggtgc cactcccact gtcctttcct aataaaatga ggaaattgca  4740
tcgcattgtc tgagtaggtg tcattctatt ctggggggtg gggtggggca ggacagcaag  4800
ggggaggatt gggaagacaa tagcaggcat gctggggatg cggtgggctc tatggcttct  4860
gaggcggaaa gaaccagctg gggctccgcg cccggggagc ccaagggcac gccctggcac  4920
ctagggggta tccccgtata ccgtcgacct ctagctagag cttggcgtaa tcatggtcat  4980
agctgtttcc tgtgtgaaat tgttatccgc tcacaattcc acacaacata cgagccggaa  5040
gcataaagtg taaagcctgg ggtgcctaat gagtgagcta actcacatta attgcgttgc  5100
gctcactgcc cgctttccag tcgggaaacc tgtcgtgcca gctgcattaa tgaatcggcc  5160
aacgcgcggg gagaggcggt ttgcgtattg ggcgctcttc cgcttcctcg ctcactgact  5220
cgctgcgctc ggtcgttcgg ctgcggcgag cggtatcagc tcactcaaag gcggtaatac  5280
ggttatccac agaatcaggg gataacgcag gaaagaacat gtgagcaaaa ggccagcaaa  5340
aggccaggaa ccgtaaaaag gccgcgttgc tggcgttttt ccataggctc cgcccccctg  5400
acgagcatca caaaaatcga cgctcaagtc agaggtggcg aaacccgaca ggactataaa  5460
gataccaggc gtttccccct ggaagctccc tcgtgcgctc tcctgttccg accctgccgc  5520
ttaccggata cctgtccgcc tttctccctt cgggaagcgt ggcgctttct catagctcac  5580
gctgtaggta tctcagttcg gtgtaggtcg ttcgctccaa gctgggctgt gtgcacgaac  5640
cccccgttca gcccgaccgc tgcgccttat ccggtaacta tcgtcttgag tccaacccgg  5700
taagacacga cttatcgcca ctggcagcag ccactggtaa caggattagc agagcgaggt  5760
atgtaggcgg tgctacagag ttcttgaagt ggtggcctaa ctacggctac actagaagaa  5820
cagtatttgg tatctgcgct ctgctgaagc cagttacctt cggaaaaaga gttggtagct  5880
cttgatccgg caaacaaacc accgctggta gcggtggttt ttttgtttgc aagcagcaga  5940
ttacgcgcag aaaaaaagga tctcaagaag atcctttgat cttttctacg gggtctgacg  6000
ctcagtggaa cgaaaactca cgttaaggga ttttggtcat gagattatca aaaaggatct  6060
tcacctagat ccttttaaat taaaaatgaa gttttaaatc aatctaaagt atatatgagt  6120
aaacttggtc tgacagttac caatgcttaa tcagtgaggc acctatctca gcgatctgtc  6180
tatttcgttc atccatagtt gcctgactcc ccgtcgtgta gataactacg atacgggagg  6240
gcttaccatc tggccccagt gctgcaatga taccgcgaga cccacgctca ccggctccag  6300
atttatcagc aataaaccag ccagccggaa gggccgagcg cagaagtggt cctgcaactt  6360
tatccgcctc catccagtct attaattgtt gccgggaagc tagagtaagt agttcgccag  6420
ttaatagttt gcgcaacgtt gttgccattg ctacaggcat cgtggtgtca cgctcgtcgt  6480
ttggtatggc ttcattcagc tccggttccc aacgatcaag gcgagttaca tgatccccca  6540
tgttgtgcaa aaaagcggtt agctccttcg gtcctccgat cgttgtcaga agtaagttgg  6600
ccgcagtgtt atcactcatg gttatggcag cactgcataa ttctcttact gtcatgccat  6660
ccgtaagatg cttttctgtg actggtgagt actcaaccaa gtcattctga gaatagtgta  6720
tgcggcgacc gagttgctct tgcccggcgt caatacggga taataccgcg ccacatagca  6780
gaactttaaa agtgctcatc attggaaaac gttcttcggg gcgaaaactc tcaaggatct  6840
taccgctgtt gagatccagt tcgatgtaac ccactcgtgc acccaactga tcttcagcat  6900
```

```
cttttacttt caccagcgtt tctgggtgag caaaaacagg aaggcaaaat gccgcaaaaa  6960
agggaataag ggcgacacgg aaatgttgaa tactcatact cttccttttt caatattatt  7020
gaagcattta tcagggttat tgtctcatga gcggatacat atttgaatgt atttagaaaa  7080
ataaacaaat aggggttccg cgcacatttc cccgaaaagt gccacctgac gtcgacggat  7140
cgggagatct cccgatcccc tatggtgcac tctcagtaca atctgctctg atgccgcata  7200
gttaagccag tatctgctcc ctgcttgtgt gttggaggtc gctgagtagt gcgcgagcaa  7260
aatttaagct acaacaaggc aaggcttgac cgacaattgc atgaagaatc tgcttagggt  7320
taggcgtttt gcgctgcttc gcgatgtacg ggccagatat                        7360

SEQ ID NO: 56          moltype = DNA  length = 7956
FEATURE                Location/Qualifiers
misc_feature           1..7956
                       note = Synthetic: minimal R6K Ori sequence between two
                        inverted repeat sequences contained dsGFP-dsRFP reporter
                        construct
source                 1..7956
                       mol_type = other DNA
                       organism = synthetic construct
SEQUENCE: 56
acgcgttgac attgattatt gactagttaa ctataacggt cctaaggtag cgaacccccca  60
actgagagaa ctcaaaggtt accccagttg ggtaaaaata cagcatagca aaactttaac  120
ctccaaatca agcctctact tgaatccttt tctgagggat gaataaggca taggcatcag  180
gggctgttgc caatgtgcat tagctgtttg cagcctcacc ttctttcatg gagtttaaga  240
tatagtgtat tttcccaagg tttgaactag ctcttcattt ctttatgttt taaatgcact  300
gacctcccac attccctttt tagtaaaata ttcagaaata atttaaatac atcattgcaa  360
tgaaaataaa tgttttttat taggcagaat ccagatgctc aaggcccttc ataatatccc  420
ccagtttagt agttggactt agggaacaaa ggaaccttta atagaaattg gacagcaaga  480
aagcgagctt agtgatactt gtgggccagg gcattagcca caccagccac cactttctga  540
taggcagcct gcactggtgg ggtgaattcg aagcttgagc tcgagatcct actagtagga  600
tctgagtccg gattacttgt acagctcgtc catgccgtga gtgatcccgg cggcggtcac  660
gaactccagc aggaccatgt gatcgcgctt ctcgttgggg tctttgctca gggcggactg  720
ggtgctcagg tagtggttgt cgggcagcag cacggggccg tcgccgatgg gggtgttctg  780
ctggtagtgg tcggcgagct gcacgctgcc gtcctcgatg ttgtggcgga tcttgaagtt  840
caccttgatg ccgttcttct gcttgtcggc catgatatag acgttgtggc tgttgtagtt  900
gtactccagc ttgtgcccca ggatgttgcc gtcctccttg aagtcgatgc ccttcagctc  960
gatgcggttc accagggtgt cgccctgcag gaggaggaac ccctagtgat ggagttggcc  1020
actccctctc tgcgcgctcg ctcgctcact gaggccgggc gaccaaaggt cgcccgacgc  1080
ccgggctttg cccgggcggc ctcagtgagc gagcgagcgc gcagccttaa ttaataccgt  1140
tcgtataatg tatgctatac gaacggtact gcagtgtcag ccgttaagtg ttcctgtgtc  1200
actcaaaatt gctttgagag gctctaaggg cttctcagtg cgttacatcc ctggcttgtt  1260
gtccacaacc gttaaacctt aaaagcttta aaagccttat atattctttt ttttcttata  1320
aaacttaaaa ccttagaggc tatttaagtt gctgatttat attaatttta ttgttcaaac  1380
atgagagctt agtacgtgaa acatgagagc ttagtacgtt agccatgaga gcttagtacg  1440
ttagccatga gggtttagtt cgttaaacat gagagcttag tacgttaaac atgagagctt  1500
agtacgtgaa acatgagagc ttagtacgta ctatcaacag gttgaactgc tgatcttcag  1560
atcttaatta aggctgcgcg ctcgctcgct cactgaggcc gcccgggcaa agcccgggcg  1620
tcgggcgacc tttggtcgcc cggcctcagt gagcgagcga gcgcgcagag agggagtggc  1680
caactccatc actaggggtt cctttcttac ctcgaacttc acctcggcgc gggtcttgta  1740
gttgccgtcg tccttgaaga agatggtgcg ctcctggacg tagccttcgg gcatggcgga  1800
cttgaagaag tcgtgctgct tcatgtggtc ggggtagcgg ctgaagcact gcacgccgta  1860
ggtgaaggtg gtcacgaggg tgggccaggg cacgggcagc ttgccggtgg tgcagatgaa  1920
cttcagggtc agcttgccgt aggtggcatc gccctcgccc tcgccggaca cgctgaactt  1980
gtggccgttt acgtcgccgt ccagctcgac caggatgggc accacccccgg tgaacagctc  2040
ctcgcccttg ctcaccatgg tggcgaccgg tagcgtgctt tgccaaagtg atgggccagc  2100
acacagacca gcacgttgcc caggagctgt gggaggaaga taagaggtat gaacatgatt  2160
agcaaaaggg cctagcttgg actcagaata atccagcctt atcccaacca taaaataaaa  2220
gcagaatggt agctggattg tagctgctat tagcaatatg aaacctctta catcagttac  2280
aatttatatg cagaaatatt tatatgcaga aatattgcta ttgccttaac ccagaaatta  2340
tcactgttat tctttagaat ggtgcaaaga ggcatgatac attgtatcat tattgccctg  2400
aaagaaagag attagggaaa gtattagaaa taagataaac aaaaaagtat attaaaagaa  2460
gaaagcattt tttaaaatta caaatgcaaa attaccctga tttggtcaat atgtgtaccc  2520
tgttacttct cccettccta tgacatgaac ttaaccatag aaaagaaggg gaaagaaaac  2580
atcaagggtc ccatagactc accctgaagt tctcaggatc cgagctcggt accacatgta  2640
agcttcgagg ggaggctgga tcggtcccgg tgtcttctat ggaggtcaaa acagcgtgga  2700
tggcgtctcc aggcgatctg acggttcact aaacgagctc tgcttatata gacctcccac  2760
cgtacacgcc taccgcccat ttgcgtcaat ggggcggagt tgttacgaca ttttggaaag  2820
tcccgttgat tttggtgcca aaacaaactc ccattgacgt caatggggtg gagacttgga  2880
aatccccgtg agtcaaaccg ctatccacgc ccattgatgt actgccaaaa ccgcatcacc  2940
atggtaatag cgatgactaa tacgtagatg tactgccaag taggaaagtc ccataaggtc  3000
atgtactggg cataatgcca ggcgggccat ttaccgtcat tgacgtcaat agggggcgta  3060
cttggcatat gatacacttg atgtactgcc aagtgggcag tttaccgtaa atagtccacc  3120
cattgacgtc aatggaaagt ccctattggc gttactatgg gaacatacgt cattattgac  3180
gtcaatgggc gggggtcgtt gggcggtcag ccaggcgggc catttaccgt aagttatgta  3240
acgcggaact ccatatatgg gctatgaact aatgaccccg taattgatta ctattaataa  3300
ctagtcaata atcaatgtct taattaaggc tccggtgccc gtcagtgggc agagcgcaca  3360
tcgcccacag tccccgagaa gttgggggga ggggtcggca attgaaccgg tgcctagaga  3420
aggtggcgcg gggtaaactg ggaaagtgat gtcgtgtact ggctccgcct ttttcccgag  3480
ggtgggggag aaccgtatat aagtgcagta gtcgccgtga acgttctttt tcgcaacggg  3540
tttgccgcca gaacacaggt aagtgccgtg tgtggttccc gcgggcctgg cctctttacg  3600
```

-continued

```
ggttatggcc cttgcgtgcc ttgaattact tccactggct gcagtacgtg attcttgatc  3660
ccgagcttcg ggttggaagt gggtgggaga gttcgaggcc ttgcgcttaa ggagcccctt  3720
cgcctcgtgc ttgagttgag gcctggcctg ggcgctgggg ccgccgcgtg cgaatctggt  3780
ggcaccttcg cgcctgtctc gctgctttcg ataagtctct agccatttaa aatttttgat  3840
gacctgctgc gacgcttttt ttctggcaag atagtcttgt aaatgcgggc caagatctgc  3900
acactggtat ttcggttttt ggggccgcgg gcggcgacgg ggcccgtgcg tcccagcgca  3960
catgttcggc gaggcggggc ctgcgagcgc ggccaccgag aatcggacgg gggtagtctc  4020
aagctggccg gcctgctctg gtgcctggcc tcgcgccgcc gtgtatcgcc ccgccctggg  4080
cggcaaggct ggcccggtcg gcaccagttg cgtgagcgga aagatggccg cttcccggcc  4140
ctgctgcagg gagctcaaaa tggaggacgc ggcgctcggg agagcgggcg ggtgagtcac  4200
ccacacaaag gaaaagggcc tttccgtcct cagccgtcgc ttcatgtgac tccacggagt  4260
accgggcgcc gtccaggcac ctcgattagt tctcgagctt ttggagtacg tcgtctttag  4320
gttgggggga ggggttttat gcgatggagt ttccccacac tgagtgggtg gagactgaag  4380
ttaggccagc ttggcacttg atgtaattct ccttggaatt tgcccttttt gagtttggat  4440
cttggttcat tctcaagcct cagacagtgg ttcaaagttt ttttcttcca tttcaggtgt  4500
cgtgagctag cgccaccatg gatagcactg agaacgtcat caagcccttc atgcgcttca  4560
aggtgcacat ggagggctcc gtgaacggcc acgagttcga gatcgagggc gagggcgagg  4620
gcaagcccta cgagggcacc cagaccgcca agctgcaggt gaccaagggc ggccccctgc  4680
ccttcgcctg ggacatcctg tccccccagt tccagtacgg ctccaaggtg tacgtgaagc  4740
accccgccga catccccgac tacaagaagc tgtccttccc cgagggcttc aagtgggagc  4800
gcgtgatgaa cttcgaggac ggcggcgtgg tgaccgtgac ccaggactcc tccctgcagg  4860
acggcacctt catctaccac gtgaagttca tcggcgtgaa cttcccctcc gacggccccg  4920
taatgcagaa gaagactctg ggctgggagc cctccaccga gcgcctgtac ccccgcgacg  4980
gcgtgctgaa gggcgagatc cacaaggcgc tgaagctgaa gggcggcggc cactacctgg  5040
tggagttcaa gtcaatctac atggccaaga agcccgtgaa gctgcccggc tactactacg  5100
tggactccaa gctggacatc acctcccaca acgaggacta caccgtggtg gagcagtacg  5160
agcgcgccga ggcccgccac cacctgttcc agtgagaatt cgtttaaacc cgctgatcag  5220
cctcgactgt gccttctagt tgccagccat ctgttgtttg cccctccccc gtgccttcct  5280
tgaccctgga aggtgccact cccactgtcc tttcctaata aaatgaggaa attgcatcgc  5340
attgtctgag taggtgtcat tctattctgg ggggtggggt ggggcaggac agcaaggggg  5400
aggattggga agacaatagc aggcatgctg gggatgcggt gggctctatg gcttctgagg  5460
cggaaagaac cagctggggc tccgcgcccg gggagcccaa gggcacgccc tggcacctag  5520
ggggtatccc cgtataccgt cgacctctag ctagagcttg gcgtaatcat ggtcatagct  5580
gtttcctgtg tgaaattgtt atccgctcac aattccacac aacatacgag ccggaagcat  5640
aaagtgtaaa gcctggggtg cctaatgagt gagctaactc acattaattg cgttgcgctc  5700
actgcccgct ttccagtcgg gaaacctgtc gtgccagctg cattaatgaa tcggccaacg  5760
cgcgggggaga ggcggtttgc gtattgggcg ctcttccgct tcctcgctca ctgactcgct  5820
gcgctcggtc gttcggctgc ggcgagcggt atcagctcac tcaaaggcgg taatacggtt  5880
atccacagaa tcaggggata acgcaggaaa gaacatgtga gcaaaaggcc agcaaaaggc  5940
caggaaccgt aaaaaggccg cgttgctggc gtttttccat aggctccgcc cccctgacga  6000
gcatcacaaa aatcgacgct caagtcagag gtggcgaaac ccgacaggac tataaagata  6060
ccaggcgttt ccccctggaa gctccctcgt gcgctctcct gttccgaccc tgccgcttac  6120
cggatacctg tccgcctttc tcccttcggg aagcgtggcg ctttctcata gctcacgctg  6180
taggtatctc agttcggtgt aggtcgttcg ctccaagctg ggctgtgtgc acgaaccccc  6240
cgttcagccc gaccgctgcg ccttatccgg taactatcgt cttgagtcca acccggtaag  6300
acacgactta tcgccactgg cagcagccac tggtaacagg attagcagag cgaggtatgt  6360
aggcggtgct acagagttct tgaagtggtg gcctaactac ggctacacta gaagaacagt  6420
atttggtatc tgcgctctgc tgaagccagt taccttcgga aaaagagttg gtagctcttg  6480
atccggcaaa caaaccaccg ctggtagcgg tggttttttt gtttgcaagc agcagattac  6540
gcgcagaaaa aaaggatctc aagaagatcc tttgatcttt tctacggggt ctgacgctca  6600
gtggaacgaa aactcacgtt aagggatttt ggtcatgaga ttatcaaaaa ggatcttcac  6660
ctagatcctt ttaaattaaa aatgaagttt taaatcaatc taaagtatat atgagtaaac  6720
ttggtctgac agttaccaat gcttaatcag tgaggcacct atctcagcga tctgtctatt  6780
tcgttcatcc atagttgcct gactccccgt cgtgtagata actacgatac gggagggctt  6840
accatctggc cccagtgctg caatgatacc gcgagaccca cgctcaccgg ctccagattt  6900
atcagcaata aaccagccag ccggaagggc cgagcgcaga agtggtcctg caactttatc  6960
cgcctccatc cagtctatta attgttgccg ggaagctaga gtaagtagtt cgccagttaa  7020
tagtttgcgc aacgttgttg ccattgctac aggcatcgtg gtgtcacgct cgtcgtttgg  7080
tatggcttca ttcagctccg gttcccaacg atcaaggcga gttacatgat cccccatgtt  7140
gtgcaaaaaa gcggttagct ccttcggtcc tccgatcgtt gtcagaagta agttggccgc  7200
agtgttatca ctcatggtta tggcagcact gcataattct cttactgtca tgccatccgt  7260
aagatgcttt tctgtgactg gtgagtactc aaccaagtca ttctgagaat agtgtatgcg  7320
gcgaccgagt tgctcttgcc cggcgtcaat acgggataat accgcgccac atagcagaac  7380
tttaaaagtg ctcatcattg gaaaacgttc ttcggggcga aaactctcaa ggatcttacc  7440
gctgttgaga tccagttcga tgtaacccac tcgtgcaccc aactgatctt cagcatcttt  7500
tactttcacc agcgtttctg ggtgagcaaa aacaggaagg caaaatgccg caaaaaaggg  7560
aataagggcg acacggaaat gttgaatact catactcttc ctttttcaat attattgaag  7620
catttatcag ggttattgtc tcatgagcgg atacatattt gaatgtattt agaaaaataa  7680
acaaataggg gttccgcgca catttccccg aaaagtgcca cctgacgtcg acggatcggg  7740
agatctcccg atcccctatg gtgcactctc agtacaatct gctctgatgc cgcatagtta  7800
agccagtatc tgctccctgc ttgtgtgttg gaggtcgctg agtagtgcgc gagcaaaatt  7860
taagctacaa caaggcaagg cttgaccgac aattgcatga agaatctgct tagggttagg  7920
cgttttgcgc tgcttcgcga tgtacgggcc agatat                            7956
```

```
SEQ ID NO: 57          moltype = DNA  length = 7379
FEATURE                Location/Qualifiers
misc_feature           1..7379
                       note = Synthetic: A BC-deleted & RBS-mutated A cruciform
                        structure contained dsGFP-dsRFP reporter construct
```

```
source                  1..7379
                        mol_type = other DNA
                        organism = synthetic construct
SEQUENCE: 57
acgcgttgac attgattatt gactagttaa ctataacggt cctaaggtag cgaaccccca  60
actgagagaa ctcaaaggtt accccagttg ggtaaaaata cagcatagca aaactttaac  120
ctccaaatca agcctctact tgaatccttt tctgagggat gaataaggca taggcatcag  180
gggctgttgc caatgtgcat tagctgtttg cagcctcacc ttctttcatg gagtttaaga  240
tatagtgtat tttcccaagg tttgaactag ctcttcattt ctttatgttt taaatgcact  300
gacctcccac attccctttt tagtaaaata ttcagaaata atttaaatac atcattgcaa  360
tgaaaataaa tgtttttat taggcagaat ccagatgctc aaggcccttc ataatatccc  420
ccagtttagt agttggactt agggaacaaa ggaaccttta atagaaattg gacagcaaga  480
aagcgagctt agtgatactt gtgggccagg gcattagcca caccagccac cactttctga  540
taggcagcct gcactggtgg ggtgaattcg aagcttgagc tcgagatcct actagtagga  600
tctgagtccg gattacttgt acagctcgtc catgccgtga gtgatcccgg cggcggtcac  660
gaactccagc aggaccatgt gatcgcgctt ctcgttgggg tctttgctca gggcggactg  720
ggtgctcagg tagtggttgt cgggcagcag cacggggccg tcgccgatgg gggtgttctg  780
ctggtagtgg tcggcgagct gcacgctgcc gtcctcgatg ttgtggcgga tcttgaagtt  840
caccttgatg ccgttcttct gcttgtcggc catgatatag acgttgtggc tgttgtagtt  900
gtactccagc ttgtgcccca ggatgttgcc gtcctccttg aagtcgatgc ccttcagctc  960
gatgcggttc accagggtgt cgccctgcag gaggaggaac ccctagtgat ggggccggcc  1020
actccctctc tcctccctcc ctccctcact gaggccgccc cgcggcctca gtgagcgagc  1080
gagcgcgcag agagggagtg gccaactcca tcactagggg tttcctttct tacctcgaac  1140
ttcacctcgg cgcgggtctt gtagttgccg tcgtccttga agaagatggt gcgctcctgg  1200
acgtagcctt cgggcatggc ggacttgaag aagtcgtgct gcttcatgtg gtcggggtag  1260
cggctgaagc actgcacgcc gtaggtgaag gtggtcacga gggtgggcca gggcacgggc  1320
agcttgccgg tggtgcagat gaacttcagg gtcagcttgc cgtaggtggc atcgccctcg  1380
ccctcgccgg acacgctgaa cttgtggccg tttacgtcgc cgtccagctc gaccaggatg  1440
ggcaccaccc cggtgaacag ctcctcgccc ttgctcacca tggtggcgac cggtagcgtg  1500
ctttgccaaa gtgatgggcc agcacacaga ccagcacgtt gcccaggagc tgtgggagga  1560
agataagagg tatgaacatg attagcaaaa gggcctagct tggactcaga ataatccagc  1620
cttatcccaa ccataaaata aaagcagaat ggtagctgga ttgtagctgc tattagcaat  1680
atgaaacctc ttacatcagt tacaatttat atgcagaaat atttatatgc agaaatattg  1740
ctattgcctt aacccagaaa ttatcactgt tattctttag aatggtgcaa agaggcatga  1800
tacattgtat cattattgcc ctgaaagaaa gagattaggg aaagtattag aaataagata  1860
aacaaaaaag tatattaaaa gaagaaagca tttttaaaa ttacaaatgc aaaattaccc  1920
tgatttggtc aatatgtgta ccctgttact tctccccttc ctatgacatg aacttaacca  1980
tagaaaagaa ggggaaagaa aacatcaagg gtcccataga ctcaccctga agttctcagg  2040
atccgagctc ggtaccacat gtaagcttcg aggggaggct ggatcggtcc cggtgtcttc  2100
tatggaggtc aaaacagcgt ggatggcgtc tccaggcgat ctgacggttc actaaacgag  2160
ctctgcttat atagacctcc caccgtacac gcctaccgcc catttgcgtc aatggggcgg  2220
agttgttacg acattttgga aagtcccgtt gattttggtg ccaaaacaaa ctcccattga  2280
cgtcaatggg gtggagactt ggaaatcccc gtgagtcaaa ccgctatcca cgcccattga  2340
tgtactgcca aaaccgcatc accatggtaa tagcgatgac taatacgtag atgtactgcc  2400
aagtaggaaa gtcccataag gtcatgtact gggcataatg ccaggcgggc catttaccgt  2460
cattgacgtc aataggggc gtacttggca tatgatacac ttgatgtact gccaagtggg  2520
cagtttaccg taaatagtcc acccattgac gtcaatggaa agtccctatt ggcgttacta  2580
tgggaacata cgtcattatt gacgtcaatg ggcgggggtc gttgggcggt cagccaggcg  2640
ggccatttac cgtaagttat gtaacgcgga actccatata tgggctatga actaatgacc  2700
ccgtaattga ttactattaa taactagtca ataatcaatg tcttaattaa ggctccggtg  2760
cccgtcagtg ggcagagcgc acatcgccca cagtccccga gaagttgggg ggaggggtcg  2820
gcaattgaac cggtgcctag agaaggtggc gcggggtaaa ctgggaaagt gatgtcgtgt  2880
actggctccg cctttttccc gagggtgggg gagaaccgta tataagtgca gtagtcgccg  2940
tgaacgttct ttttcgcaac gggtttgccg ccagaacaca ggtaagtgcc gtgtgtggtt  3000
cccgcgggcc tggcctcttt acgggttatg gcccttgcgt gccttgaatt acttccactg  3060
gctgcagtac gtgattcttg atcccgagct tcgggttgga agtgggtggg agagttcgag  3120
gccttgcgct taaggagccc cttcgcctcg tgcttgagtt gaggcctggc ctgggcgctg  3180
gggccgccgc gtgcgaatct ggtggcacct tcgcgcctgt ctcgctgctt tcgataagtc  3240
tctagccatt taaaattttt gatgacctgc tgcgacgctt tttttctggc aagatagtct  3300
tgtaaatgcg ggccaagatc tgcacactgg tatttcggtt tttggggccg cgggcggcga  3360
cggggcccgt gcgtcccagc gcacatgttc ggcgaggcgg ggcctgcgag cgcggccacc  3420
gagaatcgga cgggggtagt ctcaagctgg ccggcctgct ctggtgcctg gcctcgcgcc  3480
gccgtgtatc gccccgccct gggcggcaag gctggcccgg tcggcaccag ttgcgtgagc  3540
ggaaagatgg ccgcttcccg gccctgctgc agggagctca aaatggagga cgcggcgctc  3600
gggagagcgg gcgggtgagt cacccacaca aaggaaaagg gcctttccgt cctcagccgt  3660
cgcttcatgt gactccacgg agtaccgggc gccgtccagg cacctcgatt agttctcgag  3720
cttttggagt acgtcgtctt taggttgggg ggaggggttt tatgcgatgg agtttcccca  3780
cactgagtgg gtggagactg aagttaggcc agcttggcac ttgatgtaat tctccttgga  3840
atttgccctt tttgagtttg gatcttggtt cattctcaag cctcagacag tggttcaaag  3900
tttttttctt ccatttcagg tgtcgtgagc tagcgccacc atggatagca ctgagaacgt  3960
catcaagccc ttcatgcgct tcaaggtgca catggagggc tccgtgaacg gccacgagtt  4020
cgagatcgag ggcgagggcg agggcaagcc ctacgagggc acccagaccg ccaagctgca  4080
ggtgaccaag ggcggccccc tgcccttcgc ctgggacatc ctgtcccccc agttccagta  4140
cggctccaag gtgtacgtga agcaccccgc cgacatcccc gactacaaga agctgtcctt  4200
ccccgagggc ttcaagtggg agcgcgtgat gaacttcgag gacggcggcg tggtgaccgt  4260
gacccaggac tcctccctgc aggacggcac cttcatctac cacgtgaagt tcatcggcgt  4320
gaacttcccc tccgacggcc ccgtaatgca gaagaagact ctgggctggg agccctccac  4380
cgagcgcctg taccccgcg acggcgtgct gaagggcgag atccacaagg cgctgaagct  4440
gaagggcggc ggccactacc tggtggagtt caagtcaatc tacatggcca agaagcccgt  4500
```

```
gaagctgccc ggctactact acgtggactc caagctggac atcacctccc acaacgagga  4560
ctacaccgtg gtggagcagt acgagcgcgc cgaggcccgc caccacctgt tccagtgaga  4620
attcgtttaa acccgctgat cagcctcgac tgtgccttct agttgccagc catctgttgt  4680
ttgcccctcc cccgtgcctt ccttgaccct ggaaggtgcc actcccactg tcctttccta  4740
ataaaatgag gaaattgcat cgcattgtct gagtaggtgt cattctattc tggggggtgg  4800
ggtggggcag gacagcaagg gggaggattg ggaagacaat agcaggcatg ctggggatgc  4860
ggtgggctct atggcttctg aggcggaaag aaccagctgg ggctccgcgc ccggggagcc  4920
caagggcacg ccctggcacc tagggggtat ccccgtatac cgtcgacctc tagctagagc  4980
ttggcgtaat catggtcata gctgtttcct gtgtgaaatt gttatccgct cacaattcca  5040
cacaacatac gagccggaag cataaagtgt aaagcctggg gtgcctaatg agtgagctaa  5100
ctcacattaa ttgcgttgcg ctcactgccc gctttccagt cgggaaacct gtcgtgccag  5160
ctgcattaat gaatcggcca acgcgcgggg agaggcggtt tgcgtattgg gcgctcttcc  5220
gcttcctcgc tcactgactc gctgcgctcg gtcgttcggc tgcggcgagc ggtatcagct  5280
cactcaaagg cggtaatacg gttatccaca gaatcagggg ataacgcagg aaagaacatg  5340
tgagcaaaag gccagcaaaa ggccaggaac cgtaaaaagg ccgcgttgct ggcgtttttc  5400
cataggctcc gcccccctga cgagcatcac aaaaatcgac gctcaagtca gaggtggcga  5460
aacccgacag gactataaag ataccaggcg tttccccctg gaagctccct cgtgcgctct  5520
cctgttccga ccctgccgct taccggatac ctgtccgcct ttctcccttc gggaagcgtg  5580
gcgctttctc atagctcacg ctgtaggtat ctcagttcgg tgtaggtcgt tcgctccaag  5640
ctgggctgtg tgcacgaacc ccccgttcag cccgaccgct gcgccttatc cggtaactat  5700
cgtcttgagt ccaacccggt aagacacgac ttatcgccac tggcagcagc cactggtaac  5760
aggattagca gagcgaggta tgtaggcggt gctacagagt tcttgaagtg gtggcctaac  5820
tacggctaca ctagaagaac agtatttggt atctgcgctc tgctgaagcc agttaccttc  5880
ggaaaaagag ttggtagctc ttgatccggc aaacaaacca ccgctggtag cggtggtttt  5940
tttgtttgca agcagcagat tacgcgcaga aaaaaaggat ctcaagaaga tcctttgatc  6000
ttttctacgg ggtctgacgc tcagtggaac gaaaactcac gttaagggat tttggtcatg  6060
agattatcaa aaaggatctt cacctagatc cttttaaatt aaaaatgaag ttttaaatca  6120
atctaaagta tatatgagta aacttggtct gacagttacc aatgcttaat cagtgaggca  6180
cctatctcag cgatctgtct atttcgttca tccatagttg cctgactccc cgtcgtgtag  6240
ataactacga tacgggaggg cttaccatct ggccccagtg ctgcaatgat accgcgagac  6300
ccacgctcac cggctccaga tttatcagca ataaaccagc cagccggaag ggccgagcgc  6360
agaagtggtc ctgcaacttt atccgcctcc atccagtcta ttaattgttg ccgggaagct  6420
agagtaagta gttcgccagt taatagtttg cgcaacgttg ttgccattgc tacaggcatc  6480
gtggtgtcac gctcgtcgtt tggtatggct tcattcagct ccggttccca acgatcaagg  6540
cgagttacat gatcccccat gttgtgcaaa aaagcggtta gctccttcgg tcctccgatc  6600
gttgtcagaa gtaagttggc cgcagtgtta tcactcatgg ttatggcagc actgcataat  6660
tctcttactg tcatgccatc cgtaagatgc ttttctgtga ctggtgagta ctcaaccaag  6720
tcattctgag aatagtgtat gcggcgaccg agttgctctt gcccggcgtc aatacgggat  6780
aataccgcgc cacatagcag aactttaaaa gtgctcatca ttggaaaacg ttcttcgggg  6840
cgaaaactct caaggatctt accgctgttg agatccagtt cgatgtaacc cactcgtgca  6900
cccaactgat cttcagcatc ttttactttc accagcgttt ctgggtgagc aaaaacagga  6960
aggcaaaatg ccgcaaaaaa gggaataagg gcgacacgga aatgttgaat actcatactc  7020
ttcctttttc aatattattg aagcatttat cagggttatt gtctcatgag cggatacata  7080
tttgaatgta tttagaaaaa taaacaaata ggggttccgc gcacatttcc ccgaaaagtg  7140
ccacctgacg tcgacggatc gggagatctc ccgatcccct atggtgcact ctcagtacaa  7200
tctgctctga tgccgcatag ttaagccagt atctgctccc tgcttgtgtg ttggaggtcg  7260
ctgagtagtg cgcgagcaaa atttaagcta caacaaggca aggcttgacc gacaattgca  7320
tgaagaatct gcttagggtt aggcgttttg cgctgcttcg cgatgtacgg gccagatat   7379

SEQ ID NO: 58          moltype = DNA  length = 303
FEATURE                Location/Qualifiers
misc_feature           1..303
                       note = Synthetic: Wildtype R6K gamma origin
source                 1..303
                       mol_type = other DNA
                       organism = synthetic construct
SEQUENCE: 58
ggcttgttgt ccacaaccgt taaaccttaa aagctttaaa agccttatat attctttttt  60
ttcttataaa acttaaaacc ttagaggcta tttaagttgc tgatttatat taattttatt  120
gttcaaacat gagagcttag tacgtgaaac atgagagctt agtacgttag ccatgagagc  180
ttagtacgtt agccatgagg gtttagttcg ttaaacatga gagcttagta cgttaaacat  240
gagagcttag tacgtgaaac atgagagctt agtacgtact atcaacaggt tgaactgctg  300
atc                                                               303

SEQ ID NO: 59          moltype = DNA  length = 250
FEATURE                Location/Qualifiers
misc_feature           1..250
                       note = Synthetic: Zero-CpG R6K gamma origin
source                 1..250
                       mol_type = other DNA
                       organism = synthetic construct
SEQUENCE: 59
aaaccttaaa acctttaaaa gccttatata ttcttttttt tcttataaaa cttaaaacct  60
tagaggctat ttaagttgct gatttatatt aattttattg ttcaaacatg agagcttagt  120
acatgaaaca tgagagctta gtacattagc catgagagct tagtacatta gccatgaggg  180
tttagttcat taaacatgag agcttagtac aacaggttga attaaacatg agagcttagt  240
acatactatc                                                        250

SEQ ID NO: 60          moltype = DNA  length = 656
```

```
FEATURE                Location/Qualifiers
misc_feature           1..656
                       note = Synthetic: Two AAV2 inverted repeat sequences
                        separated by a Zero-CpG R6K gamma origin of replication
                        (Ori) sequence
source                 1..656
                       mol_type = other DNA
                       organism = synthetic construct
SEQUENCE: 60
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag ccttaattaa taccgttcgt ataatgtatg ctatacgaac ggtactgcag  180
tgtcagccgt taagtgttcc tgtgtcactc aaaattgctt tgagaggctc taagggcttc  240
tcagtgcgtt acatccctaa accttaaaac ctttaaaagc cttatatatt cttttttttc  300
ttataaaact taaaacctta gaggctattt aagttgctga tttatattaa ttttattgtt  360
caaacatgag agcttagtac atgaaacatg agagcttagt acattagcca tgagagctta  420
gtacattagc catgagggtt tagttcatta aacatgagag cttagtacaa caggttgaat  480
taaacatgag agcttagtac atactatctt cagatcttaa ttaaggctgc gcgctcgctc  540
gctcactgag gccgcccggg caaagcccgg gcgtcgggcg acctttggtc gcccggcctc  600
agtgagcgag cgagcgcgca gagagggagt ggccaactcc atcactaggg gttcct      656

SEQ ID NO: 61          moltype = DNA  length = 995
FEATURE                Location/Qualifiers
misc_feature           1..995
                       note = Synthetic: Two AAV2 inverted repeat sequences
                        separated by a pUc origin of replication (Ori) sequence
source                 1..995
                       mol_type = other DNA
                       organism = synthetic construct
SEQUENCE: 61
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag ccttaattaa taccgttcgt ataatgtatg ctatacgaac ggtactgcag  180
tgtcagccgt taagtgttcc tgtgtcactc aaaattgctt tgagaggctc taagggcttc  240
tcagtgcgtt acatcccttt tccataggct ccgcccccct gacgagcatc acaaaaatcg  300
acgctcaagt cagaggtggc gaaacccgac aggactataa agataccagg cgtttccccc  360
tggaagctcc ctcgtgcgct ctcctgttcc gaccctgccg cttaccggat acctgtccgc  420
ctttctccct tcgggaagcg tggcgctttc tcatagctca cgctgtaggt atctcagttc  480
ggtgtaggtc gttcgctcca agctgggctg tgtgcacgaa ccccccgttc agcccgaccg  540
ctgcgcctta tccggtaact atcgtcttga gtccaacccg gtaagacacg acttatcgcc  600
actggcagca gccactggta acaggattag cagagcgagg tatgtaggcg gtgctacaga  660
gttcttgaag tggtggccta actacggcta cactagaaga acagtatttg gtatctgcgc  720
tctgctgaag ccagttacct tcggaaaaag agttggtagc tcttgatccg gcaaacaaac  780
caccgctggt agcggtggtt tttttgtttg caagcagcag attacgcgca gaaaaaaagg  840
atctcaattc agatcttaat taaggctgcg cgctcgctcg ctcactgagg ccgcccgggc  900
aaagcccggg cgtcgggcga cctttggtcg cccggcctca gtgagcgagc gagcgcgcag  960
agagggagtg gccaactcca tcactagggg ttcct                             995

SEQ ID NO: 62          moltype = DNA  length = 657
FEATURE                Location/Qualifiers
misc_feature           1..657
                       note = Synthetic: Two Zero-CpG AAV2 inverted repeat
                        sequences separated by a Zero-CpG R6K gamma origin of
                        replication sequence
source                 1..657
                       mol_type = other DNA
                       organism = synthetic construct
SEQUENCE: 62
aggaacccct agtgatggag ttggccactc cctctctgca ctctctctct ctcactgagg  60
cctggggacc aaaggtcccc agactgcaga gctttgctct gcaggcctca gtgagagaga  120
gagagtgcag agccttaatt aataccgttc gtataatgta tgctatacga acggtactgc  180
agtgtcagcc gttaagtgtt cctgtgtcac tcaaaattgc tttgagaggc tctaagggct  240
tctcagtgcg ttacatccct aaaccttaaa acctttaaaa gccttatata ttcttttttt  300
tcttataaaa cttaaaacct tagaggctat ttaagttgct gatttatatt aattttattg  360
ttcaaacatg agagcttagt acatgaaaca tgagagctta gtacattagc catgagagct  420
tagtacatta gccatgaggg tttagttcat taaacatgag agcttagtac aacaggttga  480
attaaacatg agagcttagt acatactatc ttcagatctt aattaaggct ctcactgagg  540
cctgcagagc aaagctctgc agtctgggga cctttggtcc ccaggcctca gtgagagagg  600
gagagggcag agagggagtg gccaactcca tcactagggg ttcctagcct taattaa     657

SEQ ID NO: 63          moltype = DNA  length = 1524
FEATURE                Location/Qualifiers
misc_feature           1..1524
                       note = Synthetic: Zero-CpG murine secreted embryonic
                        alkaline phosphatase (SEAP)
source                 1..1524
                       mol_type = other DNA
                       organism = synthetic construct
SEQUENCE: 63
```

```
atgtggggag cctgcctgct gctgctgggc ctgagcctgc aggtgtgccc ctctgtgatc  60
cctgtggagg aggagaaccc tgccttctgg aacagaaagg ctgctgaggc cctggatgct  120
gccaagaagc tgaagcccat ccagacctct gccaagaacc tggtgatcct gatgggagat  180
ggcatgggag tgagcacagt gacagccacc agaatcctga agggccagca gcagggccac  240
ctgggccctg agacccagct ggccatggac agattccccc acatggccct gagcaagacc  300
tacaacacag acaagcagat ccctgactct gctggcacag gcacagcctt cctgtgtgga  360
gtgaagacca acatgaaggt gattggcctg tctgctgctg ccagattcaa ccagtgcaac  420
accacctggg gcaatgaggt ggtgtctgtg atgcacagag ccaagaaggc tggcaagtct  480
gtgggagtgg tgaccaccac ctctgtgcag catgccagcc ctgctggcac ctatgcccac  540
acagtgaaca gaggctggta ctctgatgcc cagatgcctg cctctgccct gcaggatggc  600
tgcaaggaca tcagcaccca gctgatcagc aacatggaca ttgatgtgat cctgggagga  660
ggcagaaagt tcatgttccc caagggcacc cctgaccagg agtaccccac agacaccaag  720
caggctggca ccagactgga tggcagaaac ctggtgcagg agtggctggc caagcaccag  780
ggagccagat atgtgtggaa cagatctgag ctgatccagg ccagcctgaa cagatctgtg  840
acccacctga tgggcctgtt tgagcccaat gacatgaagt atgagatcca cagagaccct  900
gcccaggacc ccagcctggc tgagatgaca gaggtggctg tgagaatgct gagcagaaac  960
cccaagggct tctacctgtt tgtggaggga ggcagaattg accatggcca ccatgagaca  1020
gtggcctaca gagccctgac agaggctgtg atgtttgact ctgctgtgga caaggctgac  1080
aagctgacct ctgagcagga caccatgatc ctggtgacag ctgaccacag ccatgtgttc  1140
agctttggag gctacaccca gagaggagcc agcatctttg gcctggcccc cttcaaggct  1200
gaggatggca agagcttcac cagcatcctg tatggcaatg gccctggcta caagctgcac  1260
aatggagcca gagctgatgt gacagaggag gagagcagca accccaccta ccagcagcag  1320
gctgctgtgc ccctgagctc tgagacccac tctggagagg atgtggccat ctttgccaga  1380
ggcccccagg cccacctggt gcatggagtg caggagcaga actacattgc ccatgtgatg  1440
gcctttgctg cctgcctgga gccctacaca gactgtggcc tggccagccc tgctggccag  1500
agctctgctg tgagccctgg ctga                                   1524
```

```
SEQ ID NO: 64           moltype = AA  length = 1279
FEATURE                 Location/Qualifiers
REGION                  1..1279
                        note = misc_feature - Amino acid sequence of ABCB4
source                  1..1279
                        mol_type = protein
                        organism = Homo sapiens
SEQUENCE: 64
MDLEAAKNGT AWRPTSAEGD FELGISSKQK RKKTKTVKMI GVLTLFRYSD WQDKLFMSLG  60
TIMAIAHGSG LPLMMIVFGE MTDKFVDTAG NFSFPVNFSL SLLNPGKILE EEMTRYAYYY  120
SGLGAGVLVA AYIQVSFWTL AAGRQIRKIR QKFFHAILRQ EIGWFDINDT TELNTRLTDD  180
ISKISEGIGD KVGMFFQAVA TFFAGFIVGF IRGWKLTLVI MAISPILGLS AAVWAKILSA  240
FSDKELAAYA KAGAVAEEAL GAIRTVIAFG GQNKELERYQ KHLENAKEIG IKKAISANIS  300
MGIAFLLIYA SYALAFWYGS TLVISKEYTI GNAMTVFFSI LIGAFSVGQA APCIDAFANA  360
RGAAYVIFDI IDNNPKIDSF SERGHKPDSI KGNLEFNDVH FSYPSRANVK ILKGLNLKVQ  420
SGQTVALVGS SGCGKSTTVQ LIQRLYDPDE GTINIDGQDI RNFNVNYLRE IIGVVSQEPV  480
LFSTTIAENI CYGRGNVTMD EIKKAVKEAN AYEFIMKLPQ KFDTLVGERG AQLSGGQKQR  540
IAIARALVRN PKILLLDEAT SALDTESEAE VQAALDKARE GRTTIVIAHR LSTVRNADVI  600
AGFEDGVIVE QGSHSELMKK EGVYFKLVNM QTSGSQIQSE EFELNDEKAA TRMAPNGWKS  660
RLFRHSTQKN LKNSQMCQKS LDVETDGLEA NVPPVSFLKV LKLNKTEWPY FVVGTVCAIA  720
NGGLQPAFSV IFSEIIAIFG PGDDAVKQQK CNIFSLIFLF LGIISFFTFF LQGFTFGKAG  780
EILTRRLRSM AFKAMLRQDM SWFDDHKNST GALSTRLATD AAQVQGATGT RLALIAQNIA  840
NLGTGIIISF IYGWQLTLLL LAVVPIIAVS GIVEMKLLAG NAKRDKKELE AAGKIATEAI  900
ENIRTVVSLT QERKFESMYV EKLYGPYRNS VQKAHIYGIT FSISQAFMYF SYAGCFRFGA  960
YLIVNGHMRF RDVILVFSAI VFGAVALGHA SSFAPDYAKA KLSAAHLFML FERQPLIDSY  1020
SEEGLKPDKF EGNITFNEVV FNYPTRANVP VLQGLSLEVK KGQTLALVGS SGCGKSTVVQ  1080
LLERFYDPLA GTVLLDGQEA KKLNVQWLRA QLGIVSQEPI LFDCSIAENI AYGDNSRVVS  1140
QDEIVSAAKA ANIHPFIETL PHKYETRVGD KGTQLSGGQK QRIAIARALI RQPQILLLDE  1200
ATSALDTESE KVVQEALDKA REGRTCIVIA HRLSTIQNAD LIVVFQNGRV KEHGTHQQLL  1260
AQKGIYFSMV SVQAGTQNL                                         1279
```

```
SEQ ID NO: 65           moltype = DNA  length = 3840
FEATURE                 Location/Qualifiers
misc_feature            1..3840
                        note = Synthetic: Codon-optimized ABCB4 sequence
source                  1..3840
                        mol_type = other DNA
                        organism = synthetic construct
SEQUENCE: 65
atggatctgg aggccgccaa gaatggcacc gcatggagac ccacaagcgc cgagggcgac  60
ttcgagctgg gcatcagctc caagcagaag agaaagaaga ccaagacagt gaagatgatc  120
ggcgtgctga cactgttcag gtactccgac tggcaggata agctgtttat gtctctgggc  180
accatcatgg caatcgccca cggcagcgga ctgcctctga tgatgatcgt gttcggcgag  240
atgaccgaca agtttgtgga tacagccggc aatttctcct ttcccgtgaa cttctctctg  300
agcctgctga accctggcaa gatcctggag gaggagatga caagatatgc ctactattac  360
tctggactgg gagcaggcgt gctggtggca gcatacatcc aggtgagctt ctggaccctg  420
gccgcaggcc ggcagatcag aaagatcagg cagaagttct ttcacgccat cctgcgccag  480
gagatcggct ggtttgacat caatgatacc acagagctga acacccggct gacagacgac  540
atctctaaga tcagcgaggg catcggcgat aaagtgggca tgttctttca ggccgtggcc  600
acattctttg ccggcttcat cgtgggcttt atcaggggct ggaagctgac cctggtcatc  660
atggccatct ctccaatcct gggactgagc gccgccgtgt gggcaaagat cctgtccgcc  720
ttctctgaca aggagctggc cgcctacgcc aaggcaggag cagtggcaga ggaggccctg  780
```

```
ggcgccatcc gcaccgtgat cgcctttggc ggccagaata aggagctgga gcggtatcag  840
aagcacctgg agaacgccaa ggagatcggc atcaagaagg ccatctccgc caatatctct  900
atgggcatcg ccttcctgct gatctatgcc agctacgccc tggccttttg gtatggcagc  960
accctggtca tcagcaagga gtacaccatc ggcaatgcca tgacagtgtt ctttagcatc  1020
ctgatcggag ccttctccgt gggacaggca gcaccatgca tcgacgcctt cgccaacgcc  1080
agaggcgcag cctacgtgat ctttgacatc atcgataaca atccaaagat cgactccttt  1140
tctgagcggg gccacaagcc cgattccatc aagggcaatc tggagttcaa cgacgtgcac  1200
tttagctatc cctcccgcgc caatgtgaag atcctgaagg gcctgaacct gaaggtgcag  1260
tccggacaga cagtggccct ggtgggctct agcggatgcg gcaagtctac cacagtgcag  1320
ctgatccagc ggctgtatga cccagatgag ggcaccatca acatcgacgg ccaggacatc  1380
cgcaacttca atgtgaacta cctgcgggag atcatcggcg tggtgtctca ggagcccgtg  1440
ctgtttagca ccacaatcgc cgagaatatc tgttatggcc gcggcaacgt gacaatggat  1500
gagatcaaga aggccgtgaa ggaggccaat gcctacgagt tcatcatgaa gctgccccag  1560
aagtttgaca ccctggtggg agagagaggc gcccagctga gcggaggcca gaagcagagg  1620
atcgccatcg ccagagccct ggtgaggaac cctaagatcc tgctgctgga cgaggccacc  1680
tccgccctgg atacagagtc tgaggccgag gtgcaggccg ccctggataa ggcccgcgag  1740
ggacggacca caatcgtgat cgcccacaga ctgagcacag tgaggaatgc cgacgtgatc  1800
gccggcttcg aggatggcgt gatcgtggag cagggcagcc actccgagct gatgaagaag  1860
gagggcgtgt acttcaagct ggtgaacatg cagacctctg gcagccagat ccagtccgag  1920
gagtttgagc tgaatgacga gaaggcagca acaaggatgg cacctaacgg atggaagagc  1980
agactgttca ggcactccac ccagaagaat ctgaagaact ctcagatgtg ccagaagagc  2040
ctggacgtgg agaccgatgg cctggaggca aatgtgccac ccgtgagctt cctgaaggtg  2100
ctgaagctga acaagacaga gtggccatat tttgtggtgg gcaccgtgtg cgcaatcgca  2160
aatggaggac tgcagccagc cttcagcgtg atcttttccg agatcatcgc catcttcggc  2220
cctggcgacg atgccgtgaa gcagcagaag tgtaacatct tttccctgat cttcctgttt  2280
ctgggcatca tctctttctt taccttcttt ctgcagggct tcacatttgg caaggccggc  2340
gagatcctga cacggagact gagaagcatg gccttcaagg ccatgctgag gcaggatatg  2400
tcctggtttg acgatcacaa gaacagcacc ggcgccctgt ccaccagact ggccacagac  2460
gcagcacagg tgcagggagc aaccggcaca aggctggccc tgatcgccca gaatatcgcc  2520
aacctgggca caggcatcat catctctttc atctacggat ggcagctgac cctgctgctg  2580
ctggccgtgg tgccaatcat cgccgtgagc ggcatcgtgg agatgaagct gctggccggc  2640
aatgccaaga gagacaagaa ggagctggag gcagcaggca agatcgcaac cgaggccatc  2700
gagaacatcc gcaccgtggt gagcctgaca caggagcgga agttcgagtc catgtatgtg  2760
gagaagctgt atggccccta ccgcaattcc gtgcagaagg cccacatcta cggcatcacc  2820
ttttccatct ctcaggcctt catgtatttt tcttacgccg gctgcttccg gtttggcgcc  2880
tatctgatcg tgaacggcca catgaggttc cgcgatgtga tcctggtgtt ctctgccatc  2940
gtgtttggag cagtggccct gggacacgcc tcctcttttg cccctgacta tgcaaaggca  3000
aagctgtccg ccgcacacct gttcatgctg tttgagagac agcctctgat cgatagctac  3060
tccgaggagg gcctgaagcc agacaagttc gagggcaata tcacattcaa cgaggtggtg  3120
tttaattatc caaccagggc caacgtgccc gtgctgcagg gactgagcct ggaggtgaag  3180
aagggacaga cactggccct ggtgggcagc tccggatgcg gcaagtccac cgtggtgcag  3240
ctgctggaga gattctacga ccctctggcc ggcaccgtgc tgctggatgg acaggaggcc  3300
aagaagctga atgtgcagtg gctgagggcc cagctgggca tcgtgtctca ggagccaatc  3360
ctgttcgatt gtagcatcgc cgagaatatc gcctacggcg acaactctag ggtggtgagc  3420
caggatgaga tcgtgagcgc cgcaaaggca gcaaacatcc accctttat cgagaccctg  3480
ccacacaagt atgagacacg cgtgggcgac aagggcaccc agctgtccgg aggacagaag  3540
cagaggatcg caatcgcccg cgccctgatc aggcagcccc aaatcctgct gctggacgag  3600
gccacctccg ccctggatac cgagtctgag aaggtggtgc aggaggccct ggataaagcc  3660
cgcgagggac ggacatgtat tgtcattgct cacagactga gcaccatcca gaatgccgac  3720
ctgatcgtgg tgttccagaa cggcagggtg aaggagcacg gcacacacca gcagctgctg  3780
gcccagaagg gaatctactt ttctatggtg agcgtgcagg ccggcaccca gaacctgtga  3840
```

```
SEQ ID NO: 66          moltype = DNA  length = 3840
FEATURE                Location/Qualifiers
misc_feature           1..3840
                       note = ABCB4 cDNA sequence
source                 1..3840
                       mol_type = genomic DNA
                       organism = Homo sapiens
SEQUENCE: 66
atggatcttg aggcggcaaa gaacggaaca gcctggcgcc ccacgagcgc ggagggcgac  60
tttgaactgg gcatcagcag caaacaaaaa aggaaaaaaa cgaagacagt gaaaatgatt  120
ggagtattaa cattgtttcg atactccgat tggcaggata aattgtttat gtcgctgggt  180
accatcatgg ccatagctca cggatcaggt ctcccccctca tgatgatagt atttggagag  240
atgactgaca aatttgttga tactgcagga aacttctcct ttccagtgaa cttttccttg  300
tcgctgctaa atccaggcaa aattctggaa gaagaaatga ctagatatgc atattactac  360
tcaggattgg gtgctggagt tcttgttgct gcctatatac aagtttcatt ttggactttg  420
gcagctggtc gacagatcag gaaaattagg cagaagtttt ttcatgctat tctacgacag  480
gaaataggat ggtttgacat caacgacacc actgaactca atacgcggct aacagatgac  540
atctccaaaa tcagtgaagg aattggtgac aaggttggaa tgttctttca agcagtagcc  600
acgttttttg caggattcat agtgggattc atcagaggat ggaagctcac ccttgtgata  660
atggccatca gccctattct aggactctct gcagccgttt gggcaaagat actctcggca  720
tttagtgaca aagaactagc tgcttatgca aaagcaggcg ccgtggcaga agaggctctg  780
ggggccatca ggactgtgat agctttcggg ggccagaaca aagagctgga aaggtatcag  840
aaacatttag aaaatgccaa agagattgga attaaaaaag ctatttcagc aaacatttcc  900
atgggtattg ccttcctgtt aatatatgca tcatatgcac tggccttctg gtatggatcc  960
actctagtca tatcaaaaga atatactatt ggaaatgcaa tgacagtttt tttttcaatc  1020
ctaattggag ctttcagtgt tggccaggct gccccatgta ttgatgcttt tgccaatgca  1080
agaggagcag catatgtgat ctttgatatt attgataata atcctaaaat tgacagtttt  1140
```

```
tcagagagag gacacaaacc agacagcatc aaagggaatt tggagttcaa tgatgttcac  1200
ttttcttacc cttctcgagc taacgtcaag atcttgaagg gcctcaacct gaaggtgcag  1260
agtgggcaga cggtggccct ggttggaagt agtggctgtg ggaagagcac aacggtccag  1320
ctgatacaga ggctctatga ccctgatgag ggcacaatta acattgatgg gcaggatatt  1380
aggaacttta atgtaaacta tctgagggaa atcattggtg tggtgagtca ggagccggtg  1440
ctgttttcca ccacaattgc tgaaaatatt tgttatggcc gtggaaatgt aaccatggat  1500
gagataaaga aagctgtcaa agaggccaac gcctatgagt ttatcatgaa attaccacag  1560
aaatttgaca ccctggttgg agagagaggg gcccagctga gtggtgggca gaagcagagg  1620
atcgccattg cacgtgccct ggttcgcaac cccaagatcc ttctgctgga tgaggccacg  1680
tcagcattgg acacagaaag tgaagctgag gtacaggcag ctctggataa ggccagagaa  1740
ggccggacca ccattgtgat agcacaccga ctgtctacgg tccgaaatgc agatgtcatc  1800
gctgggtttg aggatggagt aattgtggag caaggaagcc acagcgaact gatgaagaag  1860
gaaggggtgt acttcaaact tgtcaacatg cagacatcag gaagccagat ccagtcagaa  1920
gaatttgaac taaatgatga aaaggctgcc actagaatgg ccccaaatgg ctggaaatct  1980
cgcctattta ggcattctac tcagaaaaac cttaaaaatt cacaaatgtg tcagaagagc  2040
cttgatgtgg aaaccgatgg acttgaagca aatgtgccac cagtgtcctt tctgaaggtc  2100
ctgaaactga ataaaacaga atggccctac tttgtcgtgg gaacagtatg tgccattgcc  2160
aatgggggc ttcagccggc attttcagtc atattctcag agatcatagc gatttttgga  2220
ccaggcgatg atgcagtgaa gcagcagaag tgcaacatat tctctttgat tttcttattt  2280
ctgggaatta tttctttttt tactttcttc cttcagggtt tcacgtttgg gaaagctggc  2340
gagatcctca ccagaagact gcggtcaatg gcttttaaag caatgctaag acaggacatg  2400
agctggtttg atgaccataa aaacagtact ggtgcacttt ctacaagact tgccacagat  2460
gctgcccaag tccaaggagc cacaggaacc aggttggctt taattgcaca gaatatagct  2520
aaccttggaa ctggtattat catatcattt atctacggtt ggcagttaac cctattgcta  2580
ttagcagttg ttccaattat tgctgtgtca ggaattgttg aaatgaaatt gttggctgga  2640
aatgccaaaa gagataaaaa agaactggaa gctgctggaa agattgcaac agaggcaata  2700
gaaaatatta ggacagttgt gtctttgacc caggaaagaa aatttgaatc aatgtatgtt  2760
gaaaaattgt atggacctta caggaactct gtgcagaagg cacacatcta tggaattact  2820
tttagtatct cacaagcatt tatgtatttt tcctatgccg gttgttttcg atttggtgca  2880
tatctcattg tgaatggaca tatgcgcttc agagatgtta ttctggtgtt ttctgcaatt  2940
gtatttggtg cagtggctct aggacatgcc agttcatttg ctccagacta tgctaaagct  3000
aagctgtctg cagcccactt attcatgctg tttgaaagac aacctctgat tgacagctac  3060
agtgaagagg ggctgaagcc tgataaattt gaaggaaata taacatttaa tgaagtcgtg  3120
ttcaactatc ccacccgagc aaacgtgcca gtgcttcagg ggctgagcct ggaggtgaag  3180
aaaggccaga cactagccct ggtgggcagc agtggctgtg ggaagagcac ggtggtccag  3240
ctcctggagc ggttctacga ccccttggcg gggacagtgc ttctcgatgg tcaagaagca  3300
aagaaactca atgtccagtg gctcagagct caactcggaa tcgtgtctca ggagcctatc  3360
ctatttgact gcagcattgc cgagaatatt gcctatggag acaacagccg ggttgtatca  3420
caggatgaaa ttgtgagtgc agccaaagct gccaacatac atcctttcat cgagacgtta  3480
ccccacaaat atgaaacaag agtgggagat aaggggactc agctctcagg aggtcaaaaa  3540
cagaggattg ctattgcccg agccctcatc agacaacctc aaatcctcct gttggatgaa  3600
gctacatcag ctctggatac tgaaagtgaa aaggttgtcc aagaagccct ggacaaagcc  3660
agagaaggcc gcacctgcat tgtgattgct caccgcctgt ccaccatcca gaatgcagac  3720
ttaatagtgg tgtttcagaa tgggagagtc aaggagcatg gcacgcatca gcagctgctg  3780
gcacagaaag gcatctattt ttcaatggtc agtgtccagg ctgggacaca gaacttatga  3840
```

```
SEQ ID NO: 67           moltype = DNA  length = 1569
FEATURE                 Location/Qualifiers
misc_feature            1..1569
                        note = Synthetic: antiCD19-scFv-antiCD3-scFV sequence
source                  1..1569
                        mol_type = other DNA
                        organism = synthetic construct
SEQUENCE: 67
atggatatgc gcgtacccgc tcaacttctg ggtttgttgc tgctttggct caggggagcc  60
cgctgtgccg cggacatcca gctgacccag agccccgcca gcctggccgt gagcctgggc  120
cagagagcca ccatcagctg caaggccagc cagagcgtgg actacgacgg cgacagctac  180
ctgaactggt accagcagat ccccggccag ccccccaagc tgctgatcta cgacgccagc  240
aacctggtga gcggcatccc ccccagattc agcggcagcg gcagcggcac cgacttcacc  300
ctgaacatcc accccgtgga gaaggtggac gccgccacct accactgcca gcagagcacc  360
gaggacccct ggaccttcgg cggcggcacc aagctggaga tcaagggcgg cggcggcagc  420
ggcggcggcg gcagcggcgg cggcggcagc caggtgcagc tgcagcagag cggcgccgag  480
ctggtgagac ccggcagcag cgtgaagatc agctgcaagg ccagcggcta cgccttcagc  540
agctactgga tgaactgggt gaagcagaga cccggccagg gcctggagtg gatcggccag  600
atctggcccg gcgacggcga caccaactac aacggcaagt tcaagggcaa ggccaccctg  660
accgccgacg agagcagcag caccgcctac atgcagctga gcagcctggc cagcgaggac  720
agcgccgtgt acttctgcgc cagaagagag accaccaccg tgggcagata ctactacgcc  780
atggactact ggggccaggg caccaccgtg accgtgagca gcggcggcgg cggcagcgac  840
atcaagctgc agcagagcgg cgccgagctg gccagacccg gcgccagcgt gaagatgagc  900
tgcaagacca gcggctacac cttcaccaga tacaccatgc actgggtgaa gcagagaccc  960
ggccagggcc tggagtggat cggctacatc aaccccagca gaggctacac caactacaac  1020
cagaagttca aggacaaggc caccctgacc accgacaaga gcagcagcac cgcctacatg  1080
cagctgagca gcctgaccag cgaggacagc gccgtgtact actgcgccag atactacgac  1140
gaccactact gcctggacta ctggggccag ggcaccaccc tgaccgtgag cagcgtggag  1200
ggcggcagcg gcggcagcgg cggcagcggc ggcagcggcg gcgtggacga catccagctg  1260
acccagagcc ccgccatcat gagcgccagc cccggcgaga aggtgaccat gacctgcaga  1320
gccagcagca gcgtgagcta catgaactgg taccagcaga agagcggcac cagccccaag  1380
agatggatct acgacaccag caaggtggcc agcggcgtgc cctacagatt cagcggcagc  1440
ggcagcggca ccagctacag cctgaccatc agcagcatgg aggccgagga cgccgccacc  1500
```

```
tactactgcc agcagtggag cagcaacccc ctgaccttcg gcgccggcac caagctggag  1560
ctgaagtag                                                          1569

SEQ ID NO: 68           moltype = DNA  length = 4320
FEATURE                 Location/Qualifiers
misc_feature            1..4320
                        note = Synthetic: Zero-CpG B-domain-deleted Factor VIII
                         sequence
source                  1..4320
                        mol_type = other DNA
                        organism = synthetic construct
SEQUENCE: 68
atggccacca gaagatacta cctgggagct gtggagctga gctgggacta catgcagtct  60
gacctgggag agctgcctgt ggatgccaga ttcccccca gagtgcccaa gagcttcccc  120
ttcaacacct ctgtggtgta caagaagacc ctgtttgtgg agttcacaga ccacctgttc  180
aacattgcca agcccagacc cccctggatg ggcctgctgg gccccaccat ccaggctgag  240
gtgtatgaca cagtggtgat caccctgaag aacatggcca gccaccctgt gagcctgcat  300
gctgtgggag tgagctactg gaaggcctct gagggagctg agtatgatga ccagaccagc  360
cagagagaga aggaggatga caaggtgttc cctggaggca gccacaccta tgtgtggcag  420
gtgctgaagg agaatggccc catggcctct gaccccctgt gcctgaccta cagctacctg  480
agccatgtgg acctggtgaa ggacctgaac tctggcctga ttggagccct gctggtgtgc  540
agagagggca gcctggccaa ggagaagacc cagaccctgc acaagttcat cctgctgttt  600
gctgtgtttg atgagggcaa gagctggcac tctgagacca agaacagcct gatgcaggac  660
agagatgctg cctctgccag agcctggccc aagatgcaca cagtgaatgg ctatgtgaac  720
agaagcctgc ctggcctgat tggctgccac agaaagtctg tgtactggca tgtgattggc  780
atgggcacca cccctgaggt gcacagcatc ttcctggagg gccacacctt cctggtgaga  840
aaccacagac aggccagcct ggagatcagc cccatcacct tcctgacagc ccagaccctg  900
ctgatggacc tgggccagtt cctgctgttc tgccacatca gcagccacca gcatgatggc  960
atggaggcct atgtgaaggt ggacagctgc cctgaggagc cccagctgag aatgaagaac  1020
aatgaggagg ctgaggacta tgatgatgac ctgacagact ctgagatgga tgtggtgaga  1080
tttgatgatg acaacagccc cagcttcatc cagatcagat ctgtggccaa gaagcacccc  1140
aagacctggg tgcactacat tgctgctgag gaggaggact gggactatgc cccccctggtg  1200
ctggcccctg atgacagaag ctacaagagc cagtacctga acaatggccc ccagagaatt  1260
ggcagaaagt acaagaaggt gagattcatg gcctacacag atgagacctt caagaccaga  1320
gaggccatcc agcatgagtc tggcatcctg ggcccccctgc tgtatggaga ggtgggagac  1380
accctgctga tcatcttcaa gaaccaggcc agcagaccct acaacatcta cccccatggc  1440
atcacagatg tgagacccct gtacagcaga agactgccca agggagtgaa gcacctgaag  1500
gacttcccca tcctgcctgg agagatcttc aagtacaagt ggacagtgac agtggaggat  1560
ggccccacca agtctgaccc cagatgcctg accagatact acagcagctt tgtgaacatg  1620
gagagagacc tggcctctgg cctgattggc cccctgctga tctgctacaa ggagtctgtg  1680
gaccagagag gcaaccagat catgtctgac aagagaaatg tgatcctgtt ctctgtgttt  1740
gatgagaaca gaagctggta cctgacagag aacatccaga gattcctgcc caaccctgct  1800
ggagtgcagc tggaggaccc tgagttccag gccagcaaca tcatgcacag catcaatggc  1860
tatgtgtttg acagcctgca gctgtctgtg tgcctgcatg aggtggccta ctggtacatc  1920
ctgagcattg gagcccagac agacttcctg tctgtgttct tctctggcta caccttcaag  1980
cacaagatgg tgtatgagga caccctgacc ctgttcccct tctctggaga gacagtgttc  2040
atgagcatgg agaaccctgg cctgtggatc ctgggctgcc acaactctga cttcagaaac  2100
agaggcatga cagccctgct gaaggtgagc agctgtgaca agaacacagg agactactat  2160
gaggacagct atgaggacat ctctgcctac ctgctgagca agaacaatgc cattgagccc  2220
agaagcttca gccagaaccc ccctgtgctg aagagacacc agagagagat caccagaacc  2280
accctgcagt ctgaccagga ggagattgac tatgatgaca ccatctctgt ggagatgaag  2340
aaggaggact ttgacatcta tgatgaggat gagaaccaga gccccagaag cttccagaag  2400
aagaccagac actacttcat tgctgctgtg gagagactgt gggactatgg catgagcagc  2460
agcccccatg tgctgagaaa cagagcccag tctggctctg tgccccagtt caagaaggtg  2520
gtgttccagg agttcacaga tggcagcttc acccagcccc tgtacagagg agagctgaat  2580
gagcacctgg gcctgctggg cccctacatc agagctgagg tggaggacaa catcatggtg  2640
accttcagaa accaggccag cagaccctac agcttctaca gcagcctgat cagctatgag  2700
gaggaccaga gacagggagc tgagcccaga aagaactttg tgaagcccaa tgagaccaag  2760
acctacttct ggaaggtgca gcaccacatg gcccccacca aggatgagtt tgactgcaag  2820
gcctgggcct acttctctga tgtggacctg gagaaggatg tgcactctgg cctgattggc  2880
cccctgctgg tgtgccacac caacaccctg aaccctgccc atggcagaca ggtgacagtg  2940
caggagtttg ccctgttctt caccatcttt gatgagacca agagctggta cttcacagag  3000
aacatggaga gaaactgcag agccccctgc aacatccaga tggaggaccc caccttcaag  3060
gagaactaca gattccatgc catcaatggc tacatcatgg acaccctgcc tggcctggtg  3120
atggcccagg accagagaat cagatggtac ctgctgagca tgggcagcaa tgagaacatc  3180
cacagcatcc acttctctgg ccatgtgttc acagtgagaa agaaggagga gtacaagatg  3240
gccctgtaca acctgtaccc tggagtgttt gagacagtgg agatgctgcc cagcaaggct  3300
ggcatctgga gagtggagtg cctgattgga gagcacctgc atgctggcat gagcaccctg  3360
ttcctggtgt acagcaacaa gtgccagacc cccctgggca tggcctctgg ccacatcaga  3420
gacttccaga tcacagcctc tggccagtat ggccagtggg cccccaagct ggccagactg  3480
cactactctg gcagcatcaa tgcctggagc accaaggagc ccttcagctg gatcaaggtg  3540
gacctgctgg cccccatgat catccatggc atcaagaccc agggagccag acagaagttc  3600
agcagcctgt acatcagcca gttcatcatc atgtacagcc tggatggcaa gaagtggcag  3660
acctacagag gcaacagcac aggcaccctg atggtgttct ttggcaatgt ggacagctct  3720
ggcatcaagc acaacatctt caacccccccc atcattgcca gatacatcag actgcacccc  3780
acccactaca gcatcagaag caccctgaga atggagctga tgggctgtga cctgaacagc  3840
tgcagcatgc ccctgggcat ggagagcaag gccatctctg atgcccagat cacagccagc  3900
agctacttca ccaacatgtt tgccacctgg agccccagca aggccagact gcacctgcag  3960
ggcagaagca atgcctggag accccaggtg aacaacccca aggagtggct gcaggtggac  4020
```

-continued

```
ttccagaaga ccatgaaggt gacaggagtg accacccagg gagtgaagag cctgctgacc  4080
agcatgtatg tgaaggagtt cctgatcagc agcagccagg atggccacca gtggaccctg  4140
ttcttccaga atggcaaggt gaaggtgttc cagggcaacc aggacagctt cacccctgtg  4200
gtgaacagcc tggacccccc cctgctgacc agatacctga gaatccaccc ccagagctgg  4260
gtgcaccaga ttgccctgag aatggaggtg ctgggctgtg aggcccagga cctgtactga  4320
```

```
SEQ ID NO: 69          moltype = DNA  length = 4398
FEATURE                Location/Qualifiers
misc_feature           1..4398
                       note = ATP7B sequence
source                 1..4398
                       mol_type = genomic DNA
                       organism = Homo sapiens
SEQUENCE: 69
atgcccgagc aggagcggca gatcacagcc agagagggcg cctctaggaa gatcctgtct  60
aagctgagcc tgccaaccag agcctgggag cctgccatga agaagagctt cgcctttgat  120
aacgtgggat acgagggagg cctggacgga ctgggaccta gctcccaggt ggccacctcc  180
acagtgcgca tcctgggcat gacatgccag tcttgcgtga agagcatcga ggatcggatc  240
tctaatctga agggcatcat ctccatgaag gtgtctctgg agcagggcag cgccaccgtg  300
aagtatgtgc catccgtggt gtgcctgcag caggtgtgcc accagatcgg cgacatgggc  360
ttcgaggcct ctatcgcaga gggcaaggca gccagctggc cttctcgcag cctgccagca  420
caggaggcag tggtgaagct gagggtggag ggcatgacat gccagagctg cgtgagcagc  480
atcgagggca aggtgagaaa gctgcagggc gtggtgaggg tgaaggtgtc cctgtctaac  540
caggaggccg tgatcaccta ccagccctat ctgatccagc ctgaggatct gagggaccac  600
gtgaatgata tgggcttcga ggccgccatc aagtctaagg tggcaccact gagcctggga  660
ccaatcgaca tcgagcgcct gcagtccacc aacccaaagc ggcccctgtc ctctgccaac  720
cagaacttca acaattccga gacactgggc caccagggct ctcacgtggt gaccctgcag  780
ctgcgcatcg atggcatgca ctgcaagagc tgcgtgctga acatcgagga gaatatcggc  840
cagctgctgg gcgtgcagag catccaggtg tccctggaga acaagacagc ccaggtgaag  900
tacgaccctt cctgcacctc tccagtggcc ctgcagaggg caatcgaggc cctgccccct  960
ggcaatttca aggtgagcct gccagatgga gcagagggct ccggcaccga ccacagaagc  1020
tcctctagcc acagccctgg ctccccacca aggaaccagg tgcagggcac atgtagcacc  1080
acactgatcg ccatcgccgg catgacctgc gcctcttgcg tgcacagcat cgagggcatg  1140
atctcccagc tggagggcgt gcagcagatc agcgtgtccc tggccgaggg caccgcaaca  1200
gtgctgtata atccctctgt gatcagccct gaggagctga gggcagcaat cgaggatatg  1260
ggatttgagg cctccgtggt gtctgagagc tgctccacaa accccctggg caatcactcc  1320
gccggcaact ctatggtgca gaccacagat ggcaccccca caagcgtgca ggaggtggca  1380
cctcacaccg gccgcctgcc agcaaatcac gcaccagaca tcctggccaa gtccccacag  1440
tctacacggg ccgtggcacc acagaagtgt tttctgcaga tcaagggcat gacctgcgcc  1500
agctgcgtga gcaacatcga gagaaatctg cagaaggagg caggcgtgct gtccgtgctg  1560
gtggccctga tggcaggcaa ggccgagatc aagtacgatc ctgaagtgat ccagccactg  1620
gagatcgccc agttcatcca ggacctgggc tttgaggccg ccgtgatgga ggattatgcc  1680
ggcagcgacg gcaacatcga gctgaccatc acaggcatga cctgcgcctc ctgcgtgcac  1740
aacatcgagt ctaagctgac caggacaaat ggcatcacat acgcctccgt ggccctggcc  1800
acctctaagg ccctggtgaa gttcgatccc gagatcatcg gccctagaga catcatcaag  1860
atcatcgagg agatcggctt tcacgcctcc ctggcccaga ggaacccaaa tgcccaccac  1920
ctggatcaca agatggagat caagcagtgg aagaagagct tcctgtgctc cctggtgttt  1980
ggcatccccg tgatggccct gatgatctac atgctgatcc ctagcaacga gccacaccag  2040
agcatggtgc tggaccacaa catcatccct ggcctgagca tcctgaatct gatcttcttt  2100
atcctgtgca cattcgtgca gctgctgggc ggctggtact tttatgtgca ggcctataag  2160
agcctgcggc acagatccgc caatatggat gtgctgatcg tgctggccac ctctatcgcc  2220
tacgtgtata gcctggtcat cctggtggtg gcagtggcag agaaggcaga gagatccccc  2280
gtgaccttct ttgacacacc tccaatgctg ttcgtgttta tcgccctggg caggtggctg  2340
gagcacctgg ccaagtctaa gaccagcgag gccctggcca agctgatgag cctgcaggcc  2400
acagaggcca ccgtggtgac actgggcgag gataacctga tcatcagaga ggagcaggtg  2460
cctatggagc tggtgcagag gggcgacatc gtgaaggtgg tgccaggcgg caagttcccc  2520
gtggatggca aggtgctgga gggcaataca atggccgacg agagcctgat caccggagag  2580
gccatgcctg tgaccaagaa gccaggctcc acagtgatcg ccggctctat caacgcccac  2640
ggcagcgtgc tgatcaaggc caccacgtg ggcaatgata ccacactggc ccagatcgtg  2700
aagctggtgg aggaggccca gatgtccaag gcaccaatcc agcagctggc cgaccgcttc  2760
agcggctact tcgtgccttt tatcatcatc atgtccaccc tgacactggt ggtgtggatc  2820
gtgatcggct tcatcgattt tggcgtggtg cagagatatt ttcccaaccc taataagcac  2880
atcagccaga ccgaagtgat catcaggttc gcctttcaga cctctatcac agtgctgtgc  2940
atcgcatgcc cttgtagcct gggcctggcc accccaacag ccgtgatggt gggcacagga  3000
gtggcagcac agaacggcat cctgatcaag ggcggcaagc ccctggagat ggcccacaag  3060
atcaagaccg tgatgtttga taagaccggc acaatcaccc acggcgtgcc cagagtgatg  3120
agagtgctgc tgctgggcga cgtggccaca ctgccactga ggaaggtgct ggccgtggtg  3180
ggcaccgcag aggcctcctc tgagcaccca ctgggagtgg ccgtgacaaa gtactgcaag  3240
gaggagctgg gcacagagac cctgggctat tgtaccgact tccaggccgt gcccggctgc  3300
ggaatcggct gtaaggtgtc taacgtggag ggcatcctgg cacacagcga gagacccctg  3360
tctgcccctg ccagccacct gaatgaggca ggctccctgc cagcagagaa ggatgccgtg  3420
ccccagacat ttctgtgct gatcggcaac agggagtggc tgcggagaaa tggcctgacc  3480
atcagctccg acgtgagcga cgccatgaca gaccacgaga tgaagggcca gaccgccatc  3540
ctggtggcca tcgatggcgt gctgtgcggc atgatcgcca tcgcagacgc agtgaagcag  3600
gaggccgccc tggccgtgca caccctgcag agcatgggcg tggatgtggt gctgatcacc  3660
ggcgacaaca ggaagacagc cagagccatc gccacccaag tgggcatcaa taaggtgttc  3720
gccgaggtgc tgccttctca caaggtggcc aaggtgcagg agctgcagaa caagggcaag  3780
aaggtggcta tggtgggcga tggcgtgaat gacagcccag ccctggccca ggcagacatg  3840
ggagtggcaa tcggcacagg caccgatgtg gcaatcgagg cagcagacgt ggtgctgatc  3900
```

```
agaaacgatc tgctggacgt ggtggcctcc atccacctgt ctaagcgcac cgtgaggcgc  3960
atccggatca acctggtgct ggccctgatc tacaatctgg tgggcatccc aatcgcagca  4020
ggcgtgttta tgcctatcgg catcgtgctg cagccctgga tgggctccgc cgctatggcc  4080
gcctctagcg tgtctgtggt gctgtcctct ctgcagctga agtgctacaa gaagcctgac  4140
ctggagcggt acgaggcaca ggcccacggc cacatgaagc cactgaccgc ctcccaggtg  4200
tctgtgcaca tcggcatgga cgataggtgg agggatagcc cacgggccac accctgggac  4260
caggtgagct acgtgtccca ggtgagcctg agcagcctga ccagcgacaa gcctagccgc  4320
cacagcgccg ccgccgacga tgacggcgat aagtggtccc tgctgctgaa tggccgggac  4380
gaggagcagt atatctga                                                4398

SEQ ID NO: 70          moltype = DNA  length = 4398
FEATURE                Location/Qualifiers
misc_feature           1..4398
                       note = Synthetic: Zero-CpG ATP7B sequence
source                 1..4398
                       mol_type = other DNA
                       organism = synthetic construct
SEQUENCE: 70
atgcctgagc aggagagaca gatcacagcc agagagggag ccagcagaaa gatcctgagc  60
aagctgagcc tgcccaccag agcctgggag cctgccatga agaagagctt tgcctttgac  120
aatgtgggct atgagggagg cctggatggc ctgggcccca gcagccaggt ggccaccagc  180
acagtgagaa tcctgggcat gacctgccag agctgtgtga agagcattga ggacagaatc  240
agcaacctga agggcatcat cagcatgaag gtgagcctgg agcagggctc tgccacagtg  300
aagtatgtgc cctctgtggt gtgcctgcag caggtgtgcc accagattgg agacatgggc  360
tttgaggcca gcattgctga gggcaaggct gccagctggc ccagcagaag cctgcctgcc  420
caggaggctg tggtgaagct gagagtggag ggcatgacct gccagagctg tgtgagcagc  480
attgagggca aggtgagaaa gctgcaggga gtggtgagag tgaaggtgag cctgagcaac  540
caggaggctg tgatcaccta ccagccctac ctgatccagc ctgaggacct gagagaccat  600
gtgaatgaca tgggctttga ggctgccatc aagagcaagg tggccccccct gagcctgggc  660
cccattgaca ttgagagact gcagagcacc aaccccaaga gacccctgag ctctgccaac  720
cagaacttca acaactctga gaccctgggc caccagggca gccatgtggt gaccctgcag  780
ctgagaattg atggcatgca ctgcaagagc tgtgtgctga acattgagga gaacattggc  840
cagctgctgg gagtgcagag catccaggtg agcctggaga acaagacagc ccaggtgaag  900
tatgacccca gctgcaccag ccctgtggcc ctgcagagag ccattgaggc cctgcccccct  960
ggcaacttca aggtgagcct gcctgatgga gctgagggct ctggcacaga ccacagaagc  1020
agcagcagcc acagccctgg cagccccccc agaaaccagg tgcagggcac ctgcagcacc  1080
accctgattg ccattgctgg catgacctgt gccagctgtg tgcacagcat tgagggcatg  1140
atcagccagc tggagggagt gcagcagatc tctgtgagcc tggctgaggg cacagccaca  1200
gtgctgtaca acccctctgt gatcagccct gaggagctga gagctgccat tgaggacatg  1260
ggctttgagg cctctgtggt gtctgagagc tgcagcacca acccccctggg caaccactct  1320
gctggcaaca gcatggtgca gaccacagat ggcaccccca cctctgtgca ggaggtggcc  1380
ccccacacag gcagactgcc tgccaaccat gcccctgaca tcctggccaa gagcccccag  1440
agcaccagag ctgtggcccc ccagaagtgc ttcctgcaga tcaagggcat gacctgtgcc  1500
agctgtgtga gcaacattga gagaaacctg cagaaggagg ctggagtgct gtctgtgctg  1560
gtggccctga tggctggcaa ggctgagatc aagtatgacc ctgaggtgat ccagcccctg  1620
gagattgccc agttcatcca ggacctgggc tttgaggctg ctgtgatgga ggactatgct  1680
ggctctgatg gcaacattga gctgaccatc acaggcatga cctgtgccag ctgtgtgcac  1740
aacattgaga gcaagctgac cagaaccaat ggcatcacct atgcctctgt ggccctggcc  1800
accagcaagg ccctggtgaa gtttgaccct gagatcattg gccccagaga catcatcaag  1860
atcattgagg agattggctt ccatgccagc ctggcccaga gaaaccccaa tgcccaccac  1920
ctggaccaca agatggagat caagcagtgg aagaagagct tcctgtgcag cctggtgttt  1980
ggcatccctg tgatggccct gatgatctac atgctgatcc ccagcaatga gccccaccag  2040
agcatggtgc tggaccacaa catcatccct ggcctgagca tcctgaacct gatcttcttc  2100
atcctgtgca cctttgtgca gctgctggga ggctggtact tctatgtgca ggcctacaag  2160
agcctgagac acagatctgc caacatggat gtgctgattg tgctggccac cagcattgcc  2220
tatgtgtaca gcctggtgat cctggtggtg gctgtggctg agaaggctga gagaagccct  2280
gtgaccttct ttgacacccc ccccatgctg tttgtgttca ttgccctggg cagatggctg  2340
gagcacctgg ccaagagcaa gacctctgag gccctggcca agctgatgag cctgcaggcc  2400
acagaggcca cagtggtgac cctgggagag gacaacctga tcatcagaga ggagcaggtg  2460
cccatggagc tggtgcagag aggagacatt gtgaaggtgg tgcctggagg caagttccct  2520
gtggatggca aggtgctgga gggcaacacc atggctgatg agagcctgat cacaggagag  2580
gccatgcctg tgaccaagaa gcctggcagc acagtgattg ctggcagcat caatgcccat  2640
ggctctgtgc tgatcaaggc caccccatgtg ggcaatgaca ccaccctggc ccagattgtg  2700
aagctggtgg aggaggccca gatgagcaag gcccccatcc agcagctggc tgacagattc  2760
tctggctact ttgtgccctt catcatcatc atgagcaccc tgaccctggt ggtgtggatt  2820
gtgattggct tcattgactt tggagtggtg cagagatact tccccaaccc caacaagcac  2880
atcagccaga cagaggtgat catcagattt gccttccaga ccagcatcac agtgctgtgc  2940
attgcctgcc cctgcagcct gggcctggcc acccccacag ctgtgatggt gggcacagga  3000
gtggctgccc agaatggcat cctgatcaag ggaggcaagc ccctggagat ggcccacaag  3060
atcaagacag tgatgtttga caagacaggc accatcaccc atggagtgcc cagagtgatg  3120
agagtgctgc tgctgggaga tgtggccacc ctgcccctga gaaaggtgct ggctgtggtg  3180
ggcacagctg aggccagctc tgagcacccc ctgggagtgg ctgtgaccaa gtactgcaag  3240
gaggagctgg gcacagagac cctgggctac tgcacagact tccaggctgt gcctggctgt  3300
ggcattggct gcaaggtgag caatgtggag ggcatcctgg cccactctga gagacccctg  3360
tctgcccctg ccagccacct gaatgaggct ggcagcctgc ctgctgagaa ggatgctgtg  3420
ccccagacct tctctgtgct gattggcaac agagagtggc tgagaagaaa tggcctgacc  3480
atcagctctg atgtgtctga tgccatgaca gaccatgaga tgaagggcca gacagccatc  3540
ctggtggcca ttgatggagt gctgtgtggc atgattgcca ttgctgatgc tgtgaagcag  3600
gaggctgccc tggctgtgca caccctgcag agcatgggag tggatgtggt gctgatcaca  3660
```

```
ggagacaaca gaaagacagc cagagccatt gccacccagg tgggcatcaa caaggtgttt  3720
gctgaggtgc tgcccagcca caaggtggcc aaggtgcagg agctgcagaa caagggcaag  3780
aaggtggcca tggtgggaga tggagtgaat gacagccctg ccctggccca ggctgacatg  3840
ggagtggcca ttggcacagg cacagatgtg gccattgagg ctgctgatgt ggtgctgatc  3900
agaaatgacc tgctggatgt ggtggccagc atccacctga gcaagagaac agtgagaaga  3960
atcagaatca acctggtgct ggccctgatc tacaacctgg tgggcatccc cattgctgct  4020
ggagtgttca tgcccattgg cattgtgctg cagccctgga tgggctctgc tgccatggct  4080
gccagctctg tgtctgtggt gctgagcagc ctgcagctga agtgctacaa gaagcctgac  4140
ctggagagat atgaggccca ggcccatggc cacatgaagc ccctgacagc cagccaggtg  4200
tctgtgcaca ttggcatgga tgacagatgg agagacagcc ccagagccac cccctgggac  4260
caggtgagct atgtgagcca ggtgagcctg agcagcctga cctctgacaa gcccagcaga  4320
cactctgctg ctgctgatga tgatggagac aagtggagcc tgctgctgaa tggcagagat  4380
gaggagcagt acatctga                                                 4398

SEQ ID NO: 71          moltype = DNA  length = 652
FEATURE                Location/Qualifiers
misc_feature           1..652
                       note = Synthetic: a minimized cruciform structure
                        containing two inverted repeat sequences separated by a
                        minimal R6K gamma origin
source                 1..652
                       mol_type = other DNA
                       organism = synthetic construct
SEQUENCE: 71
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag cctgtcagcc gttaagtgtt cctgtgtcac tcaaaattgc tttgagaggc  180
tctaagggct tctcagtgcg ttacatccct ggcttgttgt ccacaaccgt taaaccttaa  240
aagctttaaa agccttatat attctttttt tcttataaaa cttaaaacct tagaggctat  300
ttaagttgct gatttatatt aattttattg ttcaaacatg agagcttagt acgtgaaaca  360
tgagagctta gtacgttagc catgagagct tagtacgtta gccatgaggg tttagttcgt  420
taaacatgag agcttagtac gttaaacatg agagcttagt acgtgaaaca tgagagctta  480
gtacgtacta tcaacaggtt gaactgctga tcttcagatc ggctgcgcgc tcgctcgctc  540
actgaggccg cccgggcaaa gcccgggcgt cgggcgacct ttggtcgccc ggcctcagtg  600
agcgagcgag cgcgcagaga gggagtggcc aactccatca ctaggggttc ct          652

SEQ ID NO: 72          moltype = DNA  length = 3775
FEATURE                Location/Qualifiers
misc_feature           1..3775
                       note = Synthetic: Halo sTNALP vector comprising a minimized
                        cruciform structure IR-R6K Ori-IR and EF1A-driven
                        sTNALP-(DSS)6 transgene
source                 1..3775
                       mol_type = other DNA
                       organism = synthetic construct
SEQUENCE: 72
ttcgcgcctg tctcgctgct ttcgataagt ctctagccat ttaaaatttt tgatgacctg  60
ctgcgacgct ttttttctgg caagatagtc ttgtaaatgc gggccaagat ctgcacactg  120
gtatttcggt ttttggggcc gcgggcggcg acggggcccg tgcgtcccag cgcacatgtt  180
cggcgaggcg gggcctgcga gcgcggccac cgagaatcgg acgggggtag tctcaagctg  240
gccggcctgc tctggtgcct ggcctcgcgc cgccgtgtat cgccccgccc tgggcggcaa  300
ggctggcccg gtcggcacca gttgcgtgag cggaaagatg gccgcttccc ggccctgctg  360
cagggagctc aaaatggagg acgcggcgct cgggagagcg ggcgggtgag tcacccacac  420
aaaggaaaag ggcctttccg tcctcagccg tcgcttcatg tgactccacg gagtaccggg  480
cgccgtccag gcacctcgat tagttctcga gcttttggag tacgtcgtct ttaggttggg  540
gggaggggtt ttatgcgatg gagtttcccc acactgagtg ggtggagact gaagttaggc  600
cagcttggca cttgatgtaa ttctccttgg aatttgccct ttttgagttt ggatcttggt  660
tcattctcaa gcctcagaca gtggttcaaa gtttttttct tccatttcag gtgtcgtgag  720
ctagctgcca ccatggatat gagagtacct gctcaacttc tgggtttgtt gctgctttgg  780
ctcaggggag ccagatgtgc tgccctggtt cctgagaagg aaaaggaccc caagtactgg  840
agagatcagg cacaggagac actgaagtat gccctggagc tgcagaagct gaataccaat  900
gttgccaaaa atgtgatcat gttcctggga gatgggatgg gagtcagcac agtgacagct  960
gctagaatcc tgaagggaca gctgcatcat aatcctggag aagagaccag actggaaatg  1020
gataagttcc cctttgtggc cctgagcaag acatataata ccaatgccca agtgcctgat  1080
tctgctggaa cagctacagc ttacctgtgt ggagtgaagg ccaatgaggg aacagtggga  1140
gtgtctgctg ccacagaaag aagcagatgc aacaccaccc aaggcaatga ggtgacaagc  1200
atcctgagat gggccaagga tgctggcaaa tctgtgggca ttgtgacaac aaccagagtg  1260
aaccatgcca ccccatctgc tgcttatgcc cattctgctg acagagactg gtactctgac  1320
aatgagatgc ctccagaggc tctgtcccag ggttgtaaag atattgccta tcagctgatg  1380
cacaacatca gagacattga tgtgatcatg ggaggaggca ggaagtacat gtaccccaag  1440
aacaagacag atgtggagta tgagtctgat gagaaggcca gaggcacaag actggatggc  1500
ctggacctgg tggacacctg gaagtctttt aagcccagat acaagcacag ccacttcatc  1560
tggaacagaa cagaactgct gaccctggac ccccacaatg tggactacct gctgggcctg  1620
tttgagcctg gagatatgca gtatgagctg aatagaaaca atgtgacaga cccctccctg  1680
tctgaaatgg tggtggtggc catccagatc ctgagaaaga accctaaggg ctttttcctg  1740
ctggttgagg gaggaagaat tgaccatggc catcatgagg gcaaggctaa gcaggccctg  1800
catgaggctg tggagatgga cagagccatt ggccaagctg gctctctgac cagctcagag  1860
gacaccctga cagtggtgac agctgatcac tctcatgtgt tcacttttgg aggatatacc  1920
cctagaggca acagcatctt tggcctggcc cctatgctgt ctgacacaga caaaaagccc  1980
```

```
ttcacagcca tcctgtatgg caatggccca ggatacaagg tggtgggagg agagagagag  2040
aatgtgtcta tggtggacta tgcacacaac aactaccagg cccagtctgc tgttcctctg  2100
agacatgaaa cacatggagg ggaagatgtg gcagtgtttt ctaaaggccc tatggctcac  2160
ctgctgcatg gagtccatga gcagaactat gtgccccatg tgatggccta tgctgcctgc  2220
attggagcaa acctgggcca ctgtgcccct gccagctccg actcctctga ttcttctgac  2280
agctcagact cctctgatag ctctgacagc tcttgagaat tcgtttaaac ccgctgatca  2340
gcctcgactg tgccttctag ttgccagcca tctgttgttt gcccctcccc cgtgccttcc  2400
ttgaccctgg aaggtgccac tcccactgtc ctttcctaat aaaatgagga aattgcatcg  2460
cattgtctga gtaggtgtca ttctattctg gggggtgggg tggggcagga cagcaagggg  2520
gaggattggg aagacaatag caggcatgct ggggatgcgg tgggctctat ggcttctgag  2580
gcggaaagaa ccagctgggg ctccgcgccc ggggagccca aaggttaccc cagttggggt  2640
acgtaaggaa cccctagtga tggagttggc cactccctct ctgcgcgctc gctcgctcac  2700
tgaggccggg cgaccaaagg tcgcccgacg cccgggcttt gcccgggcgg cctcagtgag  2760
cgagcgagcg cgcagcctgt cagccgttaa gtgttcctgt gtcactcaaa attgctttga  2820
gaggctctaa gggcttctca gtgcgttaca tccctggctt gttgtccaca accgttaaac  2880
cttaaaagct ttaaaagcct tatatattct ttttttctta taaaacttaa aaccttagag  2940
gctatttaag ttgctgattt atattaattt tattgttcaa acatgagagc ttagtacgtg  3000
aaacatgaga gcttagtacg ttagccatga gagcttagta cgttagccat gagggtttag  3060
ttcgttaaac atgagagctt agtacgttaa acatgagagc ttagtacgtg aaacatgaga  3120
gcttagtacg tactatcaac aggttgaact gctgatcttc agatcggctg cgcgctcgct  3180
cgctcactga ggccgcccgg gcaaagcccg ggcgtcgggc gacctttggt cgcccggcct  3240
cagtgagcga gcgagcgcgc agagagggag tggccaactc catcactagg ggttcctgcc  3300
tggagacgtt aattaaggct ccggtgcccg tcagtgggca gagcgcacat cgcccacagt  3360
ccccgagaag ttggggggag gggtcggcaa ttgaaccggt gcctagagaa ggtggcgcgg  3420
ggtaaactgg gaaagtgatg tcgtgtactg gctccgcctt tttcccgagg gtgggggaga  3480
accgtatata agtgcagtag tcgccgtgaa cgttcttttt cgcaacgggt ttgccgccag  3540
aacacaggta agtgccgtgt gtggttcccg cgggcctggc ctctttacgg gttatggccc  3600
ttgcgtgcct tgaattactt ccactggctg cagtacgtga ttcttgatcc cgagcttcgg  3660
gttggaagtg ggtgggagag ttcgaggcct tgcgcttaag gagccccttc gcctcgtgct  3720
tgagttgagg cctggcctgg gcgctggggc cgccgcgtgc gaatctggtg gcacc       3775
```

```
SEQ ID NO: 73           moltype = DNA  length = 3715
FEATURE                 Location/Qualifiers
misc_feature            1..3715
                        note = Synthetic: Halo sTNALP vector comprising a minimized
                         cruciform structure IR-R6K Ori-IR and EF1A-driven
                         cynomolgus monkey sTNALP transgene
source                  1..3715
                        mol_type = other DNA
                        organism = synthetic construct
SEQUENCE: 73
ttcgcgcctg tctcgctgct ttcgataagt ctctagccat ttaaaatttt tgatgacctg  60
ctgcgacgct ttttttctgg caagatagtc ttgtaaatgc gggccaagat ctgcacactg  120
gtatttcggt ttttggggcc gcgggcggcg acggggcccg tgcgtcccag cgcacatgtt  180
cggcgaggcg gggcctgcga gcgcggccac cgagaatcgg acgggggtag tctcaagctg  240
gccggcctgc tctggtgcct ggcctcgcgc cgccgtgtat cgccccgccc tgggcggcaa  300
ggctggcccg gtcggcacca gttgcgtgag cggaaagatg gccgcttccc ggccctgctg  360
cagggagctc aaaatggagg acgcggcgct cgggagagcg ggcgggtgag tcacccacac  420
aaaggaaaag ggcctttccg tcctcagccg tcgcttcatg tgactccacg gagtaccggg  480
cgccgtccag gcacctcgat tagttctcga gcttttggag tacgtcgtct ttaggttggg  540
gggaggggtt ttatgcgatg gagtttcccc acactgagtg ggtggagact gaagttaggc  600
cagcttggca cttgatgtaa ttctccttgg aatttgccct ttttgagttt ggatcttggt  660
tcattctcaa gcctcagaca gtggttcaaa gtttttttct tccatttcag gtgtcgtgag  720
ctagctgcca ccatgagagt gcctgcccag ctgctgggcc tgctgctgct gtggctgaga  780
ggagccagat gtgctgccct ggtgcctgag aaggagaagg accccaagta ctggagagac  840
caggcccagg agaccctgaa gtatgccctg gagctgcaga agctgaacac caatgtggcc  900
aagaatgtga tcatgttcct gggagatggc atgggagtga gcacagtgac agccaccaga  960
atcctgaagg gccagctgca ccacaaccct ggagaggaga ccagactgga gatggacaag  1020
ttcccctttg tggccctgag caagacctac aacaccaatg cccaggtgcc tgactctgct  1080
ggcacagcca cagcctacct gtgtggagtg aaggccaatg agggcacagt gggagtgtct  1140
gctgccacag agagaagcag atgcaacacc acccagggca atgaggtgac cagcatcctg  1200
agatgggcca aggatgctgg caagtctgtg ggcattgtga ccaccaccag agtgaaccat  1260
gccacccccct ctgctgccta tgcccactct gctgacagag actggtactc tgacaatgag  1320
atgcccccctg aggccctgag ccagggctgc aaggacattg cctaccagct ggtgcacaac  1380
atcagagaca ttgatgtgat catgggagga ggcagaaagt acatgtaccc caagaacaag  1440
acagatgtgg agtatgagat tgatgagaag gccagaggca ccagactgga tggcctggac  1500
ctggtgaaca tctggaagag cttcaagccc agacacaagc acagccactt catctggaac  1560
agaacagagc tgctgaccct ggacccccac aatgtggact acctgctggg cctgtttgag  1620
cctggagaca tggagtatga gctgaacaga aacaatgtga cagaccccag cctgtctgag  1680
atggtggtgg tggccatcca gatcctgaga aagaacccca agggcttctt cctgctggtg  1740
gagggaggca gaattgacca tggccaccat gagggcaagg ccaagcaggc cctgcatgag  1800
gctgtggaga tggacagagc cattggccag gctggcagca tgaccagcct ggaggacacc  1860
ctgacagtgg tgacagctga ccacagccat gtgttcacct ttggaggcta cacccccaga  1920
ggcaacagca tctttggcct ggcccccatg ctgtctgaca cagacaagaa gcccttcaca  1980
gccatcctgt atggcaatgg ccctggctac aaggtggtgg gaggagagag agagaatgtg  2040
agcatggtgg actatgccca caacaactac caggcccagt ctgctgtgcc cctgagacat  2100
gagacccatg gaggagagga tgtggctgtg ttcagcaagg gccccatggc ccacctgctg  2160
catggagtgc atgagcagaa ctacatcccc catgtgatgg cctatgctgc ctgcattgga  2220
gccaacctgg accactgtgc ccctgccagc agctgagaat tcgtttaaac ccgctgatca  2280
```

```
gcctcgactg tgccttctag ttgccagcca tctgttgttt gcccctcccc cgtgccttcc  2340
ttgaccctgg aaggtgccac tcccactgtc ctttcctaat aaaatgagga aattgcatcg  2400
cattgtctga gtaggtgtca ttctattctg gggggtgggg tggggcagga cagcaagggg  2460
gaggattggg aagacaatag caggcatgct ggggatgcgg tgggctctat ggcttctgag  2520
gcggaaagaa ccagctgggg ctccgcgccc ggggagccca aaggttaccc cagttggggt  2580
acgtaaggaa cccctagtga tggagttggc cactccctct ctgcgcgctc gctcgctcac  2640
tgaggccggg cgaccaaagg tcgcccgacg cccgggcttt gcccgggcgg cctcagtgag  2700
cgagcgagcg cgcagcctgt cagccgttaa gtgttcctgt gtcactcaaa attgctttga  2760
gaggctctaa gggcttctca gtgcgttaca tccctggctt gttgtccaca accgttaaac  2820
cttaaaagct ttaaaagcct tatatattct ttttttctta taaaacttaa aaccttagag  2880
gctatttaag ttgctgattt atattaattt tattgttcaa acatgagagc ttagtacgtg  2940
aaacatgaga gcttagtacg ttagccatga gagcttagta cgttagccat gagggtttag  3000
ttcgttaaac atgagagctt agtacgttaa acatgagagc ttagtacgtg aaacatgaga  3060
gcttagtacg tactatcaac aggttgaact gctgatcttc agatcggctg cgcgctcgct  3120
cgctcactga ggccgcccgg gcaaagcccg ggcgtcgggc gacctttggt cgcccggcct  3180
cagtgagcga gcgagcgcgc agagagggag tggccaactc catcactagg ggttcctgcc  3240
tggagacgtt aattaaggct ccggtgcccg tcagtgggca gagcgcacat cgcccacagt  3300
ccccgagaag ttggggggag gggtcggcaa ttgaaccggt gcctagagaa ggtggcgcgg  3360
ggtaaactgg gaaagtgatg tcgtgtactg gctccgcctt tttcccgagg gtgggggaga  3420
accgtatata agtgcagtag tcgccgtgaa cgttcttttt cgcaacgggt ttgccgccag  3480
aacacaggta agtgccgtgt gtggttcccg cgggcctggc ctctttacgg gttatggccc  3540
ttgcgtgcct tgaattactt ccactggctg cagtacgtga ttcttgatcc cgagcttcgg  3600
gttggaagtg ggtgggagag ttcgaggcct tgcgcttaag gagccccttc gcctcgtgct  3660
tgagttgagg cctggcctgg gcgctggggc cgccgcgtgc gaatctggtg gcacc       3715

SEQ ID NO: 74           moltype = DNA  length = 41
FEATURE                 Location/Qualifiers
misc_feature            1..41
                        note = Synthetic: synthetic dna
source                  1..41
                        mol_type = other DNA
                        organism = synthetic construct
SEQUENCE: 74
ttggccactc cctctctgcg cgctdgctcg ctcactgagg c                       41

SEQ ID NO: 75           moltype = DNA  length = 41
FEATURE                 Location/Qualifiers
misc_feature            1..41
                        note = Synthetic: synthetic dna
source                  1..41
                        mol_type = other DNA
                        organism = synthetic construct
SEQUENCE: 75
gcctcagtga gcgagcgagc gcgcagagag ggagtggcca a                       41

SEQ ID NO: 76           moltype =   length =
SEQUENCE: 76
000

SEQ ID NO: 77           moltype =   length =
SEQUENCE: 77
000

SEQ ID NO: 78           moltype =   length =
SEQUENCE: 78
000

SEQ ID NO: 79           moltype =   length =
SEQUENCE: 79
000

SEQ ID NO: 80           moltype = DNA  length = 20
FEATURE                 Location/Qualifiers
misc_feature            1..20
                        note = Synthetic: synthetic dna
source                  1..20
                        mol_type = other DNA
                        organism = synthetic construct
SEQUENCE: 80
aggaacccct agtgatggag                                               20

SEQ ID NO: 81           moltype = DNA  length = 20
FEATURE                 Location/Qualifiers
misc_feature            1..20
                        note = Synthetic: synthetic dna
source                  1..20
                        mol_type = other DNA
                        organism = synthetic construct
SEQUENCE: 81
```

```
ctccatcact aggggttcct                                        20

SEQ ID NO: 82           moltype = DNA  length = 1257
FEATURE                 Location/Qualifiers
misc_feature            1..1257
                        note = Synthetic: Zero-CpG Alpha-1 anti-trypsin sequence
source                  1..1257
                        mol_type = other DNA
                        organism = synthetic construct
SEQUENCE: 82
atgcccagct ctgtgagctg gggcatcctg ctgctggctg gcctgtgctg cctggtgcct  60
gtgagcctgg ctgaggaccc ccagggagat gctgcccaga agacagacac cagccaccat  120
gaccaggacc accccacctt caacaagatc acccccaacc tggctgagtt tgccttcagc  180
ctgtacagac agctggccca ccagagcaac agcaccaaca tcttcttcag ccctgtgagc  240
attgccacag cctttgccat gctgagcctg ggcaccaagg ctgacaccca tgatgagatc  300
ctggagggcc tgaacttcaa cctgacagag atccctgagg cccagatcca tgagggcttc  360
caggagctgc tgagaaccct gaaccagcct gacagccagc tgcagctgac cacaggcaat  420
ggcctgttcc tgtctgaggg cctgaagctg gtggacaagt tcctggagga tgtgaagaag  480
ctgtaccact ctgaggcctt cacagtgaac tttggagaca cagaggaggc caagaagcag  540
atcaatgact atgtggagaa gggcacccag ggcaagattg tggacctggt gaaggagctg  600
gacagagaca cagtgtttgc cctggtgaac tacatcttct tcaagggcaa gtgggagaga  660
ccctttgagg tgaaggacac agaggaggag gacttccatg tggaccaggt gaccacagtg  720
aaggtgccca tgatgaagag actgggcatg ttcaacatcc agcactgcaa gaagctgagc  780
agctgggtgc tgctgatgaa gtacctgggc aatgccacag ccatcttctt cctgcctgat  840
gagggcaagc tgcagcacct ggagaatgag ctgacccatg acatcatcac caagttcctg  900
gagaatgagg acagaagatc tgccagcctg cacctgccca agctgagcat cacaggcacc  960
tatgacctga agtctgtgct gggccagctg ggcatcacca aggtgttcag caatggagct  1020
gacctgtctg gagtgacaga ggaggccccc ctgaagctga gcaaggctgt gcacaaggct  1080
gtgctgacca ttgatgagaa gggcacagag gctgctggag ccatgttcct ggaggccatc  1140
cccatgagca tcccccctga ggtgaagttc aacaagccct ttgtgttcct gatgattgag  1200
cagaacacca agagccccct gttcatgggc aaggtggtga accccaccca gaagtga     1257

SEQ ID NO: 83           moltype = AA  length = 1465
FEATURE                 Location/Qualifiers
REGION                  1..1465
                        note = misc_feature - Full length ATP7B amino acid sequence
source                  1..1465
                        mol_type = protein
                        organism = Homo sapiens
SEQUENCE: 83
MPEQERQITA REGASRKILS KLSLPTRAWE PAMKKSFAFD NVGYEGGLDG LGPSSQVATS  60
TVRILGMTCQ SCVKSIEDRI SNLKGIISMK VSLEQGSATV KYVPSVVCLQ QVCHQIGDMG  120
FEASIAEGKA ASWPSRSLPA QEAVVKLRVE GMTCQSCVSS IEGKVRKLQG VVRVKVSLSN  180
QEAVITYQPY LIQPEDLRDH VNDMGFEAAI KSKVAPLSLG PIDIERLQST NPKRPLSSAN  240
QNFNNSETLG HQGSHVVTLQ LRIDGMHCKS CVLNIEENIG QLLGVQSIQV SLENKTAQVK  300
YDPSCTSPVA LQRAIEALPP GNFKVSLPDG AEGSGTDHRS SSSHSPGSPP RNQVQGTCST  360
TLIAIAGMTC ASCVHSIEGM ISQLEGVQQI SVSLAEGTAT VLYNPSVISP EELRAAIEDM  420
GFEASVVSES CSTNPLGNHS AGNSMVQTTD GTPTSVQEVA PHTGRLPANH APDILAKSPQ  480
STRAVAPQKC FLQIKGMTCA SCVSNIERNL QKEAGVLSVL VALMAGKAEI KYDPEVIQPL  540
EIAQFIQDLG FEAAVMEDYA GSDGNIELTI TGMTCASCVH NIESKLTRTN GITYASVALA  600
TSKALVKFDP EIIGPRDIIK IIEEIGFHAS LAQRNPNAHH LDHKMEIKQW KKSFLCSLVF  660
GIPVMALMIY MLIPSNEPHQ SMVLDHNIIP GLSILNLIFF ILCTFVQLLG GWYFYVQAYK  720
SLRHRSANMD VLIVLATSIA YVYSLVILVV AVAEKAERSP VTFFDTPPML FVFIALGRWL  780
EHLAKSKTSE ALAKLMSLQA TEATVVTLGE DNLIIREEQV PMELVQRGDI VKVVPGGKFP  840
VDGKVLEGNT MADESLITGE AMPVTKKPGS TVIAGSINAH GSVLIKATHV GNDTTLAQIV  900
KLVEEAQMSK APIQQLADRF SGYFVPFIII MSTLTLVVWI VIGFIDFGVV QRYFPNPNKH  960
ISQTEVIIRF AFQTSITVLC IACPCSLGLA TPTAVMVGTG VAAQNGILIK GGKPLEMAHK  1020
IKTVMFDKTG TITHGVPRVM RVLLLGDVAT LPLRKVLAVV GTAEASSEHP LGVAVTKYCK  1080
EELGTETLGY CTDFQAVPGC GIGCKVSNVE GILAHSERPL SAPASHLNEA GSLPAEKDAV  1140
PQTFSVLIGN REWLRRNGLT ISSDVSDAMT DHEMKGQTAI LVAIDGVLCG MIAIADAVKQ  1200
EAALAVHTLQ SMGVDVVLIT GDNRKTARAI ATQVGINKVF AEVLPSHKVA KVQELQNKGK  1260
KVAMVGDGVN DSPALAQADM GVAIGTGTDV AIEAADVVLI RNDLLDVVAS IHLSKRTVRR  1320
IRINLVLALI YNLVGIPIAA GVFMPIGIVL QPWMGSAAMA ASSVSVVLSS LQLKCYKKPD  1380
LERYEAQAHG HMKPLTASQV SVHIGMDDRW RDSPRATPWD QVSYVSQVSL SSLTSDKPSR  1440
HSAAADDDGD KWSLLLNGRD EEQYI                                  1465

SEQ ID NO: 84           moltype =   length =
SEQUENCE: 84
000

SEQ ID NO: 85           moltype =   length =
SEQUENCE: 85
000

SEQ ID NO: 86           moltype =   length =
SEQUENCE: 86
000

SEQ ID NO: 87           moltype =   length =
```

```
SEQUENCE: 87
000

SEQ ID NO: 88          moltype =   length =
SEQUENCE: 88
000

SEQ ID NO: 89          moltype =   length =
SEQUENCE: 89
000

SEQ ID NO: 90          moltype =   length =
SEQUENCE: 90
000

SEQ ID NO: 91          moltype =   length =
SEQUENCE: 91
000

SEQ ID NO: 92          moltype =   length =
SEQUENCE: 92
000

SEQ ID NO: 93          moltype =   length =
SEQUENCE: 93
000

SEQ ID NO: 94          moltype = DNA  length = 11
FEATURE                Location/Qualifiers
source                 1..11
                       mol_type = other DNA
                       organism = synthetic construct
SEQUENCE: 94
agtacaaatt g                                                      11

SEQ ID NO: 95          moltype = DNA  length = 13
FEATURE                Location/Qualifiers
source                 1..13
                       mol_type = other DNA
                       organism = synthetic construct
SEQUENCE: 95
accttagagg cta                                                    13
```

NON-IMMUNOGENIC CIRCULAR, NON-VIRAL DNA VECTORS

CROSS-REFERENCE TO RELATED APPLICATIONS

This application is a continuation of U.S. patent application Ser. No. 19/015,381, filed Jan. 9, 2025, which is a continuation of International Patent Application No. PCT/US2023/070238, filed in the U.S. Receiving Office on Jul. 14, 2023, which claims the benefit of the filing date of U.S. Provisional Patent Application No. 63/390,515 filed on Jul. 19, 2022. The entirety of each of these applications is incorporated herein for all purposes.

FIELD OF THE DISCLOSURE

The present disclosure relates to non-viral DNA vectors including one or more nucleotide sequences encoding one or more therapeutic proteins. In some embodiments, the non-viral DNA vectors are useful for treating hypophosphatasia or for treating, mitigating, or preventing one or more symptoms of hypophosphatasia in a subject in need of treatment thereof.

INCORPORATION BY REFERENCE

The Sequence Listing XML file named "24012-004WO1US3_ST26_2" created on Jun. 23, 2025, and having a size of 272,494 bytes, is hereby incorporated by reference.

BACKGROUND OF THE DISCLOSURE

Gene therapy is an innovative approach in medicine aimed at treating inherited and acquired diseases through the delivery of new genetic material into a patient's cells to compensate for or suppress the function of a mutant gene and/or treat a genetic disorder.

Vectors used in gene therapy are divided into two main categories, viral and non-viral ones. Viral gene therapy vectors include retroviruses, lentiviruses, adenoviruses, adeno-associated viruses, herpesviruses, poxviruses. (Lundstrom K. Viral Vectors in Gene Therapy. Diseases. 2018 May 21; 6(2)). Viral vectors can actively enter host cells and are transfected efficiently. The main advantage of viral vectors is fast and highly efficient delivery of therapeutic genetic material to a cell due to the natural properties of viruses. Viral vectors, however, have rather limited use in clinical practice given the risk of inflammation, immune response to the gene therapy, cytotoxicity, mutagenesis, and carcinogenesis. There remains a need for non-viral vectors for therapeutic gene delivery.

BRIEF SUMMARY OF THE DISCLOSURE

The present disclosure relates to circular, non-viral DNA vectors; compositions including one or more of the disclosed circular, non-viral DNA vectors; and methods for delivering and/or expressing one or more therapeutic genes in mammals, e.g., human patients, from the disclosed circular, non-viral DNA. The presently disclosed circular, non-viral DNA vectors are capable of facilitating persistent expression of a transgene which is delivered by the vector to a cell.

A first aspect of the present disclosure is an isolated, circular, non-viral DNA vector comprising: a first portion comprising an expression cassette including one or more nucleic acid sequences encoding one or more therapeutic proteins, where each of the one or more nucleic acid sequences encoding the one or more therapeutic proteins are operatively linked to a promoter; and a second portion capable of forming at least one cruciform structure. In some embodiments, the second portion comprises at least two inverted repeat sequences. In some embodiments, the at least two inverted repeat sequences are separated by a non-repeating nucleotide sequence having at least 3 nucleotides.

In some embodiments, the non-viral DNA vector is substantially devoid of CpG sequences. In some embodiments, the non-viral DNA vector comprises less than about 750 CpG per vector. In some embodiments, the non-viral DNA vector comprises less than about 700 CpG per vector. In some embodiments, the non-viral DNA vector comprises less than about 600 CpG per vector. In some embodiments, the non-viral DNA vector comprises less than about 500 CpG per vector. In some embodiments, the non-viral DNA vector comprises less than about 400 CpG per vector. In some embodiments, the non-viral DNA vector comprises less than about 300 CpG per vector. In some embodiments, the non-viral DNA vector comprises less than about 200 CpG per vector. In some embodiments, the non-viral DNA vector comprises less than about 150 CpG per vector. In some embodiments, the non-viral DNA vector comprises less than about 50 CpG per vector.

In some embodiments, the non-repeating nucleotide sequence comprises at least 5 nucleotides. In some embodiments, the non-repeating nucleotide sequence comprises at least 10 nucleotides. In some embodiments, the non-repeating nucleotide sequence comprises at least 15 nucleotides. In some embodiments, the non-repeating nucleotide sequence comprises at least 20 nucleotides. In some embodiments, the non-repeating nucleotide sequence comprises at least 25 nucleotides. In some embodiments, the non-repeating nucleotide sequence has at least 3 nucleotides and encodes at least a portion of a bacterial origin of replication. In some embodiments, origins of replication include sequences derived from pMB1, pBR322, ColE1, p15A, pSC101, or F1. In some embodiments, the non-repeating nucleotide sequence having the at least 3 nucleotides encodes a heterologous gene or a portion of a heterologous gene. In some embodiments, the non-repeating nucleotide sequence having the at least 3 nucleotides encodes a bacterial suppressor RNA. In some embodiments, the non-repeating nucleotide sequence having the at least 3 nucleotides encodes a bacterial RNAi repressor. In some embodiments, the non-repeating nucleotide sequence having the at least 3 nucleotides encodes antisense RNA. In some embodiments, the non-repeating nucleotide sequence having the at least 3 nucleotides encodes a bacterial operator sequence or a portion thereof. In some embodiments, the bacterial operator sequence comprises a lac operator. In some embodiments, the bacterial operator sequence comprises a tet operator.

In some embodiments, the non-viral DNA vector lacks a drug resistance gene. In some embodiments, the non-viral DNA vector includes one or more recombination sites. In some embodiments, the one or more recombination sites are selected from the group consisting of LoxP sites, FRT sites, attB and attP sites or their product sites attL or attR, or alternative recombination target sites derived from these sites, e.g., Lox511 or Lox66 sites. In some embodiments, the non-viral DNA vector is substantially double stranded. In some embodiments, the non-viral DNA vector is substantially supercoiled.

In some embodiments, the substantially supercoiled non-viral DNA vectors comprise one or more regions of negative supercoiling. In some embodiments, the non-viral DNA vector is non-immunogenic.

In some embodiments, each of the inverted repeat sequences are derived from nucleic acid sequences present within one or more AAV serotypes. In some embodiments, each of the inverted repeat sequences comprise a nucleotide sequence having at least 85% identity to any one of SEQ ID NOS: 1-18. In some embodiments, each of the inverted repeat sequences comprise a nucleotide sequence having at least 90% identity to any one of SEQ ID NOS: 1-18. In some embodiments, each of the inverted repeat sequences comprises a nucleotide sequence having at least 91% identity to any one of SEQ ID NOS: 1-18. In some embodiments, each of the inverted repeat sequences comprises a nucleotide sequence having at least 92% identity to any one of SEQ ID NOS: 1-18. In some embodiments, each of the inverted repeat sequences comprises a nucleotide sequence having at least 93% identity to any one of SEQ ID NOS: 1-18. In some embodiments, each of the inverted repeat sequences comprises a nucleotide sequence having at least 94% identity to any one of SEQ ID NOS: 1-18. In some embodiments, each of the inverted repeat sequences comprises a nucleotide sequence having at least 95% identity to any one of SEQ ID NOS: 1-18. In some embodiments, each of the inverted repeat sequences comprises a nucleotide sequence having at least 96% identity to any one of SEQ ID NOS: 1-18. In some embodiments, each of the inverted repeat sequences comprises a nucleotide sequence having at least 97% identity to any one of SEQ ID NOS: 1-18. In some embodiments, each of the inverted repeat sequences comprises a nucleotide sequence having at least 98% identity to any one of SEQ ID NOS: 1-18. In some embodiments, each of the inverted repeat sequences comprises a nucleotide sequence having at least 99% identity to any one of SEQ ID NOS: 1-18. In some embodiments, each of the inverted repeat sequences comprises any one of SEQ ID NOS: 1-18.

In some embodiments, the non-viral DNA vectors do not comprise a DD element. In some embodiments, the non-viral DNA vectors do not comprise a DD element but do include at least a portion of a bacterial origin of replication. In some embodiments, the non-viral DNA vectors do not comprise a DD element but do include at least a portion of a bacterial origin of replication as part of the second portion. In some embodiments, the non-viral DNA vectors do not comprise a DD element but do include at least a portion of a bacterial origin of replication, but not within the second portion.

In some embodiments, the non-repeating nucleotide sequence having the least 3 nucleotides has a nucleotide sequence having at least 85% identity to any one of SEQ ID NOS: 58-59. In some embodiments, the non-repeating nucleotide sequence having the least 3 nucleotides has a nucleotide sequence having at least 90% identity to any one of SEQ ID NOS: 58-59. In some embodiments, the non-repeating nucleotide sequence having the least 3 nucleotides has a nucleotide sequence having at least 91% identity to any one of SEQ ID NOS: 58-59. In some embodiments, the non-repeating nucleotide sequence having the least 3 nucleotides has a nucleotide sequence having at least 92% identity to any one of SEQ ID NOS: 58-59. In some embodiments, the non-repeating nucleotide sequence having the least 3 nucleotides has a nucleotide sequence having at least 93% identity to any one of SEQ ID NOS: 58-59. In some embodiments, the non-repeating nucleotide sequence having the least 3 nucleotides has a nucleotide sequence having at least 94% identity to any one of SEQ ID NOS: 58-59. In some embodiments, the non-repeating nucleotide having the least 3 nucleotides has a nucleotide sequence having at least 95% identity to any one of SEQ ID NOS: 58-59. In some embodiments, the non-repeating nucleotide sequence having the least 3 nucleotides has a nucleotide sequence having at least 96% identity to any one of SEQ ID NOS: 58-59. In some embodiments, the non-repeating nucleotide sequence having the least 3 nucleotides has a nucleotide sequence having at least 97% identity to any one of SEQ ID NOS: 58-59. In some embodiments, the non-repeating nucleotide sequence having the least 3 nucleotides has a nucleotide sequence having at least 98% identity to any one of SEQ ID NOS: 58-59. In some embodiments, the non-repeating nucleotide sequence having the least 3 nucleotides has a nucleotide sequence having at least 99% identity to any one of SEQ ID NOS: 58-59. In some embodiments, the non-repeating nucleotide sequence having the least 3 nucleotides has a nucleotide sequence having any one of SEQ ID NOS: 58-59.

In some embodiments, the second portion comprises a first nucleic acid sequence having at least 90% identity to any one of SEQ ID NOS: 1, 3, 5, 7, 9, 11, 13, 15, or 17; a second nucleic acid sequence having at least 90% identity to any one of SEQ ID NOS: 58-59; and a third nucleic acid sequence having at least 90% identity to any one of SEQ ID NOS: 2, 4, 6, 8, 10, 12, 14, 16, or 18. The isolated, circular, non-viral DNA vector of any one of the preceding claims, wherein the second portion comprises a first nucleic acid sequence having at least 92% identity to any one of SEQ ID NOS: 1, 3, 5, 7, 9, 11, 13, 15, or 17; a second nucleic acid sequence having at least 92% identity to any one of SEQ ID NOS: 58-59; and a third nucleic acid sequence having at least 92% identity to any one of SEQ ID NOS: 2, 4, 6, 8, 10, 12, 14, 16, or 18.

The isolated, circular, non-viral DNA vector of any one of the preceding claims, wherein the second portion comprises a first nucleic acid sequence having at least 95% identity to any one of SEQ ID NOS: 1, 3, 5, 7, 9, 11, 13, 15, or 17; a second nucleic acid sequence having at least 95% identity to any one of SEQ ID NOS: 58-59; and a third nucleic acid sequence having at least 95% identity to any one of SEQ ID NOS: 2, 4, 6, 8, 10, 12, 14, 16, or 18. The isolated, circular, non-viral DNA vector of any one of the preceding claims, wherein the second portion comprises a first nucleic acid sequence having at least 96% identity to any one of SEQ ID NOS: 1, 3, 5, 7, 9, 11, 13, 15, or 17; a second nucleic acid sequence having at least 96% identity to any one of SEQ ID NOS: 58-59; and a third nucleic acid sequence having at least 96% identity to any one of SEQ ID NOS: 2, 4, 6, 8, 10, 12, 14, 16, or 18. The isolated, circular, non-viral DNA vector of any one of the preceding claims, wherein the second portion comprises a first nucleic acid sequence having at least 97% identity to any one of SEQ ID NOS: 1, 3, 5, 7, 9, 11, 13, 15, or 17; a second nucleic acid sequence having at least 97% identity to any one of SEQ ID NOS: 58-59; and a third nucleic acid sequence having at least 97% identity to any one of SEQ ID NOS: 2, 4, 6, 8, 10, 12, 14, 16, or 18. The isolated, circular, non-viral DNA vector of any one of the preceding claims, wherein the second portion comprises a first nucleic acid sequence having at least 98% identity to any one of SEQ ID NOS: 1, 3, 5, 7, 9, 11, 13, 15, or 17; a second nucleic acid sequence having at least 98% identity to any one of SEQ ID NOS: 58-59; and a third nucleic acid sequence having at least 98% identity to any one of SEQ ID NOS: 2, 4, 6, 8, 10, 12, 14, 16, or 18. The isolated, circular, non-viral DNA vector of any one of the preceding claims, wherein the second portion comprises a first nucleic acid sequence having at least 99% identity to any one of SEQ ID NOS: 1, 3, 5, 7, 9, 11, 13, 15, or 17; a second nucleic acid sequence having at least 99% identity to any one of SEQ ID NOS: 58-59; and a third nucleic acid sequence having at least 99% identity to any one of SEQ ID NOS: 2, 4, 6, 8, 10, 12, 14, 16, or 18.

In some embodiments, the second portion comprises a first nucleic acid sequence having any one of SEQ ID NOS: 1, 3, 5, 7, 9, 11, 13, 15, or 17; a second nucleic acid sequence having any one of SEQ ID NOS: 58-59 and a third nucleic acid sequence having any one of SEQ ID NOS: 2, 4, 6, 8, 10, 12, 14, 16, or 18.

In some embodiments, the second portion comprises a nucleic acid sequence having at least 90% identity to any one of SEQ ID NOS: 35 and 60. In some embodiments, the second portion comprises a nucleic acid sequence having at least 95% identity to any one of SEQ ID NOS: 35 and 60. In some embodiments, the second portion comprises a nucleic acid sequence having at least 96% identity to any one of SEQ ID NOS: 35 and 60. In some embodiments, the second portion comprises a nucleic acid sequence having at least 97% identity to any one of SEQ ID NOS: 35 and 60. In some embodiments, the second portion comprises a nucleic acid sequence having at least 98% identity to any one of SEQ ID NOS: 35 and 60. In some embodiments, the second portion comprises a nucleic acid sequence having at least 99% identity to any one of SEQ ID NOS: 35 and 60. In some embodiments, the second portion comprises a nucleic acid sequence having any one of SEQ ID NOS: 35 and 60.

In some embodiments, the one or more therapeutic proteins are selected from the group consisting of ALPL, PCSK9, PCSK7, SerpinA1, ABCB4 (having at least 80%, at least 85%, at least 90%, at least 95%, at least 97%, at least 99% identity to any one of SEQ ID NOS: 64, 65, 66, or 69), ATP7B (having at least 80%, at least 85%, at least 90%, at least 95%, at least 97%, at least 99% identity to any one of SEQ ID NOS: 70 or 83), A1AT (having at least 80%, at least 85%, at least 90%, at least 95%, at least 97%, at least 99% identity to SEQ ID NO: 66), ABCB11, antiCD19-antiCD3 (having at least 80%, at least 85%, at least 90%, at least 95%, at least 97%, at least 99% identity to SEQ ID NO: 67), BDF8 (having at least 80%, at least 85%, at least 90%, at least 95%, at least 97%, at least 99% identity to SEQ ID NO: 68) and variants thereof. In some embodiments, the one or more therapeutic proteins are alkaline phosphatase or a variant thereof.

A second aspect of the present disclosure is an isolated, circular, non-viral DNA vector comprising: a first portion comprising an expression cassette including one or more nucleic acid sequences encoding one or more therapeutic proteins, where each of the one or more nucleic acid sequences encoding the one or more therapeutic proteins are operatively linked to a promoter; and a second portion capable of forming at least one cruciform structure, wherein the second portion has the Formula X—Y—X', where X and X' are each inverted repeat sequences, and where Y is not repeated and comprises a nucleotide sequence having at least 3 nucleotides.

In some embodiments, the non-viral DNA vector is substantially devoid of CpG sequences. In some embodiments, the non-viral DNA vector comprises less than about 400 CpG per vector. In some embodiments, the non-viral DNA vector comprises less than about 300 CpG per vector. In some embodiments, the non-viral DNA vector comprises less than about 200 CpG per vector. In some embodiments, the non-viral DNA vector comprises less than about 150 CpG per vector. In some embodiments, the non-viral DNA vector comprises less than about 50 CpG per vector.

In some embodiments, Y comprises at least 5 nucleotides. In some embodiments, Y comprises at least 10 nucleotides. In some embodiments, Y comprises at least 15 nucleotides. In some embodiments, Y comprises at least 20 nucleotides. In some embodiments, Y encodes at least a portion of a bacterial origin of replication. In some embodiments, Y encodes a heterologous gene or a portion of a heterologous gene. In some embodiments, Y encodes a bacterial suppressor tRNA. In some embodiments, Y encodes a bacterial RNAi repressor. In some embodiments, Y encodes antisense RNA. In some embodiments, Y encodes a bacterial operator sequence. In some embodiments, the bacterial operator sequence comprises a lac operator. In some embodiments, the bacterial operator sequence comprises a tet operator.

In some embodiments, the non-viral DNA vector lacks a drug resistance gene. In some embodiments, the non-viral DNA vector includes one or more recombination sites. In some embodiments, the one or more recombination sites are selected from the group consisting of LoxP sites, FRT sites, attB and attP sites or their product sites attL or attR, or alternative recombination target sites derived from these sites, e.g., Lox511 or Lox66 sites. In some embodiments, the non-viral DNA vector is substantially double stranded. In some embodiments, the non-viral DNA vector is substantially supercoiled. In some embodiments, the substantially supercoiled non-viral DNA vectors comprise one or more regions of negative supercoiling. In some embodiments, the non-viral DNA vector is non-immunogenic.

In some embodiments, X and X' are derived from nucleic acid sequences present within one or more AAV serotypes. In some embodiments, X and X' each comprise a nucleotide sequence having at least 85% identity to any one of SEQ ID NOS: 1-18. In some embodiments, X and X' each comprise a nucleotide sequence having at least 90% identity to any one of SEQ ID NOS: 1-18. In some embodiments, X and X' each comprise a nucleotide sequence having at least 91% identity to any one of SEQ ID NOS: 1-18. In some embodiments, X and X' each comprise a nucleotide sequence having at least 92% identity to any one of SEQ ID NOS: 1-18. In some embodiments, X and X' each comprise a nucleotide sequence having at least 93% identity to any one of SEQ ID NOS: 1-18. In some embodiments, X and X' each comprise a nucleotide sequence having at least 94% identity to any one of SEQ ID NOS: 1-18. In some embodiments, X and X' each comprise a nucleotide sequence having at least 95% identity to any one of SEQ ID NOS: 1-18. In some embodiments, X and X' each comprise a nucleotide sequence having at least 96% identity to any one of SEQ ID NOS: 1-18. In some embodiments, X and X' each comprise a nucleotide sequence having at least 97% identity to any one of SEQ ID NOS: 1-18. In some embodiments, X and X' each comprise a nucleotide sequence having at least 98% identity to any one of SEQ ID NOS: 1-18. In some embodiments, X and X' each comprise a nucleotide sequence having at least 99% identity to any one of SEQ ID NOS: 1-18. In some embodiments, the non-viral DNA vectors do not comprise a DD element. In some embodiments, the non-viral DNA vectors do not comprise a DD element but do include at least a portion of a bacterial origin of replication.

In some embodiments, Y has a nucleotide sequence having at least 85% identity to any one of SEQ ID NOS: 58-59. In some embodiments, Y has a nucleotide sequence having at least 90% identity to any one of SEQ ID NOS: 58-59. In some embodiments, Y has a nucleotide sequence having at least 91% identity to any one of SEQ ID NOS: 58-59. In some embodiments, Y has a nucleotide sequence having at least 92% identity to any one of SEQ ID NOS: 58-59. In some embodiments, Y has a nucleotide sequence having at least 93% identity to any one of SEQ ID NOS: 58-59. In some embodiments, Y has a nucleotide sequence having at least 94% identity to any one of SEQ ID NOS: 58-59. In some embodiments, Y has a nucleotide sequence having at least 95% identity to any one of SEQ ID NOS: 58-59. In some embodiments, Y has a nucleotide sequence having at least 96% identity to any one of SEQ ID NOS: 58-59. In some embodiments, Y has a nucleotide sequence having at least 97% identity to any one of SEQ ID NOS: 58-59. In some embodiments, Y has a nucleotide sequence having at least 98% identity to any one of SEQ ID NOS: 58-59. In some embodiments, Y has a nucleotide sequence having at least 99% identity to any one of SEQ ID NOS: 58-59. In some embodiments, Y has a nucleotide sequence having any one of SEQ ID NOS: 58-59. In some embodiments, Y does not include a bacterial origin of replication or any portion thereof.

In some embodiments, the non-viral DNA vector includes a bacterial origin or replication or a portion of a bacterial origin of replication, but where the bacterial origin of replication or the portion of the bacterial origin of replication is not included in the second portion. In some embodiments, the non-viral DNA vector includes a bacterial origin or replication or a portion of a bacterial origin of replication, but where the bacterial origin of replication or the portion of the bacterial origin of replication is not included in Y. In some embodiments, the one or more therapeutic proteins are selected from the group consisting of ALPL, PCSK9, PCSK7, SerpinA1, ABCB4 (having at least 80%, at least 85%, at least 90%, at least 95%, at least 97%, at least 99% identity to any one of SEQ ID NOS: 64 or 65), ATP7B (having at least 80%, at least 85%, at least 90%, at least 95%, at least 97%, at least 99% identity to any one of SEQ ID NOS: 70 or 83), A1AT (having at least 80%, at least 85%, at least 90%, at least 95%, at least 97%, at least 99% identity to SEQ ID NO: 66), ABCB11, antiCD19-antiCD3 (having at least 80%, at least 85%, at least 90%, at least 95%, at least 97%, at least 99% identity to SEQ ID NO: 67), BDF8 (having at least 80%, at least 85%, at least 90%, at least 95%, at least 97%, at least 99% identity to SEQ ID NO: 68) and variants thereof. In some embodiments, the one or more therapeutic proteins are an alkaline phosphatase or a variant thereof.

A third aspect of the present disclosure is an isolated, circular, non-viral DNA vector comprising the following elements operatively linked in a 5' to a 3' direction: (i) a first repeat sequence; (ii) a non-repeating nucleotide sequence having at least 3 nucleotides; (iii) a second repeat sequence; and (iv) an expression cassette. In some embodiments, the non-viral DNA vector comprises less than about 400 CpG per vector. In some embodiments, the non-viral DNA vector comprises less than about 300 CpG per vector. In some embodiments, the non-viral DNA vector comprises less than about 250 CpG per vector. In some embodiments, the non-viral DNA vector comprises less than about 200 CpG per vector. In some embodiments, the non-viral DNA vector comprises less than about 150 CpG per vector. In some embodiments, the non-viral DNA vector comprises less than about 100 CpG per vector. In some embodiments, the non-viral DNA vector comprises less than about 50 CpG per vector. In some embodiments, the expression cassette includes one or more nucleic acid sequences encoding one or more therapeutic proteins, where each of the one or more nucleic acid sequences encoding the one or more therapeutic proteins are operatively linked to a promoter.

In some embodiments, the non-repeating nucleotide sequence comprises at least 5 nucleotides. In some embodiments, the non-repeating nucleotide sequence comprises at least 10 nucleotides. In some embodiments, the non-repeating nucleotide sequence comprises at least 15 nucleotides. In some embodiments, the non-repeating nucleotide sequence comprises at least 20 nucleotides. In some embodiments, the non-repeating nucleotide sequence having the at least 3 nucleotides encodes at least a portion of a bacterial origin of replication. In some embodiments, the non-repeating nucleotide sequence having the at least 3 nucleotides encodes a heterologous gene or a portion of a heterologous gene. In some embodiments, the non-repeating nucleotide sequence having the at least 3 nucleotides encodes a bacterial suppressor tRNA. In some embodiments, the non-repeating nucleotide sequence having the at least 3 nucleotides encodes a bacterial suppressor RNAi repressor. In some embodiments, the non-repeating nucleotide sequence having the at least 3 nucleotides encodes antisense RNA. In some embodiments, the non-repeating nucleotide sequence having the at least 3 nucleotides encodes a bacterial operator sequence. In some embodiments, the bacterial operator sequence comprises a lac operator. In some embodiments, the bacterial operator sequence comprises a tet operator.

In some embodiments, the non-viral DNA vector lacks a drug resistance gene. In some embodiments, the non-viral DNA vector includes one or more recombination sites. In some embodiments, the one or more recombination sites are selected from the group consisting of LoxP sites, FRT sites, attB and attP sites or their product sites attL or attR, or alternative recombination target sites derived from these sites, e.g., Lox511 or Lox66 sites. In some embodiments, the non-viral DNA vector is non-immunogenic. In some embodiments, the non-viral DNA vector is substantially double stranded.

In some embodiments, the one or more therapeutic proteins are selected from the group consisting of ALPL, PCSK9, PCSK7, SerpinA1, ABCB4 (having at least 80%, at least 85%, at least 90%, at least 95%, at least 97%, at least 99% identity to any one of SEQ ID NOS: 64, 65, 66, or 69), ATP7B (having at least 80%, at least 85%, at least 90%, at least 95%, at least 97%, at least 99% identity to any one of SEQ ID NOS: 70 or 83), A1AT (having at least 80%, at least 85%, at least 90%, at least 95%, at least 97%, at least 99% identity to SEQ ID NO: 66), ABCB11, antiCD 19-antiCD3 (having at least 80%, at least 85%, at least 90%, at least 95%, at least 97%, at least 99% identity to SEQ ID NO: 67), BDF8 (having at least 80%, at least 85%, at least 90%, at least 95%, at least 97%, at least 99% identity to SEQ ID NO: 68) and their variants thereof. In some embodiments, the one or more therapeutic proteins are an alkaline phosphatase or a variant thereof.

A fourth aspect of the present disclosure is an isolated, circular, non-viral DNA vector comprising: a first portion comprising an expression cassette including one or more nucleic acid sequences encoding one or more therapeutic proteins, where each of the one or more nucleic acid sequences encoding the one or more therapeutic proteins are operatively linked to a promoter; and a second portion capable of forming at least one cruciform structure, wherein the second portion comprises at least two inverted repeat sequences, and where the at least two inverted repeat sequences are separated by at least a portion of a bacterial origin of replication.

In some embodiments, the non-viral DNA vector is substantially devoid of CpG sequences. In some embodiments, the non-viral DNA vector comprises less than about 400 CpG per vector. In some embodiments, the non-viral DNA vector comprises less than about 300 CpG per vector. In some embodiments, the non-viral DNA vector comprises less than about 250 CpG per vector. In some embodiments, the non-viral DNA vector comprises less than about 200 CpG per vector. In some embodiments, the non-viral DNA vector comprises less than about 150 CpG per vector. In some embodiments, the non-viral DNA vector comprises less than about 50 CpG per vector.

In some embodiments, the non-viral DNA vector lacks a drug resistance gene. In some embodiments, the non-viral DNA vector includes one or more recombination sites. In some embodiments, the one or more recombination sites are selected from the group consisting of LoxP sites, FRT sites, attB and attP sites or their product sites attL or attR, or alternative recombination target sites derived from these sites, e.g., Lox511 or Lox66 sites. In some embodiments, the non-viral DNA vector is substantially double stranded. In some embodiments, the non-viral DNA vector is substantially supercoiled.

In some embodiments, the substantially supercoiled non-viral DNA vectors comprise one or more regions of negative supercoiling. In some embodiments, the non-viral DNA vector is non-immunogenic.

In some embodiments, each of the inverted repeat sequences are derived from nucleic acid sequences present within one or more AAV serotypes. In some embodiments, each of the inverted repeat sequences comprise a nucleotide sequence having at least 85% identity to any one of SEQ ID NOS: 1-18. In some embodiments, each of the inverted repeat sequences comprise a nucleotide sequence having at least 90% identity to any one of SEQ ID NOS: 1-18. In some embodiments, each of the inverted repeat sequences comprise a nucleotide sequence having at least 91% identity to any one of SEQ ID NOS: 1-18. In some embodiments, each of the inverted repeat sequences comprise a nucleotide sequence having at least 92% identity to any one of SEQ ID NOS: 1-18. In some embodiments, each of the inverted repeat sequences comprise a nucleotide sequence having at least 93% identity to any one of SEQ ID NOS: 1-18. In some embodiments, each of the inverted repeat sequences comprise a nucleotide sequence having at least 94% identity to any one of SEQ ID NOS: 1-18. In some embodiments, each of the inverted repeat sequences comprise a nucleotide sequence having at least 95% identity to any one of SEQ ID NOS: 1-18. In some embodiments, each of the inverted repeat sequences comprise a nucleotide sequence having at least 96% identity to any one of SEQ ID NOS: 1-18. In some embodiments, each of the inverted repeat sequences comprise a nucleotide sequence having at least 97% identity to any one of SEQ ID NOS: 1-18. In some embodiments, each of the inverted repeat sequences comprise a nucleotide sequence having at least 98% identity to any one of SEQ ID NOS: 1-18. In some embodiments, each of the inverted repeat sequences comprise a nucleotide sequence having at least 99% identity to any one of SEQ ID NOS: 1-18. In some embodiments, the non-viral DNA vectors do not comprise a DD element. In some embodiments, the non-viral DNA vectors do not comprise a DD element but do include at least a portion of a bacterial origin of replication.

In some embodiments, the at least the portion of a bacterial origin of replication has a nucleotide sequence having at least 85% identity to any one of SEQ ID NOS: 58-59. In some embodiments, at least the portion of a bacterial origin of replication has a nucleotide sequence having at least 90% identity to any one of SEQ ID NOS: 58-59. In some embodiments, the at least the portion of a bacterial origin of replication has a nucleotide sequence having at least 95% identity to any one of SEQ ID NOS: 58-59. In some embodiments, the at least the portion of a bacterial origin of replication has a nucleotide sequence having at least 96% identity to any one of SEQ ID NOS: 58-59. In some embodiments, the at least the portion of a bacterial origin of replication has a nucleotide sequence having at least 97% identity to any one of SEQ ID NOS: 58-59. In some embodiments, the at least the portion of a bacterial origin of replication has a nucleotide sequence having at least 98% identity to any one of SEQ ID NOS: 58-59. In some embodiments, the at least the portion of a bacterial origin of replication has a nucleotide sequence having at least 99% identity to any one of SEQ ID NOS: 58-59. In some embodiments, at least the portion of a bacterial origin of replication has a nucleotide sequence having any one of SEQ ID NOS: 58-59.

In some embodiments, the second portion comprises a first nucleic acid sequence having at least 85% identity to any one of SEQ ID NOS: 1, 3, 5, 7, 9, 11, 13, 15, or 17; a second nucleic acid sequence having at least 85% identity to any one of SEQ ID NOS: 58-59; and a third nucleic acid sequence having at least 85% identity to any one of SEQ ID NOS: 2, 4, 6, 8, 10, 12, 14, 16, or 18. In some embodiments, the second portion comprises a first nucleic acid sequence having at least 90% identity to any one of SEQ ID NOS: 1, 3, 5, 7, 9, 11, 13, 15, or 17; a second nucleic acid sequence having at least 90% identity to any one of SEQ ID NOS: 58-59; and a third nucleic acid sequence having at least 90% identity to any one of SEQ ID NOS: 2, 4, 6, 8, 10, 12, 14, 16, or 18. In some embodiments, the second portion comprises a first nucleic acid sequence having at least 95% identity to any one of SEQ ID NOS: 1, 3, 5, 7, 9, 11, 13, 15, or 17; a second nucleic acid sequence having at least 95% identity to any one of SEQ ID NOS: 58-59; and a third nucleic acid sequence having at least 95% identity to any one of SEQ ID NOS: 2, 4, 6, 8, 10, 12, 14, 16, or 18. In some embodiments, the second portion comprises a first nucleic acid sequence having at least 96% identity to any one of SEQ ID NOS: 1, 3, 5, 7, 9, 11, 13, 15, or 17; a second nucleic acid sequence having at least 96% identity to any one of SEQ ID NOS: 58-59; and a third nucleic acid sequence having at least 96% identity to any one of SEQ ID NOS: 2, 4, 6, 8, 10, 12, 14, 16, or 18. In some embodiments, the second portion comprises a first nucleic acid sequence having at least 97% identity to any one of SEQ ID NOS: 1, 3, 5, 7, 9, 11, 13, 15, or 17; a second nucleic acid sequence having at least 97% identity to any one of SEQ ID NOS: 58-59; and a third nucleic acid sequence having at least 97% identity to any one of SEQ ID NOS: 2, 4, 6, 8, 10, 12, 14, 16, or 18. In some embodiments, the second portion comprises a first nucleic acid sequence having at least 98% identity to any one of SEQ ID NOS: 1, 3, 5, 7, 9, 11, 13, 15, or 17; a second nucleic acid sequence having at least 98% identity to any one of SEQ ID NOS: 58-59; and a third nucleic acid sequence having at least 98% identity to any one of SEQ ID NOS: 2, 4, 6, 8, 10, 12, 14, 16, or 18. In some embodiments, the second portion comprises a first nucleic acid sequence having at least 99% identity to any one of SEQ ID NOS: 1, 3, 5, 7, 9, 11, 13, 15, or 17; a second nucleic acid sequence having at least 99% identity to any one of SEQ ID NOS: 58-59; and a third nucleic acid sequence having at least 99% identity to any one of SEQ ID NOS: 2, 4, 6, 8, 10, 12, 14, 16, or 18. In some embodiments, the second portion comprises a first nucleic acid sequence having any one of SEQ ID NOS: 1, 3, 5, 7, 9, 11, 13, 15, or 17; a second nucleic acid sequence having any one of SEQ ID NOS: 58-59; and a third nucleic acid sequence having any one of SEQ ID NOS: 2, 4, 6, 8, 10, 12, 14, 16, or 18.

In some embodiments, the second portion comprises a nucleic acid sequence having at least 80% identity to any one of SEQ ID NOS: 35 and 60. In some embodiments, the second portion comprises a nucleic acid sequence having at least 85% identity to any one of SEQ ID NOS: 35 and 60.

In some embodiments, the second portion comprises a nucleic acid sequence having at least 90% identity to any one of SEQ ID NOS: 35 and 60. In some embodiments, the second portion comprises a nucleic acid sequence having at least 92% identity to any one of SEQ ID NOS: 35 and 60. In some embodiments, the second portion comprises a nucleic acid sequence having at least 95% identity to any one of SEQ ID NOS: 35 and 60. In some embodiments, the second portion comprises a nucleic acid sequence having at least 96% identity to any one of SEQ ID NOS: 35 and 60. In some embodiments, the second portion comprises a nucleic acid sequence having at least 97% identity to any one of SEQ ID NOS: 35 and 60. In some embodiments, the second portion comprises a nucleic acid sequence having at least 98% identity to any one of SEQ ID NOS: 35 and 60. In some embodiments, the second portion comprises a nucleic acid sequence having at least 99% identity to any one of SEQ ID NOS: 35 and 60. In some embodiments, the second portion comprises a nucleic acid sequence having any one of SEQ ID NOS: 35 and 60.

In some embodiments, the one or more therapeutic proteins are selected from the group consisting of ALPL, PCSK9, PCSK7, SerpinA1, ABCB4 (having at least 80%, at least 85%, at least 90%, at least 95%, at least 97%, at least 99% identity to any one of SEQ ID NOS: 64, 65, 66, or 69), ATP7B (having at least 80%, at least 85%, at least 90%, at least 95%, at least 97%, at least 99% identity to any one of SEQ ID NOS: 70 or 83), A1AT (having at least 80%, at least 85%, at least 90%, at least 95%, at least 97%, at least 99% identity to SEQ ID NO: 66), ABCB11, antiCD 19-antiCD3 (having at least 80%, at least 85%, at least 90%, at least 95%, at least 97%, at least 99% identity to SEQ ID NO: 67), BDF8 (having at least 80%, at least 85%, at least 90%, at least 95%, at least 97%, at least 99% identity to SEQ ID NO: 68) and their variants thereof. In some embodiments, the one or more therapeutic proteins are alkaline phosphatase or a variant thereof.

In some embodiments, the non-viral DNA vector further comprises a S/MAR element. In some embodiments, the non-viral DNA vector further comprises an insulator element. In some embodiments, the expression cassette further comprises a polyadenylation site downstream of the one or more nucleic acid sequences encoding the one or more therapeutic proteins.

A fifth aspect of the present disclosure is an isolated, circular, non-viral DNA vector comprising: a first portion comprising an expression cassette including a nucleic acid sequence encoding a polypeptide having any one of Formulas (IA) to (IE), where the nucleic acid sequence encoding the polypeptide is operatively linked to a promoter; and a second portion capable of forming at least one cruciform structure, wherein the second portion comprises at least two inverted repeat sequences, and where the at least two inverted repeat sequences are separated by a non-repeating nucleotide sequence having at least 3 nucleotides;

(IA),
[A]v-[B]-[C]w-[R]q-([D]x-[E]y)z (IB),
[A]-[B]-[C]-[R]q-([D]x-[E]y)

IC),
([A]-[B])-([D]x-[E]y)z (ID),
([A]-[B])-([E]y)
and (IE)
[A]-[B]-[R]q-([E]y)

wherein

A comprises an amino acid sequence encoding a secretion signal peptide;

B comprises an amino acid encoding an alkaline phosphatase;

C comprises an amino acid sequence encoding a GPI anchor;

R is -(Mo(Fc)Np)-, where M and N each independently include between 1 and 6 amino acids, where Fc is a Fc domain, and o and p are each independently 0, 1, or 2;

D comprises an amino acid sequence having between 4 and 6 amino acids, or is F(G)tF, where each F is the same amino acid, G is an amino acid sequence having 3, 4, or 5 amino acids, and t is an integer ranging from 2-5;

E comprises an amino acid sequence having between 1 and 8 amino acids;

q is 0 or 1;

v is 0 or 1;

w is 0 or 1;

x is 0 or an integer ranging from 1 to 6;

y is 0 or an integer ranging from 1 to 16; and z is 0 or an integer ranging from 1 to 6;

In some embodiments, when vis 1, w is 0, q is 1, o is 1, p is 1, N is the diamino acid -D-I-, M is the diamino acid -L-K-, [B] comprises SEQ ID NO: 11, Fc comprises SEQ ID NO: 130, and x is 0, then [E]y does not comprise ten to sixteen contiguous aspartic acid residues.

In some embodiments, E comprises 3 amino acids. In some embodiments, E is -D-S-S-. In some embodiments, E is -D-S-S-, and y ranges from 1 to 16. In some embodiments, E is -D-S-S-, y is 6, z is 1, q is 0, and x is 0. In other embodiments, E is -D-S-S-, y is 6, z is 1, q is 0, and x is 2. In some embodiments, E is -D-S-S-, y is 6, z is 1, x is 2, and q is 1.

A sixth aspect of the present disclosure is an isolated, circular, non-viral DNA vector having a nucleic acid sequence having at least 80% identity to any one of SEQ ID NOS: 28-30, 38, 40-48, and 72-73, e.g., at least 85%, at least 90%, at least 91%, at least 92%, at least 93%, at least 94%, at least 95%, at least 96%, at least 97%, at least 98%, at least 99% identity to any one of SEQ ID NOS: 28-30, 38, 40-48, and 72-73. In some embodiments, the isolated, circular, non-viral DNA is provided in a pharmaceutically acceptable medium. In some embodiments, the isolated, circular, non-viral DNA is formulated with one or more lipid nanoparticles. In some embodiments, the isolated, circular, non-viral DNA is formulated with one or more polymer nanoparticles. In some embodiments, the isolated, circular, non-viral DNA is formulated with one or more proteo-lipid nanoparticles.

A seventh aspect of the present disclosure is an isolated, circular, non-viral DNA vector having a nucleic acid sequence having any one of SEQ ID NOS: 28-30, 38, 40-48, and 72-73. In some embodiments, the isolated, circular, non-viral DNA is provided in a pharmaceutically acceptable medium. In some embodiments, the isolated, circular, non-viral DNA is formulated with one or more lipid nanoparticles. In some embodiments, the isolated, circular, non-viral DNA is formulated with one or more polymer nanoparticles. In some embodiments, the isolated, circular, non-viral DNA is formulated with one or more proteo-lipid nanoparticles.

An eighth aspect of the present disclosure is a pharmaceutical composition comprising any one of the isolated, circular, non-viral DNA vectors of any one of the preceding embodiments and a pharmaceutically acceptable carrier or excipient. In some embodiments, the pharmaceutical composition is formulated with a lipid-based delivery vehicle. In some embodiments, the pharmaceutical composition is formulated as lipid nanoparticles. In some embodiments, the pharmaceutical composition is formulated as lipid nanocapsules. In some embodiments, the pharmaceutical composition is formulated with one or more polymers.

A ninth aspect of the present disclosure is a method of treating a patient in need of treatment thereof, comprising administering any of the pharmaceutical compositions described above. In some embodiments, the pharmaceutical composition is administered weekly. In some embodiments, the pharmaceutical composition is administered monthly. In some embodiments, the pharmaceutical composition is administered every two months. In some embodiments, the pharmaceutical composition is administered every six months. In some embodiments, the pharmaceutical composition is administered yearly. In some embodiments, the pharmaceutical composition is administered every two years. In some embodiments, the pharmaceutical composition is administered every several years.

A tenth aspect of the present disclosure is a method of treating hypophosphatasia, comprising administering a therapeutically effective amount of any of the isolated, circular, non-viral DNA vectors described above or a pharmaceutical composition comprising the same.

An eleventh aspect of the present disclosure is a method of treating, mitigating, or preventing a symptom of hypophosphatasia, comprising administering a therapeutically effective amount of any of the isolated, circular, non-viral DNA vectors described above or a pharmaceutical composition comprising the same.

A twelfth aspect of the present disclosure is directed to the use of any of the isolated, circular, non-viral DNA vectors described above (or a pharmaceutical composition comprising the same) for treating hypophosphatasia.

BRIEF DESCRIPTION OF THE FIGURES

For a general understanding of the features of the disclosure, reference is made to the drawings. In the drawings, like reference numerals have been used throughout to identify identical elements.

FIGS. 2A, 2B, 2C, 2D, and 2E depict the predicted DNA secondary structure and calculated Gibbs free energy, normalized calculated Gibbs free energy per bp, melting temperature (Tm) of zero-CpG internal repeat sequences of circular, non-viral DNA vectors according to the present disclosure (SEQ ID NO: 29, 30, and 31). Based on this assessment, although the two long inverted repeat sequences contain smaller internal inverted repeats, when containing a portion of a bacterial origin of replication, internal secondary structure may not be formed within the two long inverted repeat sequences.

FIG. 13A shows that the cells transfected with the construct M056 (SEQ ID NO: 73) with the further optimized cruciform structure had much higher ALP secretion level in medium than those transfected with M012 (SEQ ID NO: 30) with both FUGENE™ and SM102-based lipid nanoparticle formulations. FIG. 13B shows that both constructs (M012—SEQ ID NO: 30 and M056—SEQ ID NO: 73), which have different structures, do not significant impact the viability of transfected cells.

FIG. 14A shows a representative image in which DAPI staining (blue) represents the nucleus, green foci without green circle represents the constructs of the present disclosure in cytoplasm, green foci marked with green circle represents constructs of the present disclosure in the nucleus. The fluorescence-labeled circular, non-viral DNA vector including a nucleic acid encoding TNALP and also including dual inverted repeats (M012—SEQ ID NO: 28) showed highest number of foci per nucleus at day 3 and 6 as compared with (i) a circular, non-viral DNA vector including single inverted repeats without intervening heterologous sequences (DD-ITR construct) (M013—SEQ ID NO: 29), and (ii) a control and without cruciform structure at all (M022—SEQ ID NO: 33) (FIG. 14B). There is a correlation between the number of foci per nucleus and measured ALP activity in the cell culture medium (FIG. 14C).

FIG. 19B shows that a human TNALP DNA construct according to the present disclosure (M012—SEQ ID NO: 28) with optimized cruciform structure led to a much higher ALP activity, more durable transgene expression, and no immune response (as shown by the ability to re-dose) in mouse as compared with a non-viral human TNALP DNA vector with an early version of a cruciform structure including single inverted repeats without intervening heterologous sequences (DD-ITR construct) (M013—SEQ ID NO: 29) (FIG. 19A). FIG. 19C illustrates that optimized cynomolgus monkey TNALP DNA construct according to the present disclosure (M026—SEQ ID NO: 43) with improved cruciform structure further increased potency, durability of the transgene expression while maintaining the ability to re-dose as compared with the similar construct without gene cassette optimization. Non-viral DNA constructs were administered repeatedly at 3-week intervals through hydrodynamic tail vein injection (15 μg per mouse) and plasma samples were collected weekly for assessment of ALP activity.

DETAILED DESCRIPTION

Figure 1A:
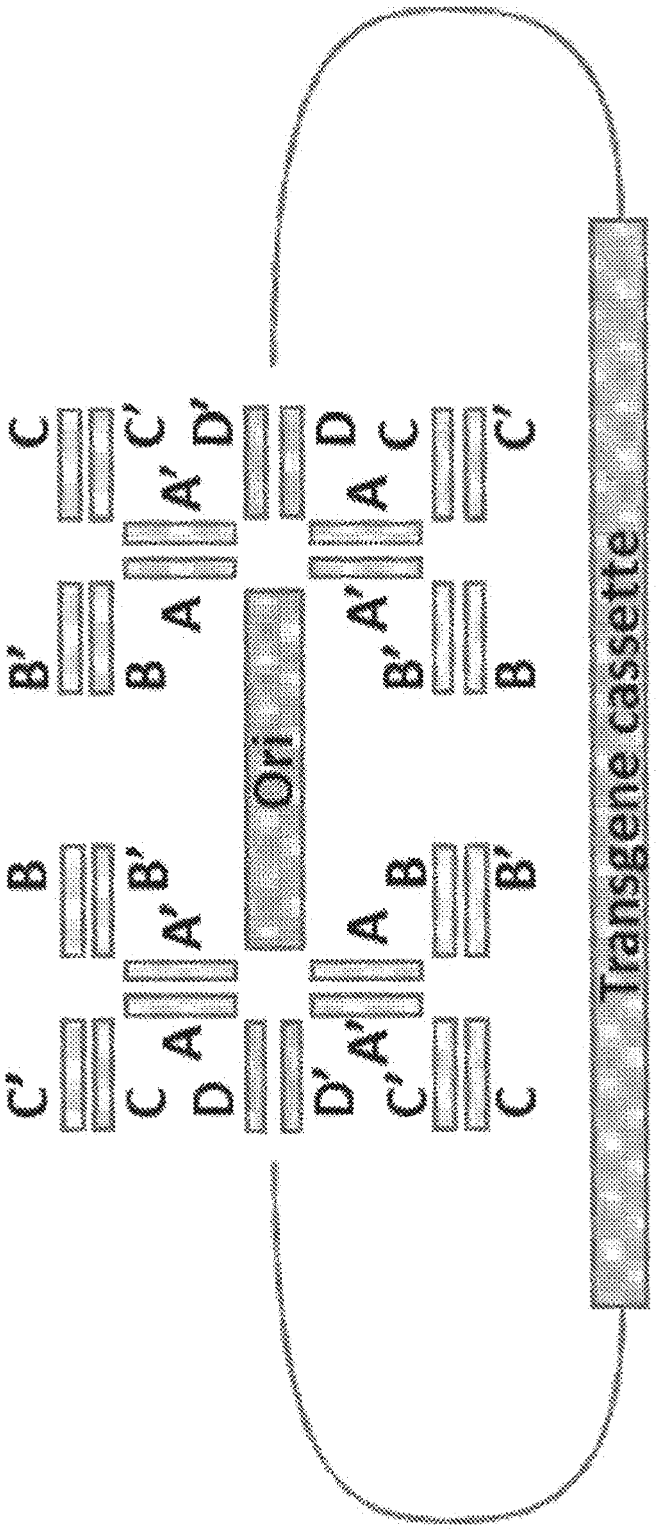
FIG. 1A illustrates a non-viral DNA vector comprising (i) a first portion comprising an expression cassette including one or more nucleic acid sequences encoding one or more therapeutic proteins, where each of the one or more nucleic acid sequences encoding the one or more therapeutic proteins are operatively linked to a promoter; and (ii) a second portion capable of forming at least one cruciform structure, wherein the second portion comprises at least two inverted repeat sequences, wherein the at least two inverted repeat sequences are separated by a non-repeating nucleotide sequence having at least 3 nucleotides. Here, the first portion includes a nucleic acid encoding the human tissue non-specific alkaline phosphatase (TNALP), the nucleic acid under control of a promoter, including any of those described herein. In some embodiments, the cruciform structure comprises a Holliday junction.
Figure 1B:
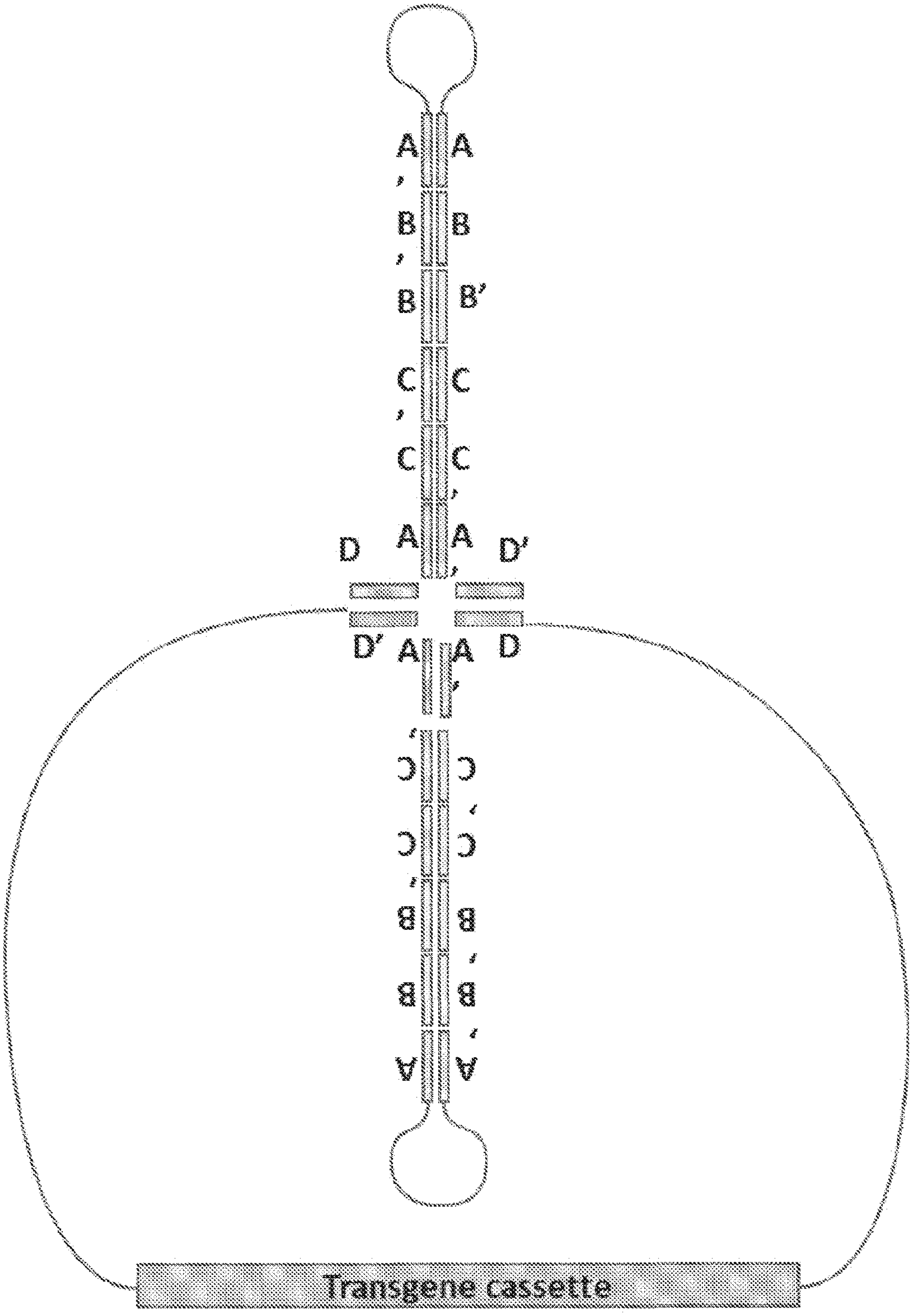
FIGS. 1B and 1C illustrate the non-viral DNA vector of FIG. 1A and illustrate the formed at least one cruciform structure. The inverted DNA repeat elements that lead to the formation of the cruciform DNA structure may contain internal inverted DNA repeats as depicted in FIG. 1B. These smaller internal inverted DNA repeat elements may form additional secondary structure that stabilizes the formation of the larger cruciform structure. As depicted in FIG. 1B, the cruciform structure is formed between specific repeat elements, however, due to the nature of these repeats, the cruciform may be formed between other repeat elements, or between the inverted repeat sequences and the remainder of the non-viral DNA vector. In some embodiments, the inverted repeat elements may also be discontinuous, with regions of non-base paired or single-stranded DNA. One such region containing non-base paired or single-stranded DNA is in the region comprising the non-repeating nucleotide sequence having at least 3 nucleotides, which is internal to the cruciform structure (sec FIG. 1A). Given the components of the non-viral DNA vectors of the present disclosure, it is believed that at least two inverted repeat sequences, each separated by a non-repeating nucleotide sequence having at least 3 nucleotides, facilitates the formation of a single cruciform structure having two long arms capped by a region of single-stranded DNA.
Figure 1C:
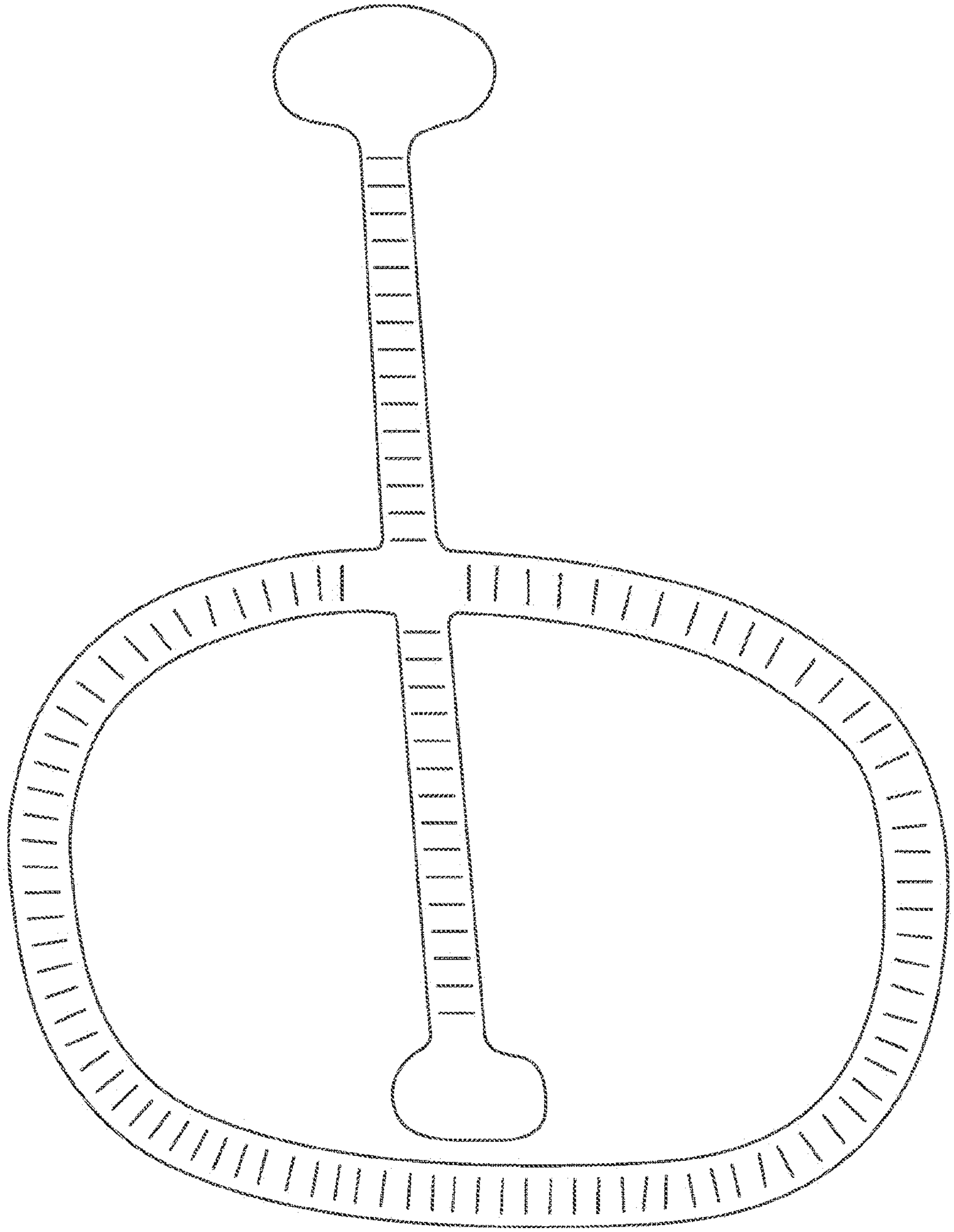
Figure 1D:
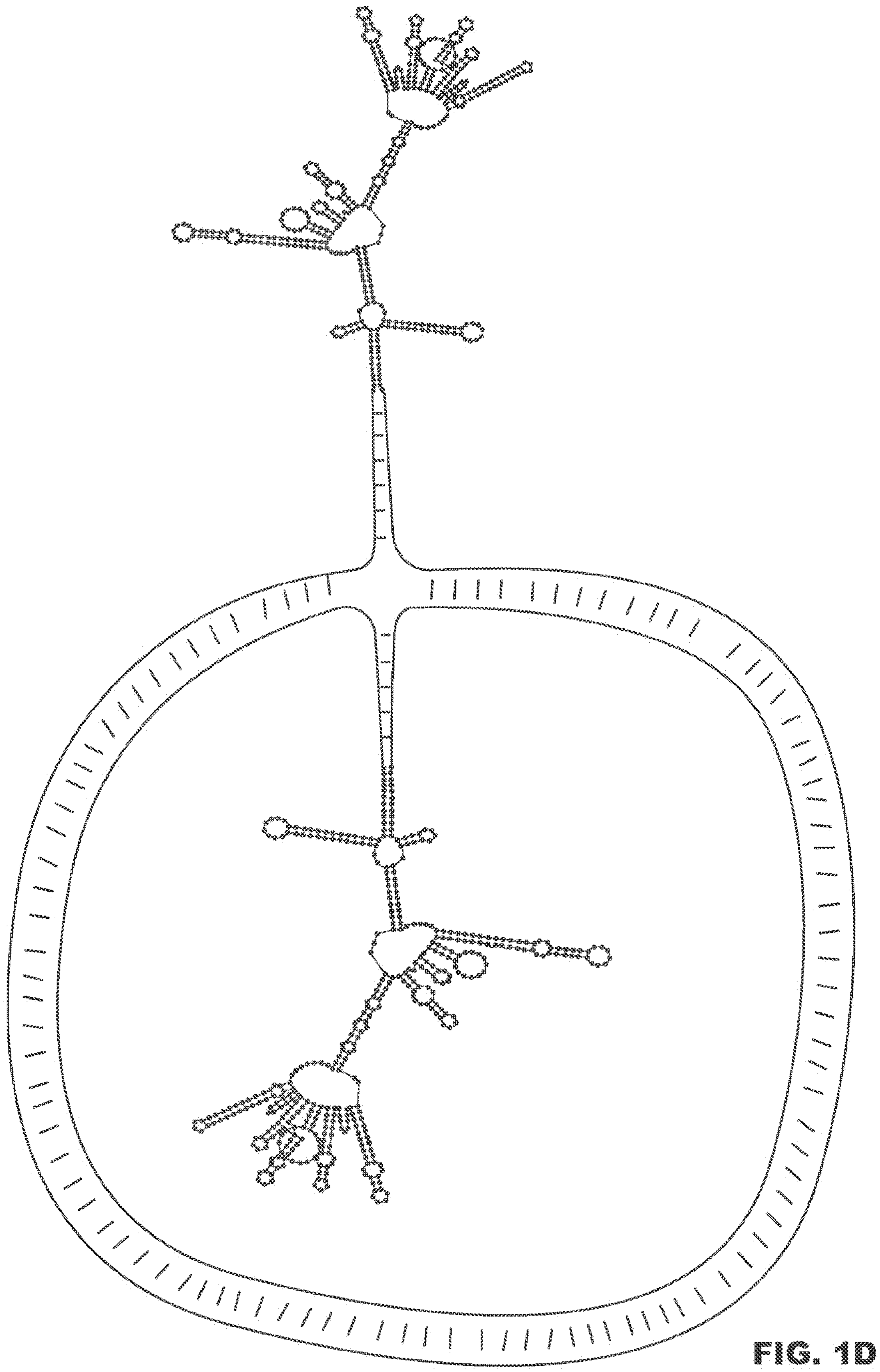
FIG. 1D illustrates the non-viral DNA vector of FIG. 1A, and illustrates the formed at least one cruciform structure, and further depicts secondary structure of the incorporated portion of the non-repeating nucleotide sequence having at least 3 nucleotides, which may be a portion of a bacterial origin of replication.
Figure 1E:
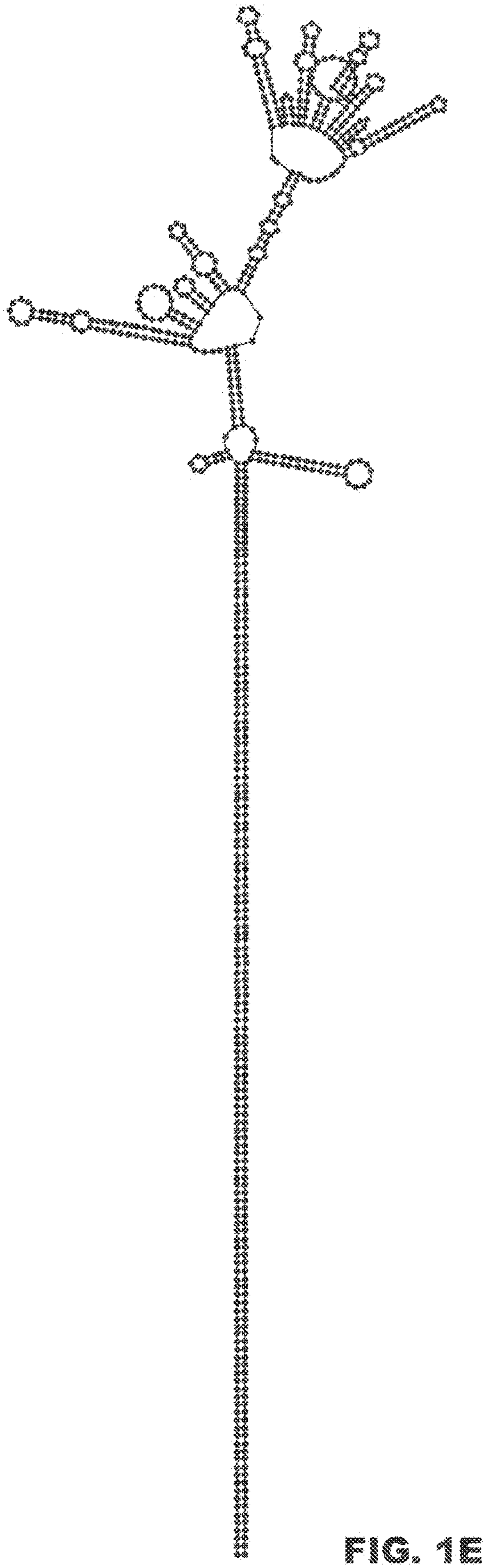
FIG. 1E depicts the predicted secondary structure of a bacterial origin of replication between two inverted terminal repeats. This single large cruciform structure contains numerous regions of single-stranded and non-repeat forming DNA in the region of the bacterial origin of replication.
Figure 2A:
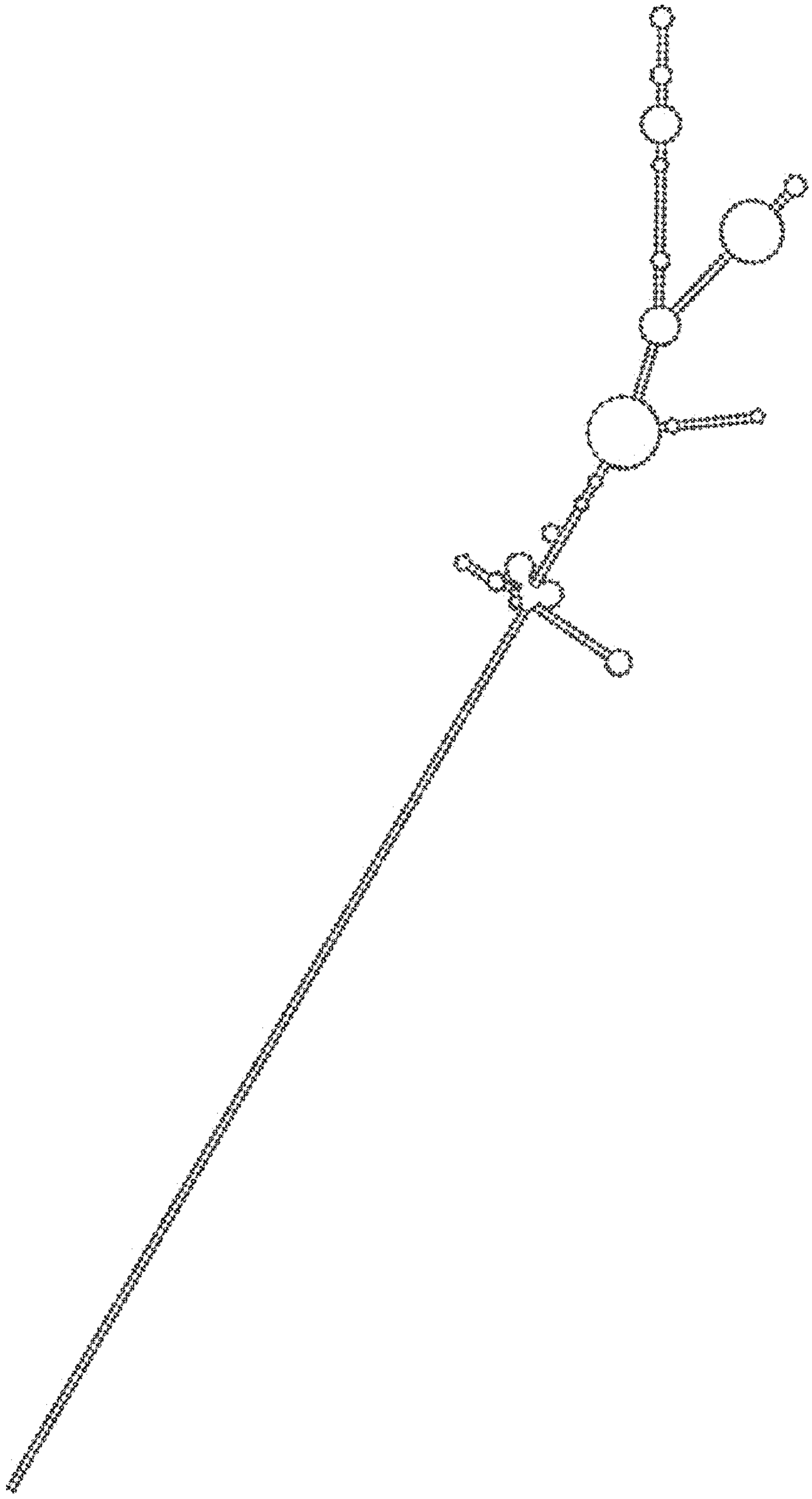
Figure 2B:
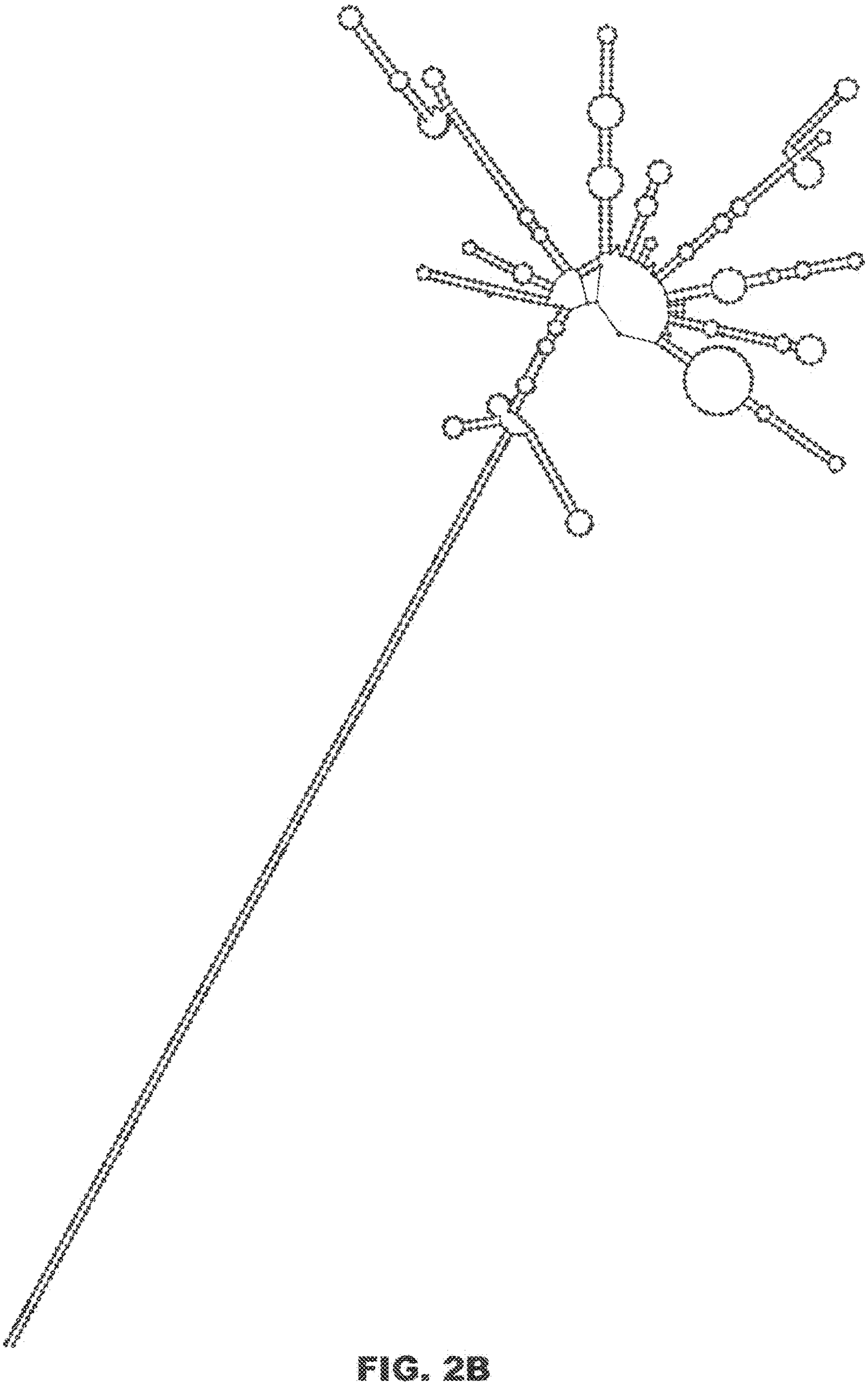
Figure 2C:
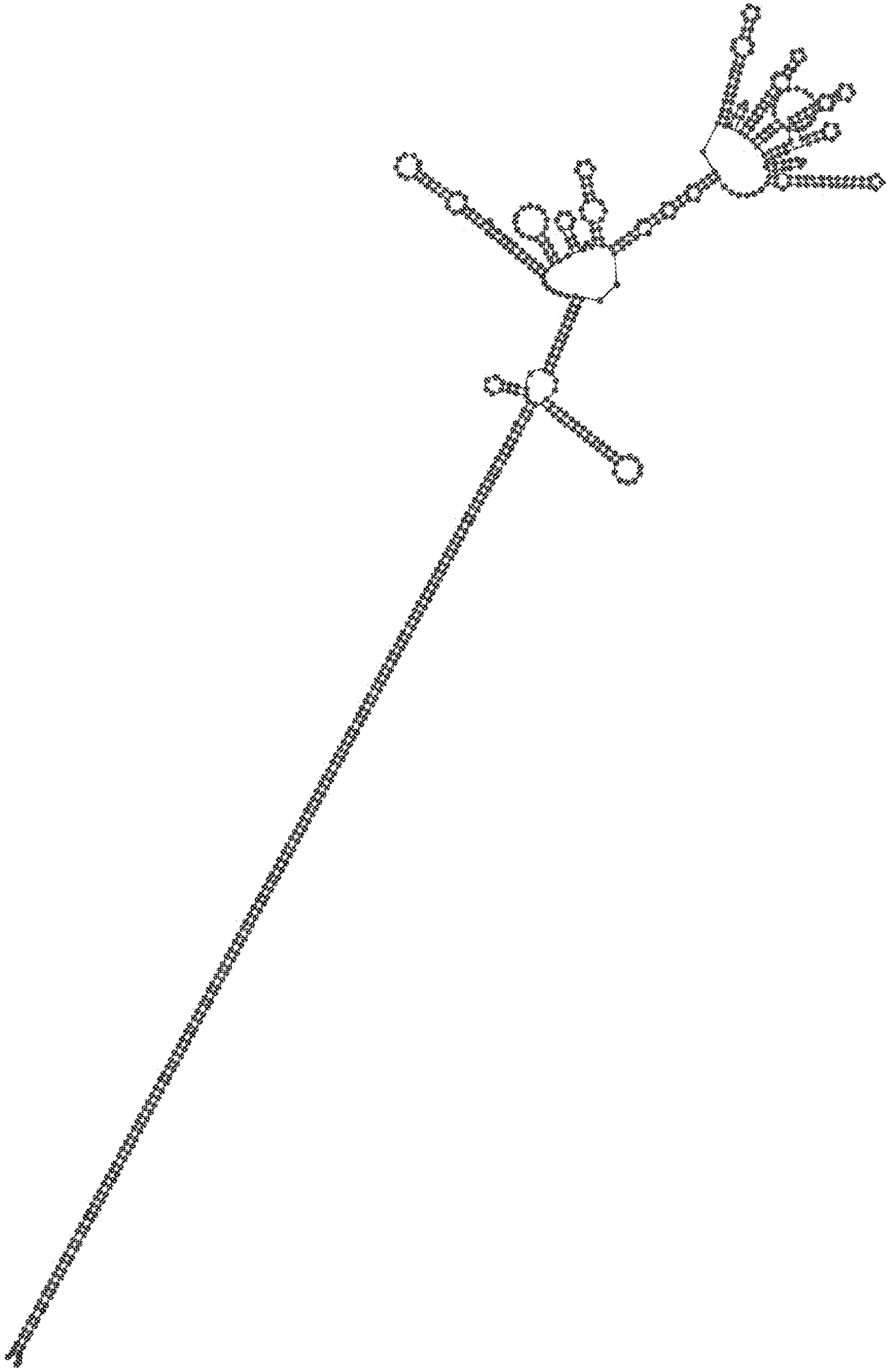
Figure 2D:
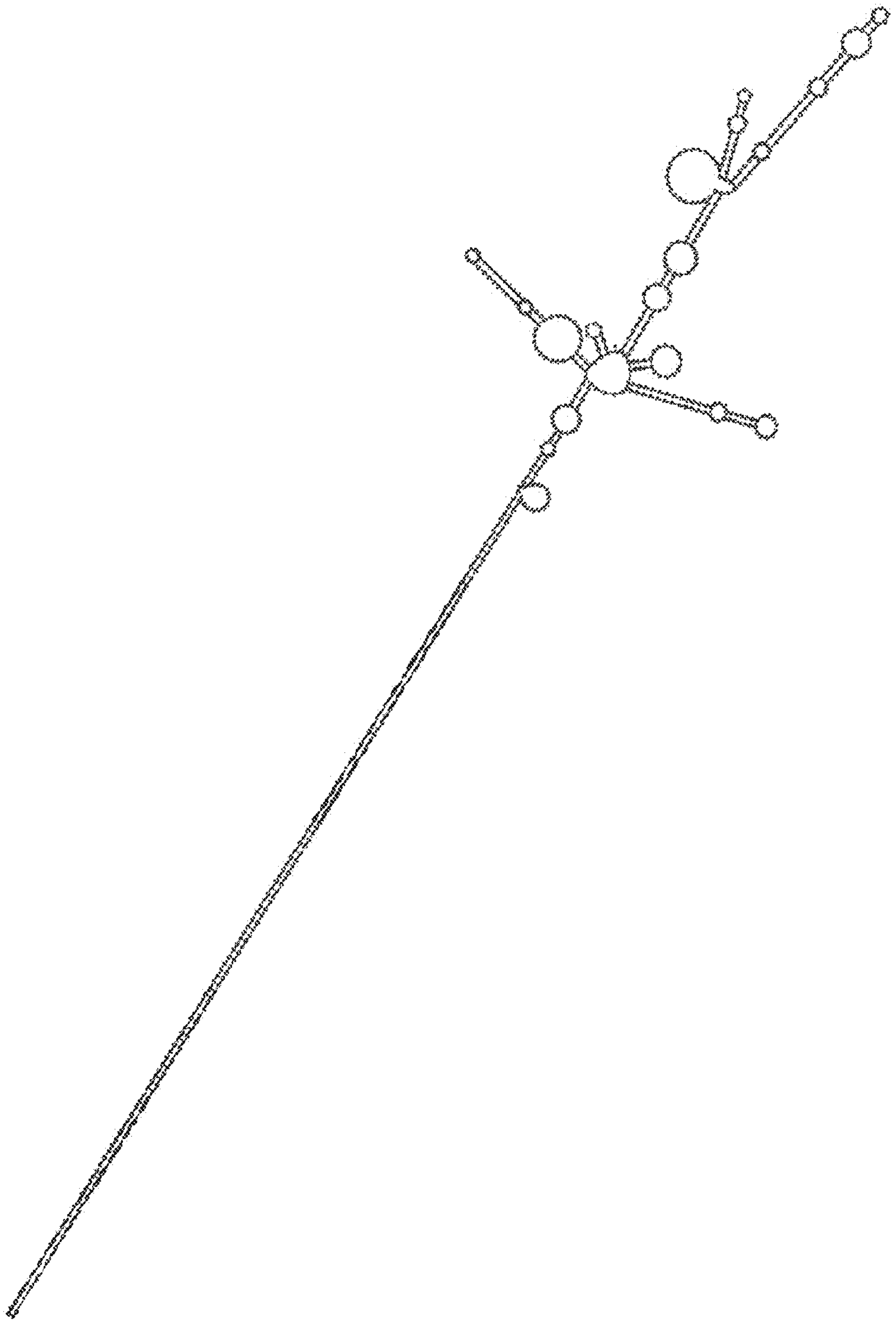
Figure 3:
FIG. 3 provides three representative transmission electron microscope photos of circular, non-viral DNA vectors of the present disclosure which include at least two inverted repeat sequences separated by at least a portion of a bacterial origin of replication (M012—SEQ ID NO: 10).
Figure 4:
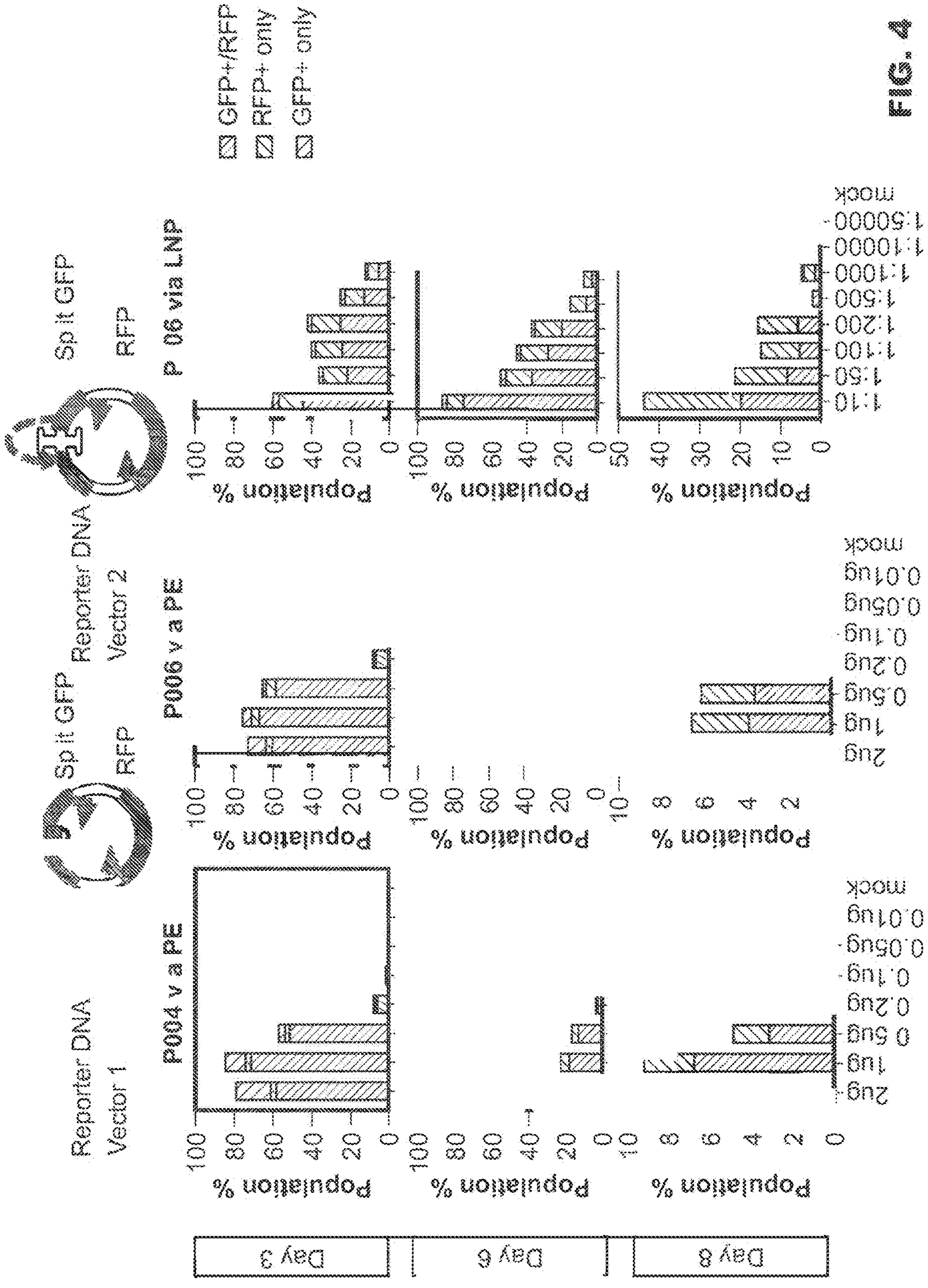
FIG. 4 illustrates resolution of circular, non-viral vector DNA reporter constructs containing cruciform structures of the present disclosure (P004—SEQ ID NO: 35; P006—SEQ ID NO: 14) delivered by polyethylenimine (PEI) and SM-102-based lipid nanoparticle (LNP) in 293 cells. The data suggests resolution of reporter constructs delivered with LNP and PEI started from day 6. The data further suggests that different inverted repeat sequences will have different resolution efficiencies.

It should also be understood that, unless clearly indicated to the contrary, in any methods claimed herein that include more than one step or act, the order of the steps or acts of the method is not necessarily limited to the order in which the steps or acts of the method are recited.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g., "one or the other but not both") when preceded by terms of exclusivity, such as "either," "one of," "only one of" or "exactly one of." "Consisting essentially of," when used in the claims, shall have its ordinary meaning as used in the field of patent law.

As used herein, the terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b, and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "about" refers to a measurable value such as an amount of the length of a nucleotide sequence, a polynucleotide or polypeptide sequence, dose, time, temperature, and the like, is meant to encompass variations of 20%, 10%, 5%, 1%, 0.5%, or even 0.1% of the specified amount.

As used herein, the term "Fc" refers to a human IgG Fc domain. Subtypes of IgG such as IgG1, IgG2, IgG3, and IgG4 are all being contemplated for usage as Fc domains.

As used herein, the term "heterologous gene" as used herein refers to a nucleotide sequence not naturally associated with a host animal into which it is introduced, including for example, exon coding sequences from a human gene introduced, as a chimeric heterologous gene, into a host nematode.

As used herein, the term "host cell" refers to any cell type that is susceptible to transformation, transfection, transduction, or the like with a nucleic acid construct or expression vector comprising a polynucleotide of the present disclosure. In some embodiments, the term "host cell" encompasses any progeny of a parent cell that is not identical to the parent cell due to mutations that occur during replication. Host cells may include packaging cells, producer cells, and cells infected with viral vectors. In particular embodiments, host cells infected with viral vector of the present disclosure are administered to a subject in need of therapy. In some embodiments, host cells are transduced ex vivo. In other embodiments, host cells are transduced in vivo.

As used herein, the terms "hypophosphatasia" and "HPP" refer to a rare, heritable skeletal disorder caused by, e.g., one or more loss-of-function mutations in the ALPL (alkaline phosphatase, liver/bone/kidney) gene, which encodes tissue-nonspecific alkaline phosphatase (TNALP). HPP can be further characterized as, e.g., infantile HPP or perinatal HPP (e.g., benign perinatal HPP or lethal perinatal HPP). For instance, "infantile HPP" describes a patient having HPP that is about three years of age or younger, whereas "perinatal HPP" describes a patient having HPP immediately before or after birth (e.g., one to four weeks after birth). The age of onset of HPP, such as when the subject exhibits symptoms of HPP, can also be categorized as, e.g., perinatal-onset HPP and infantile-onset HPP. Patients with HPP can exhibit symptoms of HPP including, but not limited to, skeletal deformity, hypotonia, mobility impairments, gait disturbance, bone deformity, joint pain, bone pain, bone fracture, muscle weakness, muscle pain, rickets (e.g., defects in growth plate cartilage), premature loss of deciduous teeth, incomplete bone mineralization, elevated blood and/or urine levels of phosphoethanolamine (PEA), PPi, pyridoxal 5'-phosphate (PLP), hypomineralization, rachitic ribs, hypercalciuria, short stature, HPP-related seizure, inadequate weight gain, craniosynostosis, and/or calcium pyrophosphate dihydrate crystal deposition (CPPD) in joints leading to, e.g., chondrocalcinosis and premature death. Symptoms of HPP can also include TBM and symptoms of TBM, such as cardio-respiratory arrest, tracheostomy, cardiac arrest, respiratory distress, sputum retention, wheezing, coughing, anoxic spells, cyanosis, bradycardia, tachyarrhythmia, spontaneous hyperextension of the neck, prolonged expiratory breathing phase, failure to thrive, sternal retractions, substernal retractions, intercostal retractions, intermittent or continuous dyspnea, and recurrent bronchitis or pneumonia.

As used herein, the term "nucleic acid" refers to polynucleotides such as DNA or RNA. Nucleic acids can be single-stranded, partly, or completely, double-stranded, and in some cases partly or completely triple-stranded. Nucleic acids include genomic DNA, cDNA, mRNA, etc. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. The term "nucleic acid sequence" as used herein can refer to the nucleic acid material itself and is not restricted to the sequence information (i.e., the succession of letters chosen among the five base letters A, G, C, T, or U) that biochemically characterizes a specific nucleic acid, e.g., a DNA or RNA molecule. A nucleic acid sequence is presented in the 5' to 3' direction unless otherwise indicated. The term "nucleic acid segment" is used herein to refer to a nucleic acid sequence that is a portion of a longer nucleic acid sequence.

As used herein, the terms "operably linked" or "operably associated" refer to a functional relationship between two nucleic acids, wherein the expression, activity, localization, etc., of one of the sequences is controlled by, directed by, regulated by, modulated by, etc., the other nucleic acid. The two nucleic acids are said to be operably linked or operably associated or in operable association. "Operably linked" or "operably associated" can also refers to a relationship between two polypeptides wherein the expression of one of the polypeptides is controlled by, directed by, regulated by, modulated by, etc., the other polypeptide. For example, transcription of a nucleic acid is directed by an operably linked promoter; post-transcriptional processing of a nucleic acid is directed by an operably linked processing sequence; translation of a nucleic acid is directed by an operably linked translational regulatory sequence such as a translation initiation sequence; transport, stability, or localization of a nucleic acid or polypeptide is directed by an operably linked transport or localization sequence such as a secretion signal sequence; and post-translational processing of a polypeptide is directed by an operably linked processing sequence. Typically, a first nucleic acid sequence that is operably linked to a second nucleic acid sequence, or a first polypeptide that is operatively linked to a second polypeptide, is covalently linked, either directly or indirectly, to such a sequence, although any effective three-dimensional association is acceptable. One of ordinary skill in the art will appreciate that multiple nucleic acids, or multiple polypeptides, may be operably linked or associated with one another.

As used herein, the terms "pharmaceutically acceptable excipient," "carrier," or "diluent" refer to pharmaceutical components which do not alter the therapeutic properties of an active agent with which it is administered. One exemplary pharmaceutically acceptable carrier substance is physiological saline. For instance, the pharmaceutically acceptable carrier can include sodium chloride (e.g., 150 mM sodium chloride) and sodium phosphate (e.g., 25 mM sodium phosphate). Other physiologically acceptable excipients, carriers, and diluents, and their formulations, are known to those skilled in the art and described, e.g., in Remington: The Science and Practice of Pharmacy (22nd Ed), Allen (2012). For instance, a pharmaceutically acceptable excipient, carrier, or diluent can include dibasic sodium phosphate, heptahydrate; monobasic sodium phosphate, monohydrate; and sodium chloride at a pH between 7.2 and 7.6.

As used herein, the term "pharmaceutical composition" it is meant a composition containing an active agent as described herein, formulated with at least one pharmaceutically acceptable excipient, carrier, or diluent. The pharmaceutical composition can be manufactured or sold with the approval of a governmental regulatory agency as part of a therapeutic regimen for the treatment or prevention of a disease or event in a patient (e.g., an infant with HPP, such as an infant having perinatal-onset HPP, or an infant having infantile-onset HPP, or juvenile-onset HPP, or a patient having childhood-onset HPP). Pharmaceutical compositions can be formulated, for example, for subcutaneous administration, intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form.

As used herein, the term "polypeptide," "polypeptide fragment," "peptide" and "protein" are used interchangeably, unless specified to the contrary, and according to conventional meaning, i.e., as a sequence of amino acids. Polypeptides arc not limited to a specific length, e.g., they may comprise a full-length protein sequence or a fragment of a full-length protein, and may include post-translational modifications of the polypeptide, for example, glycosylations, acetylations, phosphorylations and the like, as well as other modifications known in the art, both naturally occurring and non-naturally occurring. In various embodiments, the polypeptides contemplated herein comprise a signal (or leader) sequence at the N-terminal end of the protein, which co-translationally or post-translationally directs transfer of the protein. Polypeptides can be prepared using any of a variety of well-known recombinant and/or synthetic techniques. In some embodiments, the polypeptides contemplated herein encompass alkaline phosphatases, or sequences that have deletions from, additions to, and/or substitutions of one or more amino acid of a CAR as disclosed herein.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the term "promoter," as used herein, refers to a DNA sequence that determines the site of transcription initiation for an RNA polymerase. Promoter sequences comprise motifs which are recognized and bound by polypeptides, i.e., transcription factors. The said transcription factors shall upon binding recruit RNA polymerases II, preferably, RNA polymerase I, II or III, more preferably, RNA polymerase II or III, and most preferably, RNA polymerase II. Thereby will be initiated the expression of a nucleic acid operatively linked to the transcription control sequence. It is to be understood that dependent on the type of nucleic acid to be expressed, expression as meant herein may comprise transcription of DNA sequences into RNA polynucleotides (as suitable for, e.g., anti-sense approaches, RNAi approaches or ribozyme approaches) or may comprise transcription of DNA sequences into RNA polynucleotides followed by translation of the said RNA polynucleotides into polypeptides (as suitable for, e.g., gene expression and recombinant polypeptide production approaches). In order to govern expression of a nucleic acid sequence, the transcription control sequence may be located immediately adjacent to the nucleic acid to be expressed, i.e., physically linked to the said nucleic acid at its 5' end. Alternatively, it may be located in physical proximity. In the latter case, however, the sequence must be located so as to allow functional interaction with the nucleic acid to be expressed.

As used herein, the terms "regulatory sequence" or "regulatory element" refer to a nucleic acid sequence that regulates one or more steps in the expression (particularly transcription, but in some cases other events such as splicing or other processing) of nucleic acid sequence(s) with which it is operatively linked. The term includes promoters, enhancers, and other transcriptional control elements that direct or enhance transcription of an operatively linked nucleic acid. Regulatory sequences may direct constitutive expression (e.g., expression in most or all cell types under typical physiological conditions in culture or in an organism), cell type specific, lineage specific, or tissue specific expression, and/or regulatable (inducible or repressible) expression. For example, expression may be induced or repressed by the presence or addition of an inducing agent such as a hormone or other small molecule, by an increase in temperature, etc. Non-limiting examples of cell type, lineage, or tissue specific promoters appropriate for use in mammalian cells include lymphoid-specific promoters (see, for example, Calame et al., Adv. Immunol. 43:235, 1988) such as promoters of T cell receptors (see, e.g., Winoto et al., EMBO J. 8:729, 1989) and immunoglobulins (see, for example, Banerji et al., Cell 33:729, 1983; Queen et al., Cell 33:741, 1983), and neuron-specific promoters (e.g., the neurofilament promoter; Byrne et al., Proc. Natl. Acad. Sci. USA 86:5473, 1989). Developmentally regulated promoters include hox promoters (see, e.g., Kessel et al., Science 249:374, 1990) and the a-fetoprotein promoter (Campes et al., Genes Dev. 3:537, 1989). Some regulatory elements may inhibit or decrease expression of an operatively linked nucleic acid. Such regulatory elements may be referred to as "negative regulatory elements." A regulatory element whose activity can be induced or repressed by exposure to an inducing or repressing agent and/or by altering environmental conditions is referred to herein as a "regulatable" element.

As used herein, the term "signal peptide" refers to a short peptide (about 5 to about 30 amino acids long) at the N-terminus of a polypeptide that directs a polypeptide towards the secretory pathway (e.g., the extracellular space). In some embodiments, the signal peptide is typically cleaved during secretion of the polypeptide. In some embodiments, the signal sequence may direct the polypeptide to an intracellular compartment or organelle. In some embodiments, a signal sequence may be identified by homology, or biological activity, to a peptide with the known function of targeting a polypeptide to a particular region of the cell.

As used herein, the term "subject" refers to any animal subject including laboratory animals (e.g., primates, rats, mice), livestock (e.g., cows, sheep, goats, pigs, turkeys, chickens), household pets (e.g., dogs, cats, rodents, etc.), and humans.

As used herein, the term "therapeutically effective amount" refers to a virus or transduced therapeutic cell may vary according to factors such as the disease state, age, sex, and weight of the individual, and the ability of the stem and progenitor cells to elicit a desired response in the individual. In some embodiments, a therapeutically effective amount is also one in which any toxic or detrimental effects of the virus or transduced therapeutic cells are outweighed by the therapeutically beneficial effects. In some embodiments, the term "therapeutically effective amount" includes an amount that is effective to "treat" a subject (e.g., a patient).

As used herein, the terms "treatment" or "treating" refer to any beneficial or desirable effect on the symptoms or pathology of a disease or pathological condition and may include even minimal reductions in one or more measurable markers of the disease or condition being treated. In some embodiments, the treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, the terms "variants" or "variant" refer to a nucleic acid or polypeptide differing from a reference nucleic acid or polypeptide but retaining essential properties thereof. Generally, variants are overall closely similar, and, in many regions, identical to the reference nucleic acid or polypeptide. Thus, "variant" forms of a transcription factor are overall closely similar, and capable of binding DNA and activate gene transcription.

As used herein, the term "vector" refers to a nucleic acid molecule capable transferring or transporting another nucleic acid molecule. In some embodiments, the transferred nucleic acid is generally linked to, e.g., inserted into, the vector nucleic acid molecule. In some embodiments, a vector may include sequences that direct autonomous replication in a cell or may include sequences sufficient to allow integration into host cell DNA. Useful vectors include, for example, plasmids (typically DNA plasmids, but RNA plasmids are also of use), cosmids, and viral vectors. As will be evident to one of skill in the art, the term "viral vector" is widely used refer either to a nucleic acid molecule (e.g., a plasmid) that includes virus-derived nucleic acid elements that typically facilitate transfer of the nucleic acid molecule or integration into the genome of a cell or to a viral particle that mediates nucleic acid transfer. In some embodiments, the viral particles will typically include various viral components and sometimes also host cell components in addition to nucleic acid(s).

Circular, Non-Viral DNA Vectors

The present disclosure is directed to circular, non-viral DNA vectors, such as circular non-viral DNA vectors including at least two inverted repeat sequences, where the at least two inverted repeat sequences are separated by a non-repeated nucleotide sequence which is not part of the at least two inverted repeat sequences. In some embodiments, the non-repeated nucleotide sequence comprises at least 3 nucleotides. In other embodiments, the non-repeated nucleotide sequence comprises at least 4 nucleotides. In other embodiments, the non-repeated nucleotide sequence comprises at least 5 nucleotides. In other embodiments, the non-repeated nucleotide sequence comprises at least 7 nucleotides. In other embodiments, the non-repeated nucleotide sequence comprises at least 10 nucleotides. In other embodiments, the non-repeated nucleotide sequence comprises at least 15 nucleotides. In other embodiments, the non-repeated nucleotide sequence comprises at least 20 nucleotides. Examples of suitable non-repeated nucleotide sequences include, but are not limited to, TTG (SEQ ID NO: 84), AAT (SEQ ID NO: 85), TAA (SEQ ID NO: 86), TAG (SEQ ID NO: 87), AGTT (SEQ ID NO: 88), AGTA (SEQ ID NO: 89), TAAA (SEQ ID NO: 90), TCAA (SEQ ID NO: 91), GAGTA (SEQ ID NO: 92), AAGTGCA (SEQ ID NO: 93), AGTACAAATTG (SEQ ID NO: 94), and ACCTTAGAGGCTA (SEQ ID NO: 95).

In some embodiments, the non-repeated nucleotide sequence comprises a minimal bacterial origin of replication. In other embodiments, the non-repeated nucleotide sequence comprises a heterologous gene or a portion of a heterologous gene, e.g., a gene encoding a bacterial suppressor tRNA, an RNAi repressor, or an antisense RNA. In other embodiments, the non-repeated nucleotide sequence comprises a bacterial operator sequence, e.g., the lac operator or tet operator.

In some embodiments, the circular, non-viral DNA vectors are substantially devoid of CpG sequences. In some embodiments, the circular, non-viral DNA vectors comprise less than about 500 CpG per vector, less than about 450 CpG per vector, less than about 400 CpG per vector, less than about 350 CpG per vector, less than about 300 CpG per vector, less than about 250 CpG per vector, less than about 200 CpG per vector, less than about 150 CpG per vector, less than about 100 CpG per vector, less than about 75 CpG per vector, less than about 50 CpG per vector, less than about 25 CpG per vector, less than about 20 CpG per vector, less than about 15 CpG per vector, less than about 10 CpG per vector, etc.

In some embodiments, the circular, non-viral DNA vectors lack a drug resistance gene. In some embodiments, the circular, non-viral DNA vectors include the two inverted repeat sequences separated by the non-repeated nucleotide sequence; where the vector further includes at least a portion of a bacterial origin of replication, and where the at least the portion of the bacterial origin of replication is not included within either of the two inverted repeat sequences or in the non-repeated nucleotide sequence. In some embodiments, the at least the portion of the bacterial origin of replication is located adjacent to the heterologous gene. In some embodiments, the circular, non-viral DNA vector includes one or more recombination sites, e.g., LoxP sites, FRT sites, attB and attP sites or their product sites attL or attR, or alternative recombination target sites derived from these sites, e.g., Lox7, Lox511 or Lox66 sites.

In some embodiments, the circular, non-viral DNA vectors are substantially double stranded. In other embodiments, the circular, non-viral DNA vectors are substantially supercoiled. In other embodiments, the substantially supercoiled non-viral DNA vectors comprise one or more regions of negative supercoiling.

In some embodiments, the circular, non-viral DNA vectors are non-immunogenic (e.g., have a reduced likelihood of triggering an immune response as compared with other non-viral DNA vectors, or viral vectors, such as lentiviral vectors, adenoviral vectors, and adeno-associated virus (AAV) vectors). It is also believed that the circular, non-viral DNA vectors of the present disclosure are amenable to repeat dosing, as described further herein. In addition, a reduction in immune-stimulating CpG content facilitates redosing, which is believed to be critical in pediatric patients.

In some embodiments, the circular, non-viral DNA vectors of the present disclosure facilitate persistent in vivo expression of one or more heterologous genes encoding one or more therapeutic proteins. Without wishing to be bound by any particular theory, it is believed that the non-viral DNA vectors of the present disclosure act like an endogenous gene in the nucleus for enhanced persistence of gene expression. In some embodiments, the circular, non-viral DNA vectors persist for a period of at least about 4 weeks after in vivo administration. In other embodiments, the circular, non-viral DNA vectors persist for a period of at least about 6 weeks after in vivo administration. In other embodiments, the circular, non-viral DNA vectors persist for a period of at least about 8 weeks after in vivo administration. In other embodiments, the circular, non-viral DNA vectors persist for a period of at least about 10 weeks after in vivo administration. In other embodiments, the circular, non-viral DNA vectors persist for a period of at least about 12 weeks after in vivo administration. In other embodiments, the circular, non-viral DNA vectors persist for a period of at least about 14 weeks after in vivo administration. In other embodiments, the circular, non-viral DNA vectors persist for a period of at least about 16 weeks after in vivo administration. In other embodiments, the circular, non-viral DNA vectors persist for a period of at least about 20 weeks after in vivo administration. In other embodiments, the circular, non-viral DNA vectors persist for a period of at least about 24 weeks after in vivo administration. In other embodiments, the circular, non-viral DNA vectors persist for a period of at least about 36 weeks after in vivo administration. In other embodiments, the circular, non-viral DNA vectors persist for a period of at least about 48 weeks after in vivo administration. In other embodiments, the circular, non-viral DNA vectors persist for a period of at least about 1 year after in vivo administration. In other embodiments, the circular, non-viral DNA vectors persist for a period of at least about 2 years after in vivo administration. In other embodiments, the circular, non-viral DNA vectors persist for a period of at least about 4 years after in vivo administration.

It is believed that the transgenes carried by the circular, non-viral DNA vectors of the present disclosure are taken up by cells and expressed at levels similar to transgene expression from viral vectors; and persist for periods similar to those of non-integrating viral vectors. Without wishing to be bound by any particular theory, it is believed that the circular, non-viral DNA vectors of the present disclosure act similar to some non-integrating viral vectors by assuming molecular forms that allow for persistent gene expression. Such similarities may be related to chromatin factors that both the circular, non-viral DNA vectors of the present disclosure and viral vectors interact with or related to chromatin structures assumed by both viral vectors and the non-viral DNA vectors of the present disclosure. Chromatin is a term that describes structures that organize DNA within the nucleus of eukaryotic cells. In its simplest conception, chromatin is composed of histone proteins that form nucleosomes on DNA. However, the spacing and modifications of these histones is complex and non-random and provide structural and signaling capacity to the protein scaffold surrounding genes or structural elements. The role of chromatin in virus biology depends largely on the type of virus, but for all viruses that transverse the nucleus, interactions with chromatin is unavoidable. The importance of chromatin dynamics in the regulation of essential viral-vector processes, including entry, gene expression, and persistence is beginning to be understood. The circular, non-viral DNA vectors of the present disclosure are thought to utilize a variety of aspects of chromatin dynamics in a manner akin to viral vectors. Such attributes could include chromatin structures that promote interaction with the nuclear matrix, structures that regulate epigenetic factors influencing gene expression, structures that mediate nuclear organization, or structures that promote active transcriptionally active chromatin status among others.

In some embodiments, the circular, non-viral DNA vector comprises (i) a first portion comprising an expression cassette including one or more nucleic acid sequences encoding one or more therapeutic proteins, where each of the one or more nucleic acid sequences encoding the one or more therapeutic proteins are operatively linked to a promoter; and (ii) a second portion capable of forming at least one cruciform structure, wherein the second portion comprises at least two inverted repeat sequences, and where the at least two inverted repeat sequences are separated by a non-repeating nucleotide sequence having at least 3 nucleotides. In some embodiments, the non-repeating nucleotide sequence has at least 5 nucleotides. In some embodiments, the non-repeating nucleotide sequence has at least 10 nucleotides. In some embodiments, the non-repeating nucleotide sequence has at least 15 nucleotides.

In some embodiments, the second portion does not include a bacterial origin or replication or any portion thereof. In other embodiments, the non-repeating nucleotide sequence does not comprise a bacterial origin or replication or any portion thereof. In other embodiments, the circular, non-viral DNA vector includes a bacterial origin of replication or a portion thereof, but the bacterial origin of replication or the portion thereof is not located within the second portion. In yet other embodiments, at least a portion of a bacterial origin of replication is included in the first portion or within a third portion adjacent to either the first or second portions, but not within the second portion.

In some embodiments, the cruciform structure comprises a Holliday junction.

In some embodiments, each of the inverted repeat sequences comprise or are derived from nucleic acid sequences present within AAV serotypes (including any of those disclosed herein).

In some embodiments, the non-repeating nucleotide sequence is single stranded, while the remainder of the second portion is double stranded. In some embodiments, the non-viral DNA vectors are substantially devoid of CpG sequences. In some embodiments, the non-viral DNA vectors comprise less than about 500 CpG per vector, less than about 450 CpG per vector, less than about 400 CpG per vector, less than about 350 CpG per vector, less than about 300 CpG per vector, less than about 250 CpG per vector, less than about 200 CpG per vector, less than about 150 CpG per vector, less than about 100 CpG per vector, less than about 75 CpG per vector, less than about 50 CpG per vector, less than about 25 CpG per vector, less than about 20 CpG per vector, less than about 15 CpG per vector, less than about 10 CpG per vector, etc.

In other embodiments, the circular, non-viral DNA vector comprises: (i) a first portion comprising an expression cassette including one or more nucleic acid sequences encoding one or more therapeutic proteins, where each of the one or more nucleic acid sequences encoding the one or more therapeutic proteins are operatively linked to a promoter; and (ii) a second portion capable of forming at least one cruciform structure, wherein the second portion has the Formula X—Y—X', where X and X' are each inverted repeat sequences, and where Y is not repeated and comprises a nucleotide having at least 3 nucleotides, e.g., at least 5 nucleotides, at least 10 nucleotides, at least 15 nucleotides, etc. In some embodiments, the second portion does not include a bacterial origin or replication or any portion thereof. In other embodiments, the circular, non-viral DNA vector includes a bacterial origin of replication or a portion thereof, but the bacterial origin of replication or the portion thereof is not located within the second portion.

In some embodiments, the inverted repeat sequences (X and X') are derived from nucleic acid sequences present within AAV genomes. In some embodiments, the non-viral DNA vectors are substantially devoid of CpG sequences. In some embodiments, the non-viral DNA vectors comprise less than about 500 CpG per vector, less than about 450 CpG per vector, less than about 400 CpG per vector, less than about 350 CpG per vector, less than about 300 CpG per vector, less than about 250 CpG per vector, less than about 200 CpG per vector, less than about 150 CpG per vector, less than about 100 CpG per vector, less than about 75 CpG per vector, less than about 50 CpG per vector, less than about 25 CpG per vector, less than about 20 CpG per vector, less than about 15 CpG per vector, less than about 10 CpG per vector, etc.

In yet other embodiments, the non-viral DNA vector comprises the following elements operatively linked in a 5' to a 3' direction: (i) a first repeat sequence; (ii) a non-repeating nucleotide sequence having at least 3 nucleotides; (iii) a second repeat sequence; and (iv) an expression cassette. In some embodiments, the non-repeating nucleotide sequence has at least 5 nucleotides. In some embodiments, the non-repeating nucleotide sequence has at least 10 nucleotides. In some embodiments, the non-repeating nucleotide sequence has at least 15 nucleotides.

In some embodiments, the non-repeating nucleotide sequence does not comprise a bacterial origin or replication or any portion thereof. In other embodiments, the circular, non-viral DNA vector includes a bacterial origin of replication or a portion thereof, but the bacterial origin of replication or the portion thereof is not part of or included within the non-repeating nucleotide sequence. In some embodiments, the first and second repeat sequences comprise or are derived from nucleic acid sequences present within AAV genomes (including any of those disclosed herein).

In some embodiments, the expression cassette includes one or more nucleic acid sequences encoding one or more therapeutic proteins, where each of the one or more nucleic acid sequences encoding the one or more therapeutic proteins are operatively linked to a promoter. In some embodiments, the expression cassette includes one or more of an enhancer and/or promoter, a 3' untranslated region (with or without introns), a translation initiation region, a transgene (protein coding regions, which could themselves be broken down into several components), a 5' untranslated region, and a polyadenylation addition region.

In some embodiments, the non-viral DNA vectors are substantially devoid of CpG sequences. In some embodiments, the non-viral DNA vectors comprise less than about 500 CpG per vector, less than about 450 CpG per vector, less than about 400 CpG per vector, less than about 350 CpG per vector, less than about 300 CpG per vector, less than about 250 CpG per vector, less than about 200 CpG per vector, less than about 150 CpG per vector, less than about 100 CpG per vector, less than about 75 CpG per vector, less than about 50 CpG per vector, less than about 25 CpG per vector, less than about 20 CpG per vector, less than about 15 CpG per vector, less than about 10 CpG per vector, etc.

In further embodiments, the circular, non-viral DNA vector comprises (i) a first portion comprising an expression cassette including one or more nucleic acid sequences encoding one or more therapeutic proteins, where each of the one or more nucleic acid sequences encoding the one or more therapeutic proteins are operatively linked to a promoter; and (ii) a second portion capable of forming at least one cruciform structure, wherein the second portion comprises at least two inverted repeat sequences, wherein the at least two inverted repeat sequences arc separated by at least a portion of a bacterial origin of replication. In some embodiments, each of the inverted repeat sequences comprise or are derived from nucleic acid sequences present within AAV serotypes. In some embodiments, the cruciform structure comprises a Holliday junction.

In some embodiments, the at least the portion of the bacterial origin of replication is single stranded.

In some embodiments, the non-viral DNA vectors are substantially devoid of CpG sequences. In some embodiments, the non-viral DNA vectors comprise less than about 500 CpG per vector, less than about 450 CpG per vector, less than about 400 CpG per vector, less than about 350 CpG per vector, less than about 300 CpG per vector, less than about 250 CpG per vector, less than about 200 CpG per vector, less than about 150 CpG per vector, less than about 100 CpG per vector, less than about 75 CpG per vector, less than about 50 CpG per vector, less than about 25 CpG per vector, less than about 20 CpG per vector, less than about 15 CpG per vector, less than about 10 CpG per vector, etc.

In yet further embodiments, the circular, non-viral DNA vector comprises: (i) a first portion comprising an expression cassette including one or more nucleic acid sequences encoding one or more therapeutic proteins, where each of the one or more nucleic acid sequences encoding the one or more therapeutic proteins are operatively linked to a promoter; and (ii) a second portion capable of forming at least one cruciform structure, wherein the second portion has the Formula X—Y—X', where X and X' are each inverted repeat sequences, and where Y comprises at least a portion of a bacterial origin of replication. In some embodiments, the inverted repeat sequences comprise or are derived from nucleic acid sequences present within AAV genomes. In some embodiments, the at least the portion of the bacterial origin of replication is single stranded when the repeat sequences form a cruciform structure. In some embodiments, the cruciform structure comprises a Holliday junction.

In some embodiments, the non-viral DNA vectors are substantially devoid of CpG sequences. In some embodiments, the non-viral DNA vectors comprise less than about 500 CpG per vector, less than about 450 CpG per vector, less than about 400 CpG per vector, less than about 350 CpG per vector, less than about 300 CpG per vector, less than about 250 CpG per vector, less than about 200 CpG per vector, less than about 150 CpG per vector, less than about 100 CpG per vector, less than about 75 CpG per vector, less than about 50 CpG per vector, less than about 25 CpG per vector, less than about 20 CpG per vector, less than about 15 CpG per vector, less than about 10 CpG per vector, etc.

In even further embodiments, the non-viral DNA vector comprises the following elements operatively linked in a 5' to a 3' direction: (i) a first repeat sequence; (ii) a minimal bacterial origin of replication; (iii) a second repeat sequence; and (iv) an expression cassette. In some embodiments, the first and second repeat sequences comprise or are derived from nucleic acid sequences present within AAV genomes. In some embodiments, at least a portion of the minimal bacterial origin of replication is single stranded when the repeat sequences for a cruciform structure. In some embodiments, the cruciform structure comprises a Holliday junction.

In some embodiments, the expression cassette includes one or more nucleic acid sequences encoding one or more therapeutic proteins, where each of the one or more nucleic acid sequences encoding the one or more therapeutic proteins are operatively linked to a promoter. In some embodiments, the expression cassette includes one or more of an enhancer and/or promoter, a 3' untranslated region (with or without introns), a translation initiation region, a transgene (protein coding regions, which could themselves be broken down into several components), a 5' untranslated region, and a polyadenylation addition region.

In some embodiments, the non-viral DNA vectors are substantially devoid of CpG sequences. In some embodiments, the non-viral DNA vectors comprise less than about 500 CpG per vector, less than about 450 CpG per vector, less than about 400 CpG per vector, less than about 350 CpG per vector, less than about 300 CpG per vector, less than about 250 CpG per vector, less than about 200 CpG per vector, less than about 150 CpG per vector, less than about 100 CpG per vector, less than about 75 CpG per vector, less than about 50 CpG per vector, less than about 25 CpG per vector, less than about 20 CpG per vector, less than about 15 CpG per vector, less than about 10 CpG per vector, etc.

In yet even further embodiments, the circular, non-viral DNA vector comprises (i) a first portion comprising an expression cassette including one or more nucleic acid sequences encoding one or more therapeutic proteins, where each of the one or more nucleic acid sequences encoding the one or more therapeutic proteins are operatively linked to a promoter; and (ii) a second portion capable of forming at least one cruciform structure, wherein the second portion comprises at least two inverted repeat sequences separated by a non-repeating nucleotide sequence comprising a heterologous gene or a portion of a heterologous gene. In some embodiments, a least a portion of a bacterial origin of replication is included within the circular non, viral DNA vector, but not within the second portion. In some embodiments, at least a portion of a bacterial origin of replication is included in the first portion or within a third portion adjacent to either the first or second portions, but not within the second portion. In some embodiments, the cruciform structure comprises a Holliday junction. In some embodiments, the inverted repeat sequences comprise or are derived from nucleic acid sequences present within AAV serotypes. In some embodiments, the non-repeating nucleotide sequence comprising the heterologous gene, or the portion thereof is single stranded, while the remainder of the second portion is double stranded.

In some embodiments, the non-viral DNA vectors are substantially devoid of CpG sequences. In some embodiments, the non-viral DNA vectors comprise less than about 500 CpG per vector, less than about 450 CpG per vector, less than about 400 CpG per vector, less than about 350 CpG per vector, less than about 300 CpG per vector, less than about 250 CpG per vector, less than about 200 CpG per vector, less than about 150 CpG per vector, less than about 100 CpG per vector, less than about 75 CpG per vector, less than about 50 CpG per vector, less than about 25 CpG per vector, less than about 20 CpG per vector, less than about 15 CpG per vector, less than about 10 CpG per vector, etc.

In some embodiments, each of inverted repeat sequences are nucleic acid sequences which include between about 20 to about 500 bp, from between about 20 bp and about 450 bp, from between about 20 bp to about 400 bp, from between about 20 bp to about 300 bp, from between about 20 bp to about 250 bp, from between about 20 bp to about 200 bp, from between about 20 bp to about 160 bp, from between about 60 bp to about 160 bp, from about 70 bp to about 150 bp, from about 80 bp to about 140 bp, from about 90 bp to about 130 bp, etc. In some embodiments, each of the inverted repeat sequences have about 115 bp, 116 bp, 117 bp, 118 bp, 119 bp, 120 bp, 121 bp, 122 bp, 123 bp, 124 bp, 125 bp, 126 bp, 127 bp, 128 bp, 129 bp, 130 bp, 131 bp, 132 bp, 133 bp, 134 bp, 135 bp, 136 bp, 137 bp, 138 bp, 139 bp, 140 bp, 141 bp, 142 bp, etc.

In some embodiments, each of the inverted repeat sequences have a nucleic acid sequence having at least 80% identity to any one of SEQ IDS NO: 1-18. In some embodiments, each of the inverted repeat sequences have a nucleic acid sequence having at least 85% identity to any one of SEQ IDS NO: 1-18. In some embodiments, each of the inverted repeat sequences have a nucleic acid sequence having at least 90% identity to any one of SEQ IDS NO: 1-18.

In some embodiments, each of the inverted repeat sequences have a nucleic acid sequence having at least 91% identity to any one of SEQ IDS NO: 1-18. In some embodiments, each of the inverted repeat sequences have a nucleic acid sequence having at least 92% identity to any one of SEQ IDS NO: 1-18. In some embodiments, each of the inverted repeat sequences have a nucleic acid sequence having at least 93% identity to any one of SEQ IDS NO: 1-18. In some embodiments, each of the inverted repeat sequences have a nucleic acid sequence having at least 94% identity to any one of SEQ IDS NO: 1-18. In some embodiments, each of the inverted repeat sequences have a nucleic acid sequence having at least 95% identity to any one of SEQ IDS NO: 1-18. In some embodiments, each of the inverted repeat sequences have a nucleic acid sequence having at least 96% identity to any one of SEQ IDS NO: 1-18. In some embodiments, each of the inverted repeat sequences have a nucleic acid sequence having at least 97% identity to any one of SEQ IDS NO: 1-18. In some embodiments, each of the inverted repeat sequences have a nucleic acid sequence having at least 98% identity to any one of SEQ IDS NO: 1-18. In some embodiments, each of the inverted repeat sequences have a nucleic acid sequence having at least 99% identity to any one of SEQ IDS NO: 1-18. In some embodiments, each of the inverted repeat sequences have a nucleic acid sequence having any one of SEQ IDS NO: 1-18.

In some embodiments, each of the inverted repeat sequences comprise or are derived from AAV inverted terminal repeat elements (e.g., derived from elements of an AAV serotype, such as any one of AAV1, AAV2, AAV3, AAV4, AAV5, AAV6, and/or AAV7). For instance, each of the inverted repeat groups may include one or more of the A, A', B, B', C, C', D, and/or D' elements of inverted terminal repeat elements from one or more AAV serotypes.

In some embodiments, a 5' A element comprises at least 90% identity to TTGGCCACTCCCTCTCTGCGCGCTDGCTCGCTCACTGAGGC (SEQ ID NO: 74). In some embodiments, a 5' A element comprises TTGGCCACTCCCTCTCTGCGCGCTDGCTCGCTCACTGAGGC (SEQ ID NO: 74). In some embodiments, a 3' A element comprises at least 90% identity to GCCTCAGTGAGCGAGCGAGCGCGCAGAGAGGGAGTGGCCAA (SEQ ID NO: 75). In some embodiments, a 3' A element comprises GCCTCAGTGAGCGAGCGAGCGCGCAGAGAGGGAGTGGCCAA (SEQ ID NO: 75). In some embodiments, a 5' B element comprises at least 90% identity to CGGGCGACC (SEQ ID NO: 76). In some embodiments, a 5' B element comprises CGGGCGACC (SEQ ID NO: 76). In some embodiments, a 3' B element comprises at least 90% identity to GGTCGCCCG (SEQ ID NO: 77). In some embodiments, a 3' B element comprises GGTCGCCCG (SEQ ID NO: 77. In some embodiments, a 5' C element comprises at least 90% identity to CGCCCGGGC (SEQ ID NO: 78). In some embodiments, a 5' C element comprises CGCCCGGGC (SEQ ID NO: 78). In some embodiments, a 3' C element comprises at least 90% identity to GCCCGGGCG (SEQ ID NO: 79). In some embodiments, a 3' C element comprises GCCCGGGCG (SEQ ID NO: 79). In some embodiments, a 5' D element comprises at least 90% identity to AGGAACCCCTAGTGATGGAG (SEQ ID NO: 80). In some embodiments, a 5' D element comprises identity to AGGAACCCCTAGTGATGGAG (SEQ ID NO: 80). In some embodiments, a 3' D element comprises at least 90% identity to CTCCATCACTAGGGGTTCCT (SEQ ID NO: 81). In some embodiments, a 3' D element comprises identity to CTCCATCACTAGGGGTTCCT (SEQ ID NO: 81).

In some embodiments, a 5' A element comprises at least 95% identity to TTGGC-CACTCCCTCTCTGCGCGCTDGCTCGCTCACT-GAGGC (SEQ ID NO: 74). In some embodiments, a 5' A element comprises TTGGC-CACTCCCTCTCTGCGCGCTDGCTCGCTCACT-GAGGC (SEQ ID NO: 74). In some embodiments, a 3' A element comprises at least 95% identity to GCCTCAGT-GAGCGAGCGAGCGCGCAGAGAGGGAGTGGCCAA (SEQ ID NO: 75). In some embodiments, a 3' A element comprises GCCTCAGT-GAGCGAGCGAGCGCGCAGAGAGGGAGTGGCCAA (SEQ ID NO: 75). In some embodiments, a 5' B element comprises at least 95% identity to CGGGCGACC (SEQ ID NO: 76). In some embodiments, a 5' B element comprises CGGGCGACC (SEQ ID NO: 76). In some embodiments, a 3' B element comprises at least 95% identity to GGTCGCCCG (SEQ ID NO: 77). In some embodiments, a 3' B element comprises GGTCGCCCG (SEQ ID NO: 77. In some embodiments, a 5' C element comprises at least 95% identity to CGCCCGGGC (SEQ ID NO: 78). In some embodiments, a 5' C element comprises CGCCCGGGC (SEQ ID NO: 78). In some embodiments, a 3' C element comprises at least 95% identity to GCCCGGGCG (SEQ ID NO: 79). In some embodiments, a 3' C element comprises GCCCGGGCG (SEQ ID NO: 79). In some embodiments, a 5' D element comprises at least 95% identity to AGGAACCCCTAGTGATGGAG (SEQ ID NO: 80). In some embodiments, a 5' D element comprises identity to AGGAACCCCTAGTGATGGAG (SEQ ID NO: 80). In some embodiments, a 3' D element comprises at least 95% identity to CTCCATCACTAGGGGTTCCT (SEQ ID NO: 81). In some embodiments, a 3' D element comprises identity to CTCCATCACTAGGGGTTCCT (SEQ ID NO: 81).

In some embodiments, a 5' A element comprises at least 97% identity to TTGGC-CACTCCCTCTCTGCGCGCTDGCTCGCTCACT-GAGGC (SEQ ID NO: 74). In some embodiments, a 5' A element comprises TTGGC-CACTCCCTCTCTGCGCGCTDGCTCGCTCACT-GAGGC (SEQ ID NO: 74). In some embodiments, a 3' A element comprises at least 97% identity to GCCTCAGT-GAGCGAGCGAGCGCGCAGAGAGGGAGTGGCCAA (SEQ ID NO: 75). In some embodiments, a 3' A element comprises GCCTCAGT-GAGCGAGCGAGCGCGCAGAGAGGGAGTGGCCAA (SEQ ID NO: 75). In some embodiments, a 5' B element comprises at least 97% identity to CGGGCGACC (SEQ ID NO: 76). In some embodiments, a 5' B element comprises CGGGCGACC (SEQ ID NO: 76). In some embodiments, a 3' B element comprises at least 97% identity to GGTCGCCCG (SEQ ID NO: 77). In some embodiments, a 3' B element comprises GGTCGCCCG (SEQ ID NO: 77. In some embodiments, a 5' C element comprises at least 97% identity to CGCCCGGGC (SEQ ID NO: 78). In some embodiments, a 5' C element comprises CGCCCGGGC (SEQ ID NO: 78). In some embodiments, a 3' C element comprises at least 97% identity to GCCCGGGCG (SEQ ID NO: 79). In some embodiments, a 3' C element comprises GCCCGGGCG (SEQ ID NO: 79). In some embodiments, a 5' D element comprises at least 97% identity to AGGAACCCCTAGTGATGGAG (SEQ ID NO: 80). In some embodiments, a 5' D element comprises identity to AGGAACCCCTAGTGATGGAG (SEQ ID NO: 80). In some embodiments, a 3' D element comprises at least 97% identity to CTCCATCACTAGGGGTTCCT (SEQ ID NO: 81). In some embodiments, a 3' D element comprises identity to CTCCATCACTAGGGGTTCCT (SEQ ID NO: 81).

In some embodiments, a 5' A element comprises at least 99% identity to TTGGC-CACTCCCTCTCTGCGCGCTDGCTCGCTCACT-GAGGC (SEQ ID NO: 74). In some embodiments, a 5' A element comprises TTGGC-CACTCCCTCTCTGCGCGCTDGCTCGCTCACT-GAGGC (SEQ ID NO: 74). In some embodiments, a 1' A element compnses at least 99% identity to GCCTCAGT-GAGCGAGCGAGCGCGCAGAGAGGGAGTGGCCAA (SEQ ID NO: 75). In some embodiments, a 3' A element comprises GCCTCAGT-GAGCGAGCGAGCGCGCAGAGAGGGAGTGGCCAA (SEQ ID NO: 75). In some embodiments, a 5' B element comprises at least 99% identity to CGGGCGACC (SEQ ID NO: 76). In some embodiments, a 5' B element comprises CGGGCGACC (SEQ ID NO: 76). In some embodiments, a 3' B element comprises at least 99% identity to GGTCGCCCG (SEQ ID NO: 77). In some embodiments, a 3' B element comprises GGTCGCCCG (SEQ ID NO: 77. In some embodiments, a 5' C element comprises at least 99% identity to CGCCCGGGC (SEQ ID NO: 78). In some embodiments, a 5' C element comprises CGCCCGGGC (SEQ ID NO: 78). In some embodiments, a 3' C element comprises at least 99% identity to GCCCGGGCG (SEQ ID NO: 79). In some embodiments, a 3' C element comprises GCCCGGGCG (SEQ ID NO: 79). In some embodiments, a 5' D element comprises at least 99% identity to AGGAACCCCTAGTGATGGAG (SEQ ID NO: 80). In some embodiments, a 5' D element comprises identity to AGGAACCCCTAGTGATGGAG (SEQ ID NO: 80). In some embodiments, a 3' D element comprises at least 99% identity to CTCCATCACTAGGGGTTCCT (SEQ ID NO: 81). In some embodiments, a 3' D element comprises identity to CTCCATCACTAGGGGTTCCT (SEQ ID NO: 81).

In some embodiments, a first inverted repeat sequence may have the Formula D-A-C-C'-B-B'-A', whereas a second inverted repeat sequence may have the Formula-A-B-B'-C-C'-A'-D'. In some embodiments, a first inverted repeat sequence may have the Formula D-A-C-C'-B-B'-A', whereas a second inverted repeat sequence may have the Formula-A-B-B'-C-C'-A'-D', but do not include a DD element as described herein. As noted herein, each of these first and second inverted repeat sequences are separated by a non-repeating nucleotide sequence having at least 3 nucleotides (e.g., at least a portion of a bacterial origin of replication, such as at least a portion of a bacterial origin of replication derived from R6K0).

In some embodiments, the non-viral DNA vectors of the present disclosure do not include or form a DD-ITR, "double D" ITR, or "DD element." In some embodiments, the non-viral DNA vectors do not comprise a DD element but do include at least a portion of a bacterial origin of replication. In some embodiments, the circular, non-viral DNA vectors lack a drug resistance gene and do not include a DD element. Said another way, the D and D' elements included within the inverted repeat sequences of the presently disclosed non-viral DNA vector are separated by a heterologous, non-repeat element which may contain at least a portion of a bacterial origin of replication. Surprisingly, Applicant has discovered that the presently disclosed non-viral vectors which are devoid of a “DD element” direct higher amounts of linked heterologous gene expression and may persist in vivo as long, or longer, as those vectors which do include a “DD element.” Furthermore, the structure of the repeat elements within the non-viral DNA vector of the present disclosure are not formed through the process of circularization of a viral genome (e.g., an AAV genome, or AAV vector genome) or linear DNA fragment via the inverted terminal repeat sequences.

In some embodiments, the inverted repeat sequences are contiguous with and flank the non-repeated nucleic acid sequence having at least three nucleotides. In some embodiments, the non-repeating nucleic acid sequence having the at least three nucleotides comprises at least a portion of a bacterial origin of replication. In some embodiments, the at least the portion of the bacterial origin of replication is derived from plasmid R6K (e.g., its y origin of replication (oriR6Ky). In some embodiments, the R6K-derived bacterial origin of replication has been modified to reduce CpG content, e.g., to reduce CpG content by at least 60%, at least 50%, at least 40%, at least 30%, at least 25%, at least 20%, at least 10%, at least 5%, etc. In some embodiments, the at least the portion of the bacterial origin of replication includes one or more internal direct repeat sequences. In some embodiments, the at least the portion of the bacterial origin of replication includes one or more regions of internal secondary structure which, it are believed to be important in helping to maintain the cruciform structure.

In some embodiments, the at least the portion of the bacterial origin of replication has at least 90% identity to any of one SEQ ID NOS: 58-59. In some embodiments, the at least the portion of the bacterial origin of replication has at least 91% identity to any of one SEQ ID NOS: 58-59. In some embodiments, the at least the portion of the bacterial origin of replication has at least 92% identity to any of one SEQ ID NOS: 58-59. In some embodiments, the at least the portion of the bacterial origin of replication has at least 93% identity to any of one SEQ ID NOS: 58-59. In some embodiments, the at least the portion of the bacterial origin of replication has at least 94% identity to any of one SEQ ID NOS: 58-59. In some embodiments, the at least the portion of the bacterial origin of replication has at least 95% identity to any of one SEQ ID NOS: 58-59. In some embodiments, the at least the portion of the bacterial origin of replication has at least 96% identity to any of one SEQ ID NOS: 58-59. In some embodiments, the at least the portion of the bacterial origin of replication has at least 97% identity to any of one SEQ ID NOS: 58-59. In some embodiments, the at least the portion of the bacterial origin of replication has at least 98% identity to any of one SEQ ID NOS: 58-59. In some embodiments, the at least the portion of the bacterial origin of replication has at least 99% identity to any of one SEQ ID NOS: 58-59. In some embodiments, the at least the portion of the bacterial origin of replication has any of one SEQ ID NOS: 58-59.

In some embodiments, the second portion comprises a first nucleic acid sequence having at least 90% identity to any one of SEQ ID NOS: 1, 3, 5, 7, 9, 11, 13, 15, or 17; a second nucleic acid sequence having at least 90% identity to any one of SEQ ID NOS: 58-59; and a third nucleic acid sequence having at least 90% identity to any one of SEQ ID NOS: 2, 4, 6, 8, 10, 12, 14, 16, or 18. In some embodiments, the second portion comprises a first nucleic acid sequence having at least 91% identity to any one of SEQ ID NOS: 1, 3, 5, 7, 9, 11, 13, 15, or 17; a second nucleic acid sequence having at least 91% identity to any one of SEQ ID NOS: 58-59; and a third nucleic acid sequence having at least 91% identity to any one of SEQ ID NOS: 2, 4, 6, 8, 10, 12, 14, 16, or 18. In some embodiments, the second portion comprises a first nucleic acid sequence having at least 92% identity to any one of SEQ ID NOS: 1, 3, 5, 7, 9, 11, 13, 15, or 17; a second nucleic acid sequence having at least 92% identity to any one of SEQ ID NOS: 58-59; and a third nucleic acid sequence having at least 92% identity to any one of SEQ ID NOS: 2, 4, 6, 8, 10, 12, 14, 16, or 18. In some embodiments, the second portion comprises a first nucleic acid sequence having at least 93% identity to any one of SEQ ID NOS: 1, 3, 5, 7, 9, 11, 13, 15, or 17; a second nucleic acid sequence having at least 93% identity to any one of SEQ ID NOS: 58-59; and a third nucleic acid sequence having at least 93% identity to any one of SEQ ID NOS: 2, 4, 6, 8, 10, 12, 14, 16, or 18. In some embodiments, the second portion comprises a first nucleic acid sequence having at least 94% identity to any one of SEQ ID NOS: 1, 3, 5, 7, 9, 11, 13, 15, or 17; a second nucleic acid sequence having at least 94% identity to any one of SEQ ID NOS: 58-59; and a third nucleic acid sequence having at least 94% identity to any one of SEQ ID NOS: 2, 4, 6, 8, 10, 12, 14, 16, or 18.

In some embodiments, the second portion comprises a first nucleic acid sequence having at least 95% identity to any one of SEQ ID NOS: 1, 3, 5, 7, 9, 11, 13, 15, or 17; a second nucleic acid sequence having at least 95% identity to any one of SEQ ID NOS: 58-59; and a third nucleic acid sequence having at least 95% identity to any one of SEQ ID NOS: 2, 4, 6, 8, 10, 12, 14, 16, or 18. In some embodiments, the second portion comprises a first nucleic acid sequence having at least 96% identity to any one of SEQ ID NOS: 1, 3, 5, 7, 9, 11, 13, 15, or 17; a second nucleic acid sequence having at least 96% identity to any one of SEQ ID NOS: 58-59; and a third nucleic acid sequence having at least 96% identity to any one of SEQ ID NOS: 2, 4, 6, 8, 10, 12, 14, 16, or 18. In some embodiments, the second portion comprises a first nucleic acid sequence having at least 97% identity to any one of SEQ ID NOS: 1, 3, 5, 7, 9, 11, 13, 15, or 17; a second nucleic acid sequence having at least 97% identity to any one of SEQ ID NOS: 58-59; and a third nucleic acid sequence having at least 97% identity to any one of SEQ ID NOS: 2, 4, 6, 8, 10, 12, 14, 16, or 18. In some embodiments, the second portion comprises a first nucleic acid sequence having at least 98% identity to any one of SEQ ID NOS: 1, 3, 5, 7, 9, 11, 13, 15, or 17; a second nucleic acid sequence having at least 98% identity to any one of SEQ ID NOS: 58-59; and a third nucleic acid sequence having at least 98% identity to any one of SEQ ID NOS: 2, 4, 6, 8, 10, 12, 14, 16, or 18. In some embodiments, the second portion comprises a first nucleic acid sequence having at least 99% identity to any one of SEQ ID NOS: 1, 3, 5, 7, 9, 11, 13, 15, or 17; a second nucleic acid sequence having at least 99% identity to any one of SEQ ID NOS: 58-59; and a third nucleic acid sequence having at least 99% identity to any one of SEQ ID NOS: 2, 4, 6, 8, 10, 12, 14, 16, or 18. In some embodiments, the second portion comprises a first nucleic acid sequence having any one of SEQ ID NOS: 1, 3, 5, 7, 9, 11, 13, 15, or 17; a second nucleic acid sequence having any one of SEQ ID NOS: 58-59; and a third nucleic acid sequence having any one of SEQ ID NOS: 2, 4, 6, 8, 10, 12, 14, 16, or 18.

In some embodiments, the second portion comprises a nucleic acid sequence having at least 90% identity to any one of SEQ ID NOS: 35 and 60. In some embodiments, the second portion comprises a nucleic acid sequence having at least 91% identity to any one of SEQ ID NOS: 35 and 60. In some embodiments, the second portion comprises a nucleic acid sequence having at least 92% identity to any one of SEQ ID NOS: 35 and 60. In some embodiments, the second portion comprises a nucleic acid sequence having at least 93% identity to any one of SEQ ID NOS: 35 and 60. In some embodiments, the second portion comprises a nucleic acid sequence having at least 94% identity to any one of SEQ ID NOS: 35 and 60. In some embodiments, the second portion comprises a nucleic acid sequence having at least 95% identity to any one of SEQ ID NOS: 35 and 60. In some embodiments, the second portion comprises a nucleic acid sequence having at least 96% identity to any one of SEQ ID NOS: 35 and 60. In some embodiments, the second portion comprises a nucleic acid sequence having at least 97% identity to any one of SEQ ID NOS: 35 and 60. In some embodiments, the second portion comprises a nucleic acid sequence having at least 98% identity to any one of SEQ ID NOS: 35 and 60. In some embodiments, the second portion comprises a nucleic acid sequence having at least 99% identity to any one of SEQ ID NOS: 35 and 60. In some embodiments, the second portion comprises a nucleic acid sequence having SEQ ID NO: 60.

In some embodiments, the circular, non-viral DNA vectors comprise a nucleic acid sequence having at least 85% identity to any one of SEQ ID NOS: 28-30, 38, 40-48, and 72-73. In some embodiments, the circular, non-viral DNA vectors comprise a nucleic acid sequence having at least 90% identity to any one of SEQ ID NOS: 28-30, 38, 40-48, and 72-73. In some embodiments, the circular, non-viral DNA vectors comprise a nucleic acid sequence having at least 91% identity to any one of SEQ ID NOS: 28-30, 38, 40-48, and 72-73. In some embodiments, the circular, non-viral DNA vectors comprise a nucleic acid sequence having at least 92% identity to any one of SEQ ID NOS: 28-30, 38, 40-48, and 72-73. In some embodiments, the circular, non-viral DNA vectors comprise a nucleic acid sequence having at least 93% identity to any one of SEQ ID NOS: 28-30, 38, 40-48, and 72-73. In some embodiments, the circular, non-viral DNA vectors comprise a nucleic acid sequence having at least 94% identity to any one of SEQ ID NOS: 28-30, 38, 40-48, and 72-73. In some embodiments, the circular, non-viral DNA vectors comprise a nucleic acid sequence having at least 95% identity to any one of SEQ ID NOS: 28-30, 38, 40-48, and 72-73. In some embodiments, the circular, non-viral DNA vectors comprise a nucleic acid sequence having at least 96% identity to any one of SEQ ID NOS: 28-30, 38, 40-48, and 72-73. In some embodiments, the circular, non-viral DNA vectors comprise a nucleic acid sequence having at least 97% identity to any one of SEQ ID NOS: 28-30, 38, 40-48, and 72-73. In some embodiments, the circular, non-viral DNA vectors comprise a nucleic acid sequence having at least 98% identity to any one of SEQ ID NOS: 28-30, 38, 40-48, and 72-73. In some embodiments, the circular, non-viral DNA vectors comprise a nucleic acid sequence having at least 99% identity to any one of SEQ ID NOS: 28-30, 38, 40-48, and 72-73. In some embodiments, the circular, non-viral DNA vectors comprise a nucleic acid sequence having any one of SEQ ID NOS: 28-30, 38, 40-48, and 72-73.

One or More Nucleic Acid Sequences Encoding One or More Peptides or Polypeptides In some embodiments, the circular, non-viral DNA vectors of the present disclosure include one or more nucleic acid sequences encoding one or more peptides, polypeptides, etc. In some embodiments, the circular, non-viral DNA vectors of the present disclosure include one or more nucleic acid sequences encoding one or more reporter genes. In yet other embodiments, the circular, non-viral DNA vectors of the present disclosure include one or more heterologous genes encoding one or more therapeutic proteins.

In some embodiments, the one or more nucleic acid sequences encoding the one or more therapeutic proteins ranges in size from between about 1 Kb to about 150 Kb, e.g., from between about 1 Kb to about 120 Kb, from between about 1 Kb to about 100 Kb, from between about 1 Kb to about 80 Kb, from between about 1 Kb to about 60 Kb, from between about 1 Kb to about 40 Kb, from between about 1 Kb to about 30 Kb, from between about 1 Kb to about 25 Kb, from between about 1 Kb to about 20 Kb, from between about 1 Kb to about 15 Kb, from between about 1 Kb to about 12 Kb, from between about 1 Kb to about 11 Kb, from between about 1 Kb to about 10 Kb, from between about 1 Kb to about 9 Kb, from between about 1 Kb to about 8 Kb, from between about 1 Kb to about 7 Kb, from between about 1 Kb to about 6 Kb, etc. In some embodiments, the one or more nucleic acid sequences encoding the one or more therapeutic proteins has a size of about 5 Kb, about 6 Kb, about 7 Kb, about 7.5 Kb, about 8 Kb, about 8.5 Kb, about 9 Kb, about 9.5 Kb, about 10 Kb, about 10.5 Kb, about 11 Kb, about 12 Kb, about 13 Kb, about 14 Kb, about 15 Kb, about 16 Kb, about 17 Kb, about 18 Kb, about 19 Kb, about 20 Kb, about 21 Kb, etc.

Therapeutic proteins include, but are not limited to, ALPL, PCSK9, PCSK7, SerpinA1, ABCB4 (having at least 80%, at least 85%, at least 90%, at least 95%, at least 97%, at least 99% identity to any one of SEQ ID NOS: 64, 65, 66, or 69), ATP7B (having at least 80%, at least 85%, at least 90%, at least 95%, at least 97%, at least 99% identity to any one of SEQ ID NOS: 69, 70, or 83), A1AT (having at least 80%, at least 85%, at least 90%, at least 95%, at least 97%, at least 99% identity to any one of SEQ ID NOS: 66), ABCB11, antiCD19-antiCD3 (having at least 80%, at least 85%, at least 90%, at least 95%, at least 97%, at least 99% identity to any one of SEQ ID NOS: 67), BDFS (having at least 80%, at least 85%, at least 90%, at least 95%, at least 97%, at least 99% identity to any one of SEQ ID NOS: 68) and variants thereof. Examples of diseases which may be treated according to the methods of the claimed invention include, but are not limited to, hypophosphatasia, anti-alpha-1 antitrypsin deficiency disease (treated such as with a protein having at least 80%, at least 85%, at least 90%, at least 95%, at least 97%, at least 99% identity to that of SEQ ID NO: 82), familiar hypercholesterolemia, hyperlipidemia, and progressive familial intrahepatic cholestasis types 1, 2, and 3.

In some embodiments, the non-viral DNA vectors of the present disclosure include one or more nucleic acid sequences encoding an alkaline phosphatase or a variant thereof. In other embodiments, the non-viral DNA vectors of the present disclosure include a nucleic acid sequence encoding a polypeptide including amino acid sequence encoding an alkaline phosphatase.

For example, in some embodiments the polypeptide including an amino acid sequence encoding an alkaline phosphatase has any one of the Formulas (IA) to (IE):

```
(IA),
[A]v-[B]-[C]w-[R]q-([D]x-[E]y)z

(IB),
[A]-[B]-[C]-[R]q-([D]x-[E]y)

(IC),
([A]-[B])-([D]x-[E]y)z

(ID),
([A]-[B])-([E]y)
and

(IE)
[A]-[B]-[R]q-([E]y)
```

wherein

A comprises an amino acid sequence encoding a secretion signal peptide;

B comprises an amino acid encoding an alkaline phosphatase;

C comprises an amino acid sequence encoding a GPI anchor;

R is -(Mo(Fc)Np)-, where M and N each independently include between 1 and 6 amino acids, where Fc is a Fc domain, and o and pare each independently 0, 1, or 2;

D comprises an amino acid sequence having between 4 and 6 amino acids, or is F(G)tF, where each F is the same amino acid, G is an amino acid sequence having 3, 4, or 5 amino acids, and tis an integer ranging from 2-5;

E comprises an amino acid sequence having between 1 and 8 amino acids; q is 0 or 1;

v is 0 or 1; w is 0 or 1;

x is 0 or an integer ranging from 1 to 6;

y is 0 or an integer ranging from 1 to 16; and z is 0 or an integer ranging from 1 to 6;

provided that when vis 1, w is 0, q is 1, o is 1, p is 1, Nis the diamino acid -D-I-, M is the diamino acid -L-K-, [B] comprises SEQ ID NO: 11, Fc comprises SEQ ID NO: 130, and x is 0, then [E]y does not comprise ten to sixteen contiguous aspartic acid residues.

In some embodiments, the polypeptide of any one of the Formulas (IA) to (IE) is not conjugated to a dextran. In other embodiments, the polypeptide of any one of the Formulas (IA) to (IE) is catalytically competent to allow formation of hydroxyapatite crystals in bone.

In some embodiments, E comprises 3 amino acids. In some embodiments, the 3 amino acids are selected from aspartic acid, serine, lysine, threonine, tyrosine, alanine, methionine, valine, tryptophan, praline, arginine, glutamine. In other embodiments, the 3 amino acid is selected from aspartic acid and serine. In some embodiments, E is -D-S-S-. In other embodiments, E is -D-D-S-. In other embodiments, E is -D-D-D. In other embodiments, E is -D-S-S-.

In some embodiments, E comprises 3 amino acids, and y ranges from 1 to 16. In some embodiments, E comprises 3 amino acids, and y ranges from 1 to 12. In some embodiments, E comprises 3 amino acids, and y ranges from 2 to 12. In some embodiments, E comprises 3 amino acids, and y ranges from 1 to 10. In some embodiments, E comprises 3 amino acids, and y ranges from 2 to 10. In some embodiments, E comprises 3 amino acids, and y ranges from 1 to 8. In some embodiments, E comprises 3 amino acids, and y ranges from 2 to 8. In some embodiments, E comprises 3 amino acids, and y ranges from 1 to 6. In some embodiments, E comprises 3 amino acids, and y ranges from 3 to 6. In some embodiments, E comprises 3 amino acids, and y ranges from 3 to 6 and q is 0.

In some embodiments, E is -D-S-S-, and y ranges from 1 to 16. In some embodiments, E is -D-S-S-, and y ranges from 1 to 12. In some embodiments, E is -D-S-S-, and y ranges from 1 to 10. In some embodiments, E is aspartic acid, and y ranges from 1 to 8. In some embodiments, E is -D-S-S-, and y is 6, i.e. [E]y is [-DSS-] 6. In other embodiments, E is -D-S-S-, y is 6 and z is 1. In some embodiments, E is -D-S-S-, y is 6 and q is 0. In other embodiments, E is -D-S-S-, y is 6, z is 1, and q is 0. In other embodiments, E is -D-S-S-, y is 6, z is 1, q is 0, and x is 0. In other embodiments, E is -D-S-S-, y is 6, z is 1, q is 0, and x is 2.

In some embodiments, E is -D-S-S-, y is 6 and q is 1. In other embodiments, E is -D-S-S-, y is 6, z is 1, and q is 1. In other embodiments, E is -D-S-S-, y is 6, z is 1, x is 0, and q is 1. In other embodiments, E is -D-S-S-, y is 6, z is 1, x is 2, and q is 1.

Other examples of polypeptides encoding a soluble alkaline phosphatase are described m PCT Publication No. WO/2022/051555, the disclosure of which is hereby incorporated by reference herein in its entirety.

In some embodiments, the non-viral DNA vectors comprise a nucleic acid sequence encode an amino acid sequence having at least 90% identity to any one of SEQ ID NOS: 19-21 and 23-24. In some embodiments, the non-viral DNA vectors comprise a nucleic acid sequence encode an amino acid sequence having at least 95% identity to any one of SEQ ID NOS: 19-21 and 23-24. In some embodiments, the non-viral DNA vectors comprise a nucleic acid sequence encode an amino acid sequence having at least 96% identity to any one of SEQ ID NOS: 19-21 and 23-24. In some embodiments, the non-viral DNA vectors comprise a nucleic acid sequence encode an amino acid sequence having at least 97% identity to any one of SEQ ID NOS: 19-21 and 23-24. In some embodiments, the non-viral DNA vectors comprise a nucleic acid sequence encode an amino acid sequence having at least 98% identity to any one of SEQ ID NOS: 19-21 and 23-24. In some embodiments, the non-viral DNA vectors comprise a nucleic acid sequence encode an amino acid sequence having at least 99% identity to any one of SEQ ID NOS: 19-21 and 23-24. In some embodiments, the non-viral DNA vectors comprise a nucleic acid sequence encode an amino acid sequence having SEQ ID NOS: 20-21 and 23-24.

In some embodiments, the one or more heterologous genes are reporter genes. As used herein, a "reporter gene" is any gene whose expression can be measured. In some embodiments, a reporter gene can have a previously determined reference range of detectable expression. In some embodiments, a reporter gene can express a selectable or screenable marker. In some embodiments, selectable markers may also be used to select for organisms or cells that contain exogenous genetic material.

Reporter genes can encode enzymes such as beta-lactamase, beta-galactosidase, murine secreted embryonic alkaline phosphatase (MUSEAP), and luciferase (for beta-lactamase, see WO 96/30540 to Tsien, published Oct. 3, 1996). Reporter genes can also encode fluorescent proteins, such as green fluorescent protein (GFP) or mutants thereof as they are known in the art or are later developed (see, U.S. Pat. No. 5,625,048. to Tsien, issued Apr. 29, 1997; WO 96/23810 to Tsien, published Aug. 8, 1996; WO 97/28261 to Tsien, published Aug. 7, 1997; and PCT/US97/12410 to Tsien, filed Jul. 16, 1996). The products of reporter genes can be detected using methods known in the art, such as the use of chromogenic or fluorogenic substrates for enzymes. Chromogenic or fluorogenic readouts can be detected using, for example, optical methods such as absorbance or fluorescence.

Examples of selectable markers include, but are not limited to, a neo gene, which codes for kanamycin resistance and can be selected for using kanamycin, GUS, green fluorescent protein (GFP), neomycin phosphotransferase II (nptII), luciferase (LUX), or an antibiotic resistance coding sequence. In some embodiments, screenable markers can be used to monitor expression. In some embodiments, exemplary screenable markers include, by way of example, a P-glucuronidase or uidA gene (GUS) which encodes an enzyme for which various chromogenic substrates are known; a P-lactamase gene, a gene which encodes an enzyme for which various chromogenic substrates are known (e.g., PADAC, a chromogenic cephalosporin); a luciferase gene; a tyrosinase gene, which encodes an enzyme capable of oxidizing tyrosine to DOPA and dopaquinone which in turn condenses to melanin; and a-galactosidase, which can turn a chromogenic a-galactose substrate.

Promoters

Any promoter utilized in the art may be utilized to drive expression of one or nucleic acid sequences within the expression vectors described herein, e.g., to drive expression of the nucleic acid sequence encoding the polypeptide. In some embodiments, the promoter is one which is functional in mammalian cells. High-level constitutive promoters arc preferred for use in the vectors according to the present disclosure. Examples of such promoters include, without limitation, the retroviral Rous sarcoma virus (RSN) LTR promoter (optionally with the RSV enhancer), the cytomegalovirus (CMV) promoter (optionally with the CMV enhancer) [see, e.g., Boshart et al, Cell, 41:521-530 (1985)], the SN40 promoter, the dihydrofolate reductase promoter, the beta-actin promoter, the beta-active promoter linked to the enhancer derived from the cytomegalovirus (CMN) immediate early (IE) promoter, the phosphoglycerol kinase (PGK) promoter, and the EF1a promoter [Invitrogen]. Inducible promoters are regulated by exogenously supplied compounds, including, the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, Proc. Natl. Acad. Sci. USA, 93:3346-3351 (1996)], the tetracycline-repressible system [Gossen et al, Proc. Natl. Acad. Sci. USA, 89:5547-5551 (1992)], the tetracycline-inducible system [Gossen et al, Science, 268:1766-1769 (1995); see also Harvey et al, Curr. Opin. Chem. Biol, 2:512-518 (1998)], the RU486-inducible system [Wang et al, Nat. Biotech., 15:239-243 (1997) and Wang et al, Gene Ther., 4:432-441 (1997)] and the rapamycin-inducible system [Magari et al, J Clin. Invest., 100:2865-2872 (1997)]. Other types of inducible promoters which may be useful in the present disclosure are those which are regulated by a specific physiological state, e.g., temperature, acute phase, a particular differentiation state of the cell, or in replicating cells only.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, a short elongation factor 1-alpha (EF1α-short) promoter, a long elongation factor 1-alpha (EF1 α-long) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), B-kinesin ((3-KIN), the human ROSA 26 locus Orions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, a B-actin promoter and a myeloproliferative sarcoma virus enhancer, negative control region deleted, d1587rev primer-binding site substituted (MND) promoter (Challita et al., J Viral. 69(2): 748-55 (1995)).

In some embodiments, the promoter may be selected from a Cytomegalovirus (CMV) minimal promoter and, more preferably, from human CMV (hCMV) such as the hCMV immediate early promoter derived minimal promoter as described in, e.g., Gossen and Bujard (Proc. Natl. Acad. Sci. USA, 1992, 89:5547-5551). Modified promoters also may be utilized, including insertion and deletion mutation of native promoters and combinations or permutations thereof. One example of a modified promoter is the “minimal CMV promoter” as described by Gossen and Bujard (Proc. Natl. Acad. Sci. USA, 1992, 89:5547-5551). In any case, any promoter can be tested readily for its effectiveness in the tetracycline-responsive expression system described herein by substitution for the minimal CMV promoter described herein.

In some embodiments, the promoter is an MND promoter. In some embodiments, the promoter is an EF1a promoter. In some embodiments, the promoter is a CD11b promoter. In some embodiments, the promoter is a EFS promoter. In some embodiments, the promoter is a Ubc promoter. In some embodiments, the promoter is a CD68LPp promoter.

In some embodiments, the promoter is a tissue-specific promoter, where the tissue-specific promoter is used to achieve cell type specific, lineage specific, or tissue-specific expression of a desired polynucleotide sequence (e.g., to express a particular nucleic acid encoding a polypeptide in only a subset of cell types or tissues or during specific stages of development). Illustrative examples of tissue specific promoters include, but are not limited to: an B29 promoter (B cell expression), a runt transcription factor (CBFa2) promoter (stem cell specific expression), an CD14 promoter (monocytic cell expression), an CD43 promoter (leukocyte and platelet expression), an CD45 promoter (hematopoietic cell expression), an CD68 promoter (macrophage expression), a CYP450 3A4 promoter (hepatocyte expression), an desmin promoter (muscle expression), an elastase 1 promoter (pancreatic acinar cell expression, an endoglin promoter (endothelial cell expression), a fibroblast specific protein 1 promoter (FSP1) promoter (fibroblast cell expression), a fibronectin promoter (fibroblast cell expression), a fms-related tyrosine kinase 1 (FLT1) promoter (endothelial cell expression), a glial fibrillary acidic protein (GFAP) promoter (astrocyte expression), an insulin promoter (pancreatic beta cell expression), an integrin, alpha 2b (ITGA2B) promoter (megakaryocytes), an intracellular adhesion molecule 2 (ICAM-2) promoter (endothelial cells), an interferon beta (IFN-P) promoter (hematopoietic cells), a keratin 5 promoter (keratinocyte expression), a myoglobin (MB) promoter (muscle expression), a myogenic differentiation 1 (MYOD1) promoter (muscle expression), a nephrin promoter (podocyte expression), a bone gamma-carboxyglutamate protein 2 (OG-2) promoter (osteoblast expression), an 3-oxoacid CoA transferase 2B (Oxct2B) promoter, (haploid-spermatid expression), a surfactant protein B (SP-B) promoter (lung expression), a synapsin promoter (neuron expression), a Wiskott-Aldrich syndrome protein (WASP) promoter (hematopoietic cell expression).

In some embodiments, the native promoter for the transgene is utilized. In some embodiments, the native promoter may be preferred when it is desired that expression of the gene should mimic the native expression. In some embodiments, the native promoter may be used when expression of the gene must be regulated temporally or developmentally, or in a tissue-specific manner, or in response to specific transcriptional stimuli. In some embodiments, other native expression control elements, such as enhancer elements, polyadenylation sites or Kozak consensus sequences may also be used to mimic the native expression. In some embodiments, the transgene product or other desirable product to be expressed is operably linked to a tissue-specific promoter. For instance, if expression in skeletal muscle is desired, a promoter active in muscle should be used. These include the promoters from genes encoding skeletal a-actin, myosin light chain 2A, dystrophin, muscle creatine kinase, as well as synthetic muscle promoters with activities higher than naturally occurring promoters [see Li et al., Nat. Biotech, 17:241-245 (1999)]. Examples of promoters that are tissue-specific are known for liver [albumin, Miyatake et al. J Viral, 71:5124-32 (1997); Human thyroxine binding globulin (TBG) promoter (see Yan et al, Gene. 2012 15; 506(2):289-94 (2012), the disclosure of which is hereby incorporated by reference herein in its entirety; hepatitis B virus core promoter, Sandig et al, Gene Ther., 3:1002-9 (1996); and alpha-fetoprotein (AFP), Arbuthnot et al, Hum. Gene Ther, 7:1503-14 (1996)], bone [osteocalcin, Stein et al, Mol. Biol. Rep., 24:185-96 (1997); and bone sialoprotein, Chen et al, J Bone Miner. Res., 11:654-64 (1996)], lymphocytes [CD2, Hansal et al., J Immunol, 161:1063-8 (1998); immunoglobulin heavy chain; T cell receptor a chain], neuronal [neuron-specific enolase (NSE) promoter, Andersen et al. Cell. Mol. Neurobiol, 13:503-15 (1993); neurofilament light-chain gene, Piccioli et al., 1991, Proc. Natl. Acad. Sci. USA, 88:5611-5 (1991); and the neuron-specific vgf gene, Piccioli et al, Neuron 15:373-84 (1995)]; among others.

Transcription may be increased by inserting an enhancer sequence into the non-viral DNA vectors of the present disclosure. Enhancers are typically cis-acting elements of DNA, usually about 10 to 300 bp in length, that act on a promoter to increase its transcription. Many enhancer sequences are now known from mammalian genes (globin, elastase, albumin, alpha-fetoprotein, and insulin) and from eukaryotic cell viruses. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence but is preferably located at a site 5' from the promoter.

In some embodiments, the vectors of the present disclosure include an insulator element, e.g., a cHS insulator.

Inhibitory Sequences of Toll-Like Receptor 9

It has been well demonstrated a central role for Toll-like receptor 9 (TLR9), an immune sensor of DNA, in detecting non-viral DNA vectors and activating innate immune and CD8+ T cell responses. TLRs are a family of innate immune sensors preserved across mammalian species that are found on endosomal or plasma membranes of immune or other cells. TLR9 normally senses DNA from invasion of pathogenic DNA viruses and bacteria containing unmethylated cytosine-phosphate-guanine (CpG) motifs. After binding to TLR9, CpG-rich motifs of DNA lead to its dimerization and activates TLR9 signaling through MyD88, promoting induction of type I interferons and pro-inflammatory cytokines. Innate immune responses, such as interferon induction, trigger an antiviral state among cells, while inflammation recruits other immune cells to the site of infection and primes adaptive immune responses.

One solution blocking TLR9 activation is to include specific short DNA oligonucleotides that antagonize TLR9 activation into the non-viral DNA vectors of the present disclosure. In some embodiments, the vectors of the present disclosure comprise one copy of such sequence (SEQ ID NO: 39). In some embodiments, the vectors of the present disclosure comprise two or more copies of such sequence (SEQ ID NO: 39).

In Vivo Resolution

The non-viral DNA vectors of the present disclosures are resolved in vivo. In some embodiments, the non-viral DNA vectors enter the cell through an endosomal mechanism (receptor-mediated endocytosis, pinocytosis, phagocytosis, etc.) or a non-endosomal mechanism (electroporation, ultrasonication-induced microbubble, membrane fusion through fusogenic complex etc.). Once inside an endosome, the non-viral DNA vector “escapes” the endosome and enters into the cytosol before the endosome fuses with a lysosome and the DNA is degraded. It is believed that the formulation of the non-viral DNA vector determines how the DNA escapes the endosome.

Once in the cytosol, the DNA needs to make its way into the nucleus in order to be expressed. It is believed that this process is assisted by the cruciform structure (repeat elements) of the presently disclosed circular, non-viral DNA vector. It is believed that cellular proteins, or protein complexes, known to bind this cruciform structure or known to be involved in Holliday junction resolution, have nuclear localization motifs. In other words, it believed that this structure is bound by proteins that direct its transport into the nucleus. As the proteins that help mediate nuclear translocation are the same (or a subset of) that mediate resolution, it’s unclear if resolution happens in the cytoplasm or in the nucleus, although the expectation is that this occurs in the nucleus. For example, PARP1 was identified to co-localized with constructs according to the present disclosure in the cytoplasm of 293 cells post-transfection (see, e.g., FIG. 18). Generally speaking, PARP1 is a nuclear protein and might shuttle out to the cytoplasm to help DNA traffic into the nucleus.

Figure 10:
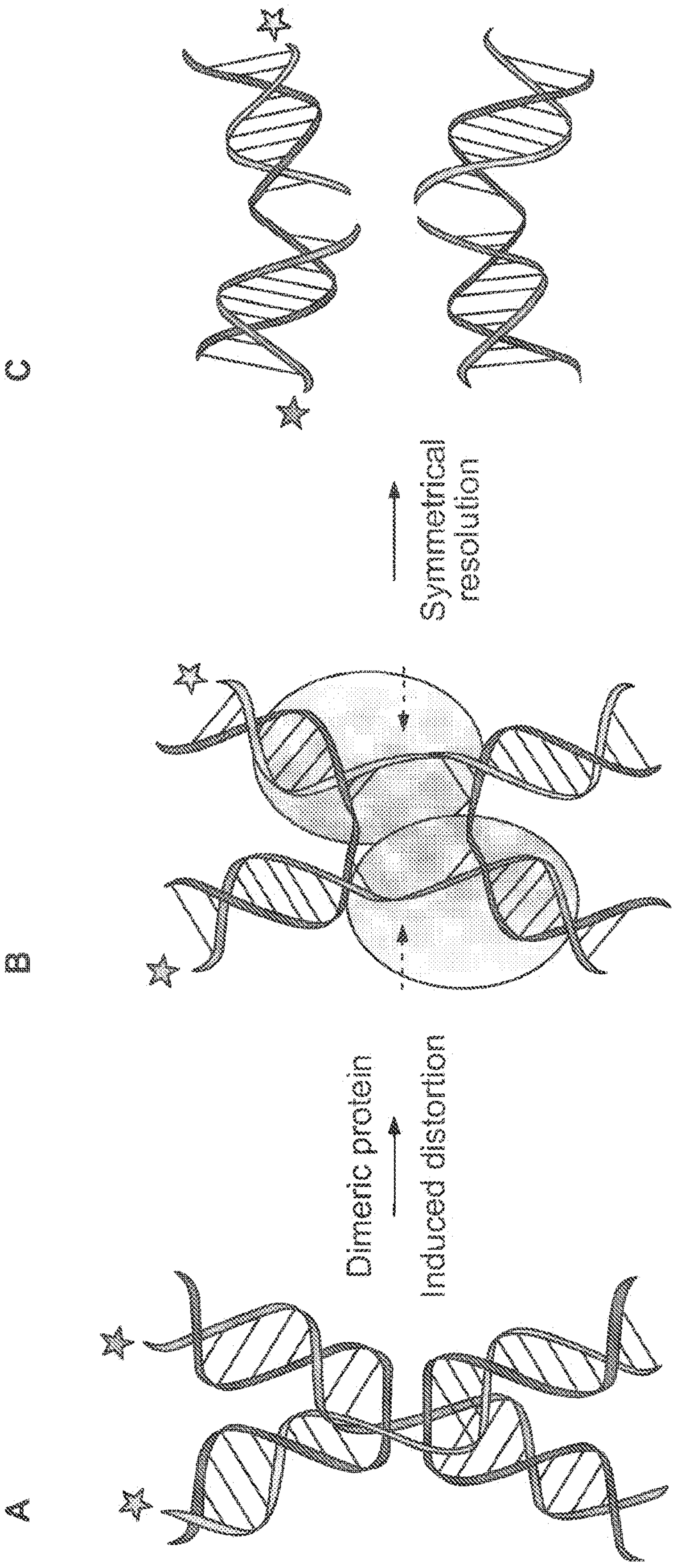
FIG. 10 illustrates the canonical mechanism of Holliday junction resolution (A) Antiparallel stacked-X Holliday junction with twofold symmetry. (B) Canonical Holliday junction resolvases are dimeric enzymes that induce structural changes to the junction on binding, causing the junction to unfold. Resolution occurs by the introduction of two coordinated and symmetrically related nicks in strands of like polarity at, or very near, the branchpoint. (C) Symmetrical resolution gives a pair of nicked DNA duplexes, each of which can be directly repaired by nick ligation, or homologous sequences can serve as templates for non-homologous end-joining (NHEJ) or homology-directed repair (HDR). Asterisks signify a given strand of DNA.

Although the process of “resolution” is largely unknown we can speak to the events that it would seem need to occur. Note that the process of normal endogenous Holliday junction resolution is also largely unknown and may occur through multiple pathways involving multiple different proteins/enzymes either in different cell types, or at different stages of the cell cycle. For instance, the first step is the recognition of the cruciform structure by proteins or protein complexes. This binding may be involved in nuclear localization as described above but is believed to be necessary to unwind the DNA a little to permit the next enzymatic steps. In some embodiments, the first enzymatic activity would cut the structure (see, e.g., FIGS. 10-11). After cutting, it is believed that a linear molecule is formed through a ligation process. It is believed that there are several DNA topoisomerases and/or DNA ligases that could been implicated in this process. It is also believed that there also several potential process/pathways via which this could occur. It is believed that DNA protein kinase (DNA-PK) is implicated in these pathways to convert the circular, non-viral vectors of the present disclosure into a linear form. In particular, DNA-PK is thought to be involved in the non-homologous end-joining (NHEJ) reaction and is believed to be part of a large multiprotein complex.

Figure 11:
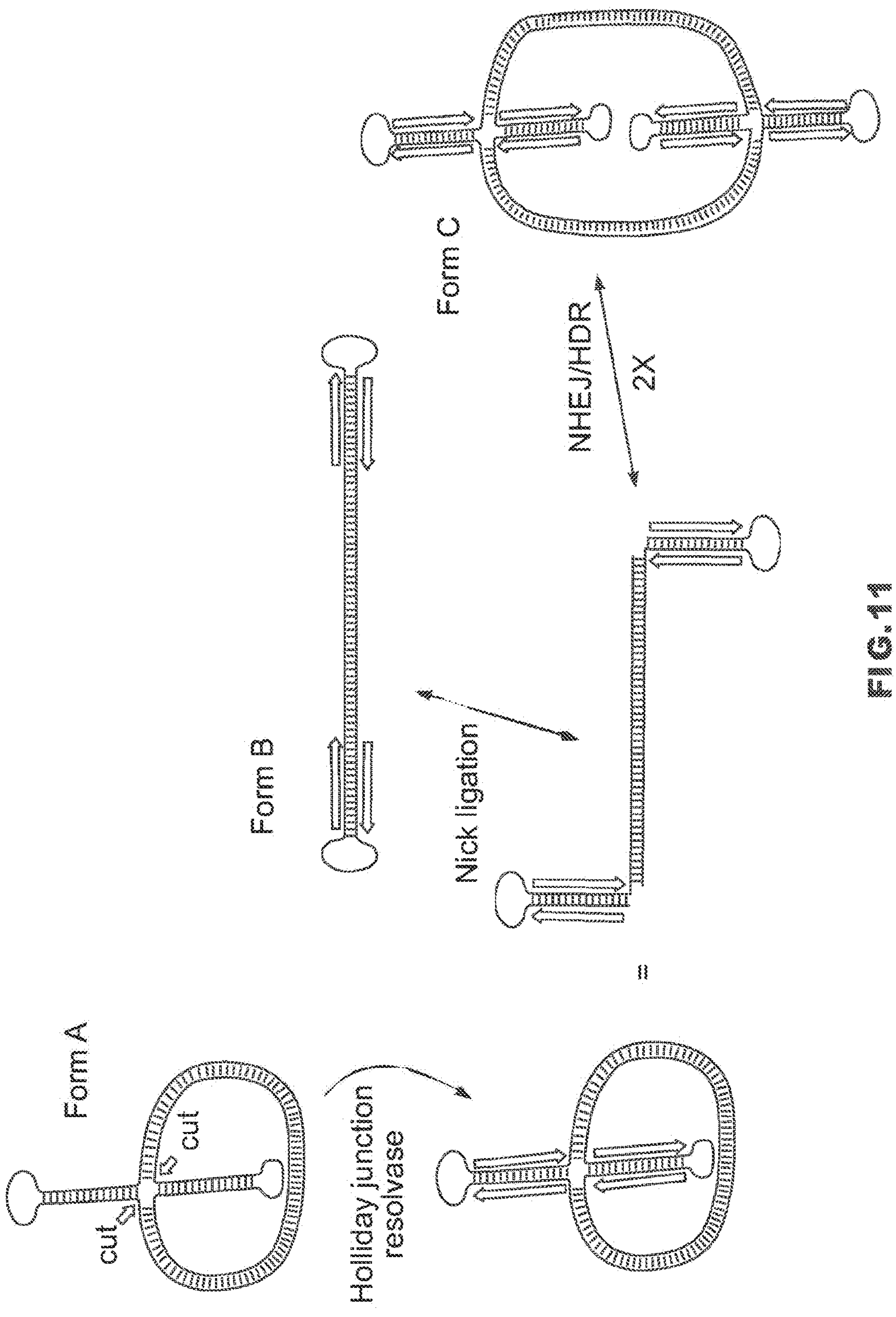
FIG. 11 illustrates the mechanism of resolution of the presently disclosed circular, non-viral DNA vector containing at least one cruciform structure (Holliday junction) (Form A) Once introduced into a eukaryotic cell, Holliday junction resolvases introduce two coordinated and symmetrically related nicks in strands of like polarity at, or very near, the branchpoint. Symmetrical resolution gives a nicked circular or linear DNA duplex, which can be directly repaired by nick ligation (yielding Form B), or homologous sequences can serve as templates for NHEJ or HDR (yielding Form C). It is further anticipated that this process could be repeated yielding higher molecular weight linear or circular forms.

In some embodiments, other homology-mediated pathways may be involved in the formation of concatemers (see, e.g., FIG. 11).

Pharmaceutical Compositions Comprising a Circular, Non-Viral DNA Vector

Another aspect of the present disclosure is directed to compositions comprising one or more circular, non-viral DNA vectors, e.g., circular, non-viral DNA vectors having at least 95%, 96%, 97%, 98%, or 99% identity to any one of SEQ ID NOS: 28-30, 38, 40-48 and 72-73.

In some embodiments, the present disclosure provides a composition comprising one or more of the circular, non-viral DNA vectors described herein and a carrier therefor (e.g., a pharmaceutically acceptable carrier). The composition desirably is a physiologically acceptable (e.g., pharmaceutically acceptable) composition, which comprises a carrier, e.g., a physiologically (e.g., pharmaceutically) acceptable carrier, and the non-viral DNA vector. Any suitable carrier can be used within the context of the present disclosure, and such carriers are well known in the art, including any of those described above.

In some embodiments, the non-viral DNA vectors may be formulated with a delivery vehicle. In some embodiments, the delivery vehicle is a lipid-based delivery vehicle. In some embodiments, the delivery vehicle is a lipid nanoparticle. As used herein, the term "lipid nanoparticle" or "LNP" refers to any lipid composition that can be used to deliver a therapeutic product, including, but not limited to, liposomes or vesicles, wherein an aqueous volume is encapsulated by amphipathic lipid bilayers, or wherein the lipids coat an interior that comprises a therapeutic product, or lipid aggregates or micelles, wherein the lipid-encapsulated therapeutic product is contained within a relatively disordered lipid mixture.

In some embodiments, lipid nanoparticles include lipid-based compositions with a solid lipid core stabilized by a surfactant. In some embodiments, the core lipids can be fatty acids, acyiglycerols, waxes, and mixtures of these surfactants. In some embodiments, biological membrane lipids such as phospholipids, sphingomyelins, bile salts (sodium taurocholate), and sterols (cholesterol) can be utilized as stabilizers.

In some embodiments, lipid nanoparticles can be formed using defined ratios of different lipid molecules, including, but not limited to, defined ratios of one or more cationic, anionic, or neutral lipids. In some embodiments, lipid nanoparticles can encapsulate molecules, such as the disclosed non-viral DNA vectors, within an outer-membrane shell and subsequently can be contacted with target cells to deliver the encapsulated molecules (e.g., the disclosed non-viral DNA vectors) to the host cell cytosol. In some embodiments, lipid nanoparticles can be modified or functionalized with non-lipid molecules, including on their surface (e.g., CD3, CD4, CD8, CD19, CD20, CD22, CD38, CD47, CDl 17, transferrin, ApoE, folate, etc.). In some embodiments, lipid nanoparticles can be modified to specifically bind to one or more receptors on the surface of the target cell (e.g., 1 or more receptors, 2 or more receptors, 3 or more receptors, 4 or more receptors, etc.). By "specifically bind" is meant that the lipid nanoparticle binds to the receptors on surface of the target cell with at least 2-fold greater affinity relative to the receptors on the surface of a non-target cell, e.g., at least 3-fold, 4-fold, 6-fold, 7-fold, 8-fold, 9-fold, 10-fold, 20-fold, 25-fold, 50-fold, or 100-fold higher. Cell surface receptors to which the modified lipid nanoparticles can bind include, but are not limited, to an integrin, transferrin receptor type land 2, EGF receptor, a VEGF receptor, an NGF receptor, CD3, CD4, CD7, CD8, CD19, CD20, CD22, CD33, CD43, CD38, CD56, CD69, the asialoglycoprotein receptor (ASGPR), N-acetyl-D-galactose (GalNAc) receptor, a folate receptor, and a sigma receptor. In some embodiments, the first and/or the second targeting ligand bind to the asialoglycoprotein receptor (ASGPR) or GalNAc receptor. Accordingly, in some embodiments, the modified lipid nanoparticles specifically bind to ASGPR or GalNAc receptor on surface of hepatocytes. In some embodiments, the targeting ligand used to modify the lipid nanoparticles is a carbohydrate or a carbohydrate conjugate. Carbohydrate based targeting ligands include, but are not limited to, glucose, multivalent glucose, fucose, D-mannose, multivalent mannose, lactose, multivalent lactose, D-galactose, multivalent galactose, GalNAc, multivalent GalNAc (e.g., GalNAc2 and GalNAc3), acetyl-galactosamine, N-acetylgulucosamine, glycosylated polyaminoacids and lectins. The term multivalent indicates that one, two, three or four monosaccharide units is present. Such monosaccharide subunits may be linked to each other through glycosidic linkages or linked to a scaffold molecule. In some embodiments, lipid nanoparticles can be single layered (unilamellar) or multi-layered (multilamellar). In some embodiments, lipid nanoparticles can be complexed with nucleic acid. Unilamellar lipid nanoparticles can be complexed with nucleic acid, wherein the nucleic acid is in the aqueous interior. In some embodiments, multilamellar lipid nanoparticles can be complexed with nucleic acid, wherein the nucleic acid is in the aqueous interior, or to form or sandwiched between.

In some embodiments, liposomal particles can, for example, be formed of a mixture of zwitterionic, cationic and anionic lipids which can be saturated or unsaturated, for example 1,2-distearoyl-sn-glycero-3-phosphocholine (DSPC) (zwitterionic, saturated), 1,2-dilinoleyoxy-3-dimethylaminopropane (DlinDMA) (cationic, unsaturated), and/or 1,2-dimyristoyl-rac-glycerol (DMG) (anionic, saturated). In some embodiments, the liposomes will typically comprise helper lipids. Useful helper lipids include zwitterionic lipids, such as DPPC, DOPC, DSPC, dodecylphosphocholine, 1,2-dioleoyl-sn-glycero-3-phosphatidylethanolamine (DOPE), and 1,2-diphytanoyl-sn-glycero-3-phosphoethanolamine (DPyPE); sterols, such as cholesterol; and PEGylated lipids, such as PEG-DMPE (PEG-conjugated 1, 2-dimyristoyl-Sn-glycero-3-phosphoethanolamine-N-[methoxy (polyethylene glycol)]) or PEG-DMG (PEG-conjugated 1,2-Dimyristoyl-sn-glycerol, methoxypolyethylene Glycol). In some embodiments, suitable PEGylated lipids include PEG2K-DMPE (PEG-conjugated 1, 2-dimyristoyl-Sn-glycero-3-phosphoethanolamine-N-[methoxy (polyethylene glycol)-2000]) or PEG2K-DMG (PEG-conjugated 1,2-Dimyristoyl-sn-glycerol, methoxypolyethylene Glycol-2000). In some embodiments, LNPs for use with the non-viral DNA vectors of the present disclosure include a zwitterionic lipid which can form liposomes, optionally in combination with at least one cationic lipid (such as N-[1-(2,3-Dioleoyloxy) propyl]-N,N,N-trimethylammonium methyl-sulfate (DOTAPBis(2-methacryloyl)oxyethyl disulfide (DSDMA), 2,3-Dioleyloxy-1-(dimethylamino) propane (DODMA), 1,2-dilinoleyoxy-3-dimethylaminopropane (DLinDMA), N,N-dimethyl-3-aminopropane (DLenDMA), etc.).

In some embodiments, the lipid nanoparticles have a mean diameter ranging from between about 20 nm to about 300 nm, e.g., from between about 20 nm to about 250 nm from between about 30 nm to about 200 nm, from between about 40 nm to about 180 nm, from between about 50 nm to about 150 nm, from between about 60 nm to about 140 nm, etc. Lipid nanoparticle particle size can be determined by quasi-elastic light scattering using, for example, a Malvern ZETASIZER® Nano ZS (Malvern, UK) system or electron microscope using, for example, FEI QUANTA® 200 Scanning Electron Microscope or FEI TECNAI™ Twin 120 kV Transmission Electron Microscope.

Examples of LNPs are described by Schoeenmaker et. al., "mRNA-lipid nanoparticle COVID-19 vaccines: Structure and stability," Int J Pharm. 2021 May 15; 601:120586, the disclosure of which is hereby incorporated by reference herein in its entirety. Other exemplary LNPs are described by Eygeris et. al., "Chemistry of Lipid Nanoparticles for RNA Delivery," Ace Chem Res. 2022 Jan. 4; 55(1):2-12. doi: 10.1021/acs.accounts.lc00544. Epub 2021 Dec. 1. PMID: 34850635, the disclosure of which is hereby incorporated by reference herein in its entirety. Yet other suitable LNPs for use with the non-viral DNA vectors of the present disclosure are described in United States Patent Publication Nos. 2021/0371877, 2022/0175968, 2022/0042035, and 2022/0062409, the disclosures of which are hereby incorporated by reference herein in their entireties.

The non-viral DNA vectors of the present disclosure may also be formulated with one or more polymers. Various polymers or copolymers may be adapted as a vehicle for the non-viral DNA vectors of the present disclosure. Exemplary polymeric materials include poly(D,L-lactic acid-co-glycolic acid) (PLGA), poly(caprolactone) (PCL), ethylene vinyl acetate polymer (EVA), poly(lactic acid) (PLA), poly (L-lactic acid) (PLLA), poly(glycolic acid) (PGA), poly(L-lactic acid-co-glycolic acid) (PLLGA), poly(D,L-lactide) (PDLA), poly(L-lactide) (PLLA), PLGA-b-poly(ethylene glycol)-PLGA (PLGA-bPEG-PLGA), PLLA-bPEG-PLLA, PLGA-PEG-maleimide (PLGA-PEG-mal), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) (polyacrylic acids), and copolymers and mixtures thereof, polydioxanone and its copolymers, polyhydroxyalkanoates, polypropylene fumarate), polyoxymethylene, poloxamers, poly (ortho) esters, poly(butyric acid), poly(valeric acid), poly (lactide-co-caprolactone), trimethylene carbonate, polyvinylpyrrolidone, polyorthoesters, polyphosphazenes, Poly([beta]-amino esters (PBAE), and polyphosphoesters, and blends and/or block copolymers of two or more such polymers. Polymer-based systems may also include Cyclodextrin polymer (CDP)-based nanoparticles such as, for example, CDP-admantane (AD)-PEG conjugates and CDP-AD-PEG-transferrin conjugates.

Non-limiting examples of polymeric particle systems for delivery of the disclosed non-viral DNA vectors include the systems described in U.S. Pat. Nos. 5,543,158, 6,007,845, 6,254,890, 6,998,115, 7,727,969, 7,427,394, 8,323,698, 8,071,082, 8,105,652, US 2008/0268063, us 2009/0298710, us 2010/0303723, us 2011/0027172, us 2011/0065807, us 2012/0156135, US 2014/0093575, WO 2013/090861, the disclosures of which are hereby incorporated by reference herein in their entireties.

In some embodiments, the non-viral DNA vectors may be formulated as pharmaceutically acceptable nanocapsule formulations. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention. Such particles may be easily made, as described (Couvreur et al., 1980; Couvreur, 1988; zur Muhlen et al., 1998; Zambaux et al. 1998; Pinto-Alphandry et al., 1995 and U.S. Pat. No. 5,145,684, specifically incorporated herein by reference in its entirety).

In some embodiments, the pharmaceutical compositions including the non-viral DNA vectors of the present disclosure, and which are suitable for injectable use include sterile aqueous solutions or dispersions and sterile powders for the extemporaneous preparation of sterile injectable solutions or dispersions (see U.S. Pat. No. 5,466,468, the disclosure of which is hereby incorporated by reference herein in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils.

In some embodiments, the non-viral DNA vectors may be given to the patients with physical methods, such as electroporation, sonoporation with microbubbles, sonoporation without microbubbles, magnetofection, hydroporation, photoporation, mechanical massage, jet injection, biolistics (gene gun), hydrodynamic injection, needle injection or microinjections.

Methods of Treatment

The present disclosure is also directed to administering therapeutically effective amounts of a circular, non-viral DNA vector capable of expressing one or more transgenes or a pharmaceutical composition comprising a circular, non-viral DNA vector capable of expressing one or more transgenes to a patient in need of treatment thereof.

In some embodiments, the present disclosure is directed to treating a condition or disease related to a bone defect characterized by a lack of or an insufficient amount of functional alkaline phosphatase. Another aspect of the present disclosure is directed to a method of treating hypophosphatasia in a mammal, e.g., a human, in need thereof. Another aspect of the present disclosure is directed to a method of treating, mitigating, or preventing a symptom of hypophosphatasia in a mammal, e.g., a human.

Hypophosphatasia (HPP) is a rare, heritable skeletal disease with an incidence of 1 per 100,000 births for the most severe forms of the disease. The disorder results from loss-of-function mutations in the gene encoding tissue-nonspecific alkaline phosphatase (TNALP). HPP patients present a remarkable range of symptoms, from teeth loss or osteomalacia (rickets) to almost complete absence of bone mineralization in utero. Many patients with HPP present the characteristics of skeletal deformities, short stature, muscle and bone pain, impaired mobility, and premature loss of teeth. Perinatal-onset or infantile-onset HPP can also be characterized by the presence of rachitic chest deformity, vitamin B6-dependent seizures, and failure to thrive. In particular, HPP presenting at less than six months of age is often lethal due to respiratory insufficiency, with a low survival rate at one year of age.

In some embodiments, the methods of the present disclosure provide for the treatment of hypophosphatasia in the mammal. As used herein, the terms “treatment,” “treating,” and the like refer to obtaining a desired pharmacologic and/or physiologic effect. In some embodiments, the effect is therapeutic, i.e., the effect partially or completely cures a disease and/or adverse symptom attributable to the disease. In some embodiments, a “therapeutically effective amount” of the composition comprising the non-viral DNA vector are administered to the subject in need of treatment thereof. A “therapeutically effective amount” refers to an amount effective, at dosages and for periods of time necessary, to achieve a desired therapeutic result.

In some embodiments, hypophosphatasia may be treated by administering a therapeutically effective amount of a pharmaceutical composition including a circular, non-viral DNA vector including one or more nucleic acid sequences encoding TNALP or a polypeptide having an amino acid sequence encoding TNALP (see, e.g., SEQ ID NOS: 28-30, 38, 40-48, and 72-73). In other embodiments, treating, mitigating, or preventing a symptom of hypophosphatasia in a mammal comprises administering a therapeutically effective amount of a pharmaceutical composition including a circular, non-viral DNA vector including one or more nucleic acid sequences encoding TNALP or a polypeptide having an amino acid sequence encoding TNALP (see, e.g., SEQ ID NOS: 28-30, 38, 40-48, and 72-73).

In some embodiments, the therapeutically effective amount may vary according to factors such as the disease state, age, sex, and weight of the individual.

The methods provided herein may be carried out by administering the pharmaceutical compositions by any suitable routes of administration. The route of administration can be local or systemic. Exemplary routes of administration include, for example, the nasal, pulmonary, inhalation, intraarterial, intradermal, intralesional, intramuscular, intraperitoneal, intravenous, intrathecal, intravesical, parenteral, rectal, subcutaneous, and transmucosal. In some embodiments, the non-viral DNA vectors are administered in suitably formulated pharmaceutical compositions disclosed herein either subcutaneously, intraocularly, intravitreally, parenterally, subcutaneously, intravenously, intracerebroventricularly, intramuscularly, intrathecally, orally, intraperitoneally, by oral or nasal inhalation, or by direct injection to one or more cells, tissues, or organs by direct injection. The methods of administration may also include those modalities as described in U.S. Pat. Nos. 5,543,158; 5,641,515 and 5,399,363, each of which are incorporated by reference herein in their entireties.

In some embodiments, a subject in need of treatment is treated over a particular duration of time. In some embodiments, the duration of treatment is from about 1 week to about 10 years. In some embodiments, the duration of treatment is from about 1 week to about 5 years. In some embodiments, the duration of treatment is from about 1 week to about 1 year. In some embodiments, the duration of treatment is from about 1 week to about 6 months. In some embodiments, the duration of treatment is from about 1 week to about 3 months. In some embodiments, the duration of treatment is from about 1 week to about 1 month. In some embodiments, the duration of treatment is from about 3 months to about 5 years. In some embodiments, the duration of treatment is from about 6 months to about 5 years. In some embodiments, the duration of treatment is from about 1 year to about 5 years.

Each dose may be administered over any suitable period of time. In some embodiments, the dose is administered as a bolus dose. In some embodiments, the dose is administered over a period of about 1 minute to about 4 hours. In some embodiments, the dose is administered over a period of about 1 minute to about 2 hours. In some embodiments, the dose is administered over a period of about 1 minute to about 1 hour. In some embodiments, the dose is administered over a period of about 1 minute to about 30 minutes. In some embodiments, the dose is administered over a period of about 1 minute to about 15 minutes.

As noted herein, the circular, non-viral DNA vectors are amenable to redosing. In some embodiments, the circular, non-viral DNA vectors are redosed for a time period ranging from between about two weeks to about five years. In some embodiments, the pharmaceutical composition is administered according to a particular frequency. In some embodiments, the frequency is daily, every 2 days, every 3 days, every 4 days, every 5 days, every 6 days, every 7 days, every 8 days, every 9 days, every 10 days, every 11 days, every 12 days, every 13 days, or every 14 days. In some embodiments, the frequency is every 3 weeks, every 4 weeks, every 5 weeks, every 6 weeks, every 7 weeks, every 8 weeks, every 9 weeks, every 10 weeks, every 11 weeks, or every 12 weeks. In some embodiments, the frequency is every 1 month, every 2 months, every 3 months, every 4 months, every 5 months, every 6 months, every 7 months, every 8 months, every 9 months, every 10 months, every 11 months, every 12 months, every 13 months, every 14 months, every 15 months, every 16 months, every 17 months, or every 18 months. In some embodiments, the frequency is every 2 years, every 3 years, every 4 years, or every 5 years.

EXAMPLES

Figure 5:
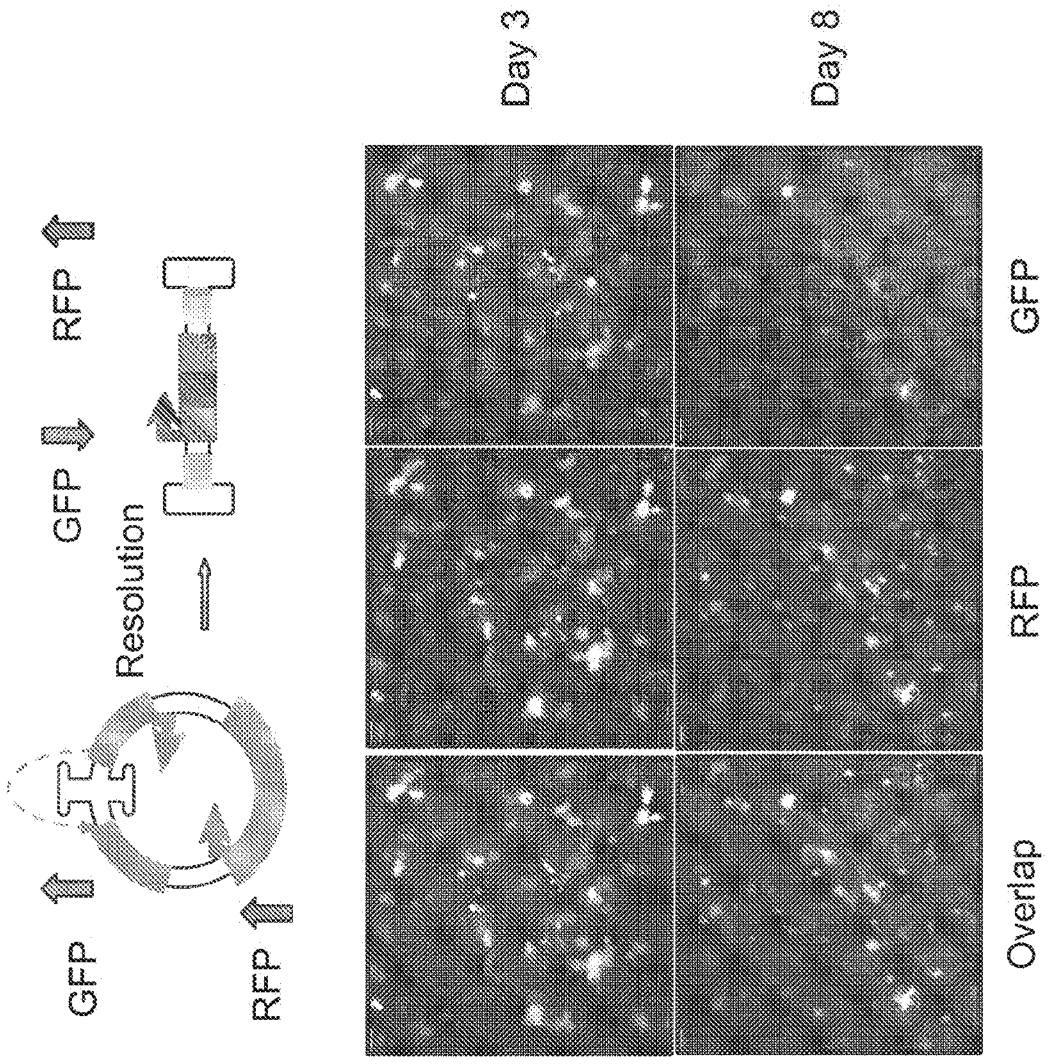
FIG. 5 illustrates simultaneous green fluorescent protein (GFP) and red fluorescent protein (RFP) expression at day 3, and largely RFP expression at day 8, in non-dividing induced pluripotent stem cell (iPSC)-derived human hepatocytes transfected with a circular, non-viral DNA vector including an RFP/GFP reporter (SEQ ID NO: 32).

Example 1—In Vitro Resolution of a Reporter Non-Viral DNA Construct in IPSC-Derived Hepatocytes Non-dividing iPSC-derived hepatocytes transfected with a circular, non-viral DNA vector of the present disclosure including an RFP/GFP reporter (SEQ ID NO: 32) showed simultaneous GFP and RFP expression at day 3 and mainly RFP at day 8 in FIG. 5. The data suggested that the circular, non-viral DNA vector containing a cruciform structure could be resolved into linear form in non-dividing primary human iPSC-derived hepatocytes.

A reporter system was developed for assessing resolution of a circular, non-viral DNA vector to a linear form once introduced into a mammalian cell. The circular molecule would express both a red fluorescent protein (RFP) and a green fluorescent protein (GFP) while GFP expression in the circular form proceeded via splicing the mRNA across the cruciform DNA structure would be interrupted and the linearized molecule would only express the RFP.

Method

Non-dividing iPSC-derived human hepatocytes were purchased from Fujifilm. At day 0, plating medium was prepared by adding 1.5 mL of B27 supplement, 0.15 mL of 10 μg/mL of oncostatin stock solution, 1.5 μL of 5 mM of dexamethasone stock solution, 37.5 μL of 25 μg/mL of gentamicin and 1.5 mL of ICELL® Hepatocytes 2.0 medium supplement into 72 mL of RPMI medium according to Fujifilm's recommendation.

Plating medium was filtered via 0.22 μm PES filter unit. At day 1, the ICELL® Hepatocytes 2.0 cryovial was removed from the liquid nitrogen storage tank. The cryovial was immersed in a 37° C. water bath for exactly 3 minutes. Using a 2 mL serological pipette, the ICELL® Hepatocytes 2.0 cryovial contents was gently transferred into the 15 mL centrifuge tube containing 10 mL of 37° C. Plating Medium. The cell suspension was centrifuged at 200×g for 3 minutes at room temperature. The supernatant was carefully aspirated under vacuum. 2 mL of 37° C. Plating Medium was slowly added with a wide-bore pipette to resuspend the cell pellet. Hepatocytes were seeded in pre-warmed collagen-coated 24/48-well plate. The medium was refreshed daily from day 1 to 7 and every other day starting from day 8.

TRANSIT™-LTI Reagent and non-viral vector DNA complex was prepared following Mirus manufacturer's recommendation. The TRANSIT™-LTI Reagent:DNA complex was added dropwise to different areas of the wells. The culture vessel was gently rocked back-and-forth and from side-to-side to evenly distribute the TRANSIT™-LTI Reagent:DNA complexes.

Results

FIG. 5 demonstrated that iPSC-derived hepatocytes transfected with a circular, non-viral DNA reporter vector of the present disclosure including an RFP/GFP reporter (SEQ ID NO: 32) showed simultaneous GFP and RFP expression at day 3 but mainly RFP only at day 8. The data suggested that the circular, non-viral DNA vector containing a cruciform structure could be resolved into linear form in non-dividing primary human iPSC-derived hepatocytes.

Figure 6:
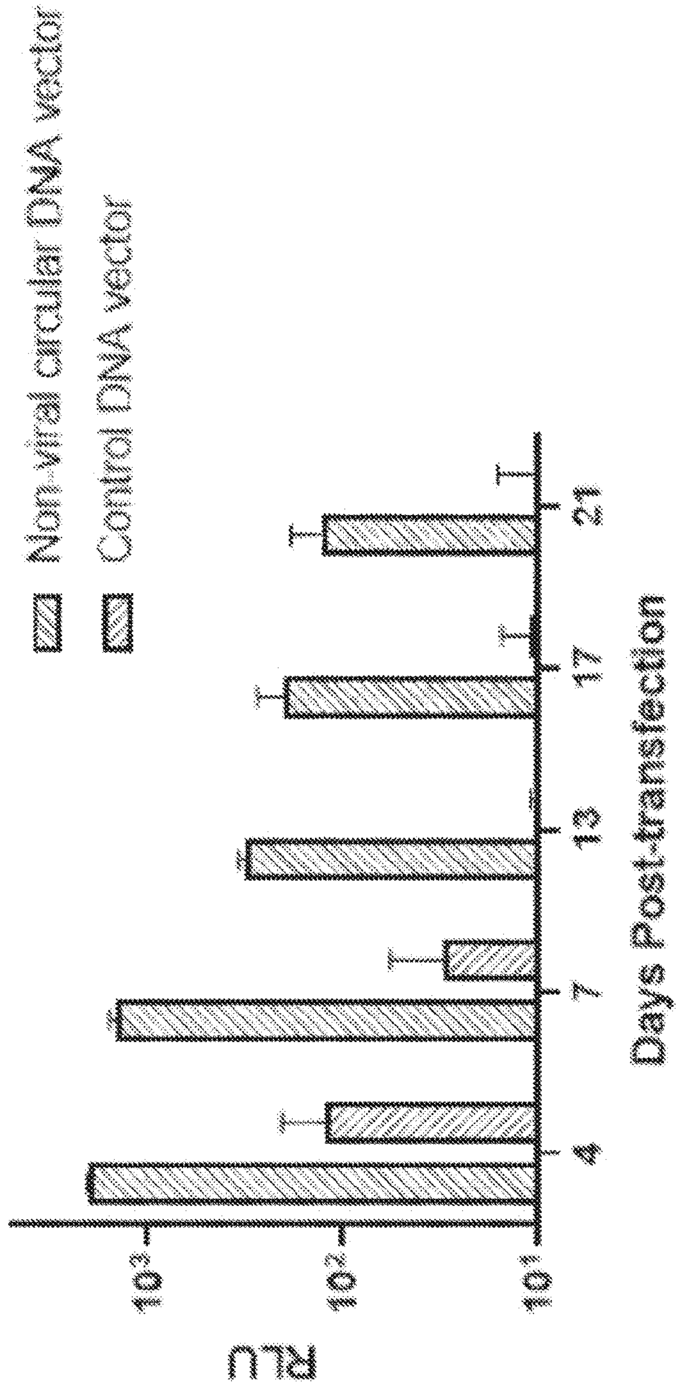
FIG. 6 compares the gene expression and durability of firefly luciferase from two different constructs, namely from a circular, non-viral DNA vector of the present disclosure (SEQ ID NO: 30) and from a plasmid (SEQ ID NO: 31) in post-mitotic human iPSC-derived hepatocytes. The data reveals that transgene expression from the circular, non-viral DNA vectors of the present disclosure (SEQ ID NO: 30) with the cruciform structure is much higher and more stable than the plasmid construct (SEQ ID NO: 31).

Example 2—In Vitro Durable Gene Expression of Firefly Luciferase DNA Construct in IPSC-Derived Hepatocytes Transfection of a circular, non-viral DNA vector of the present disclosure encoding TNALP (M014—SEQ ID NO: 30) led to strong bioluminescent emission in iPSC-derived hepatocytes from day 3; and this signal was maintained from day 12 to day 21 while Relative Luminescence Unit (RLU) from cells transfected with a control circular, non-viral DNA vector of the present disclosure encoding TNALP (P021—SEQ ID NO: 31) dropped significantly from day 7 shown in FIG. 6. The circular, non-viral DNA vectors of the present disclosure including a luciferase reporter gene showed robust and durable luciferase expression whereas the same control construct carrying antibiotics-resistance gene were far less potent and did not last.

Method

Non-dividing iPSC-derived human hepatocytes were purchased from Fujifilm. At day 0, plating medium was prepared by adding 1.5 mL of B27 supplement, 0.15 mL of 10 μg/mL of oncostatin stock solution, 1.5 μL of 5 mM of dexamethasone stock solution, 37.5 μL of 25 μg/mL of gentamicin and 1.5 mL of ICELL® Hepatocytes 2.0 medium supplement into 72 mL of RPMI medium according to Fujifilm's recommendation.

Plating medium was filtered via 0.22 μm PES filter unit. At day 1, the ICELL® Hepatocytes 2.0 cryovial was removed from the liquid nitrogen storage tank. The cryovial was immersed in a 37° C. water bath for exactly 3 minutes. Using a 2 mL serological pipette, the ICELL® Hepatocytes 2.0 cryovial contents was gently transferred into the 15 mL centrifuge tube containing 10 mL of 37° C. Plating Medium. The cell suspension was centrifuged at 200×g for 3 minutes at room temperature. The supernatant was carefully aspirated under vacuum. 2 mL of 37° C. Plating Medium was slowly added with a wide-bore pipette to resuspend the cell pellet. Hepatocytes were seeded in pre-warmed collagen-coated 24/48-well plate. The medium was refreshed daily from day 1 to 7 and every other day starting from day 8.

TRANSIT™-LTI Reagent and non-viral vector DNA complex was prepared following Mirus manufacturer's recommendation. The TRANSIT™-LTI Reagent:DNA complex was added dropwise to different areas of the wells. The culture vessel was gently rocked back-and-forth and from side-to-side to evenly distribute the TRANSIT™-LTI Reagent:DNA complexes.

For non-invasive bioluminescent readout, luciferin substrate stock solution was added into the cell plate to reach 5 mM final concentration then RLU from each well of the plate was measured by Molecular Device plate reader iD5.

Figure 7:
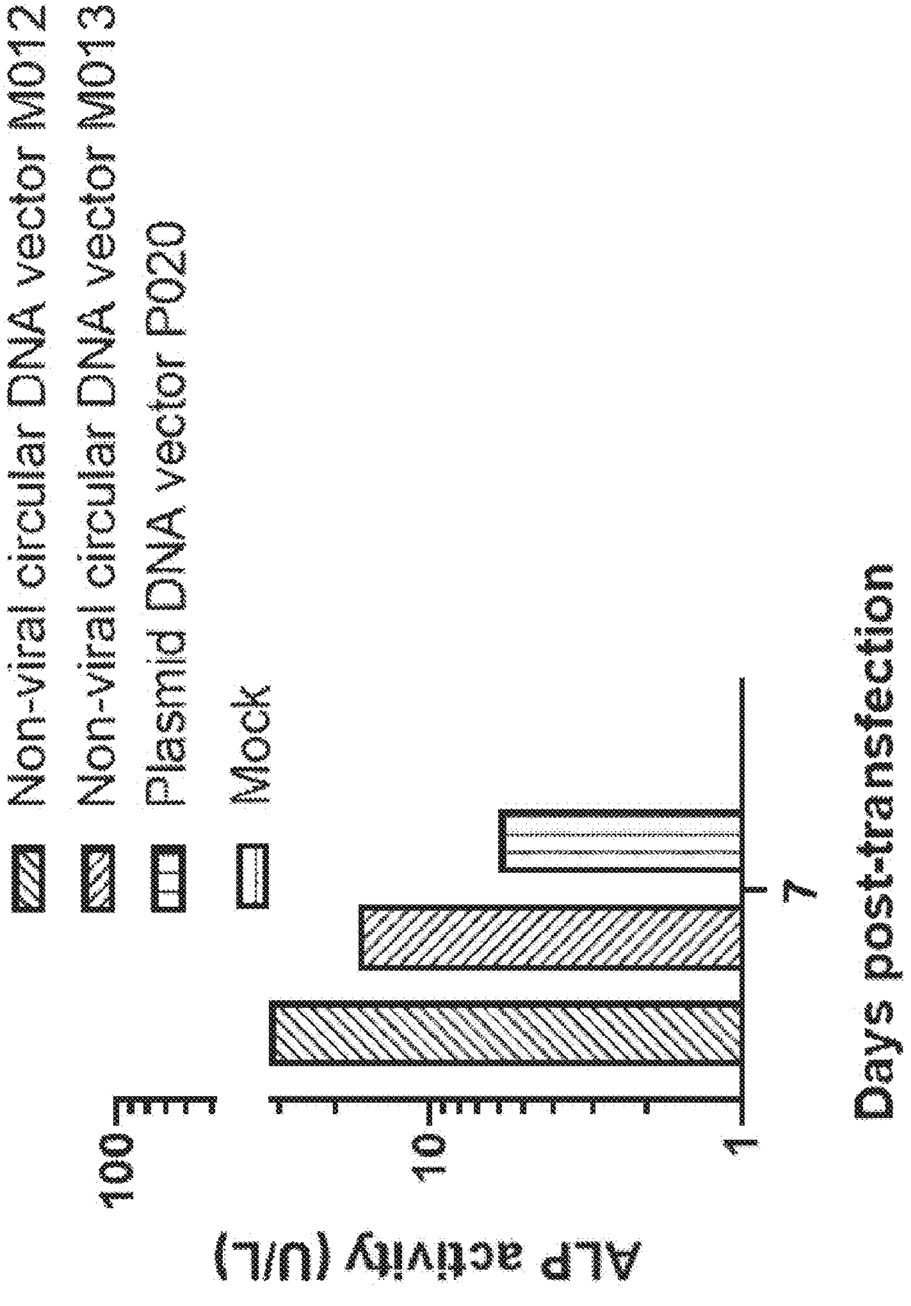
FIG. 7 compares the secretive ALP activity of human tissue non-specific alkaline phosphatase (TNALP) in post-mitotic iPSC-derived hepatocytes from three different constructs, namely from a circular, non-viral DNA vector of the present disclosure containing a cruciform structure comprised of a long inverted repeat containing a bacterial origin of replication (M012—SEQ ID NO: 28), from a circular, non-viral DNA vector of the present disclosure containing a cruciform structure comprised of a shorter inverted repeat not containing a bacterial origin (M013—SEQ ID NO: 29), and from a regular plasmid vector (P020—SEQ ID NO: 33), respectively. The data suggest significantly enhanced transgene (TNALP) expression from vectors comprised of a long-inverted repeat containing a bacterial origin of replication.

Example 3—In Vitro Durable Gene Expression of TNALP DNA Constructs in IPSC-Derived Hepatocytes Non-dividing iPSC-derived hepatocytes transfected with circular, non-viral DNA vectors of the present disclosure including a nucleic acid encoding TNALP and also including dual inverted repeats (M012—SEQ ID NO: 28) showed higher ALP secretion as compared with hepatocytes transfected with a circular, non-viral DNA vector including a nucleic acid encoding TNALP and also including a series of single inverted repeats without intervening heterologous sequences (M013—SEQ ID NO: 29) in FIG. 7. Cells transfected with both constructs comprising the inverted repeat sequences showed higher ALP secretion than cells transfected with a control TNALP construct comprising ampicillin resistance gene (P020—SEQ ID NO: 33).

Method

Non-dividing iPSC-derived human hepatocytes were purchased from Fujifilm. At day 0, plating medium was prepared by adding 1.5 mL of B27 supplement, 0.15 mL of 10 μg/mL of oncostatin stock solution, 1.5 μL of 5 mM of dexamethasone stock solution, 37.5 μL of 25 μg/mL of gentamicin and 1.5 mL of ICELL® Hepatocytes 2.0 medium supplement into 72 mL of RPMI medium according to Fujifilm's recommendation.

Plating medium was filtered via 0.22 μm PES filter unit. At day 1, the ICELL® Hepatocytes 2.0 cryovial was removed from the liquid nitrogen storage tank the cryovial was immersed in a 37° C. water bath for exactly 3 minutes. Using a 2 mL serological pipette, the ICELL® Hepatocytes 2.0 cryovial contents was gently transferred into the 15 mL centrifuge tube containing 10 mL of 37° C. Plating Medium. The cell suspension was centrifuged at 200×g for 3 minutes at room temperature. The supernatant was carefully aspirated under vacuum. 2 mL of 37° C. Plating Medium was slowly added with a wide-bore pipette to resuspend the cell pellet. Hepatocytes were seeded in pre-warmed collagen-coated 24/48-well plate. The medium was refreshed daily from day 1 to 7 and every other day starting from day 8.

TRANSIT™-LTI Reagent and non-viral vector DNA complex was prepared following Mirus manufacturer's recommendation. The TRANSIT™-LTI Reagent:DNA complex was added dropwise to different areas of the wells. The culture vessel was gently rocked back-and-forth and from side-to-side to evenly distribute the TRANSIT™-LTI Reagent:DNA complexes.

At different timepoints, the cell culture medium was taken out and ALP activity in the cell culture medium was determined by ALP colorimetric assay carried out on a Molecular Device plate reader iD5.

Figure 8A:
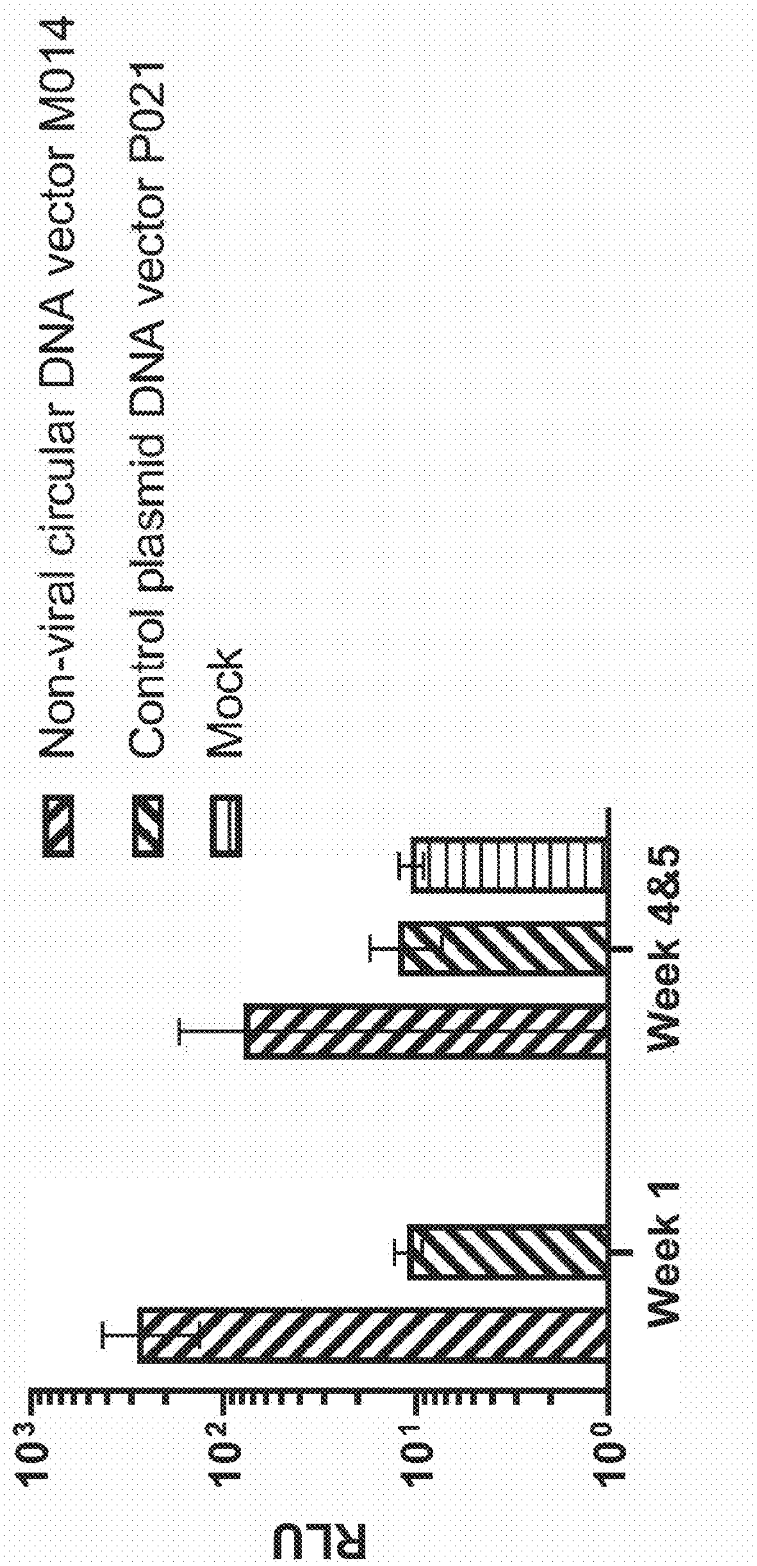
FIG. 8A illustrates that a circular, non-viral DNA vector encoding a luciferase reporter (M014—SEQ ID NO: 30) in accordance with the present disclosure showed persistent bioluminescent signal from mouse liver tissue harvested from week 1 to weeks 4 and 5 after dosing through hydrodynamic tail vein injection compared with the fast decay of control luciferase plasmid.
Figure 8B:
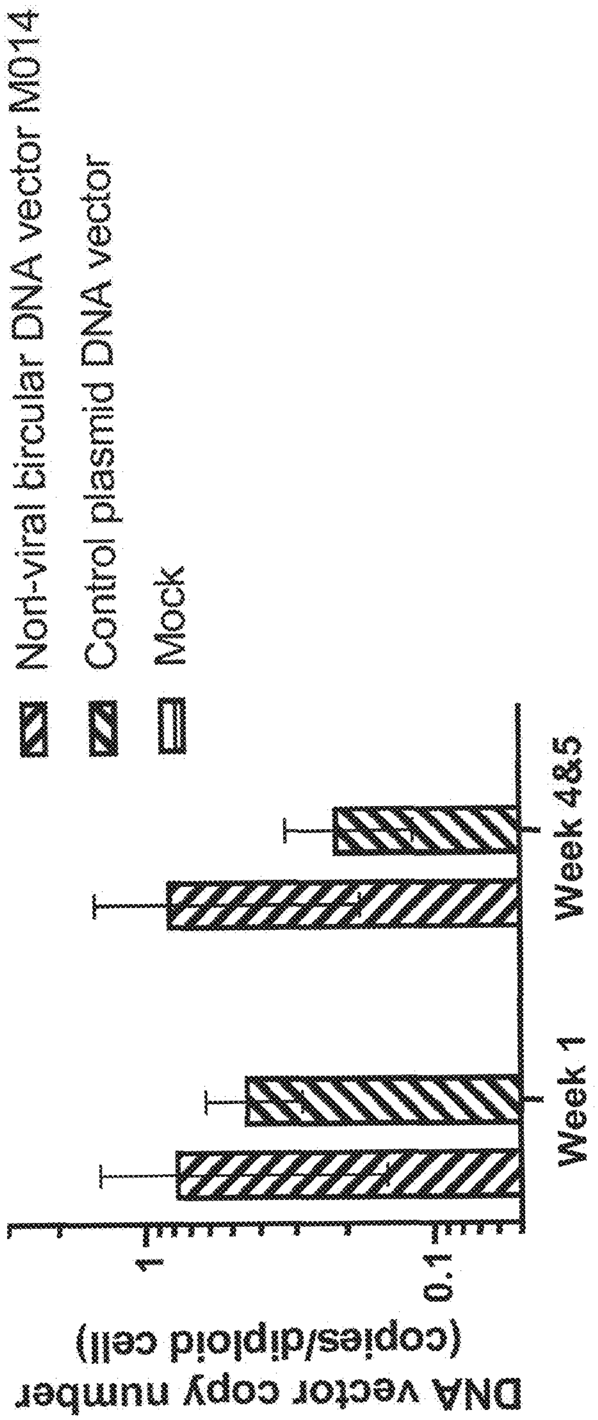
FIG. 8B shows that DNA copy number results matched gene expression of two DNA vectors. The DNA copy number of the circular, non-viral DNA vector was maintained for one month in mouse liver tissue while the copy number of a control luciferase plasmid (P021—SEQ ID NO: 31) in mouse liver cells dropped significantly from week 1 to week 5 as shown in FIG. 8B.

Example 4—Persistence of Liver Luciferase Expression from Luciferase-Containing Constructs in Adult Mice A circular, non-viral DNA vector encoding a luciferase reporter (M014—SEQ ID NO: 30) in accordance with the present disclosure showed persistent bioluminescent signal from mouse liver tissue harvested from week 1 to weeks 4 and 5 after dosing through hydrodynamic tail vein injection (15 μg per mouse) while mice injected with control luciferase plasmid showed background level of luminescence shown in FIG. 8A. Further DNA copy number per diploid cell analysis showed that the M014 construct was maintained for one month in mouse liver tissue while the copy number of a control luciferase plasmid (P021—SEQ ID NO: 31) in mouse liver cells dropped significantly from week 1 to week 5 shown in FIG. 8B.

Method

Adult mice (strain: BALB/c) at age of 9-11 weeks were ordered from The Jackson Laboratory. Prior to study start, animals were randomized into groups using a random number generator. Non-viral DNA vector constructs were administered to adult mice by hydrodynamic injection through the tail vein at dose of 15 μg per animal and volume of 80 mL/kg. At several terminal timepoints, luciferase activity and the non-viral DNA vector copy number were measured ex-vivo in the liver tissues.

For constructs according to the present disclosure DNA copy number measurement, about 25 mg of each liver lobe from each animal were collected and stored below −65° C. before ddPCR assay was carried out on a Biorad ddPCR system. Primers/probe targeting polyA region of non-viral DNA vector construct were used to measure non-viral DNA vector construct copy number while mouse RPP30 was used as a reference gene.

For luciferase, the remaining tissue from each liver lobe was stored at below −65° C. for lysate generation/luciferase. Spectra Max GLO STEADY-LUC™ Reporter Assay Kit was used to measure bioluminescence from the liver lysate after homogenization.

Figure 9:
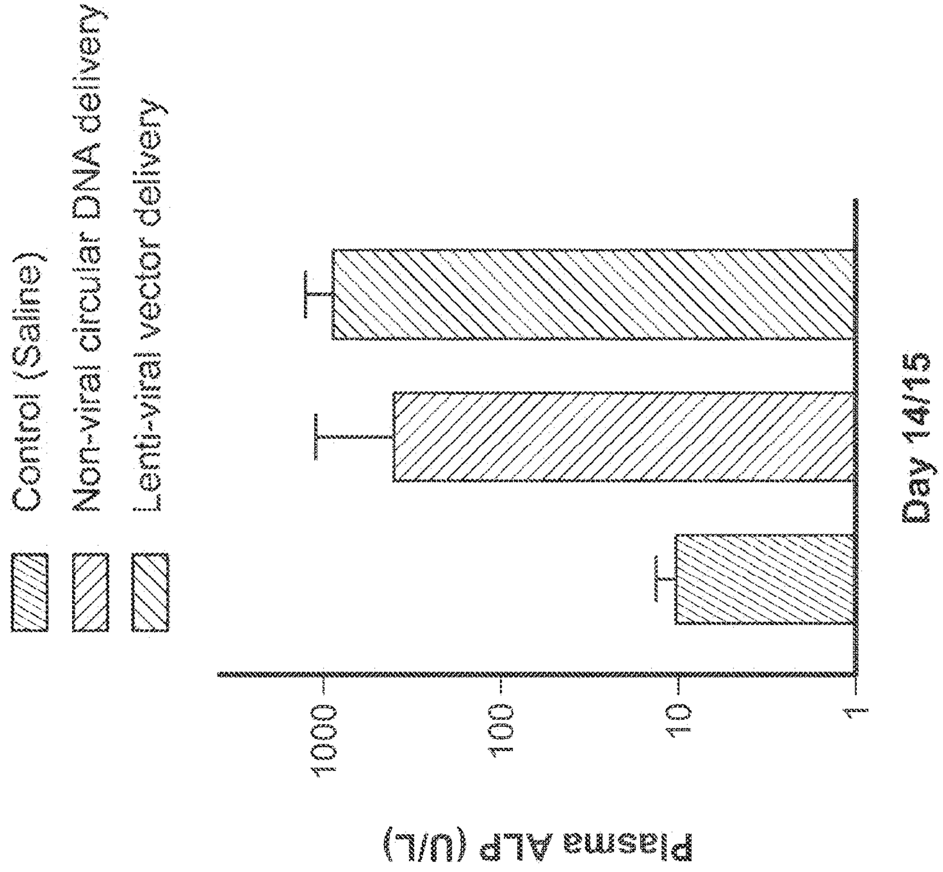
FIG. 9 shows data from a single time point comparing between two different studies. The first study used a circular, non-viral DNA vector including a nucleic acid encoding TNALP; while the second study utilized mobilized human hematopoietic stem cells transduced with a lentiviral vector expressing TNALP. Similar plasma ALP activities were mediated in mice in the two different studies.

Example 5—Comparison of Alp Levels in Mice Treated with a Circular, Non-Viral DNA Vector Expressing TNALP and a Lentiviral Vector Expressing TNALP FIG. 9 shows that similar plasma ALP levels were found in mice (n=3) dosed with a circular, non-viral DNA vector including a nucleic acid encoding TNALP (M013—SEQ ID NO: 29) as compared with mice treated with $1\times10^6$ cells transduced with a lentiviral vector expressing TNALP (SEQ TD NO: 34) (transduced hematopoietic stem/progenitor cells at 2 weeks post-dosing).

Method

Adult mice (strain: B6129SF2/J) at age of 9-11 weeks were ordered from The Jackson Laboratory. Prior to study start, animals were randomized into groups using a random number generator. Non-viral DNA vector constructs were administered to adult mice by hydrodynamic injection through the tail vein at dose of 15 μg per animal and volume of 80 mL/kg. At several terminal timepoints, luciferase activity and non-viral DNA vector copy number were measured in the liver.

For DNA vector copy number measurement, 25 mg of each liver lobe from each animal were collected and stored below −65° C. before ddPCR assay was carried out on a Biorad ddPCR system. Primers/probe targeting the poly A region of the non-viral DNA vector construct were used to measure non-viral DNA vector construct copy number while mouse RPP30 was used as a reference gene.

At different timepoints, plasma samples were collected from the animals and stored below −65° C. before ALP measurement was carried out. ALP concentration was determined by colorimetric assay carried out on a Molecular Device plate reader iD5.

Example 6—Production of Construct According to the Present Disclosure

In some embodiments, a circular, non-viral DNA vector can be generated from a parental plasmid including both a marker gene and high copy number origin of replication (e.g., pUC or pMB1) between two loxP sites by "Cre-lox recombination." The Cre recombinase can be induced through metabolic control in the bacterial cells harboring the parental plasmid. In this instance, recombination produces two circular and supercoiled DNA molecules which are topologically unlinked, each containing a single loxP site. The one resulting circular supercoiled DNA molecule comprises the marker gene and the high copy number origin of replication, while the other comprises the circular non-viral DNA vector of this disclosure.

In some embodiments, other LoxP sites such as Lox511, Lox 5171, Lox 2272, M2, M3, M7, M11, Lox 71, Lox 66, LoxPsym, or others could be used to generate the non-viral DNA vector from a parental DNA plasmid. In some embodiments, other recombinases such as PhiC31, A integrase, and Flp recombinase could be used to generate the non-viral DNA vector. In some embodiments, recombinases such as Cre, PhiC31, A integrase, and Flp recombinase could be produced recombinantly and applied directly to purified parental plasmid DNA to generate the non-viral DNA vector. In some embodiments, marker genes would include those the encode kanamycin resistance, spectinomycin resistance, streptomycin resistance, carbenicillin resistance, bleomycin resistance, erythromycin resistance, polymyxin B resistance, tetracycline resistance, or chloramphenicol resistance among others. In some embodiments, origins of replication would include those sequences from pMB1, pBR322, ColE1, p15A, pSC101, or F1.

Figure 12A:
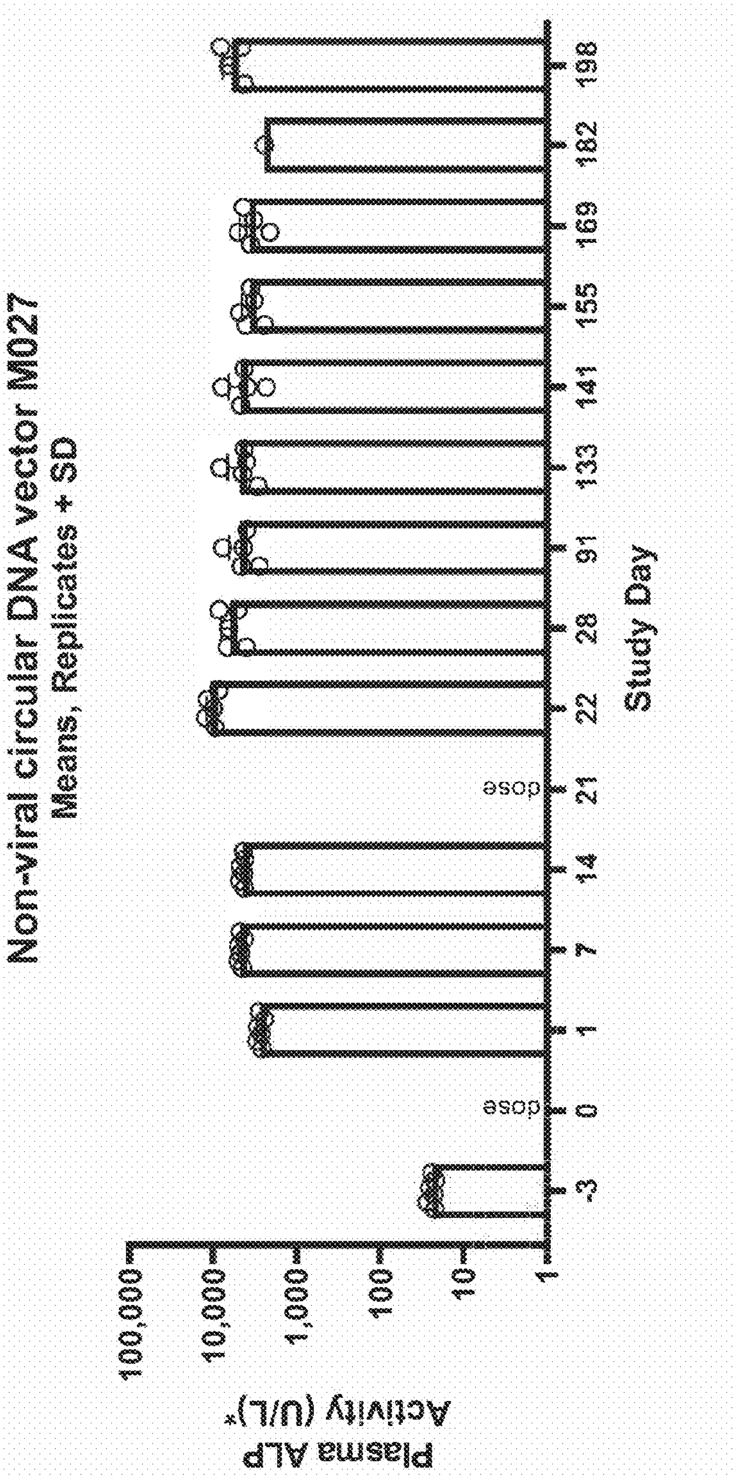
FIGS. 12A and 12B illustrate the persistence of circular, non-viral DNA vectors of the present disclosure encoding a murine secreted embryonic alkaline phosphatase (SEAP) reporter (M027 and M032—SEQ ID NO: 74 and SEQ ID NO: 75) in a rodent model through hydrodynamic tail vein injection at 15 μg DNA per mouse per dose. High plasma SEAP activity in mouse plasma was maintained from day 1 to day 190 after double dosing through hydrodynamic tail vein injection (15 μg of DNA per mouse per dose). Further, DNA vector copy number per diploid cell analysis showed that the three constructs according to the present disclosure (M027—SEQ ID NO: 74; M032—SEQ ID NO: 75) were maintained for 183 days in mouse liver (FIG. 12C).
Figure 12B:
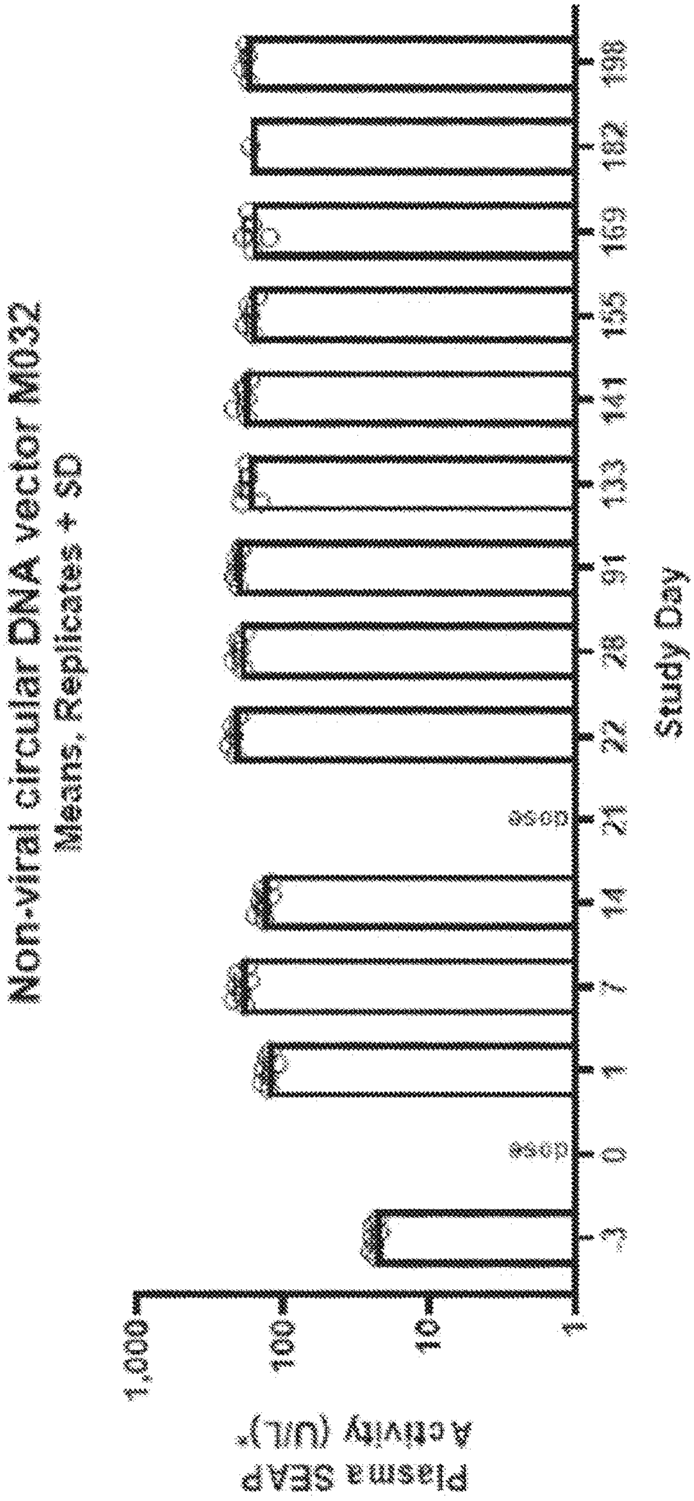
Figure 12C:
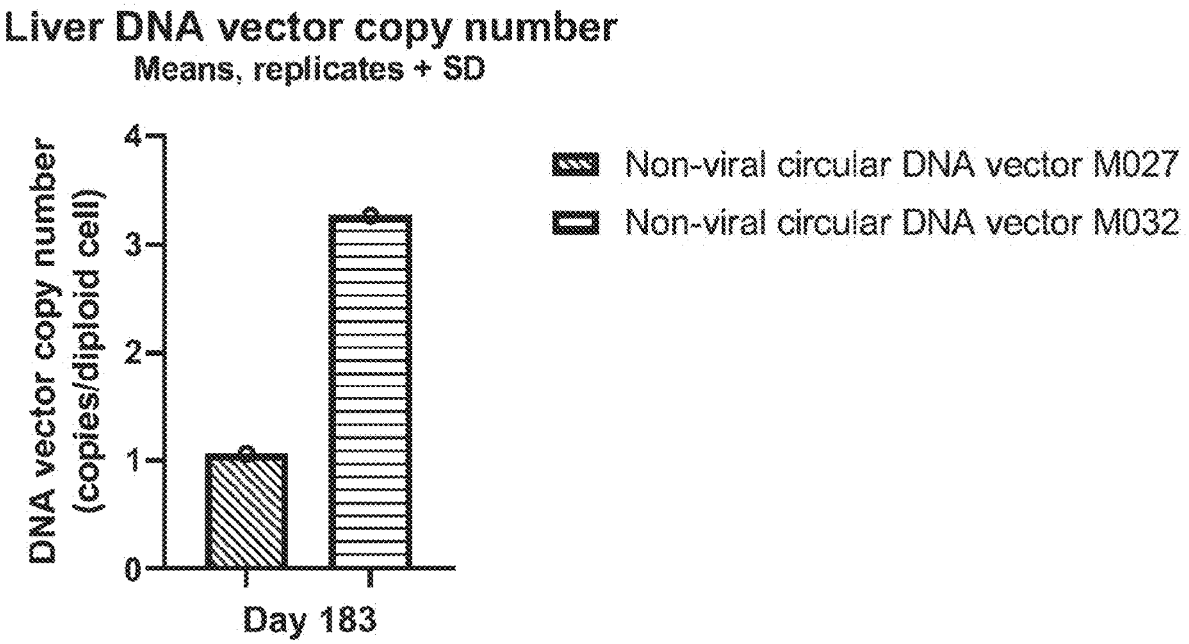

Example 7—Persistence of Liver Murine SEAP Expression from Murine SEAP Constructs in Adult Mice Circular, non-viral DNA vectors using EF1a and TBG promoters encoding a murine SEAP reporter (M027 and M032—SEQ ID NO: 74 and SEQ ID NO: 75) showed persistence of high plasma SEAP activity in mouse samples collected from day 1 to day 190 after dosing through hydrodynamic tail vein injection (15 μg per mouse) (FIGS. 12A and 12B), respectively. DNA copy number per diploid cell analysis showed that the two constructs according to the present disclosure (M027—SEQ ID NO: 74; and M032—SEQ ID NO: 75) were maintained for 189 days in mouse liver (FIG. 12C).

Method

Adult mice (strain: BALB/c) at age of 9-11 weeks were ordered from The Charles River Laboratories. Prior to study start, animals were randomized into groups using a random number generator. Non-viral DNA vector constructs were administered to adult mice by hydrodynamic injection through the tail vein at dose of 15 μg per animal and volume of 100 ml/kg. At several terminal timepoints, SEAP activity were measured in plasma samples and the non-viral DNA vector copy number was measured in liver tissue samples.

For constructs according to the present disclosure, copy number measurement, 25 mg of each liver lobe from each animal were collected and stored below −65° C. before ddPCR assay was carried out on a BioRad ddPCR system. Primers/probe targeting the poly A region of a reference gene.

At different timepoints, plasma samples were collected and stored below −65° C. before the SEAP assay was carried out. SEAP activity was determined by SEAP fluorescence assays carried out on a Molecular Device plate reader iD5.

Example 8—Nuclear Entry of Constructs According to the Present Disclosure

Figure 14A:
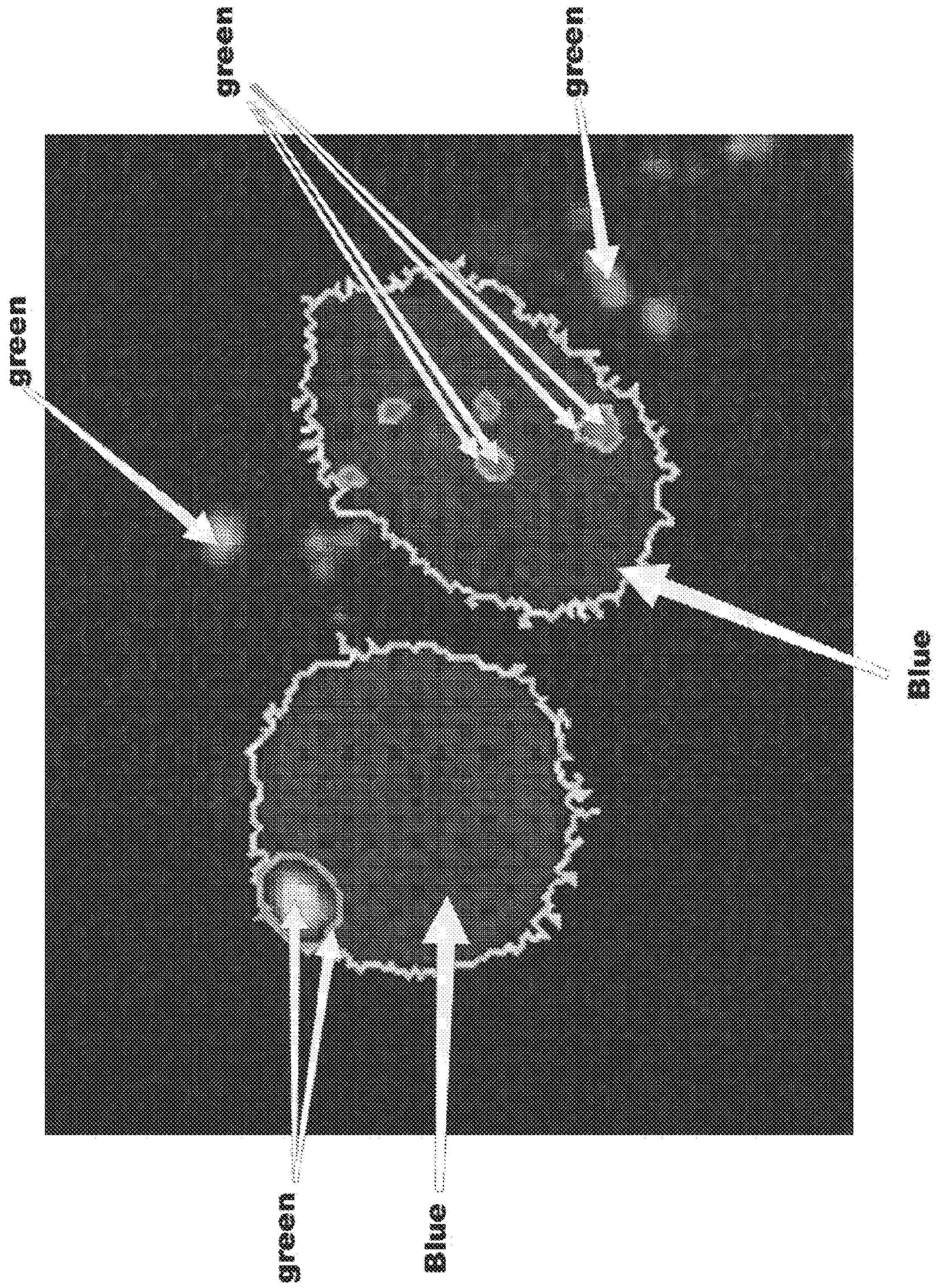
FIGS. 14A, 14B and 14C illustrate the enhanced nuclear entry of constructs according to the present disclosure having a cruciform structure (M012—SEQ ID NO: 28; M013—SEQ ID NO: 29) as compared with DNA without a crucifom1 structure (M022—SEQ ID NO: 33) in post-mitotic non-dividing iPSC-derived hepatocytes after transfection.
Figure 14B:
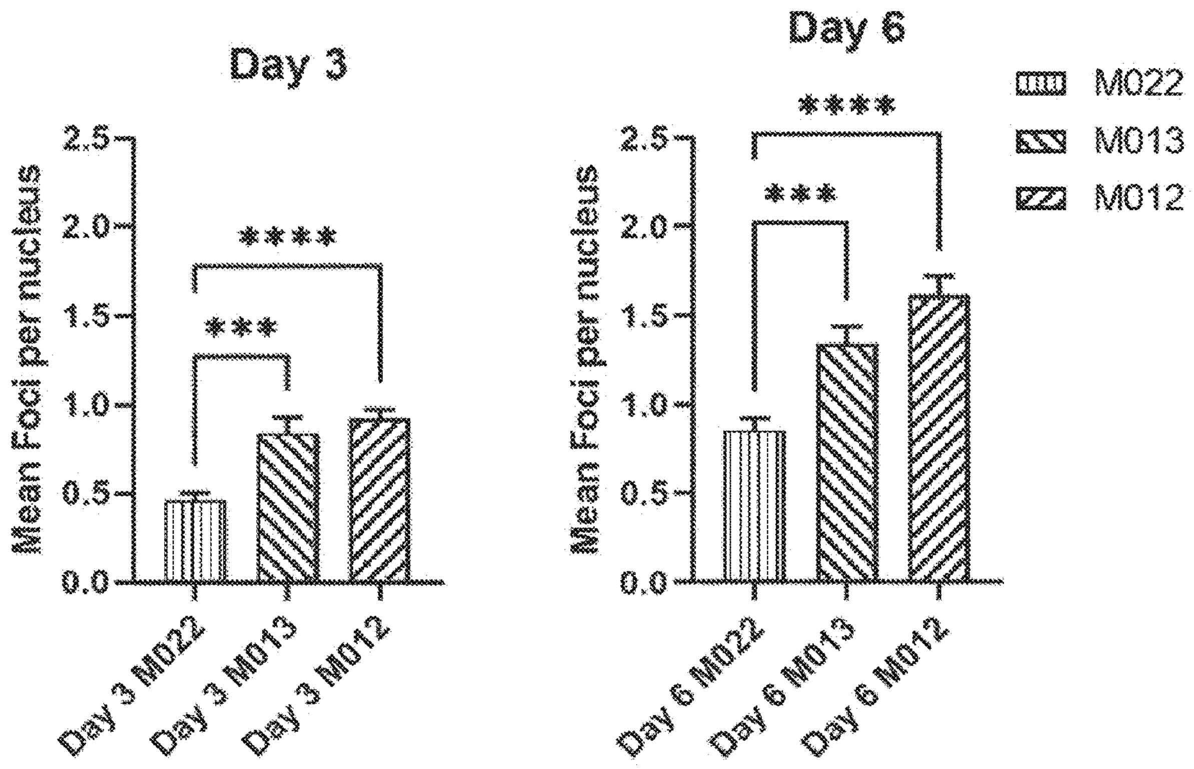
Figure 14C:
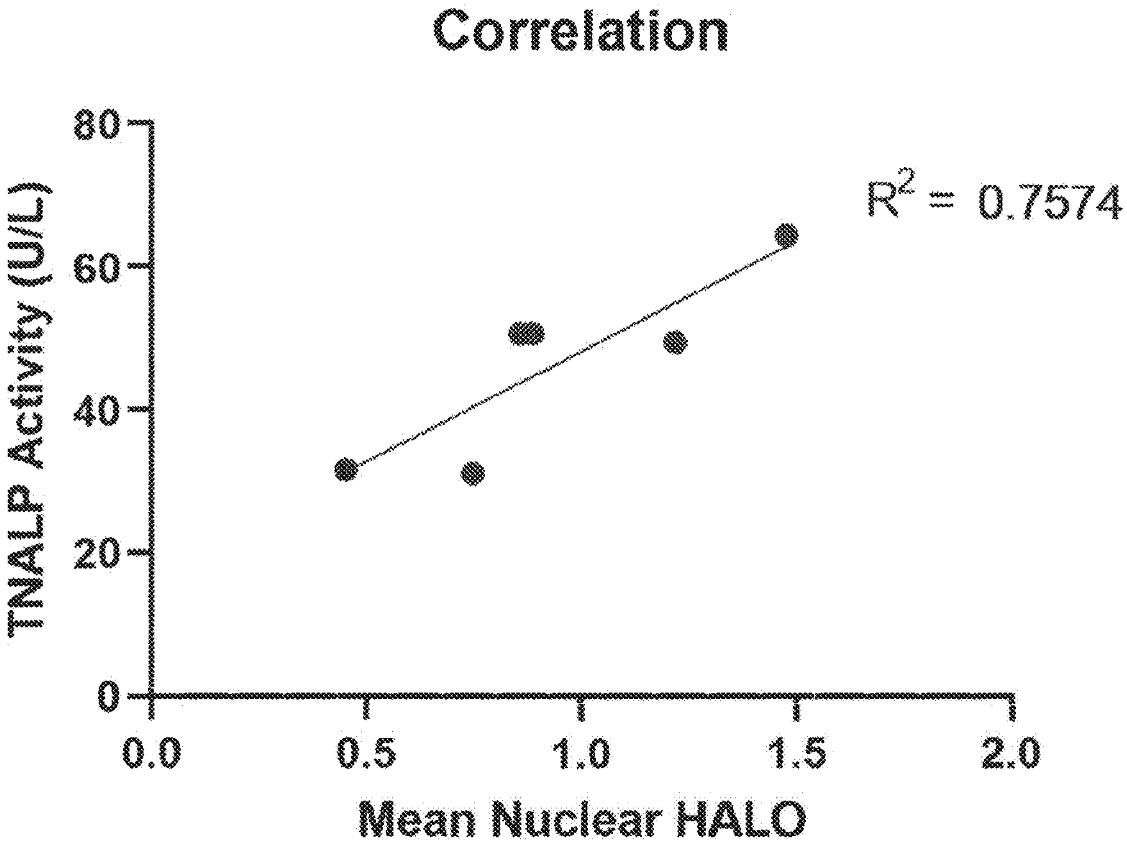

To determine the extent to which the cruciform structure impacts nuclear entry and retention, post-mitotic non-dividing iPSC-derived hepatocytes transfected with fluorescence-labeled circular, non-viral DNA vectors including a nucleic acid encoding TNALP and also including dual inverted repeats (M012—SEQ ID NO: 28) showed higher number of foci per nucleus as compared with hepatocytes transfected with a circular, non-viral DNA vector including a nucleic acid encoding TNALP and also including a series of single inverted repeats without intervening heterologous sequences (DD-ITR construct) (M013—SEQ ID NO: 29) and a control TNALP construct comprising ampicillin resistance gene (M022—SEQ ID NO: 33) at day 1, 3 and 6 (FIG. 14B). The number of foci per nucleus correlates with ALP activity of medium (FIG. 14C).

Method

Non-dividing iPSC-derived human hepatocytes were purchased from Fujifilm. At day 0, plating medium was prepared by adding 1.5 mL of B27 supplement, 0.15 mL of 10 μg/mL of oncostatin stock solution, 1.5 μL of 5 mM of dexamethasone stock solution, 37.5 μL of 25 μg/mL of gentamicin and 1.5 mL of ICELL® Hepatocytes 2.0 medium supplement into 72 mL of RPMI according to Fujifilm's recommendation.

After ICELL® Hepatocytes 2.0 Medium Supplement (1×3.0 mL) was thawed, plating medium was filtered via 0.22 μm PES filter unit. At day 1, the ICELL® Hepatocytes 2.0 cryovial was taken out from the liquid nitrogen storage tank. The cryovial was immersed in a 37° C. water bath for exactly 3 minutes. Using a 2 mL serological pipette, the ICELL® Hepatocytes 2.0 cryovial contents were gently transferred into the 15 mL centrifuge tube containing 10 mL of 37° C. Plating Medium. The cell suspension was centrifuged at 200×g for 3 minutes at room temperature. After the supernatant was carefully aspirated, 2 mL of warm plating medium with a wide-bore pipette was used to resuspend the cell pellet. Hepatocytes were seeded in pre-warmed collagen-coated 24/48-well plate.

Transfection Reagent was purchased from FuGENE and DNA transfection followed manufacturer's recommendation.

At different timepoints, the cell culture medium was taken out and ALP level was determined by ALP colorimetric assay carried out on a Molecular Device plate reader iD5.

Cells were fixed on day 1, 3, and 6 post-transfection, stained with DAPI, and mounted for confocal images. DAPI staining (blue) represents the nucleus and green foci represent the constructs of the present disclosure inside the cell, both in the nucleus and cytoplasm (FIG. 14A).

Images were analyzed using ImagePro 11 smart segmentation. Nuclei regions of interest (ROIs) were identified on the blue channel using a minimum area cut-off of 58 $\mu m^2$. ROIs including the constructs of the present disclosure were identified on the green channel using a minimum area cut-off of 0.04 $\mu m^2$. Only foci including constructs of the present disclosure located within nuclei were counted.

An average of 400 cells were analyzed per condition. Data are graphed as the average number of foci per nucleus for each condition. Outliers were excluded from the dataset using 3 criteria (nuclei area, # of foci, and foci % area of nuclei).

Figure 13A:
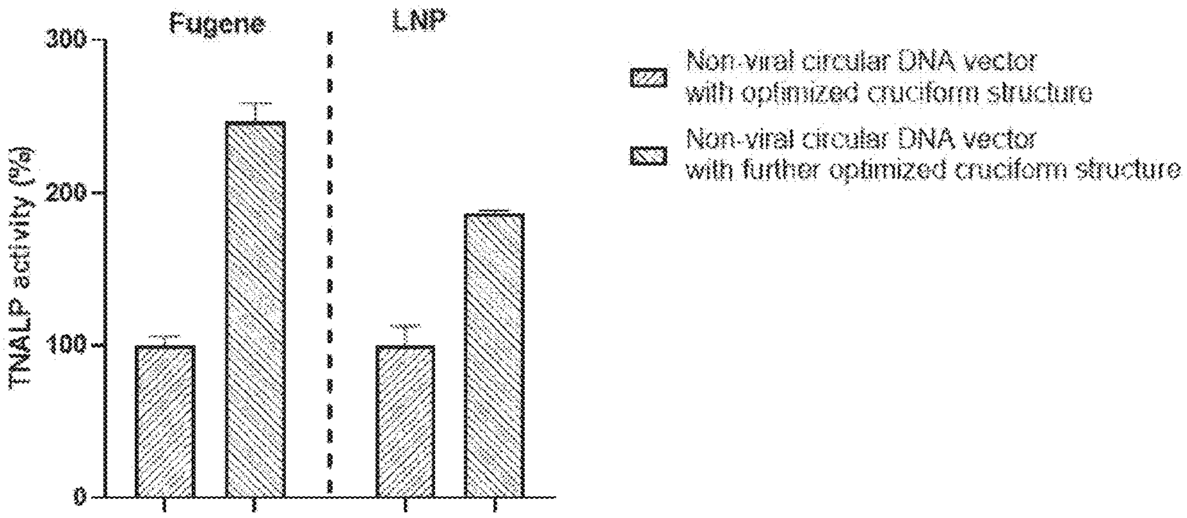
FIGS. 13A and 13B illustrate a comparison of two constructs according to the present disclosure, where the two constructs have two different cruciform structures, namely M012 (SEQ ID NO: 30) and M056 (SEQ ID NO: 73) in iPSC-derived hepatocytes at day 3.
Figure 13B:
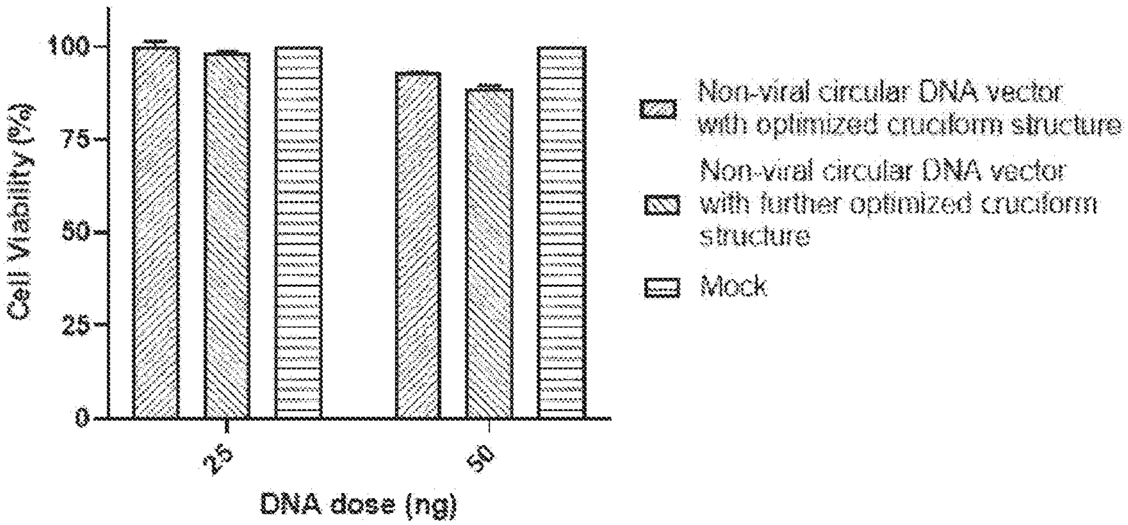

Example 9—In Vitro Gene Expression of Reporter Constructs with Different Cruciforvi Structures in IPSC-Derived Hepatocytes FIG. 13A shows that transfection of a circular non-viral DNA vector with further improved cruciform structure (M056—SEQ ID NO:73) led to stronger ALP level in culture medium in iPSC-derived hepatocytes at day 3 than a circular non-viral DNA vector with improved cruciform structure (M012—SEQ ID NO: 30) with FUGENE™ or SM102-based lipid nanoparticle formulation. Both of circular, non-viral DNA vectors with FUGENE™ or SM102-based lipid nanoparticle formulation do not induce significant toxicity in iPSC-derived human hepatocytes shown in FIG. 13B.

Method

Non-dividing iPSC-derived human hepatocytes were purchased from Fujifilm. At day 0, plating medium was prepared by adding 1.5 mL of B27 supplement, 0.15 mL of 10 μg/mL of oncostatin stock solution, 1.5 μL of 5 mM of dexamethasone stock solution, 37.5 μL of 25 μg/mL of gentamicin and 1.5 mL of ICELL® Hepatocytes 2.0 medium supplement into 72 mL of RPMI according to Fujifilm's recommendation.

After ICELL® Hepatocytes 2.0 Medium Supplement (1×3.0 mL) was thawed, plating medium was filtered via 0.22 μm PES filter unit. At day 1, the ICELL® Hepatocytes 2.0 cryovial was taken out from the liquid nitrogen storage tank. The cryovial was immersed in a 37° C. water bath for exactly 3 minutes. Using a 2 mL serological pipette, the ICELL® Hepatocytes 2.0 cryovial contents were gently transferred into the 15 mL centrifuge tube containing 10 mL of 37° C. Plating Medium. The cell suspension was centrifuged at 200×g for 3 minutes at room temperature. After the supernatant was carefully aspirated, 2 mL of warm plating medium with a wide-bore pipette was used to resuspend the cell pellet. Hepatocytes were seeded in pre-warmed collagen-coated 24/48-well plate.

Prepare FUGENE™ or SM-102-based lipid nanoparticle transfection Reagent and a non-viral vector DNA complex following supplier's recommendation. Add the transfection reagent:DNA complexes (prepared in Step A) dropwise to different areas of the wells. Gently rock the culture vessel back-and-forth and from side-to-side to evenly distribute the transfection reagent:DNA complexes.

At day 3, the cell culture medium was taken out and ALP level was determined by ALP colorimetric assay carried out on a Molecular Device plate reader iD5.

Figure 15A:
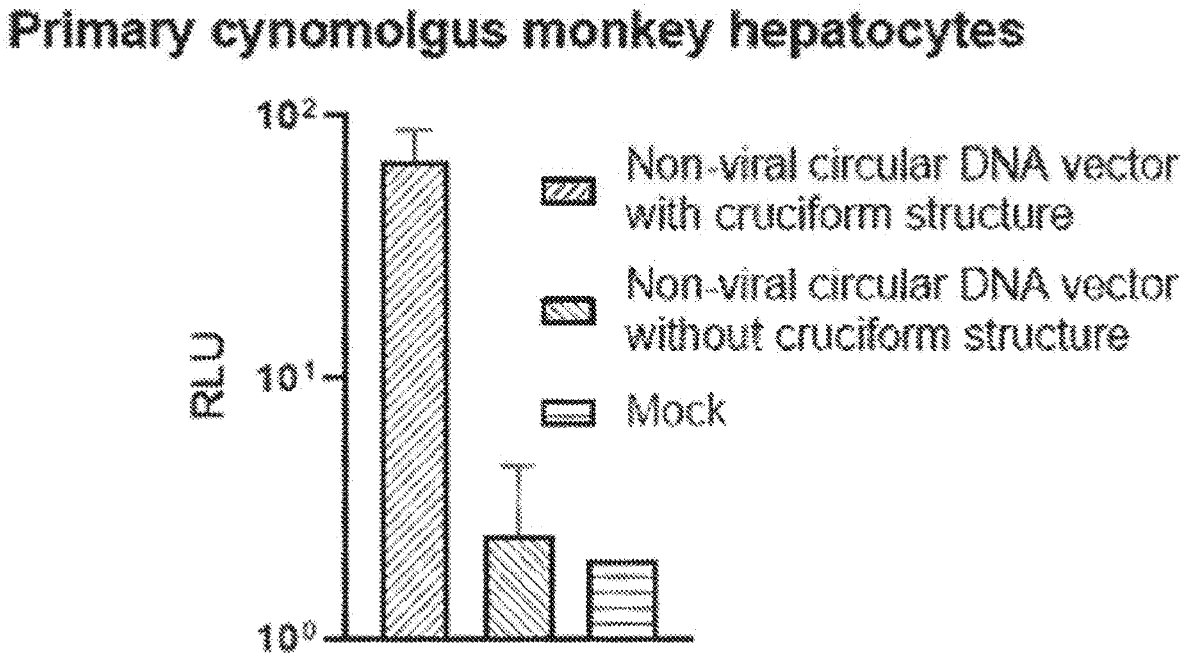
FIGS. 15A and 15B illustrate that constructs of the present disclosure including firefly luciferase DNA (SEQ ID NO: 73) with improved cruciform structure led to a much higher luciferase activity than control DNA without cruciform structure (SEQ ID NO: 74) across species both in human and cynomolgus monkey hepatocytes. Both the constructs according to the present disclosure with luciferase DNA (SEQ ID NO: 73) and control luciferase DNA without cruciform structure (SEQ ID NO: 74) were transfected to hepatocytes with SM102-based lipid nanoparticle formulation.
Figure 15B:
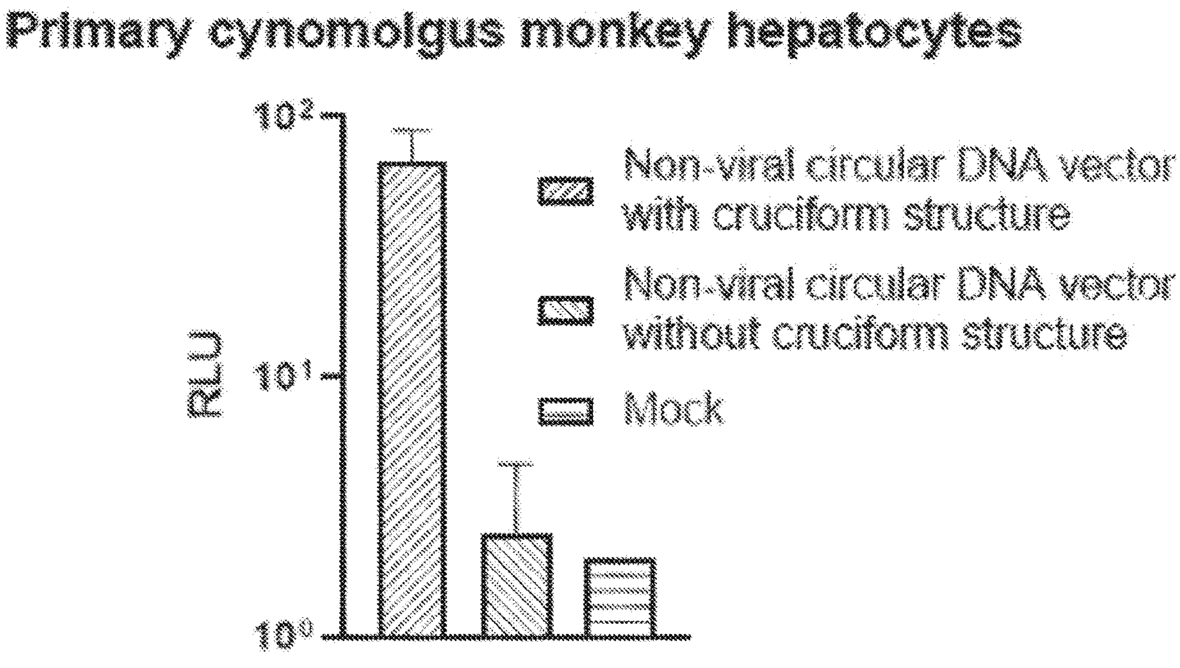

Example 10—In Vitro Gene Expression of a Reporter Constructs with or without Cruciform Structure in Primary Human and Cynomolgus Monkey Hepatocytes Transfection of constructs of the present disclosure which included luciferase DNA (SEQ ID NO: 73) with improved cruciform structure led to a much higher luciferase level in primary human hepatocytes (FIG. 15A) and cynomolgus monkey hepatocytes (FIG. 15B) at day 3 than control luciferase DNA without cruciform structure (SEQ ID NO: 74) using SM102-based lipid nanoparticle formulation.

Method

Primary human hepatocytes (Lonza) and primary cynomolgus monkey hepatocytes (GIBCO) were seeded on day 0 in duplicate wells of collagen type I-coated 96 well plates at 80,000 and 70,000 cells per well. One day post seeding, constructs of the present disclosure and control constructs were delivered by LNP mix.

Prepare SM-102-based lipid mix (SM102, DSPC, NIP 6, 1.5% DMG-PEG2K) and use pipette to mix DNA with lipid mix. Add lipid mix:DNA complexes dropwise to different areas of the wells. Gently rock the culture vessel back-and-forth and from side-to-side to evenly distribute lipid DNA mix.

Endpoint luciferase activity was measured in cell lysate of primary human hepatocytes (FIG. 16A) and primary cynomolgus monkey hepatocytes (FIG. 16B) on day 6 post LNP delivery with Molecular Devices GLO STEADY-LUC™ kit, respectively.

Figure 16:
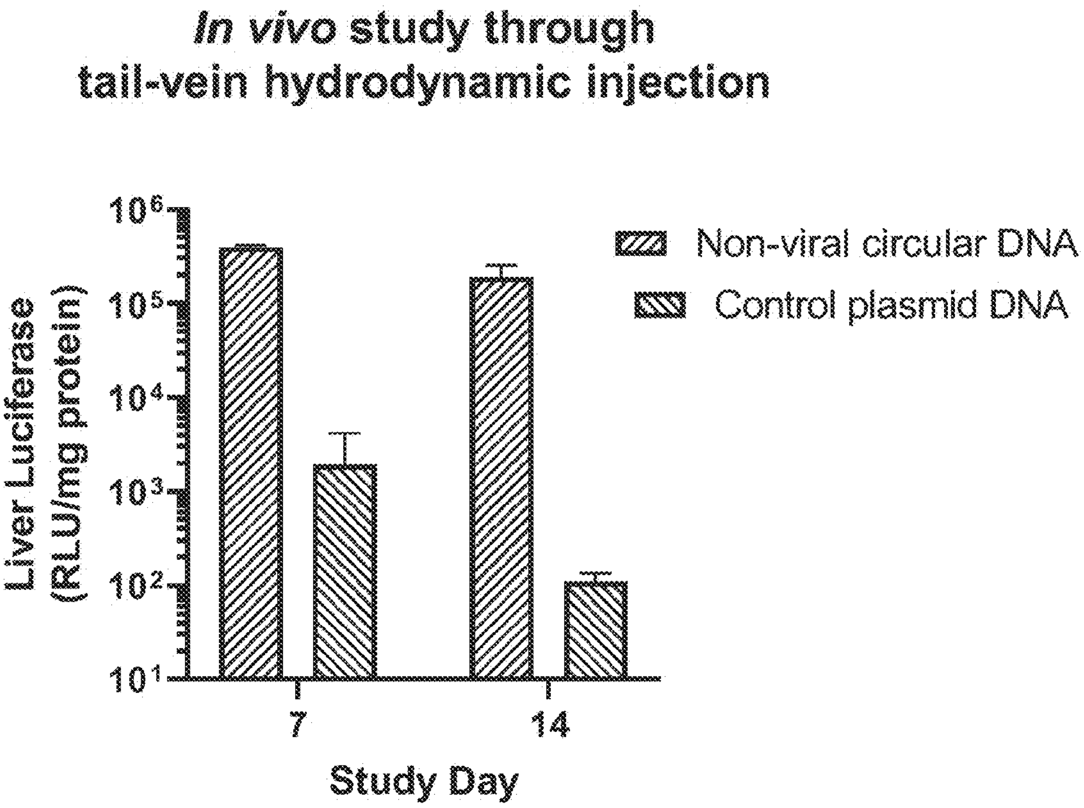
FIG. 16 illustrates that a construct according to the present disclosure with luciferase DNA (SEQ ID NO: 73) with improved cruciform structure also led to a much higher luciferase activity in mouse than control DNA without a cruciform structure (SEQ ID NO: 74). A circular, non-viral DNA vector including a firefly luciferase reporter (SEQ ID NO: 73) and a control DNA without cruciform structure (SEQ ID NO: 74) were dosed to mice through hydrodynamic tail vein injection (15 μg per mouse) and mouse liver tissues were harvested at day 7 and 14 before luciferase activity assay was carried out.

Example 11—Enhanced Liver Luciferase Expression from Firefly Luciferase Constructs in Adult Mice A circular, non-viral DNA vector including a firefly luciferase reporter (SEQ ID NO: 73) showed higher expression of luciferase activity in mouse liver tissue harvested from day 7 and 14 after dosing through tail vein-based hydrodynamic injection (15 μg per mouse) compared to a control firefly luciferase construct (SEQ ID NO: 73) (FIG. 16).

Method

Adult mice (strain: BALB/c) at age of 9-11 weeks were ordered from The Charles River Laboratories. Prior to study start, animals were randomized into groups using a random number generator. Non-viral DNA vector constructs were administered to adult mice by hydrodynamic injection through the tail vein at dose of 15 μg per animal and volume of 100 mL/kg. On day 7 and 14, firefly luciferase activity was measured in liver samples.

At day 7 and day 14, the mice were euthanized, and liver samples were collected and stored at below −65° C. before bioluminescent measurement was determined by a bioluminescence assay carried out on a Molecular Device plate reader iD5.

Figure 17:
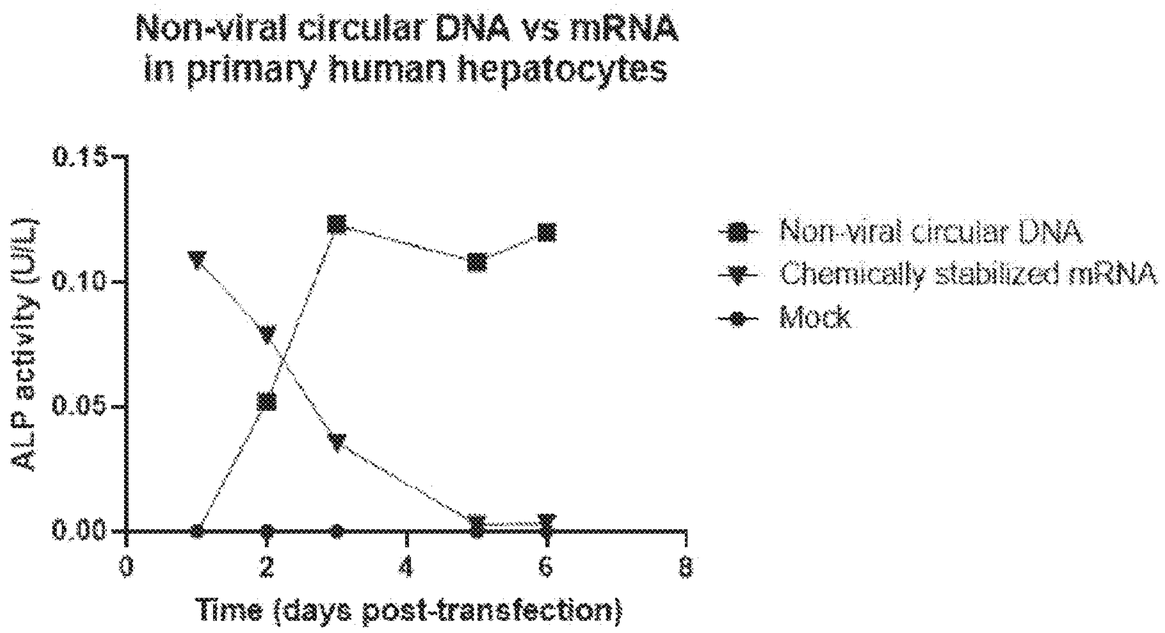
FIG. 17 illustrates the great durability of constructs according to the present disclosure (SEQ ID NO: 43) as compared with mRNA. Constructs according to the present disclosure (SEQ ID NO: 43) and chemically modified mRNA encoding cynomolgus monkey soluble TNALP transgene were transfected via SM102-based lipid nanoparticle formulation to primary human hepatocytes. ALP activity from constructs according to the present disclosure in culture medium increased from day 1 to 3, then was maintained from day 3 to day 6. At the same time, ALP activity of mRNA-transfected cells decreased from day 1 to 5 and diminished at day 6.

Example 12—In Vitro Gene Expression Comparison of DNA Construct and Chemically Modified mRNA Encoding a Cynomolgus Monkey Soluble TNALP Transgene in Primary Human Hepatocytes (i) A construct of the present disclosure including Cynomolgus Monkey Soluble TNALP DNA (SEQ ID NO: 43) with improved cruciform structure, and (ii) chemically modified mRNA encoding the same transgene were delivered to primary human hepatocytes using SM102-based lipid nanoparticle formulation. ALP activity from constructs according to the present disclosure in culture medium increased from day 1 to 3, then was maintained from day 3 to day 6. At the same time, ALP activity of mRNA-transfected cells kept dropping from day 1 to 5 and diminished at day 6 (FIG. 17).

Method

Primary human hepatocytes (Lonza) were seeded on day 0 in duplicate wells of collagen type I-coated 96 well plates at 80,000 cells per well. One day post seeding, constructs of the present disclosure and control constructs were delivered by LNP mix.

Prepare SM-102-based lipid mix (SM102, DSPC, N/P 6, 1.5% DMG-PEG2K) and use pipette to mix DNA with lipid mix. Add lipid mix:DNA complexes dropwise to different areas of the wells. Gently rock the culture vessel back-and-forth and from side-to-side to evenly distribute lipid DNA mix.

Between day 1 and day 6, the cell culture medium was taken out and ALP level was determined by ALP fluorescence assay carried out on a Molecular Device plate reader iD5.

Example 13—In Vitro Colocalization of Constructs According to the Present Disclosure with PARP1

Figure 18:
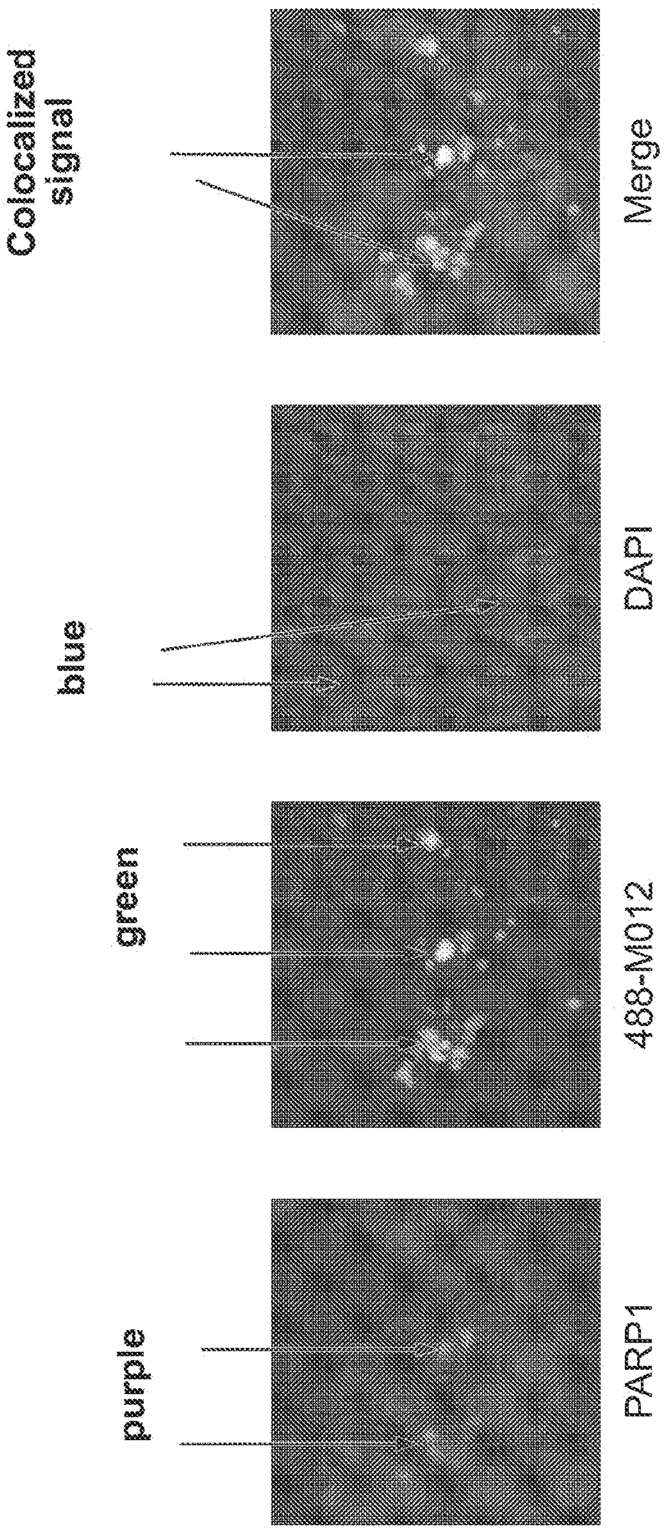
FIG. 18 illustrates that co-localization of PARP1 (purple color) and constructs according to the present disclosure (green color) (M012—SEQ ID NO: 28) in the cytoplasm of 293 cells 24 hours post-transfection. PARP1 is a well-known first responder that detects DNA damage and then facilitates genomic DNA repair pathway. The colocalization data suggests that PARP1 might be one of the factors involved in the innate immune evasion, resolution, nuclear entry, recombination, and nuclear retention of constructs according to the present disclosure.

FIG. 18 shows a representative confocal image of 293T cells transfected with a fluorescence-labelled construct according to the present disclosure (M012—SEQ ID NO: 28). Cells were stained with anti-PARP1-AF647 (Purple). As the area of PARP1 overlapped with the construct according to the present disclosure, it suggested that PARP1 might be involved in the intracellular pathway of constructs according to the present disclosure post-transfection.

Method

A construct according to the present disclosure (M012—SEQ ID NO: 28) was labeled with green fluorescence DNA conjugation reagent before the transfection. Transfection Reagent was purchased from FuGENE and DNA transfection followed the manufacturer's recommendation. 293T cells were fixed on day 3 post-transfection, stained with DAPI and anti-PARP1 antibody, and mounted for confocal images. Purple color represents PARP1, DAPI staining (blue) represents the nucleus and green color represent the constructs according to the present disclosure inside the cell (FIG. 18).

Figure 19A:
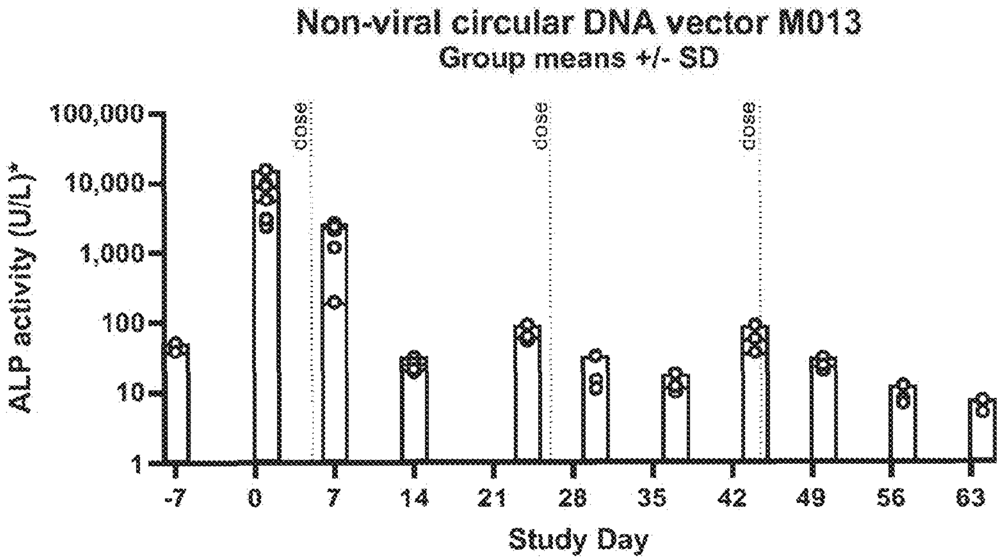
FIGS. 19A, 19B and 19C illustrate immunomodulatory effects of circular, non-viral constructs according to the present disclosure.
Figure 19B:
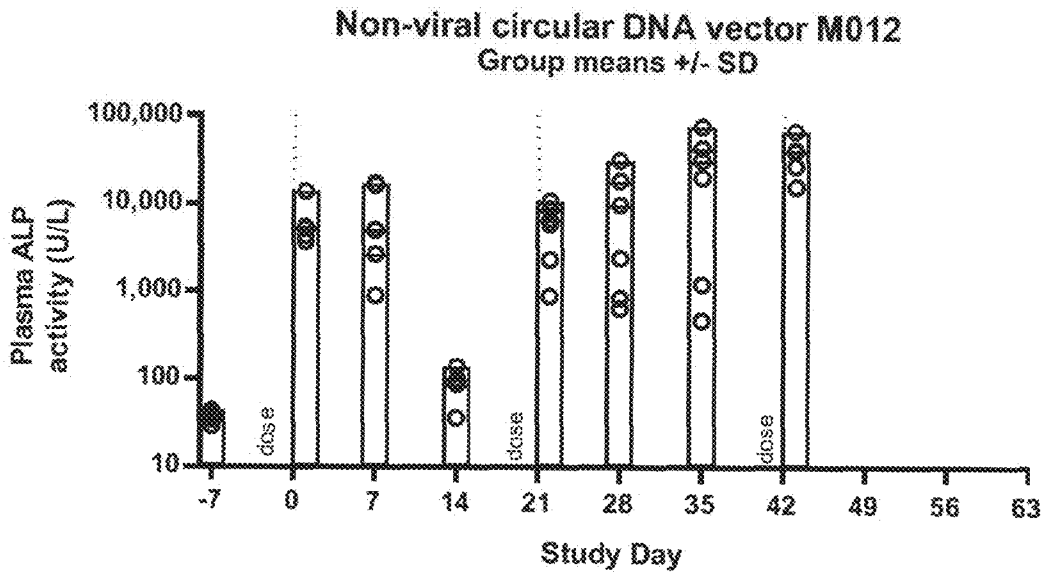
Figure 19C:
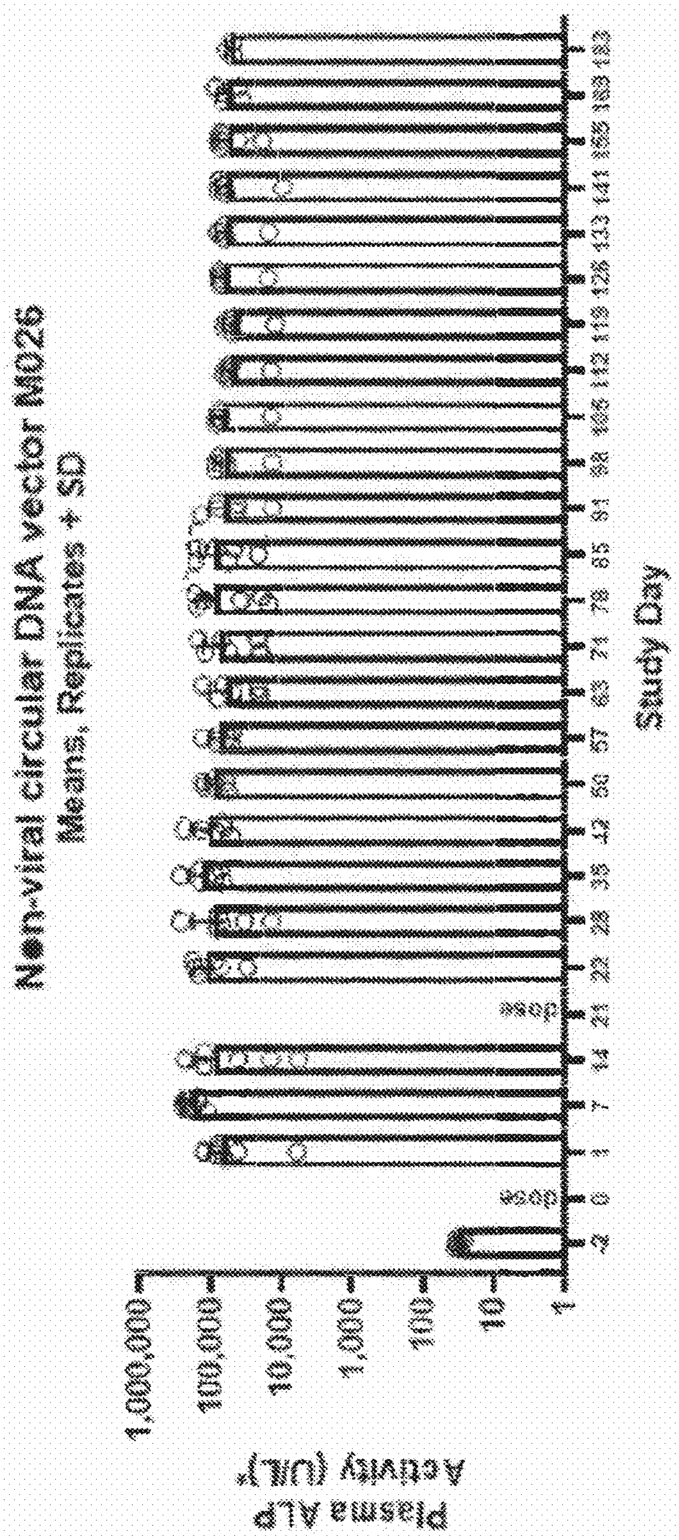

Example 14—Immunomodulatory Effects of Constructs According to the Present Disclosure To determine the extent to which the cruciform structure and cassette gene impact immune response, adult mice (n=7 per group) were dosed three times with three different constructs: (i) a circular, non-viral DNA vector carrying the human TNALP with single inverted repeats without intervening heterologous sequences (M013—SEQ ID NO: 29)

with high CpG content, bone-tag, and with lg-Fc domain (FIG. 19A); (ii) a circular, non-viral DNA vector according to the present disclosure carrying the human TNALP transgene with improved cruciform structure (M012—SEQ ID NO: 28) and high CpG content, bone-tag and Fc-domain (FIG. 19B), or (iii) a circular, non-viral DNA vector according to the present disclosure carrying cynomolgus monkey TNALP with improved cruciform structure (SEQ ID NO: 43), but with zero CpG content in transgene coding, no bone-tag, and no Ig-Fc-domain in the gene cassette to increase TNALP protein expression and reduce the immunostimulatory properties of the DNA (FIG. 19C). Plasma ALP activity from the DNA construct with single inverted repeats without intervening heterologous sequences cruciform structure was modest, non-durable and showed inability to re-dose likely due to the development of a humoral or cellular immune response against the inflammatory transgene product or transgene expressing cells. Plasma ALP activity from construct according to the present disclosure with improved cruciform structure showed increased potency, more durable transgene expression and ability to re-dose likely due to invasion of cytosolic DNA signaling (CDS) pathway mediated by the cGAS-STING pathway. Optimization of the gene expression cassette in that construct further improved plasma protein secretion and decreased immune response, leading to the highest observed levels of ALP activity.

Method

Adult mice (strain: BALB/c) at age of 9-11 weeks were ordered from The Charles River Laboratories. Prior to study start, animals were randomized into groups using a random number generator. Non-viral DNA vector constructs were administered three times at 3-week interval to adult mice by hydrodynamic injection through the tail vein at dose of 15 μg per animal and volume of 100 mL/kg.

At different timepoints, plasma samples were collected and stored below −65° C. before the ALP assay was carried out. ALP activity was determined by TNALP fluorescence assays carried out on a Molecular Device plate reader iD5.

Additional Embodiments

In some embodiments, the present disclosure is directed to an amino acid sequence having at least 85% identity to any one of SEQ ID NOS: 19-27. In some embodiments, the present disclosure is directed to an amino acid sequence having at least 90% identity to any one of SEQ ID NOS: 19-27. In some embodiments, the present disclosure is directed to an amino acid sequence having at least 91% identity to any one of SEQ ID NOS: 19-27. In some embodiments, the present disclosure is directed to an amino acid sequence having at least 92% identity to any one of SEQ ID NOS: 19-27. In some embodiments, the present disclosure is directed to an amino acid sequence having at least 93% identity to any one of SEQ ID NOS: 19-27. In some embodiments, the present disclosure is directed to an amino acid sequence having at least 94% identity to any one of SEQ ID NOS: 19-27. In some embodiments, the present disclosure is directed to an amino acid sequence having at least 95% identity to any one of SEQ ID NOS: 19-27. In some embodiments, the present disclosure is directed to an amino acid sequence having at least 96% identity to any one of SEQ ID NOS: 19-27. In some embodiments, the present disclosure is directed to an amino acid sequence having at least 97% identity to any one of SEQ ID NOS: 19-27. In some embodiments, the present disclosure is directed to an amino acid sequence having at least 98% identity to any one of SEQ ID NOS: 19-27. In some embodiments, the present disclosure is directed to an amino acid sequence having at least 99% identity to any one of SEQ ID NOS: 19-27. In some embodiments, the present disclosure is directed to an amino acid sequence having any one of SEQ ID NOS: 19-27.

In some embodiments, the present disclosure is directed to a circular, non-viral DNA vector which includes a nucleus acid sequence encoding an amino acid having at least 85% identity to any one of SEQ ID NOS: 19-27. In some embodiments, the present disclosure is directed to a circular, non-viral DNA vector which includes a nucleus acid sequence encoding encoding an amino acid having at least 90% identity to any one of SEQ ID NOS: 19-27. In some embodiments, the present disclosure is directed to a circular, non-viral DNA vector which includes a nucleus acid sequence encoding encoding an amino acid having at least 91% identity to any one of SEQ ID NOS: 19-27. In some embodiments, the present disclosure is directed to a circular, non-viral DNA vector which includes a nucleus acid sequence encoding encoding an amino acid having at least 92% identity to any one of SEQ ID NOS: 19-27. In some embodiments, the present disclosure is directed to a circular, non-viral DNA vector which includes a nucleus acid sequence encoding encoding an amino acid having at least 93% identity to any one of SEQ ID NOS: 19-27. In some embodiments, the present disclosure is directed to a circular, non-viral DNA vector which includes a nucleus acid sequence encoding encoding an amino acid having at least 94% identity to any one of SEQ ID NOS: 19-27. In some embodiments, the present disclosure is directed to a circular, non-viral DNA vector which includes a nucleus acid sequence encoding encoding an amino acid having at least 95% identity to any one of SEQ ID NOS: 19-27. In some embodiments, the present disclosure is directed to a circular, non-viral DNA vector which includes a nucleus acid sequence encoding encoding an amino acid having at least 96% identity to any one of SEQ ID NOS: 19-27. In some embodiments, the present disclosure is directed to a circular, non-viral DNA vector which includes a nucleus acid sequence encoding encoding an amino acid having at least 97% identity to any one of SEQ ID NOS: 19-27. In some embodiments, the present disclosure is directed to a circular, non-viral DNA vector which includes a nucleus acid sequence encoding encoding an amino acid having at least 98% identity to any one of SEQ ID NOS: 19-27. In some embodiments, the present disclosure is directed to a circular, non-viral DNA vector which includes a nucleus acid sequence encoding encoding an amino acid having at least 99% identity to any one of SEQ ID NOS: 19-27. In some embodiments, the present disclosure is directed to a circular, non-viral DNA vector which includes a nucleus acid sequence encoding encoding an amino acid having any one of SEQ ID NOS: 19-27.

In some embodiments, the present disclosure is directed to a nucleic acid sequence having at least 80% identity to any one of SEQ ID NOS: 28-73. In some embodiments, the present disclosure is directed to a nucleic acid sequence having at least 85% identity to any one of SEQ ID NOS: 28-73. In some embodiments, the present disclosure is directed to a nucleic acid sequence having at least 86% identity to any one of SEQ ID NOS: 28-73. In some embodiments, the present disclosure is directed to a nucleic acid sequence having at least 87% identity to any one of SEQ ID NOS: 28-73. In some embodiments, the present disclosure is directed to a nucleic acid sequence having at least 88% identity to any one of SEQ ID NOS: 28-73. In some embodiments, the present disclosure is directed to a nucleic acid sequence having at least 89% identity to any one of SEQ ID NOS: 28-73. In some embodiments, the present disclosure is directed to a nucleic acid sequence having at least 90% identity to any one of SEQ ID NOS: 28-73. In some embodiments, the present disclosure is directed to a nucleic acid sequence having at least 91% identity to any one of SEQ ID NOS: 28-73. In some embodiments, the present disclosure is directed to a nucleic acid sequence having at least 92% identity to any one of SEQ ID NOS: 28-73. In some embodiments, the present disclosure is directed to a nucleic acid sequence having at least 93% identity to any one of SEQ ID NOS: 28-73. In some embodiments, the present disclosure is directed to a nucleic acid sequence having at least 94% identity to any one of SEQ ID NOS: 28-73. In some embodiments, the present disclosure is directed to a nucleic acid sequence having at least 95% identity to any one of SEQ ID NOS: 28-73. In some embodiments, the present disclosure is directed to a nucleic acid sequence having at least 96% identity to any one of SEQ ID NOS: 28-73. In some embodiments, the present disclosure is directed to a nucleic acid sequence having at least 97% identity to any one of SEQ ID NOS: 28-73. In some embodiments, the present disclosure is directed to a nucleic acid sequence having at least 98% identity to any one of SEQ ID NOS: 28-73. In some embodiments, the present disclosure is directed to a nucleic acid sequence having at least 99% identity to any one of SEQ ID NOS: 28-73. In some embodiments, the present disclosure is directed to a nucleic acid sequence having at least any one of SEQ ID NOS: 28-73.

A circular, non-viral DNA vector comprising a nucleic acid sequence having at least 80% identity to any one of SEQ ID NOS: 28-30. A circular, non-viral DNA vector comprising a nucleic acid sequence having at least 81% identity to any one of SEQ ID NOS: 28-30. A circular, non-viral DNA vector comprising a nucleic acid sequence having at least 80% identity to any one of SEQ ID NOS: 28-30. A circular, non-viral DNA vector comprising a nucleic acid sequence having at least 81% identity to any one of SEQ ID NOS: 28-30. A circular, non-viral DNA vector comprising a nucleic acid sequence having at least 82% identity to any one of SEQ ID NOS: 28-30. A circular, non-viral DNA vector comprising a nucleic acid sequence having at least 83% identity to any one of SEQ ID NOS: 28-30. A circular, non-viral DNA vector comprising a nucleic acid sequence having at least 84% identity to any one of SEQ ID NOS: 28-30. A circular, non-viral DNA vector comprising a nucleic acid sequence having at least 85% identity to any one of SEQ ID NOS: 28-30. A circular, non-viral DNA vector comprising a nucleic acid sequence having at least 86% identity to any one of SEQ ID NOS: 28-30. A circular, non-viral DNA vector comprising a nucleic acid sequence having at least 87% identity to any one of SEQ ID NOS: 28-30. A circular, non-viral DNA vector comprising a nucleic acid sequence having at least 88% identity to any one of SEQ ID NOS: 28-30. A circular, non-viral DNA vector comprising a nucleic acid sequence having at least 89% identity to any one of SEQ ID NOS: 28-30. A circular, non-viral DNA vector comprising a nucleic acid sequence having at least 90% identity to any one of SEQ ID NOS: 28-30. A circular, non-viral DNA vector comprising a nucleic acid sequence having at least 91% identity to any one of SEQ ID NOS: 28-30. A circular, non-viral DNA vector comprising a nucleic acid sequence having at least 92% identity to any one of SEQ ID NOS: 28-30. A circular, non-viral DNA vector comprising a nucleic acid sequence having at least 93% identity to any one of SEQ ID NOS: 28-30. A circular, non-viral DNA vector comprising a nucleic acid sequence having at least 94% identity to any one of SEQ ID NOS: 28-30. A circular, non-viral DNA vector comprising a nucleic acid sequence having at least 95% identity to any one of SEQ ID NOS: 28-30. A circular, non-viral DNA vector comprising a nucleic acid sequence having at least 96% identity to any one of SEQ ID NOS: 28-30. A circular, non-viral DNA vector comprising a nucleic acid sequence having at least 97% identity to any one of SEQ ID NOS: 28-30. A circular, non-viral DNA vector comprising a nucleic acid sequence having at least 98% identity to any one of SEQ ID NOS: 28-30. A circular, non-viral DNA vector comprising a nucleic acid sequence having at least 99% identity to any one of SEQ ID NOS: 28-30. A circular, non-viral DNA vector comprising a nucleic acid sequence having any one of SEQ ID NOS: 28-30.

A circular, non-viral DNA vector comprising a nucleic acid sequence having at least 80% identity to any one of SEQ ID NOS: 72-73. A circular, non-viral DNA vector comprising a nucleic acid sequence having at least 81% identity to any one of SEQ ID NOS: 72-73. A circular, non-viral DNA vector comprising a nucleic acid sequence having at least 80% identity to any one of SEQ ID NOS: 72-73. A circular, non-viral DNA vector comprising a nucleic acid sequence having at least 81% identity to any one of SEQ ID NOS: 72-73. A circular, non-viral DNA vector comprising a nucleic acid sequence having at least 82% identity to any one of SEQ ID NOS: 72-73. A circular, non-viral DNA vector comprising a nucleic acid sequence having at least 83% identity to any one of SEQ ID NOS: 72-73. A circular, non-viral DNA vector comprising a nucleic acid sequence having at least 84% identity to any one of SEQ ID NOS: 72-73. A circular, non-viral DNA vector comprising a nucleic acid sequence having at least 85% identity to any one of SEQ ID NOS: 72-73. A circular, non-viral DNA vector comprising a nucleic acid sequence having at least 86% identity to any one of SEQ ID NOS: 72-73. A circular, non-viral DNA vector comprising a nucleic acid sequence having at least 87% identity to any one of SEQ ID NOS: 72-73. A circular, non-viral DNA vector comprising a nucleic acid sequence having at least 88% identity to any one of SEQ ID NOS: 72-73. A circular, non-viral DNA vector comprising a nucleic acid sequence having at least 89% identity to any one of SEQ ID NOS: 72-73. A circular, non-viral DNA vector comprising a nucleic acid sequence having at least 90% identity to any one of SEQ ID NOS: 72-73. A circular, non-viral DNA vector comprising a nucleic acid sequence having at least 91% identity to any one of SEQ ID NOS: 72-73. A circular, non-viral DNA vector comprising a nucleic acid sequence having at least 92% identity to any one of SEQ ID NOS: 72-73. A circular, non-viral DNA vector comprising a nucleic acid sequence having at least 93% identity to any one of SEQ ID NOS: 72-73. A circular, non-viral DNA vector comprising a nucleic acid sequence having at least 94% identity to any one of SEQ ID NOS: 72-73. A circular, non-viral DNA vector comprising a nucleic acid sequence having at least 95% identity to any one of SEQ ID NOS: 72-73. A circular, non-viral DNA vector comprising a nucleic acid sequence having at least 96% identity to any one of SEQ ID NOS: 72-73. A circular, non-viral DNA vector comprising a nucleic acid sequence having at least 97% identity to any one of SEQ ID NOS: 72-73. A circular, non-viral DNA vector comprising a nucleic acid sequence having at least 98% identity to any one of SEQ ID NOS:

72-73. A circular, non-viral DNA vector comprising a nucleic acid sequence having at least 99% identity to any one of SEQ ID NOS: 72-73. A circular, non-viral DNA vector comprising a nucleic acid sequence having any one of SEQ ID NOS: 72-73.

In some embodiments, is an isolated, circular, non-viral DNA vector comprises: a first portion consisting essentially of an expression cassette including one or more nucleic acid sequences encoding one or more therapeutic proteins, where each of the one or more nucleic acid sequences encoding the one or more therapeutic proteins are operatively linked to a promoter; and a second portion capable of forming at least one cruciform structure, wherein the second portion consists essentially of at least two inverted repeat sequences, and where the at least two inverted repeat sequences are separated by a non-repeating nucleotide sequence having at least 3 nucleotides.

In some embodiments, is an isolated, circular, non-viral DNA vector consisting essentially of: a first portion consisting essentially of an expression cassette including one or more nucleic acid sequences encoding one or more therapeutic proteins, where each of the one or more nucleic acid sequences encoding the one or more therapeutic proteins are operatively linked to a promoter; and a second portion capable of forming at least one cruciform structure, wherein the second portion consists essentially of at least two inverted repeat sequences, and where the at least two inverted repeat sequences arc separated by a non-repeating nucleotide sequence having at least 3 nucleotides.

In some embodiments, is an isolated, circular, non-viral DNA vector comprises: a first portion consisting of an expression cassette including one or more nucleic acid sequences encoding one or more therapeutic proteins, where each of the one or more nucleic acid sequences encoding the one or more therapeutic proteins are operatively linked to a promoter; and a second portion capable of forming at least one cruciform structure, wherein the second portion consists of at least two inverted repeat sequences, and where the at least two inverted repeat sequences are separated by a non-repeating nucleotide sequence having at least 3 nucleotides.

In some embodiments, is an isolated, circular, non-viral DNA vector consists of: a first portion consisting of an expression cassette including one or more nucleic acid sequences encoding one or more therapeutic proteins, where each of the one or more nucleic acid sequences encoding the one or more therapeutic proteins are operatively linked to a promoter; and a second portion capable of forming at least one cruciform structure, wherein the second portion consists of at least two inverted repeat sequences, and where the at least two inverted repeat sequences are separated by a non-repeating nucleotide sequence having at least 3 nucleotides.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications, and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure.

What is claimed is:

1. An isolated, circular, non-viral, non-integrating DNA vector comprising:

(i) a first portion comprising an expression cassette comprising a nucleic acid sequence encoding a therapeutic protein, wherein the nucleic acid sequence encoding the therapeutic protein is operably linked to a promoter; and (ii) a second portion comprising a nucleic acid sequence consisting essentially of a first adeno-associated virus (AAV) inverted repeat sequence, an R6Kγ bacterial origin of replication (oriR6Kγ) sequence, and a second AAV inverted repeat sequence;

wherein the first AAV inverted repeat sequence, oriR6Kγ sequence, and second AAV inverted repeat sequence are contiguous, and wherein the oriR6Kγ sequence is flanked by, and in between, the first AAV inverted repeat sequence and the second AAV inverted repeat sequence.

2. The DNA vector of claim 1, wherein the oriR6Kγ sequence comprises a nucleic acid sequence that is at least 90% identical to a sequence selected from the group consisting of SEQ ID NO: 58 and SEQ ID NO: 59.

3. The DNA vector of claim 2, wherein the oriR6Kγ sequence comprises a nucleic acid sequence selected from the group consisting of SEQ ID NO: 58 and SEQ ID NO: 59.

4. The DNA vector of claim 1, wherein each of the AAV inverted repeat sequences is independently at least 90% identical to a sequence selected from the group consisting of SEQ ID NOS: 1-18.

5. The DNA vector of claim 4, wherein each of the AAV inverted repeat sequences is independently selected from the group consisting of SEQ ID NOS: 1-18.

6. The DNA vector of claim 1, wherein the first AAV inverted repeat sequence is at least 90% identical to a sequence selected from the group consisting of SEQ ID NOS: 1, 3, 5, 7, 9, 11, 13, 15, and 17; wherein the oriR6Kγ sequence comprises a nucleic acid sequence at least 90% identical to a sequence selected from the group consisting of SEQ ID NO: 58 and SEQ ID NO: 59; and wherein the second AAV inverted repeat sequence is at least 90% identical to a sequence selected from the group consisting of SEQ ID NOS: 2, 4, 6, 8, 10, 12, 14, 16, and 18.

7. The DNA vector of claim 6, wherein the first AAV inverted repeat sequence is selected from the group consisting of SEQ ID NOS: 1, 3, 5, 7, 9, 11, 13, 15, and 17; wherein the oriR6Kγ sequence comprises a nucleic acid sequence selected from the group consisting of SEQ ID NO: 58 and SEQ ID NO: 59; and wherein the second AAV inverted repeat sequence is selected from the group consisting of SEQ ID NOS: 2, 4, 6, 8, 10, 12, 14, 16, and 18.

8. The DNA vector of claim 1, wherein the second portion comprises a sequence at least 95% identical to a sequence selected from the group consisting of SEQ ID NOS: 35, 60, 62, and 71.

9. The DNA vector of claim 8, wherein the second portion comprises a sequence selected from the group consisting of SEQ ID NOS: 35, 60, 62, and 71.

10. An isolated, circular, non-viral, non-integrating DNA vector comprising:

(i) a first portion comprising an expression cassette comprising a nucleic acid sequence encoding a therapeutic protein, wherein the nucleic acid sequence encoding the therapeutic protein is operably linked to a promoter; and (ii) a second portion comprising a nucleic acid sequence comprising the Formula X—Y—X';

wherein X and X' are each separately an AAV inverted repeat sequence and Y consists essentially of an oriR6Kγ sequence.

11. The DNA vector of claim 10, wherein the oriR6Kγ sequence comprises a nucleic acid sequence that is at least 90% identical to a sequence selected from the group consisting of SEQ ID NO: 58 and SEQ ID NO: 59.

12. The DNA vector of claim 11, wherein the oriR6Kγ sequence comprises a nucleic acid sequence selected from the group consisting of SEQ ID NO: 58 and SEQ ID NO: 59.

13. The DNA vector of claim 10, wherein X and X' are independently at least 90% identical to a sequence selected from the group consisting of SEQ ID NOS: 1-18.

14. The DNA vector of claim 13, wherein X and X' are independently selected from the group consisting of SEQ ID NOS: 1-18.

15. The DNA vector of claim 10, wherein X is at least 90% identical to a sequence selected from the group consisting of SEQ ID NOS: 1, 3, 5, 7, 9, 11, 13, 15, and 17; wherein the oriR6Kγ sequence comprises a nucleic acid sequence at least 90% identical to a sequence selected from the group consisting of SEQ ID NO: 58 and SEQ ID NO: 59; and wherein X' is at least 90% identical to a sequence selected from the group consisting of SEQ ID NOS: 2, 4, 6, 8, 10, 12, 14, 16, and 18.

16. The DNA vector of claim 15, wherein X is selected from the group consisting of SEQ ID NOS: 1, 3, 5, 7, 9, 11, 13, 15, and 17; wherein the oriR6Kγ sequence comprises a nucleic acid sequence selected from the group consisting of SEQ ID NO: 58 and SEQ ID NO: 59; and wherein X' is selected from the group consisting of SEQ ID NOS: 2, 4, 6, 8, 10, 12, 14, 16, and 18.

17. The DNA vector of claim 10, wherein the second portion comprises a sequence at least 95% identical to a sequence selected from the group consisting of SEQ ID NOS: 35, 60, 62, and 71.

18. The DNA vector of claim 17, wherein the second portion comprises a sequence selected from the group consisting of SEQ ID NOS: 35, 60, 62, and 71.

19. An isolated, circular, non-viral, non-integrating DNA vector comprising:

(i) a first portion comprising an expression cassette comprising a nucleic acid sequence encoding a therapeutic protein, wherein the nucleic acid sequence encoding the therapeutic protein is operably linked to a promoter; and (ii) a second portion comprising a nucleic acid sequence consisting essentially of, operably linked in a 5' to a 3' direction:

(a) a first AAV inverted repeat sequence;

(b) an oriR6Kγ sequence; and (c) a second AAV inverted repeat sequence.

20. The DNA vector of claim 19, wherein the oriR6Kγ sequence comprises a nucleic acid sequence that is at least 90% identical to a sequence selected from the group consisting of SEQ ID NO: 58 and SEQ ID NO: 59.

21. The DNA vector of claim 20, wherein the oriR6Kγ sequence comprises a nucleic acid sequence selected from the group consisting of SEQ ID NO: 58 and SEQ ID NO: 59.

22. The DNA vector of claim 19, wherein each of the AAV inverted repeat sequences is independently at least 90% identical to a sequence selected from the group consisting of SEQ ID NOS: 1-18.

23. The DNA vector of claim 22, wherein each of the AAV inverted repeat sequences is independently selected from the group consisting of SEQ ID NOS: 1-18.

24. The DNA vector of claim 19, wherein the first AAV inverted repeat sequence is at least 90% identical to a sequence selected from the group consisting of SEQ ID NOS: 1, 3, 5, 7, 9, 11, 13, 15, and 17; wherein the oriR6Kγ sequence comprises a nucleic acid sequence at least 90% identical to a sequence selected from the group consisting of SEQ ID NO: 58 and SEQ ID NO: 59; and wherein the second AAV inverted repeat sequence is at least 90% identical to a sequence selected from the group consisting of SEQ ID NOS: 2, 4, 6, 8, 10, 12, 14, 16, and 18.

25. The DNA vector of claim 24, wherein the first AAV inverted repeat sequence is selected from the group consisting of SEQ ID NOS: 1, 3, 5, 7, 9, 11, 13, 15, and 17; wherein the oriR6Kγ sequence comprises a nucleic acid sequence selected from the group consisting of SEQ ID NO: 58 and SEQ ID NO: 59; and wherein the second AAV inverted repeat sequence is selected from the group consisting of SEQ ID NOS: 2, 4, 6, 8, 10, 12, 14, 16, and 18.

26. The DNA vector of claim 19, wherein the second portion comprises a sequence at least 95% identical to a sequence selected from the group consisting of SEQ ID NOS: 35, 60, 62, and 71.

27. The DNA vector of claim 26, wherein the second portion comprises a sequence selected from the group consisting of SEQ ID NOS: 35, 60, 62, and 71.

* * * * *